(12) United States Patent
Fela et al.

(10) Patent No.: US 11,179,339 B2
(45) Date of Patent: Nov. 23, 2021

(54) COMPOSITIONS AND METHODS FOR LYOPHILIZATION OF BACTERIA OR LISTERIA STRAINS

(71) Applicant: ADVAXIS, INC., Princeton, NJ (US)

(72) Inventors: David Fela, Califon, NJ (US); Anu Wallecha, Yardley, PA (US); Mike Grace, Princeton, NJ (US); Melissa Gosse, Jackson, NJ (US)

(73) Assignee: Advaxis, Inc., Princeton, NJ (US)

( * ) Notice: Subject to any disclaimer, the term of this patent is extended or adjusted under 35 U.S.C. 154(b) by 11 days.

(21) Appl. No.: 16/647,977

(22) PCT Filed: Aug. 29, 2018

(86) PCT No.: PCT/US2018/048586
§ 371 (c)(1),
(2) Date: Mar. 17, 2020

(87) PCT Pub. No.: WO2019/060115
PCT Pub. Date: Mar. 28, 2019

(65) Prior Publication Data
US 2020/0261369 A1 Aug. 20, 2020

Related U.S. Application Data

(60) Provisional application No. 62/560,318, filed on Sep. 19, 2017.

(51) Int. Cl.
| | | |
|---|---|---|
| *A01N 1/02* | (2006.01) | |
| *A61K 9/19* | (2006.01) | |
| *A61K 35/74* | (2015.01) | |
| *C12N 1/20* | (2006.01) | |

(52) U.S. Cl.
CPC ............... *A61K 9/19* (2013.01); *A61K 35/74* (2013.01); *C12N 1/20* (2013.01)

(58) Field of Classification Search
CPC ...................................................... A61K 9/19
See application file for complete search history.

(56) References Cited

U.S. PATENT DOCUMENTS

| | | | |
|---|---|---|---|
| 4,205,132 A | 5/1980 | Sandine et al. | |
| 5,830,702 A | 11/1998 | Portnoy et al. | |
| 6,051,237 A | 4/2000 | Paterson | |
| 6,099,848 A | 8/2000 | Frankel et al. | |
| 6,504,020 B1 | 1/2003 | Frankel et al. | |
| 6,565,852 B1 | 5/2003 | Paterson | |
| 6,635,749 B2 | 10/2003 | Frankel et al. | |
| 6,767,542 B2 | 7/2004 | Paterson et al. | |
| 6,855,320 B2 | 2/2005 | Paterson et al. | |
| 7,135,188 B2 | 11/2006 | Paterson | |
| 7,488,487 B2 | 2/2009 | Frankel et al. | |
| 7,588,930 B2 | 9/2009 | Paterson et al. | |
| 7,635,479 B2 | 12/2009 | Paterson et al. | |
| 7,655,238 B2 | 2/2010 | Paterson et al. | |
| 7,662,396 B2 | 2/2010 | Paterson et al. | |
| 7,700,344 B2 | 4/2010 | Paterson et al. | |
| 7,794,729 B2 | 9/2010 | Paterson et al. | |
| 7,820,180 B2 | 10/2010 | Paterson et al. | |
| 7,855,064 B2 | 12/2010 | Paterson et al. | |
| 7,858,097 B2 | 12/2010 | Paterson et al. | |
| 8,114,414 B2 | 2/2012 | Paterson et al. | |
| 8,241,636 B2 | 8/2012 | Paterson et al. | |
| 8,268,326 B2 | 9/2012 | Paterson et al. | |
| 8,337,861 B2 | 12/2012 | Paterson et al. | |
| 8,771,702 B2 | 7/2014 | Paterson et al. | |
| 8,778,329 B2 | 7/2014 | Seavey et al. | |
| 8,791,237 B2 | 7/2014 | Paterson et al. | |
| 8,906,664 B2 | 12/2014 | Paterson et al. | |
| 8,956,621 B2 | 2/2015 | Paterson et al. | |
| 9,012,141 B2 | 4/2015 | Paterson et al. | |
| 9,017,660 B2 | 4/2015 | Shahab et al. | |
| 9,084,747 B2 | 7/2015 | Shahabi et al. | |
| 9,226,958 B2 | 1/2016 | Harn et al. | |
| 9,408,898 B2 | 8/2016 | Seavey et al. | |
| 9,463,227 B2 | 10/2016 | Rothman et al. | |
| 9,492,527 B2 | 11/2016 | Paterson et al. | |
| 9,499,602 B2 | 11/2016 | Paterson et al. | |
| 9,549,973 B2 | 1/2017 | Paterson et al. | |
| 9,644,212 B2 | 5/2017 | Maciag et al. | |
| 9,650,639 B2 | 5/2017 | Maciag et al. | |
| 9,700,608 B2 | 7/2017 | Paterson et al. | |
| 9,919,038 B2 | 3/2018 | Seavey et al. | |

(Continued)

FOREIGN PATENT DOCUMENTS

| | | | |
|---|---|---|---|
| EP | 2148923 A1 | 11/2008 | |
| WO | WO 1996/014087 A1 | 5/1996 | |

(Continued)

OTHER PUBLICATIONS

Bedu-Addo, "Understanding Lyophilization Formulation Development," Pharmaceutical Technology, Lyophilization, www.pharmtech.com, pp. 10-18, (2004).
Bhat, et al., "Bacillus subtilis natto: a non-toxic source of poly-γ-glutamic acid that could be used as a cryoprotectant for probiotic bacteria," AMB Express, 3(1):36 (2013).
Borges, et al., "Effects of Processing and Storage on Pediococcus pentosaceus SB83 in Vaginal Formulations: Lyophilized Powder and Tablets," Biomed. Res. Int., 2013:680767, (2013).
Broeckx, et al., "Drying techniques of probiotic bacteria as an important step towards the development of novel pharmabiotics," Int. J. Pharm., 505(1-2):303-318, (2016).
Cabrefiga, et al., "Improvement of a dry formulation of Pseudomonas fluorescens EPS62e for fire blight disease biocontrol by combination of culture osmoadaptation with a freeze-drying lyoprotectant,"J. Appl. Microbiol., 117(4):1122-1131, (2014).

(Continued)

*Primary Examiner* — Albert M Navarro
(74) *Attorney, Agent, or Firm* — Alston & Bird LLP

(57) ABSTRACT

Methods and compositions are provided for lyophilization of bacteria or *Listeria* strains, such as *Listeria monocytogenes*. Provided are methods for producing a lyophilized composition comprising a bacteria or *Listeria* strain, formulations for lyophilization comprising a bacteria or *Listeria* strain, lyophilized bacteria or *Listeria* strains, and methods of preparing frozen bacteria or *Listeria* strains for lyophilization.

26 Claims, 83 Drawing Sheets

Specification includes a Sequence Listing.

(56) References Cited

U.S. PATENT DOCUMENTS

| | | |
|---|---|---|
| 9,943,590 B2 | 4/2018 | Harn et al. |
| 9,981,024 B2 | 5/2018 | Seavey et al. |
| 10,010,593 B2 | 7/2018 | Paterson |
| 10,016,617 B2 | 7/2018 | Mason et al. |
| 10,058,599 B2 | 8/2018 | Singh et al. |
| 10,064,898 B2 | 9/2018 | Rothman et al. |
| 10,143,734 B2 | 12/2018 | Petit |
| 10,166,276 B2 | 1/2019 | Paterson et al. |
| 10,189,885 B2 | 1/2019 | Paterson et al. |
| 10,258,679 B2 | 4/2019 | Wallecha et al. |
| 10,900,044 B2 | 1/2021 | Petit et al. |
| 2002/0025323 A1 | 2/2002 | Paterson et al. |
| 2002/0028206 A1 | 3/2002 | Paterson |
| 2002/0136737 A1 | 9/2002 | Frankel et al. |
| 2003/0202985 A1 | 10/2003 | Paterson |
| 2005/0048081 A1 | 3/2005 | Frankel et al. |
| 2005/0118184 A1 | 6/2005 | Paterson et al. |
| 2005/0129715 A1 | 6/2005 | Paterson et al. |
| 2006/0093582 A1 | 5/2006 | Paterson et al. |
| 2006/0104991 A1 | 5/2006 | Paterson et al. |
| 2006/0121053 A1 | 6/2006 | Sweeney et al. |
| 2006/0204516 A1 | 9/2006 | Paterson et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2006/0269561 A1 | 11/2006 | Paterson et al. |
| 2007/0003567 A1 | 1/2007 | Paterson et al. |
| 2007/0253976 A1 | 11/2007 | Paterson et al. |
| 2007/0264279 A1 | 11/2007 | Paterson et al. |
| 2008/0131456 A1 | 6/2008 | Paterson et al. |
| 2009/0081248 A1 | 3/2009 | Paterson et al. |
| 2009/0081250 A1 | 3/2009 | Paterson et al. |
| 2009/0186051 A1 | 7/2009 | Paterson et al. |
| 2009/0202587 A1 | 8/2009 | Paterson et al. |
| 2010/0189739 A1 | 7/2010 | Frankel et al. |
| 2010/0291140 A1 | 11/2010 | Paterson et al. |
| 2010/0297231 A1 | 11/2010 | Vehring et al. |
| 2011/0129499 A1 | 6/2011 | Maciag et al. |
| 2011/0142791 A1 | 6/2011 | Shahabi et al. |
| 2011/0177119 A1 | 7/2011 | Dhere et al. |
| 2011/0305724 A1 | 12/2011 | Paterson et al. |
| 2012/0014984 A1 | 1/2012 | Shahabi et al. |
| 2012/0114685 A1 | 5/2012 | Sewell |
| 2012/0135033 A1 | 5/2012 | Wallecha |
| 2012/0177678 A1 | 7/2012 | Paterson et al. |
| 2013/0259891 A1 | 10/2013 | Harn et al. |
| 2014/0199258 A1 | 7/2014 | Rothman |
| 2014/0199286 A1 | 7/2014 | Zhao et al. |
| 2014/0234370 A1 | 8/2014 | Shahabi |
| 2014/0248304 A1 | 9/2014 | Paterson et al. |
| 2014/0314708 A1 | 10/2014 | Maciag et al. |
| 2014/0335120 A1 | 11/2014 | Maciag et al. |
| 2015/0079034 A1 | 3/2015 | Seavey et al. |
| 2015/0098964 A1 | 4/2015 | Singh et al. |
| 2015/0125480 A1 | 5/2015 | Paterson et al. |
| 2015/0196628 A1 | 7/2015 | Mason et al. |
| 2015/0238584 A1 | 8/2015 | Shahabi et al. |
| 2015/0297702 A1 | 10/2015 | Shahabi |
| 2015/0335721 A1 | 11/2015 | Paterson et al. |
| 2015/0343047 A1 | 12/2015 | Paterson et al. |
| 2015/0366955 A9 | 12/2015 | Shahabi et al. |
| 2016/0022814 A1 | 1/2016 | Petit et al. |
| 2016/0024173 A1 | 1/2016 | Paterson et al. |
| 2016/0158331 A1 | 6/2016 | Paterson et al. |
| 2016/0206716 A1 | 7/2016 | Seavey et al. |
| 2016/0220652 A1 | 8/2016 | Petit et al. |
| 2016/0228530 A1 | 8/2016 | Paterson |
| 2016/0256538 A1 | 9/2016 | Harn et al. |
| 2016/0324903 A1 | 11/2016 | Rothman et al. |
| 2016/0361401 A1 | 12/2016 | Shahabi et al. |
| 2016/0367650 A1 | 12/2016 | Paterson |
| 2017/0028045 A1 | 2/2017 | Paterson et al. |
| 2017/0042996 A1 | 2/2017 | Wallecha et al. |
| 2017/0049867 A1 | 2/2017 | Seavey et al. |
| 2017/0080064 A1 | 3/2017 | Petit et al. |
| 2017/0100469 A1 | 4/2017 | Paterson et al. |
| 2017/0106072 A1 | 4/2017 | Petit |
| 2017/0204361 A1 | 7/2017 | Eapen et al. |
| 2017/0246273 A1 | 8/2017 | Wallecha et al. |
| 2017/0281691 A1 | 10/2017 | Paterson et al. |
| 2017/0368157 A1 | 12/2017 | Khleif et al. |
| 2018/0064765 A1 | 3/2018 | Petit et al. |
| 2018/0104284 A1 | 4/2018 | Wallecha et al. |
| 2018/0153974 A1 | 6/2018 | Petit et al. |
| 2018/0305702 A1 | 10/2018 | Petit et al. |
| 2018/0325964 A1 | 11/2018 | Eapen et al. |
| 2018/0360940 A1 | 12/2018 | Petit et al. |
| 2019/0002891 A1 | 1/2019 | Petit et al. |
| 2019/0032064 A1 | 1/2019 | Petit et al. |
| 2019/0240303 A1 | 8/2019 | Wallecha et al. |
| 2019/0248856 A1 | 8/2019 | Princiotta et al. |
| 2019/0322714 A1 | 10/2019 | Petit et al. |
| 2020/0061167 A1 | 2/2020 | Hayes et al. |
| 2020/0069785 A1 | 3/2020 | Paterson et al. |
| 2020/0261369 A1 | 8/2020 | Fela et al. |
| 2021/0003558 A1 | 1/2021 | Molli et al. |
| 2021/0177955 A1 | 6/2021 | Petit et al. |
| 2021/0239681 A1 | 8/2021 | Wallecha et al. |
| 2021/0246457 A1 | 8/2021 | Petit et al. |

FOREIGN PATENT DOCUMENTS

| | | |
|---|---|---|
| WO | WO 1999/025376 A1 | 5/1999 |
| WO | WO 2001/072329 A1 | 10/2001 |
| WO | WO 2004/062597 A2 | 7/2004 |
| WO | WO 2006/017856 A2 | 2/2006 |
| WO | WO 2006/036550 A2 | 4/2006 |
| WO | WO 2007/061848 A2 | 5/2007 |
| WO | WO 2007/106476 A2 | 9/2007 |
| WO | WO 2007/130455 A2 | 11/2007 |
| WO | WO 2008/079172 A2 | 7/2008 |
| WO | WO 2008/109155 A2 | 9/2008 |
| WO | WO 2008/130551 A2 | 10/2008 |
| WO | WO 2008/140812 A2 | 11/2008 |
| WO | WO 2009/143167 A2 | 11/2009 |
| WO | WO 2010/008782 A1 | 1/2010 |
| WO | WO 2010/040135 A1 | 4/2010 |
| WO | WO 2010/102140 A1 | 9/2010 |
| WO | WO 2011/060260 A2 | 5/2011 |
| WO | WO 2011/100754 A1 | 8/2011 |
| WO | WO 2012/125551 A1 | 9/2012 |
| WO | WO 2012/138377 A2 | 10/2012 |
| WO | WO 2013/025925 A1 | 2/2013 |
| WO | WO 2013/138337 A1 | 9/2013 |
| WO | WO 2014/029758 A1 | 2/2014 |
| WO | WO 2015/126921 A1 | 8/2015 |
| WO | WO 2015/130810 A2 | 9/2015 |
| WO | WO 2015/134722 A2 | 9/2015 |
| WO | WO 2015/164121 A1 | 10/2015 |
| WO | WO 2015/167748 A1 | 11/2015 |
| WO | WO 2016/011320 A1 | 1/2016 |
| WO | WO 2016/011353 A1 | 1/2016 |
| WO | WO 2016/011357 A1 | 1/2016 |
| WO | WO 2016/011362 A1 | 1/2016 |
| WO | WO 2016/061182 A1 | 4/2016 |
| WO | WO 2016/061277 A1 | 4/2016 |
| WO | WO 2016/100924 A1 | 6/2016 |
| WO | WO 2016/100929 A1 | 6/2016 |
| WO | WO 2016/105510 A2 | 6/2016 |
| WO | WO 2016/126876 A2 | 8/2016 |
| WO | WO 2016/126878 A2 | 8/2016 |
| WO | WO 2016/141121 A1 | 9/2016 |
| WO | WO 2016/154412 A2 | 9/2016 |
| WO | WO 2016/183361 A1 | 11/2016 |
| WO | WO 2016/191545 A1 | 12/2016 |
| WO | WO 2016/207859 A1 | 12/2016 |
| WO | WO 2017/048714 A1 | 3/2017 |
| WO | WO 2017/048850 A1 | 3/2017 |
| WO | WO 2017/049218 A2 | 3/2017 |
| WO | WO 2017/066706 A1 | 4/2017 |
| WO | WO 2017/085691 A1 | 5/2017 |
| WO | WO 2017/106754 A2 | 6/2017 |
| WO | WO 2017/132547 A1 | 8/2017 |
| WO | WO 2018/009461 A1 | 1/2018 |

(56) References Cited

FOREIGN PATENT DOCUMENTS

| WO | WO 2018/085854 A1 | 5/2018 |
|---|---|---|
| WO | WO 2018/102584 A1 | 6/2018 |
| WO | WO 2018/102585 A1 | 6/2018 |
| WO | WO 2018/129306 A1 | 7/2018 |
| WO | WO 2019/006401 A1 | 1/2019 |
| WO | WO 2019/060115 A1 | 3/2019 |
| WO | WO 2019/094607 A2 | 5/2019 |
| WO | WO 2019/157098 A1 | 8/2019 |
| WO | WO 2019/173684 A1 | 9/2019 |
| WO | WO 2019/210034 A1 | 10/2019 |

OTHER PUBLICATIONS

Cabuk, et al., "Improved viability of Lactobacillus acidophilus NRRL-B 4495 during freeze-drying in whey protein-pullulan microcapsules," J. Microencapsul., 32(3):3, 300-307, (2015).

Celik, et al., "Factors influencing the stabilty of freeze-dried stress-resilient and stree-sensitive strains of bifidobacteria," J. Dairy Sci., 96(6):3506-3516, (2013).

Dianawati, et al., "Role of Calcium Alginate and Mannitol in Protecting Bifidobacterium," Appl. Ennviron. Microbiol., 78(19):6914-6921, (2012).

Dimitrieva-Moats, et al., "Development of Freeze-Dried Bacteriocin-Containing Preparations from Lactic Acid Bacteria to Inhibit Listeria monocytogenes and Staphylococcus aureus," Probiotics Antimicrob. Proteins, 4(1):27-38, (2012).

Gheorghiu, et al., "Stabilisation of BCG Vaccines," Dev. Biol. Stand., 87:251-261, (1996).

Jalali, et al., "Stability evaluation of freeze-dried *Lactobacillus paracasei* subsp. tolerance and *Lactobacillus delbrueckii* subsp. Bulgaricus in oral capsules," Res. Pharm. Sci., 7(1):31-36, (2012).

Kochs, et al., "The influence of the freezing process on vapour transport during sublimation in vacuum-freeze-drying of macroscopic samples," Int. J. Heat Mass Transfer, 36(7):1727-1738, (1993).

Lewis, et al., "Characterizing the Freeze-Drying Behavior of Model Protein Formulations," AAPS PharmSciTech, 11(4):1580-1590, (2010).

Li, et al., "NaCl stress impact on the key enzymes in glycolysis from Lactobacillus bulgaricus during freeze-drying," Braz. J. Microbiol., 46(4):1193-1199, (2015).

Maus, et al., "Employment of stressful conditions during culture production to enhance subsequent cold- and acid-tolerance of bifidobacteria," J. Appl. Microbiol., 95(1):146-154, (2003).

Mayeresse, et al., "Considerations for Transferring a Bulk Freeze-Drying Process from a Glass Container to a Tray," Pharmaceutical Engineering, 29(2):36-47, (2009).

McDonald, et al., "Freeze substitution in 3 hours or less," J. Microsc., 243(3):227-233, (2011).

Merabishvili, et al., "Stability of *Staphylococcus aureus* Phage ISP after Freeze-Drying (Lyophilization)," PLoS ONE, 8(7):e68797, (2013).

Navarta, et al., "Freezing and freeze-drying of the bacterium Rahnella aquatilis BNM 0523: study of protecting agents, rehydration media and freezing temperatures," Lett. Appl. Microbiol., 53(5):565-571, (2011).

Ohtake, et al., "Formulation and Stabilization of Francisella tularensis Live Vaccine Strain," J. Pharm. Sci., 100(8):3076-3087, (2011).

Ohtake, et al., "Room Temperature Stabilization of Oral, Live Attenuated *Salmonella enterica* serovar Typhi-Vectored Vaccines," Vaccine, 29(15):2761-2771, (2011).

Onneby, et al., "Effects of di- and polysaccharide formulations and storage conditions on survival of freeze-dried *Sphingobium* sp.," World J. Microbiol. Biotechnol., 29(8):1399-1408, (2013).

Patapoff, et al., "The Importance of Freezing on Lyophilization Cycle Development," BioPharm, 15(3):16-21+72, (2002).

Pehkonen, et al., "State transitions and physicochemical aspects of cryoprotection and stabilization in freeze-drying of Lactobacillus rhamnosus GG (LGG)," J. Appl. Microbiol., 104(6):1732-1743, (2008).

Peiren, et al., "Impact of the freeze-drying process on product appearance, residual moisture content, viability, and batch uniformity of freeze-dried bacterial cultures safeguarded at culture collections," Appl. Microbiol. Biotechnol., 100(14):6239-6249, (2016).

Peiren, et al., "Improving survival and storage stability of bacteria recalcitrant to freeze-drying: a coordinated study by European culture collections," Appl. Microbiol. Biotechnol., 99(8):3559-3571, (2015).

Pingitore, et al., "Effect of lyophilization and storage temperature on the activity of salivaricin CRL 1328, a potential bioactive ingredient of a urogenital probiotic product," J. Gen. Appl. Microbiol., 58(2):71-81, (2012).

Tseng, et al., "Effect of Different Drying Methods and Storage Time on the Retention of Bioactive Compounds and Antibacterial Activity of Wine Grape Pomace (Pinot Noir and Merlot)," J. Food Sci., 77(9):H192-H201, (2012).

Wessman, et al., "Formulations for Freeze-drying of Bacteria and Their Influence on Cell Survival," J. Vis. Exp., 78:e4058, (2013).

Wiedmann, et al., "Listeria monocytogenes Grown at 7oC Shows Reduced Acid Survival and an Altered Transcriptional Response to Acid Shock Compared to L. monocytogenes Grown at 37oC," Appl. Environ. Microbiol., 78(11):3824-3836, (2012).

Zhan, et al., "Screening of freeze-dried protective agents for the formulation of biocontrol strains, Bacillus cereus AR156, Burkholderia vietnamiensis B418 and Pantoea agglomerans 2Re40," Lett. Appl. Microbiol., 54(1):10-17, (2012).

Zhang, et al., "Effect of microencapsulation methods on the survival of freeze-dried Bifidobacterium bifidum," J. Microencapsul., 30(6):511-518, (2013).

WIPO Application No. PCT/US2018/048586, PCT International Search Report and Written Opinion of the International Searching Authority dated Nov. 30, 2018.

WO Application No. PCT/US2019/048586 International Preliminary Report on Patentability and Written Opinion dated Mar. 24, 2020.

EP 18859475.9 Extended European Search Report dated Mar. 17, 2021.

COMPOSITIONS AND METHODS FOR LYOPHILIZATION OF BACTERIA OR LISTERIA STRAINS

CROSS-REFERENCE TO RELATED APPLICATIONS

This application is a national stage entry of PCT/US2018/048586 filed Aug. 29, 2018, which claims the benefit of U.S. Application No. 62/560,318, filed Sep. 19, 2017, herein incorporated by reference in its entirety for all purposes.

REFERENCE TO A SEQUENCE LISTING SUBMITTED AS A TEXT FILE VIA EFS WEB

The Sequence Listing written in file 545193SEQL-ST.TXT is 11,733,993 bytes, was created on Mar. 17, 2020, and is hereby incorporated by reference.

BACKGROUND

Lyophilization is a process that removes solvent from a solution to form solid or powder that is stable and easier to store at elevated temperature than liquid. Lyophilization, also known as freeze drying, involves freezing followed by sublimation. The resulting lyophilized matter may be stored without refrigeration or at higher temperatures than liquid, reducing storage and transportation costs of the substance as well as the storage space required for the product. It also can reduce the weight of the product, which similarly reduces shipping and related costs. Lyophilization is particularly useful for preserving and storing various biological molecules, because it increases their shelf-life.

Compared to liquid formulations, solid formulations have multiple advantages such as superior storage stability, reduced molecular mobility and unwanted chemical reactions, and less package weight for increased ease in shipping and distribution. Furthermore, as all currently available commercial vaccines require low temperature storage, the goal is to utilize solid state stabilization techniques to enhance their room temperature or high temperature stability and to reduce the reliance on cold-chain to maintain efficacy and ensure safety. Although lyophilization is the preferred preservation method because the low storage and transport costs of freeze-dried bacterial cultures are a major advantage compared to cryopreservation, lyophilization is a very complex physical process affected by many parameters requiring specific equipment and trained personnel. Freeze-drying can cause many types of damage to cells, including a loss of viability, reduction of metabolic activity, and changes in cell morphology, which can affect the physiology, characterization, and functions of cells such as bacteria.

In addition, the effect of varying different lyophilization parameters is highly strain-specific, and this strain dependency makes it difficult to draw general conclusions or guidelines from any one particular strain. The high biological and metabolic diversity of bacteria makes it difficult and laborious to develop strain-specific optimized freeze-drying procedures. There are very limited data on the lyophilization of *Listeria* bacteria strains such as *Listeria monocytogenes* and what parameters need to be optimized and how to optimize them to make lyophilization a viable option for *Listeria*.

SUMMARY

Methods and compositions are provided for lyophilization of bacteria or *Listeria* strains, such as *Listeria monocytogenes*. In one aspect, provided are methods for producing a lyophilized composition comprising a bacteria or *Listeria* strain. Some such methods can comprise providing a composition comprising a bacteria or *Listeria* strain in a formulation comprising a buffer, cooling the composition in a freezing step, exposing the cooled composition to a vacuum and a first increased temperature in a primary drying step, and exposing the composition from the primary drying step to a vacuum and a second increased temperature in a secondary drying step, whereby the lyophilized composition is produced.

In some such methods, the bacteria or *Listeria* strain used in the composition is a frozen *Listeria* strain that is thawed prior to the freezing step. In a specific example, the frozen bacteria or *Listeria* strain can be thawed at a temperature of about 2° C. to about 37° C., about 20° C. to about 37° C., about 23° C. to about 37° C., about 25° C. to about 37° C., about 32° C. to about 37° C., or about 37° C. Optionally, the thawing is for no more than about 8 hours. Optionally, the thawed bacteria or *Listeria* strain is held at temperature of between about 2° C. and about 8° C. for no more than about 24 hours. In a specific example, the concentration of the bacteria or *Listeria* strain being thawed can be between about 1×10E9 and about 1×10E10 colony forming units (CFU) per milliliter.

In some such methods, the formulation comprises a buffer and sucrose. For example, the formulation buffer can comprise about 1% to about 5% w/v sucrose, about 2% to about 3% w/v sucrose, or about 2.5% w/v sucrose. Optionally, the formulation does not comprise one or more other excipients such as trehalose, monosodium glutamate (MSG), or recombinant human serum albumin (rHSA).

In some such methods, the formulation comprises about 1×10E9 to about 1×10E10 colony forming units (CFU) of bacteria or *Listeria* per milliliter.

In some such methods, the holding temperature in the primary drying step is between about −10° C. and about −30° C., between about −12° C. and about −22° C., between about −17° C. and about −19° C., or about −18° C.

In some such methods, the residual moisture in the lyophilized composition is at least about 2.5%, at least about 3%, or at least about 3.5%. In some such methods, the residual moisture is between about 1% and about 5% or between about 2% and about 4%.

In some such methods, the lyophilized composition shows at least about 60%, 70%, 80%, or 90% viability after storage at between about −20° C. and about 4° C. or after storage at about −20° C. or about 4° C. for about 6 months, 12 months, 18 months, or 24 months.

Such methods can comprise, for example: (a) providing a composition comprising a *Listeria* strain in a formulation comprising a buffer and sucrose; (b) cooling the composition provided in step (a) to a holding temperature between about −32° C. and about −80° C. in a freezing step; (c) exposing the composition produced by step (b) to a vacuum at a holding temperature between about −10° C. and about −30° C. in a primary drying step; and (d) exposing the composition produced by step (c) to a vacuum at a holding temperature between about −5° C. and about 25° C. in a secondary drying step whereby the lyophilized composition is produced. Such methods can alternatively comprise, for example: (a) providing a composition comprising a *Listeria* strain in a formulation comprising a buffer and sucrose; (b) cooling the composition provided in step (a) to a holding temperature between about −32° C. and about −80° C. in a freezing step; (c) exposing the composition produced by step (b) to a vacuum at a holding temperature between about −10° C. and about −30° C. in a primary drying step; and (d) exposing the composition produced by step (c) to a vacuum at a holding temperature between about 5° C. and about 25° C. in a secondary drying step whereby the lyophilized composition is produced. In some such methods, the *Listeria* strain is a recombinant *Listeria monocytogenes* strain, a stress response is induced in the *Listeria* strain by exposing the *Listeria* strain to a decreased temperature, the buffer is a phosphate buffer, the formulation comprises 2% to 3% w/v sucrose, the formulation does not comprise trehalose, MSG, or rHSA, the temperature in the primary drying step (c) is between −17° C. and −19° C., and the residual moisture in the lyophilized composition is between 3% and 4%. Some such methods have one or more or all of the following elements: the *Listeria* strain is a recombinant *Listeria monocytogenes* strain; the buffer is a phosphate buffer; the formulation comprises about 2% to about 3% w/v sucrose; the formulation does not comprise trehalose, MSG, or rHSA; the formulation comprises about 1×10E9 to about 1×10E10 colony forming units (CFU) of *Listeria* per milliliter; the holding temperature in the freezing step (a) is between about −40° C. and about −50° C.; the holding temperature in the primary drying step (c) is between about −17° C. and about −19° C.; the holding temperature in the secondary drying step (d) is between −1° C. and 1° C.; and the residual moisture in the lyophilized composition is between about 2.5% and about 4%. In some such methods, the *Listeria* strain used in the composition in step (a) is a frozen *Listeria* strain that is thawed prior to step (a). Optionally, such methods have one or more or all of the following elements: the concentration of the frozen *Listeria* strain being thawed is between about 1×10E9 to about 1×10E10 colony forming units (CFU) per milliliter; the frozen *Listeria* strain is thawed at about 37° C.; the frozen *Listeria* strain is thawed for no more than 8 hours; and the frozen *Listeria* strain is held at about 2° C. to about 8° C. for no more than 24 hours after thawing. Also provided are lyophilized bacteria or *Listeria* strains produced by the lyophilization methods disclosed herein.

In another aspect, provided are formulations for lyophilization comprising a bacteria or *Listeria* strain. Such formulations can comprise, for example: (1) the *Listeria* strain; (2) a phosphate buffer; and (3) sucrose. In some such formulations, the *Listeria* strain is a recombinant *Listeria monocytogenes* strain, the formulation comprises about 2% to about 3% w/v sucrose, and the formulation does not comprise trehalose, MSG, or rHSA.

In another aspect, provided are lyophilized compositions comprising a bacteria or *Listeria* strain. Some such lyophilized compositions have a residual moisture of at least about 2.5% or at least about 3%. Some such lyophilized compositions can further comprise a phosphate buffer and sucrose. In some such lyophilized compositions, the *Listeria* strain is a recombinant *Listeria monocytogenes* strain, the lyophilized composition does not comprise trehalose, MSG, or rHSA, and the residual moisture in the lyophilized composition is between 3% and 4%.

In another aspect, provided are methods of preparing a frozen *Listeria* strain for lyophilization, comprising thawing the frozen *Listeria* strain at a temperature between about 20° C. and about 37° C. Optionally, such methods have one or more or all of the following elements: the concentration of the frozen *Listeria* strain being thawed is between about 1×10E9 to about 1×10E10 colony forming units (CFU) per milliliter; the frozen *Listeria* strain is thawed at about 37° C.; the frozen *Listeria* strain is thawed for no more than 8 hours; and the frozen *Listeria* strain is held at about 2° C. to about 8° C. for no more than 24 hours after thawing.

BRIEF DESCRIPTION OF THE FIGURES

FIG. 7A shows results for formulations having 2.5% weight per volume (w/v) sucrose. FIG. 7B shows results for formulations having 5% to lyophilization (Part B) and Lm samples with no temperature shift (Part A) in the Lyo10 experiment.

Figure 14:
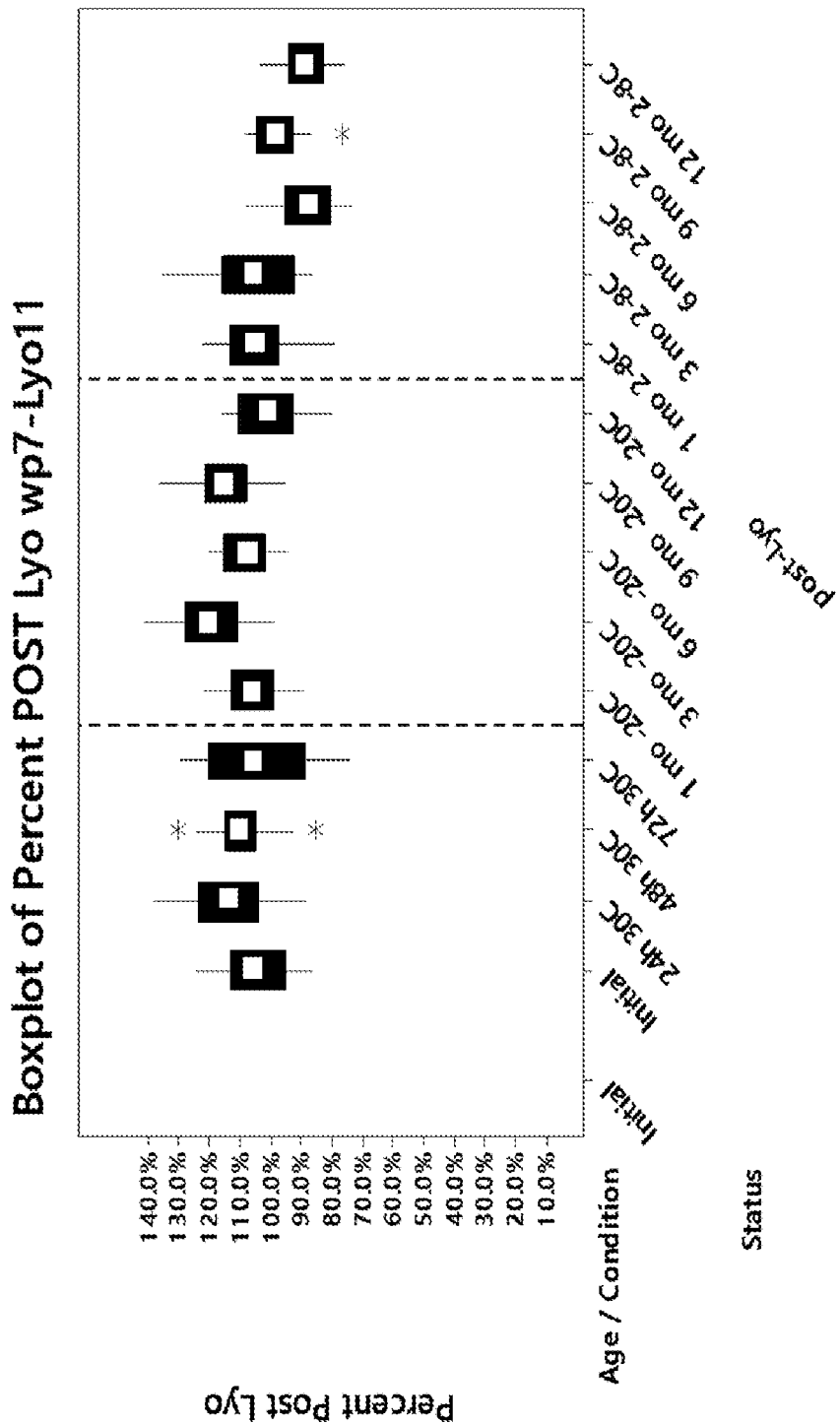

FIG. 14 shows VCC data post-lyophilization after storage at different temperatures for different amounts of time in the Lyo11 experiment.

Figure 15:
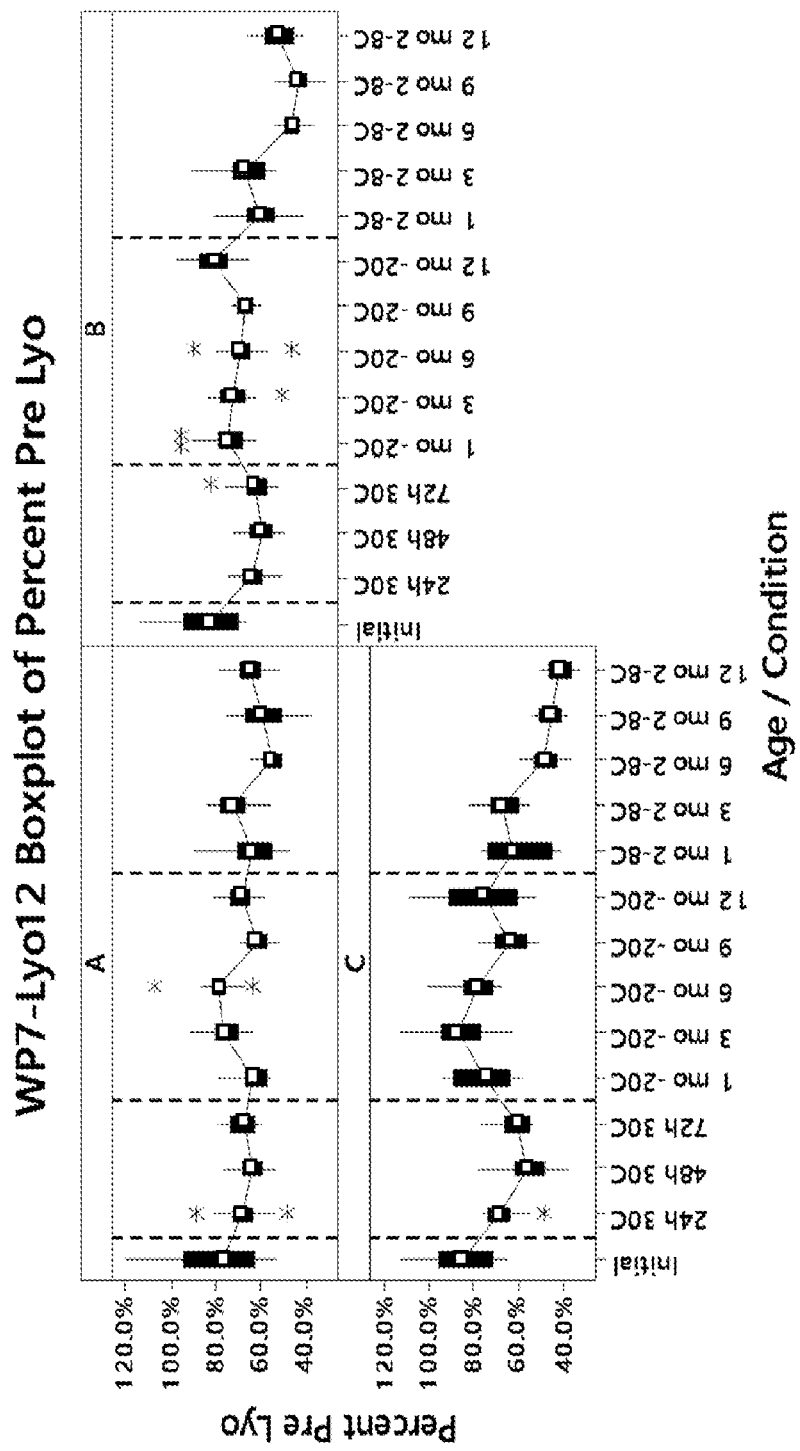

FIG. 15 shows VCC data post-lyophilization after storage at different temperatures for different amounts of time in fresh Lm samples (Part A), frozen Lm samples thawed at 2-8° C. prior to lyophilization (Part B), and frozen Lm samples thawed at 37° C. and incubated 4 hours prior to lyophilization (Part C) in the Lyo12 experiment.

Figure 16:
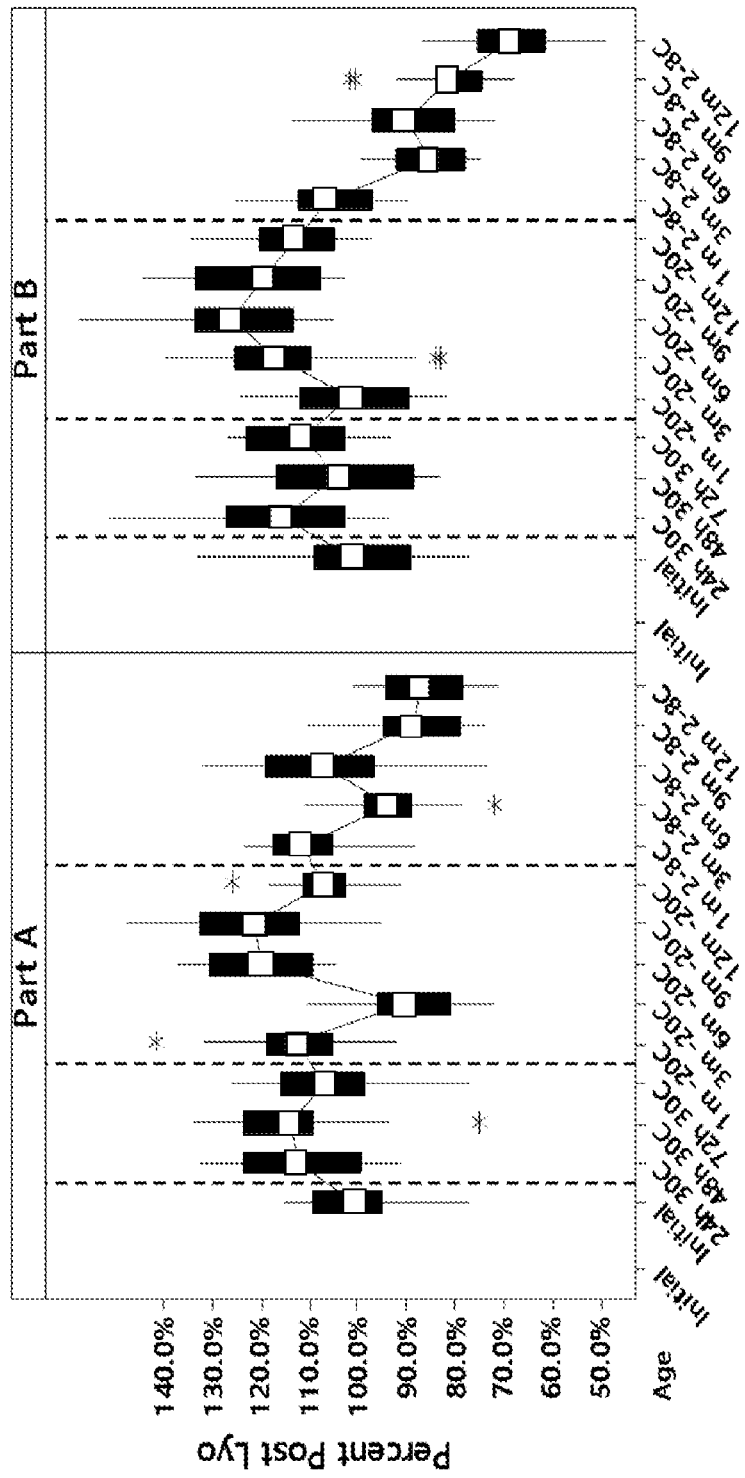

FIG. 16 shows VCC data post-lyophilization after storage at different temperatures for different amounts of time in fresh Lm samples (Part A) and Lm samples stored at 2-8° C. for 3 days.

Figure 17:
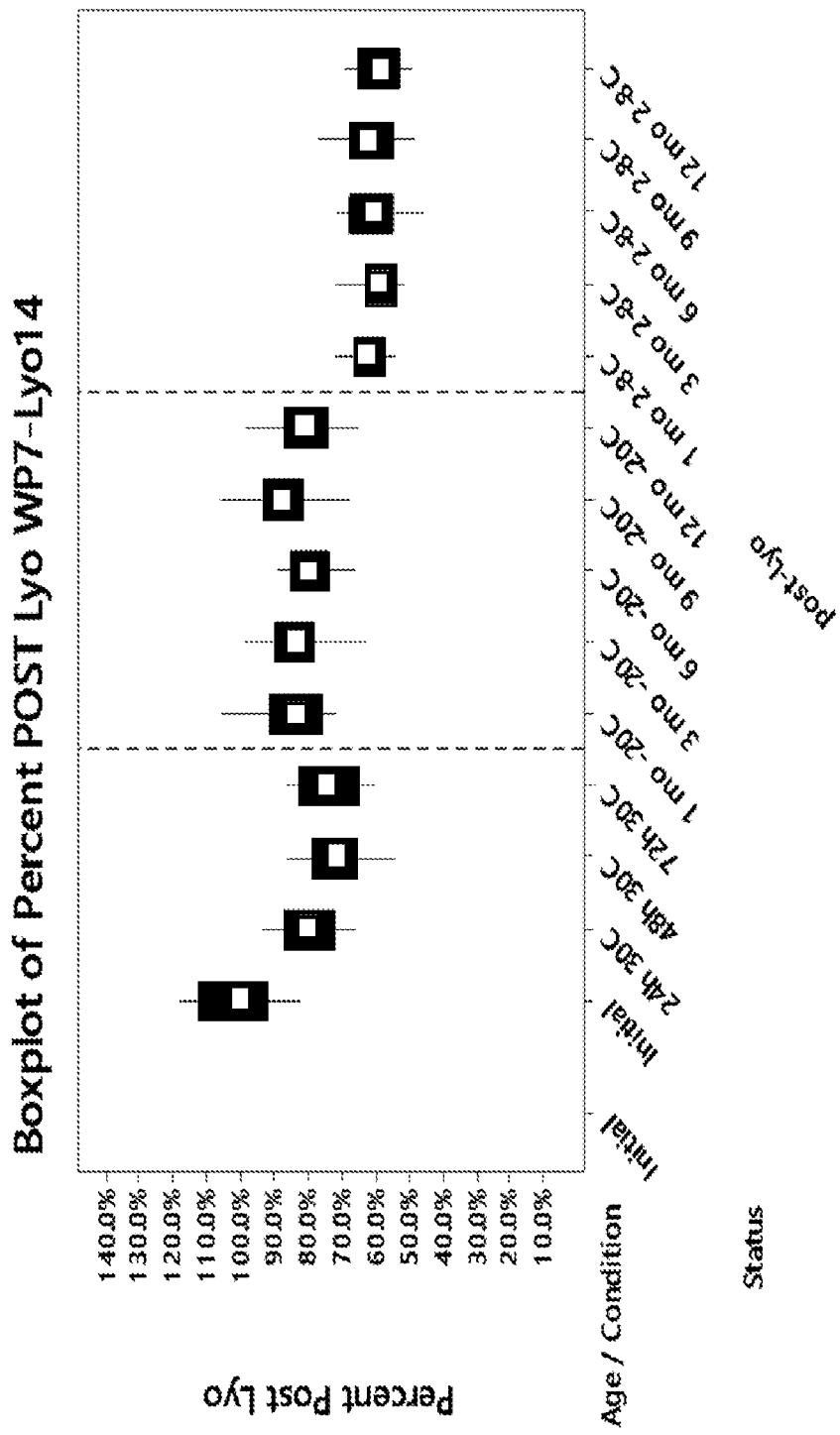

FIG. 17 shows VCC data post-lyophilization after storage at different temperatures for different amounts of time in Lm samples under the following conditions: 2R vials, $1 \times 10^9$ VCC, and 1.2 mL fill.

Figure 18:
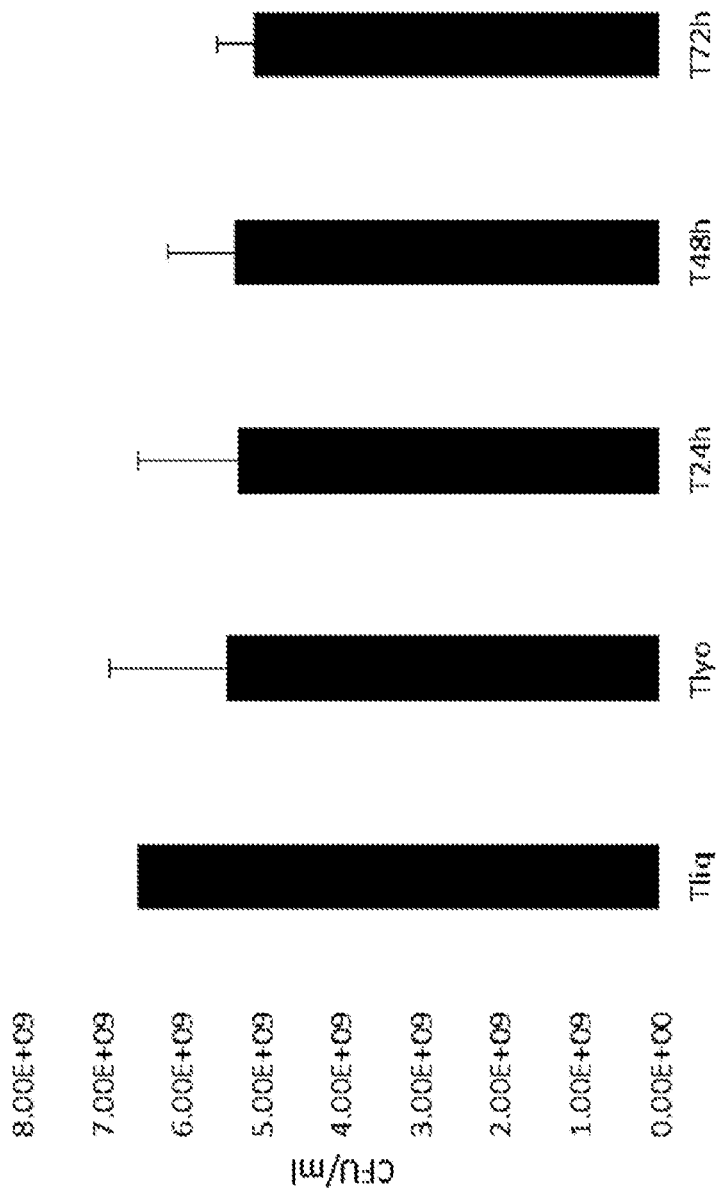

FIG. 18 shows VCC data (CFU/mL) before lyophilization, after lyophilization, and at accelerated conditions for 1, 2, and 3 days at 30° C. ($T_{liq}$, $T_{lyo}$, T42 h, T48 h, and T72 h, respectively).

Figure 19:
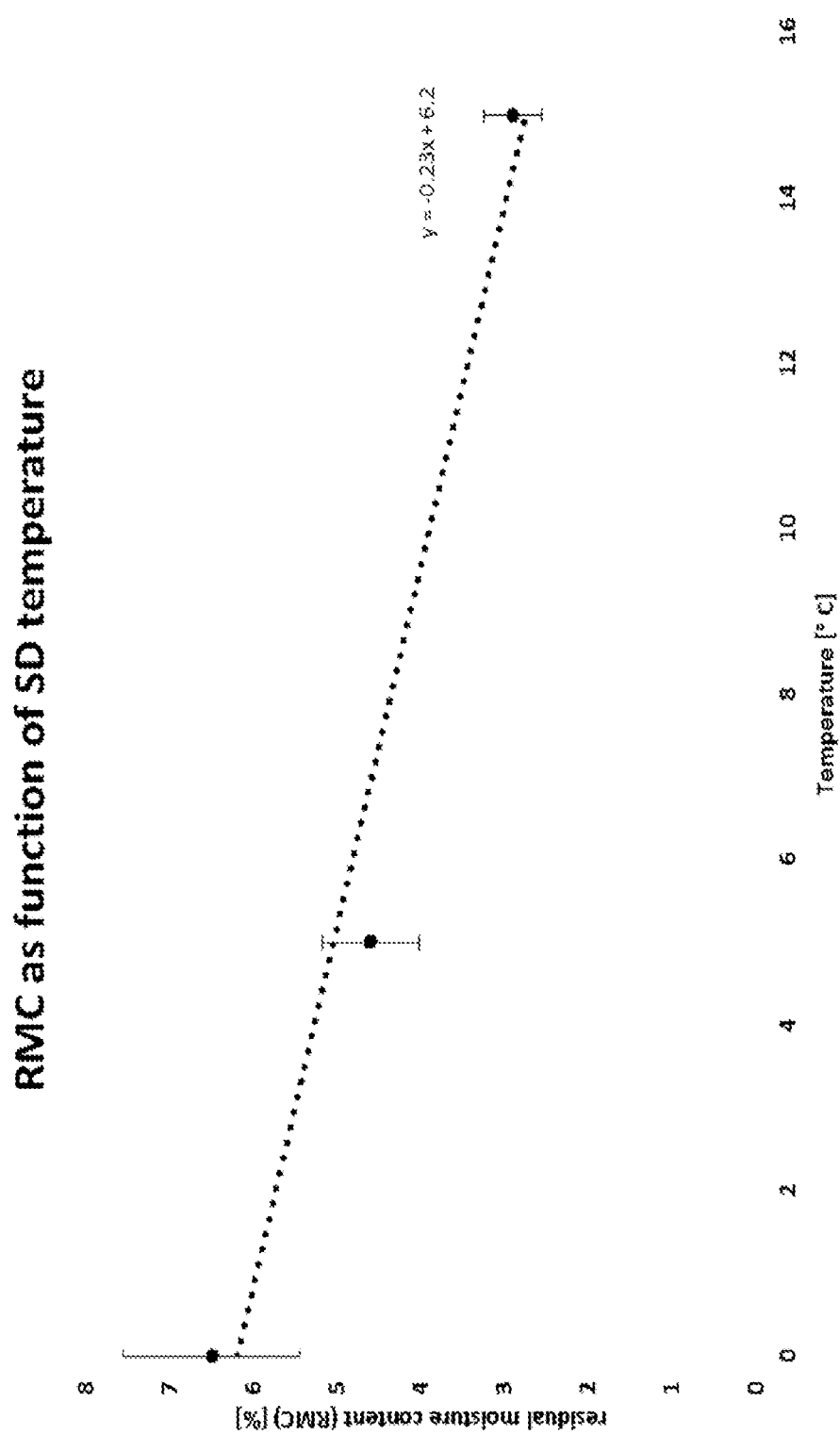

FIG. 19 shows residual moisture content (RM) as a function of the shelf temperature in the secondary drying step (SD temperature).

Figure 20:
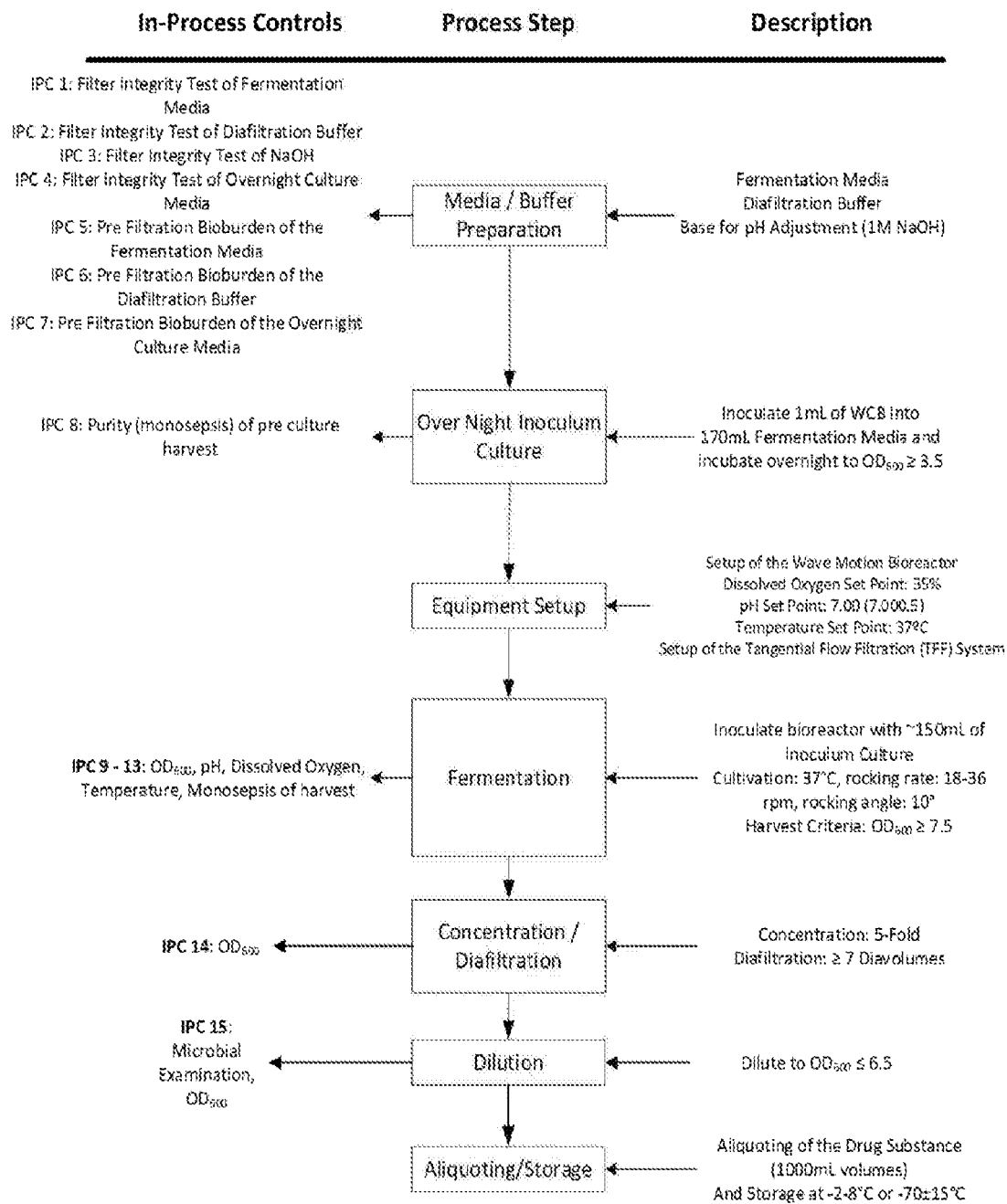

FIG. 20 shows the drug substance manufacturing process flow for Axalimogene Filolisbac (ADXS-HPV).

Figure 21:
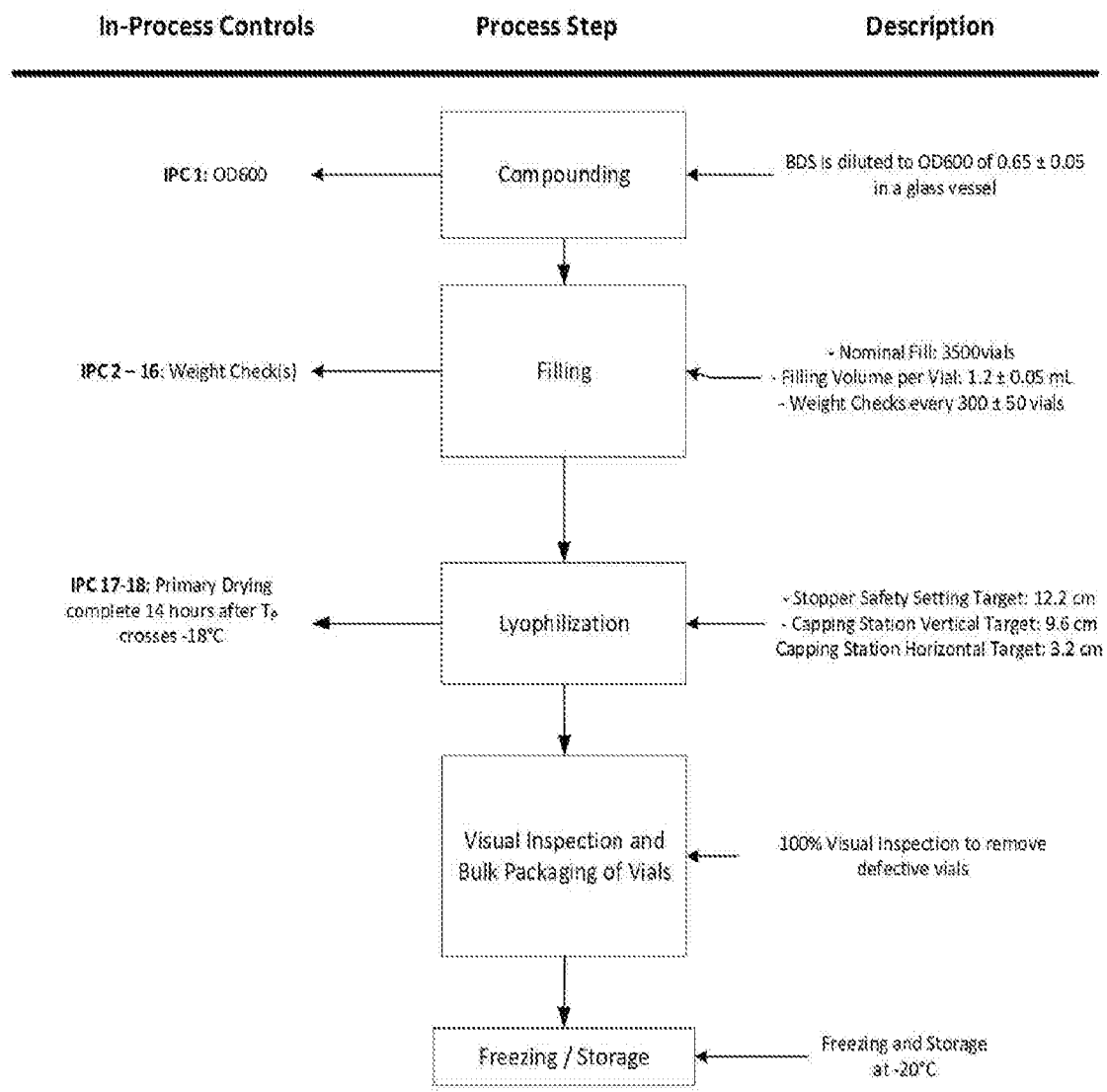

FIG. 21 shows a flow diagram for manufacture of the Axalimogene Filolisbac (ADXS-HPV) drug product.

Figure 22A:
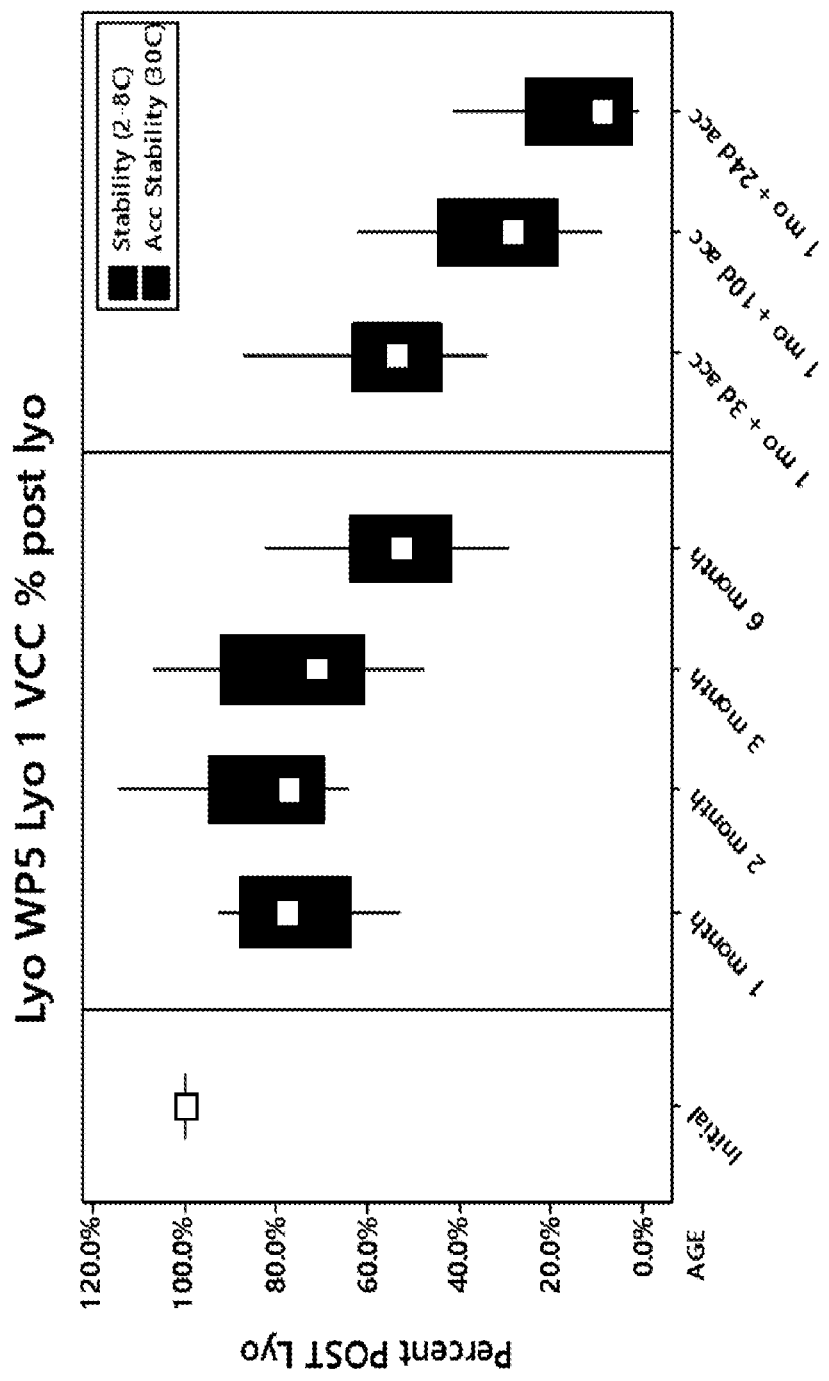

FIG. 22A shows VCC data (percent of average pre-lyophilization VCC) before lyophilization and post-lyophilization after storage at different temperatures for different amounts of time in the Lyo1 experiment.

Figure 22B:
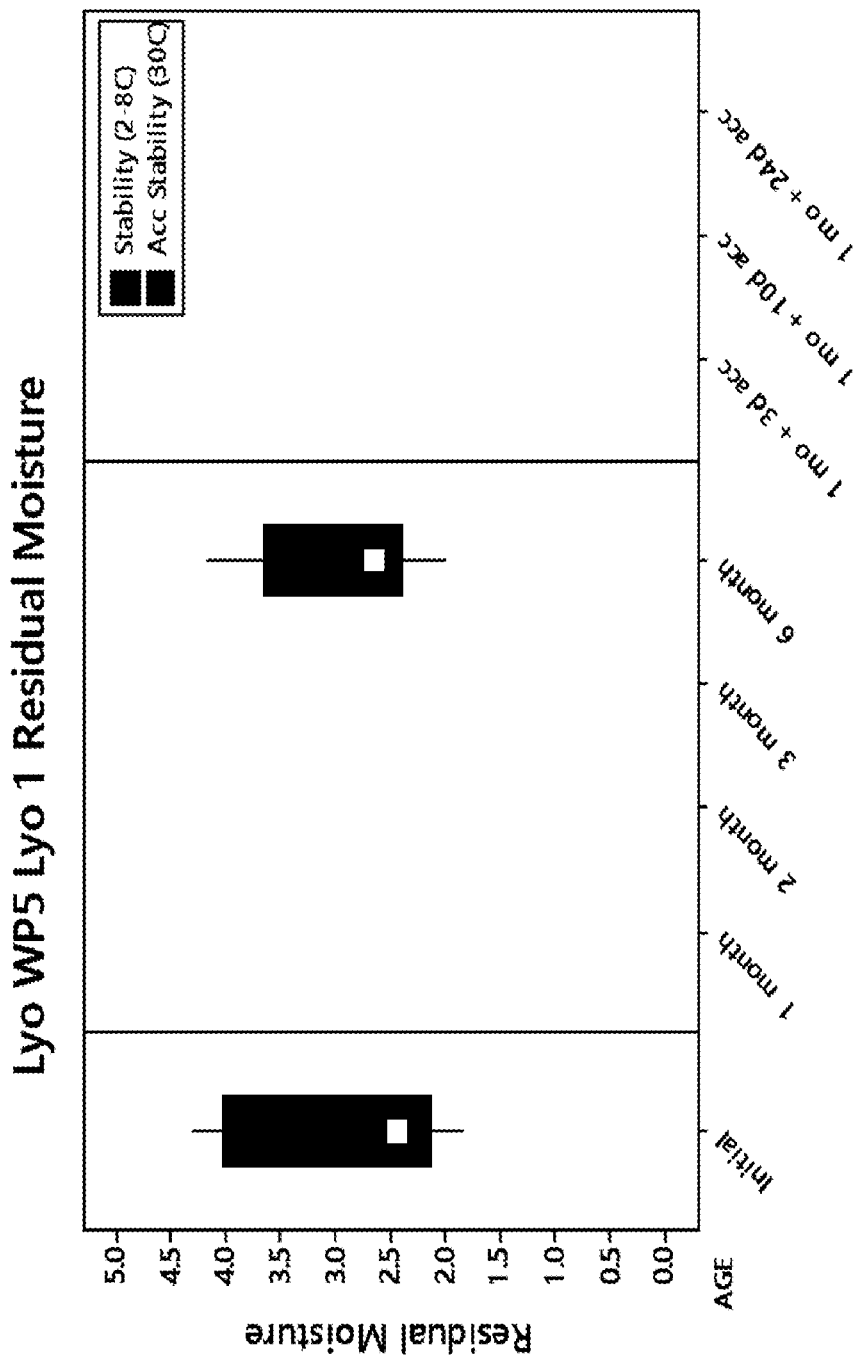

FIG. 22B shows residual moisture immediately after lyophilization and after 6 months at 2-8° C. in the Lyo1 experiment.

Figure 23A:
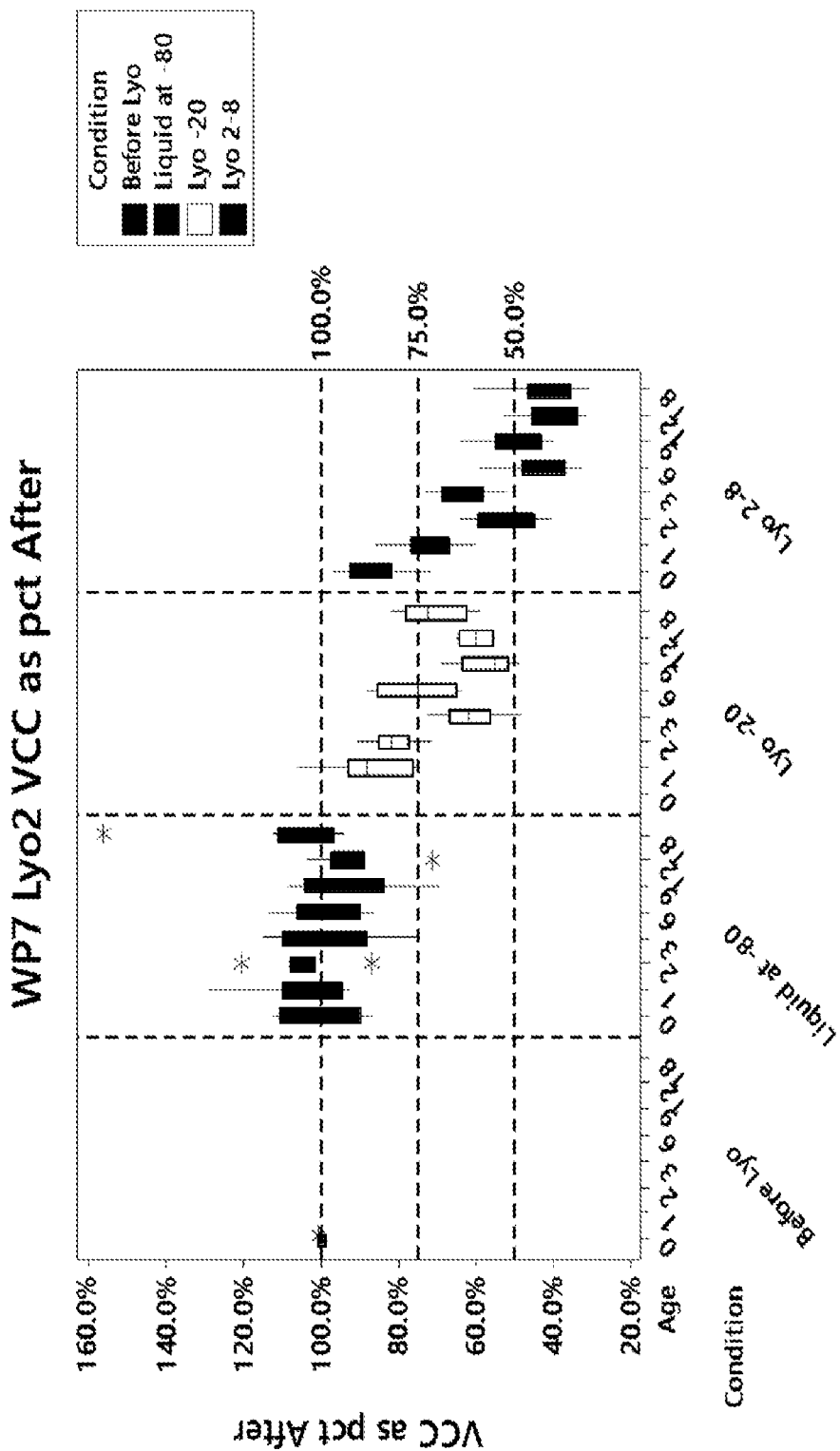

FIG. 23A shows VCC data (percent of average pre-lyophilization VCC) before lyophilization and post-lyophilization after storage at different temperatures for different amounts of time (months) in the Lyo2 experiment.

Figure 23B:
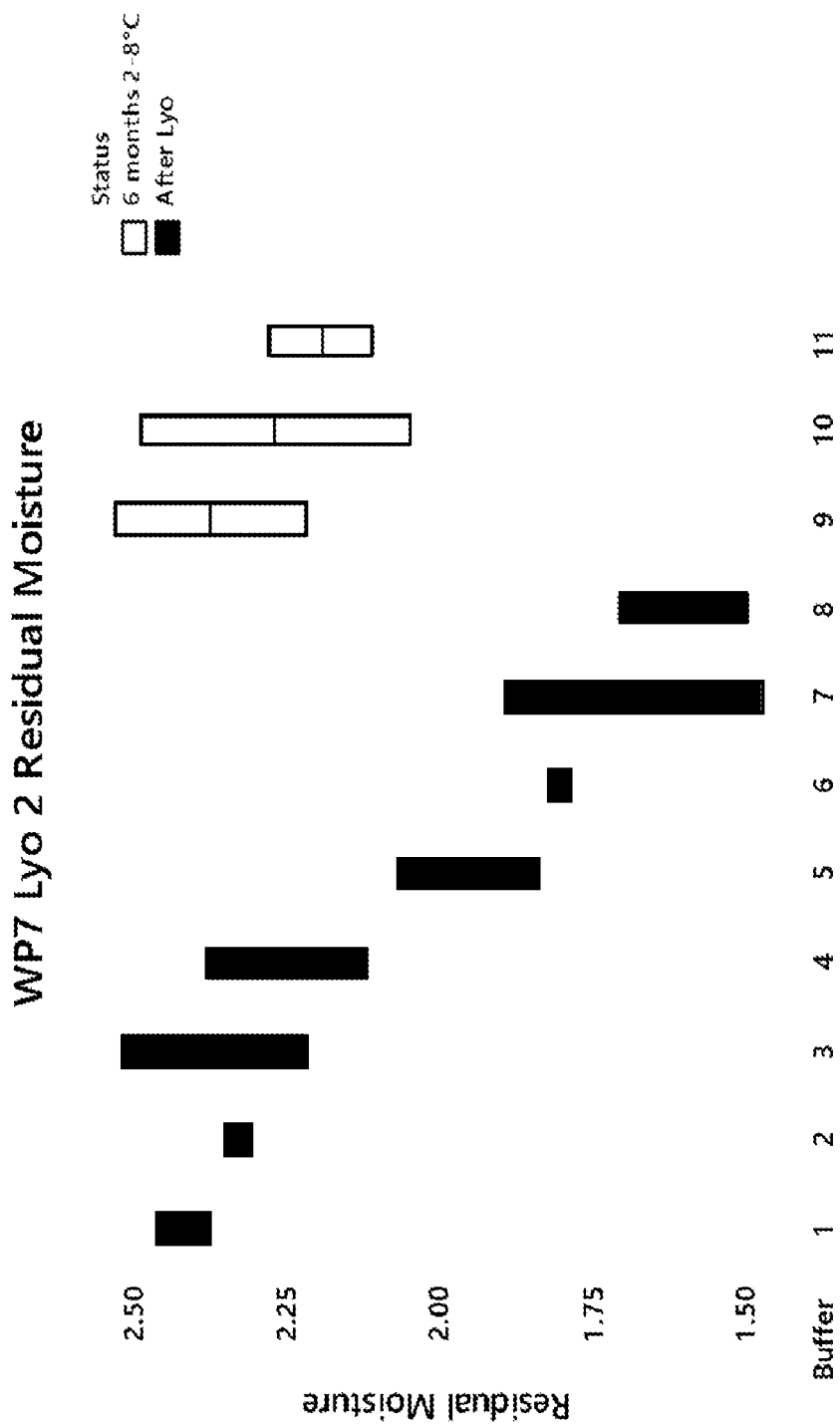

FIG. 23B shows residual moisture immediately after lyophilization and after 6 months at 2-8° C. in the Lyo2 experiment.

Figure 24A:
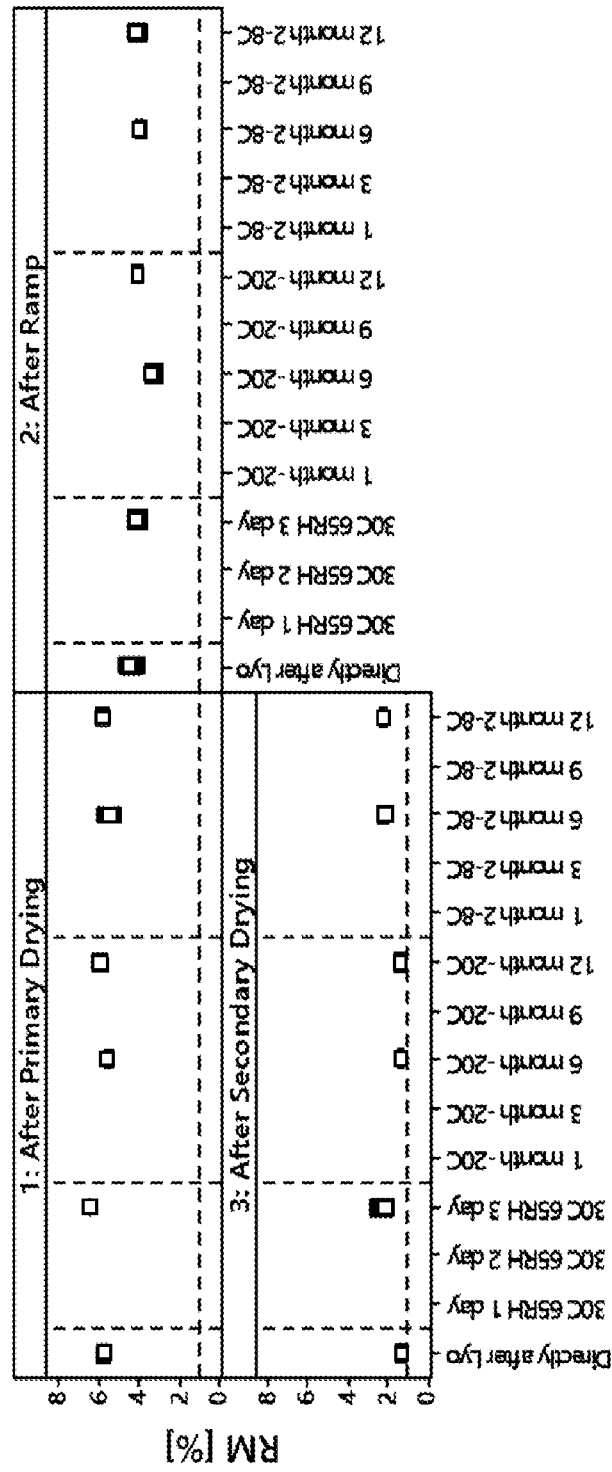

FIG. 24A shows residual moisture (RM) using 2.5% sucrose after primary drying, after ramp, and after secondary drying after storage at different temperatures for different amounts of time in the Lyo4 experiment.

Figure 24B:
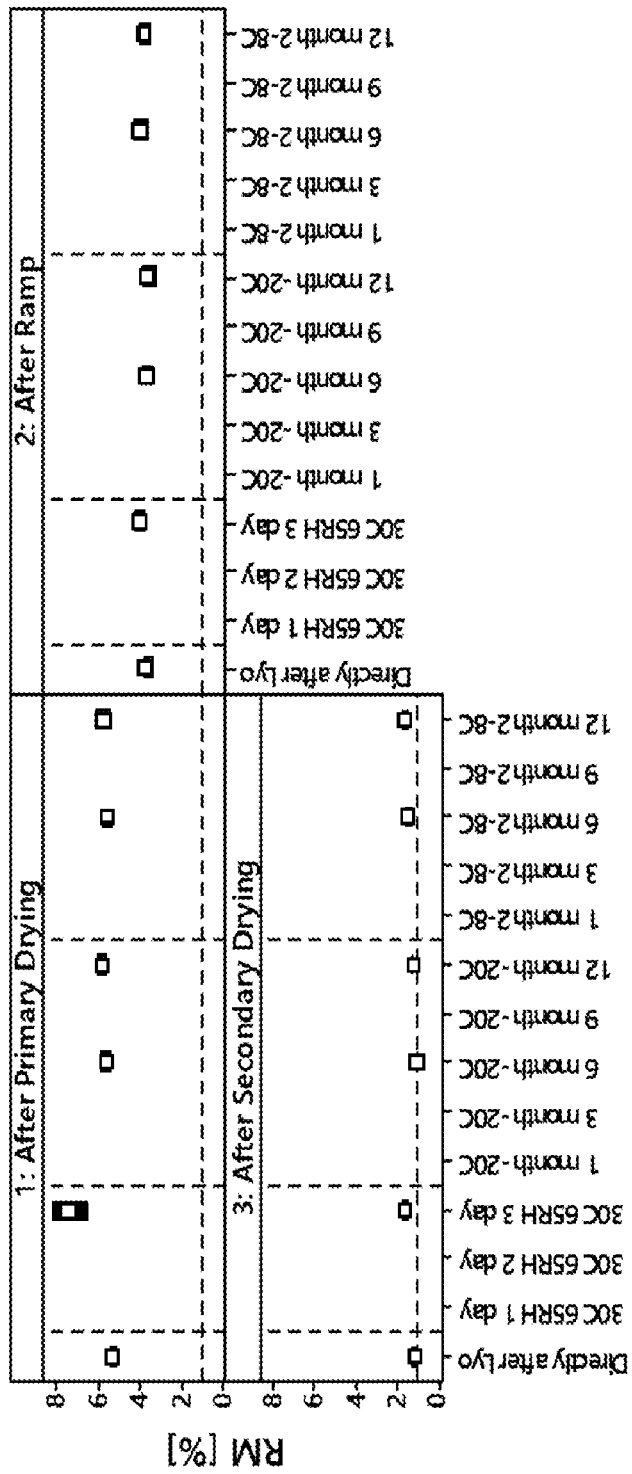

FIG. 24B shows residual moisture (RM) using 5.0% sucrose after primary drying, after ramp, and after secondary drying after storage at different temperatures for different amounts of time in the Lyo4 experiment.

Figure 25:
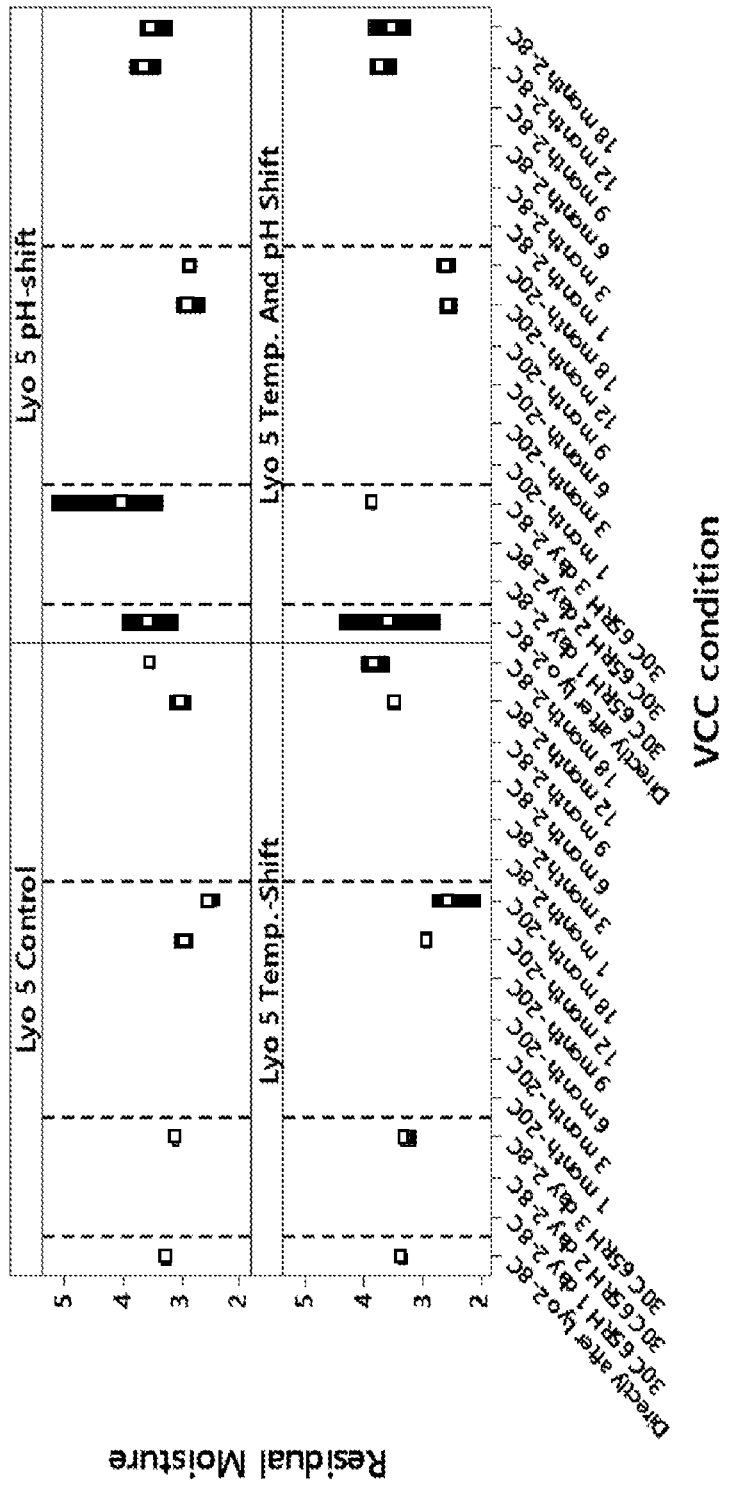

FIG. 25 shows residual moisture after various stress treatments after storage at different temperatures for different amounts of time in the Lyo5 experiment.

Figure 26:
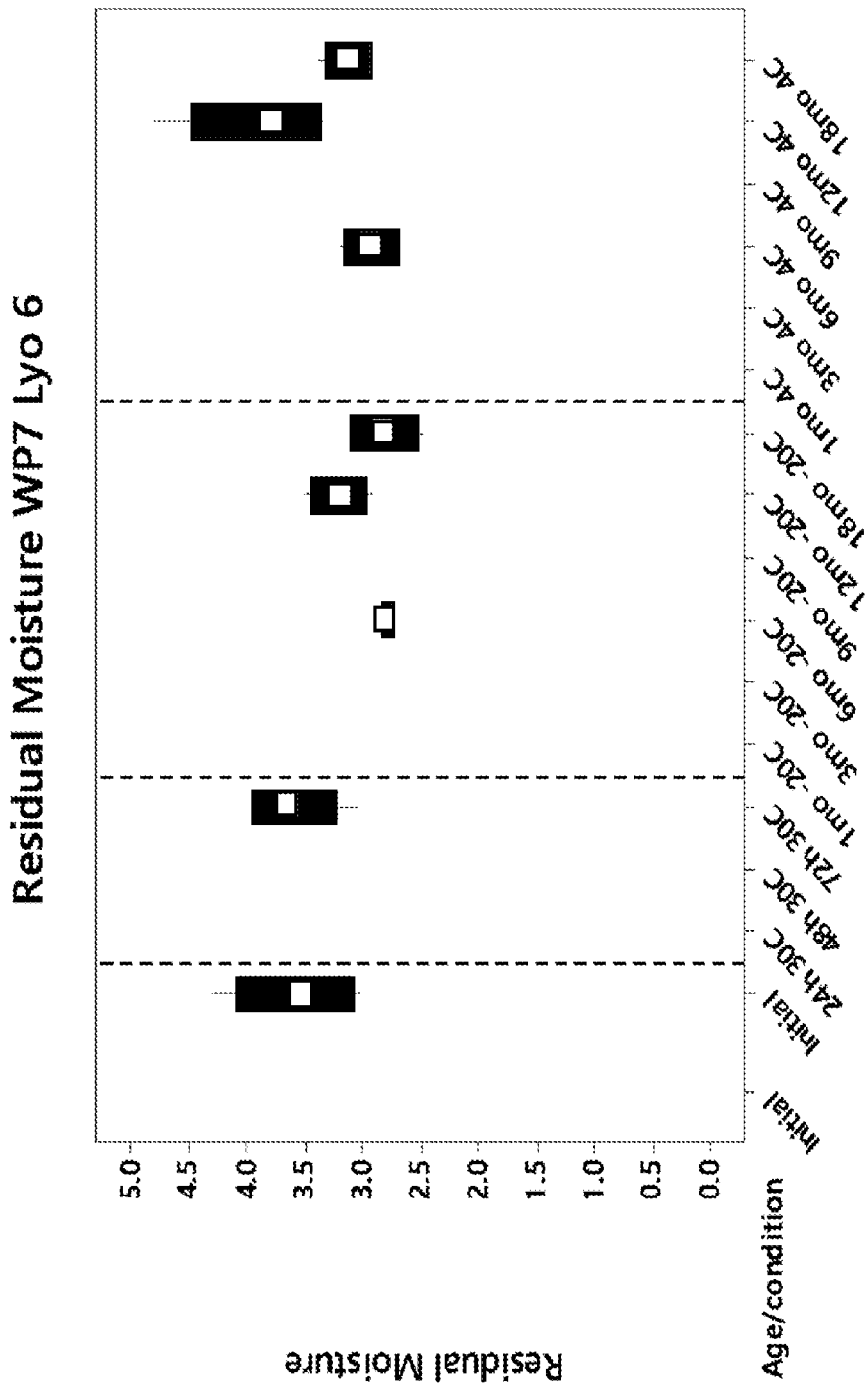

FIG. 26 shows residual moisture following temperature shift treatment pre-lyophilization after storage at different temperatures for different amounts of time in the Lyo6 experiment.

Figure 27:
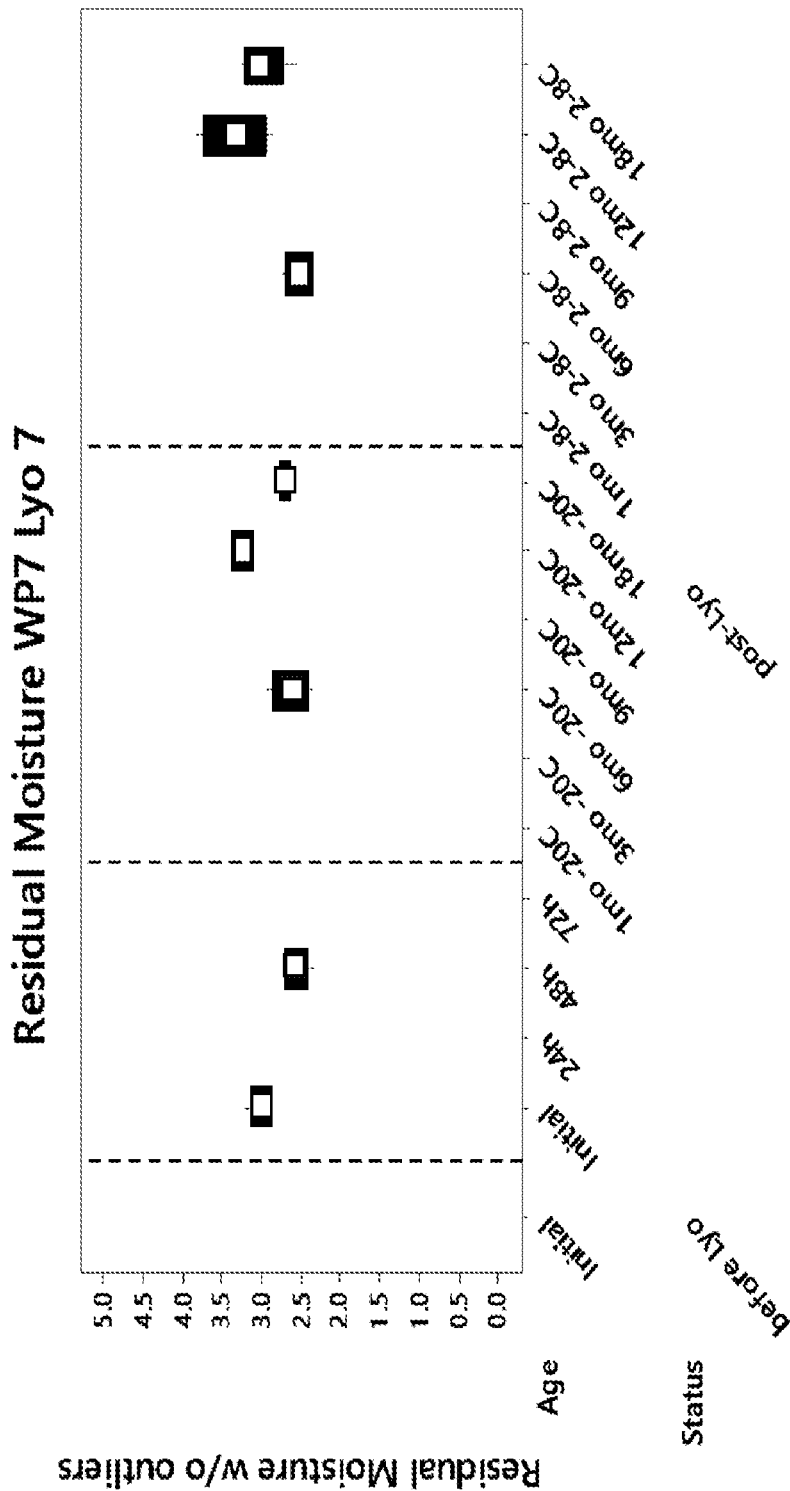

FIG. 27 shows residual moisture after storage at different temperatures for different amounts of time in the Lyo7 experiment.

Figure 28:
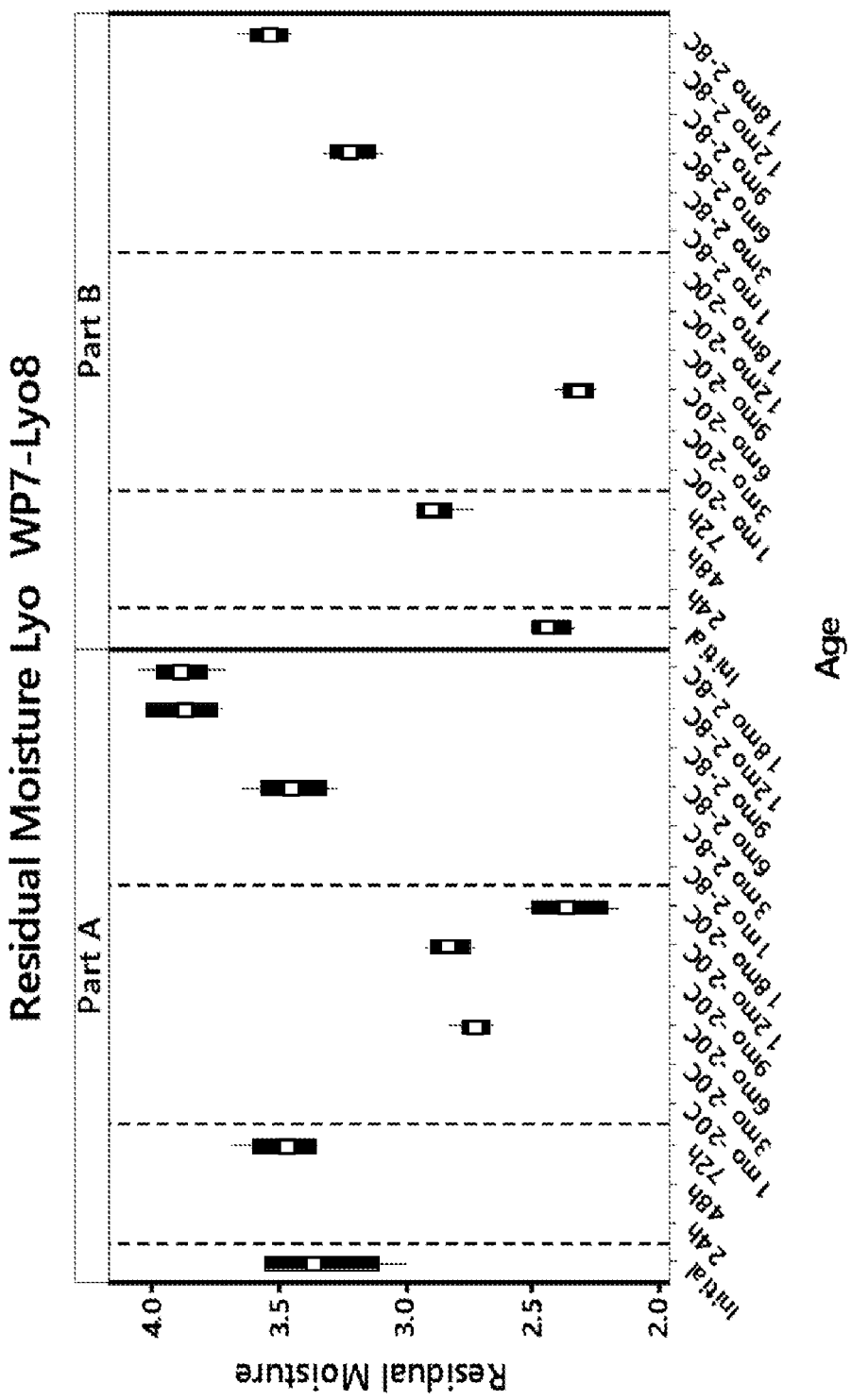

FIG. 28 shows residual moisture for samples were lyophilized immediately (part A) or samples that were frozen, thawed, and then lyophilized (part B) after storage at different temperatures for different amounts of time in the Lyo8 experiment.

Figure 29:
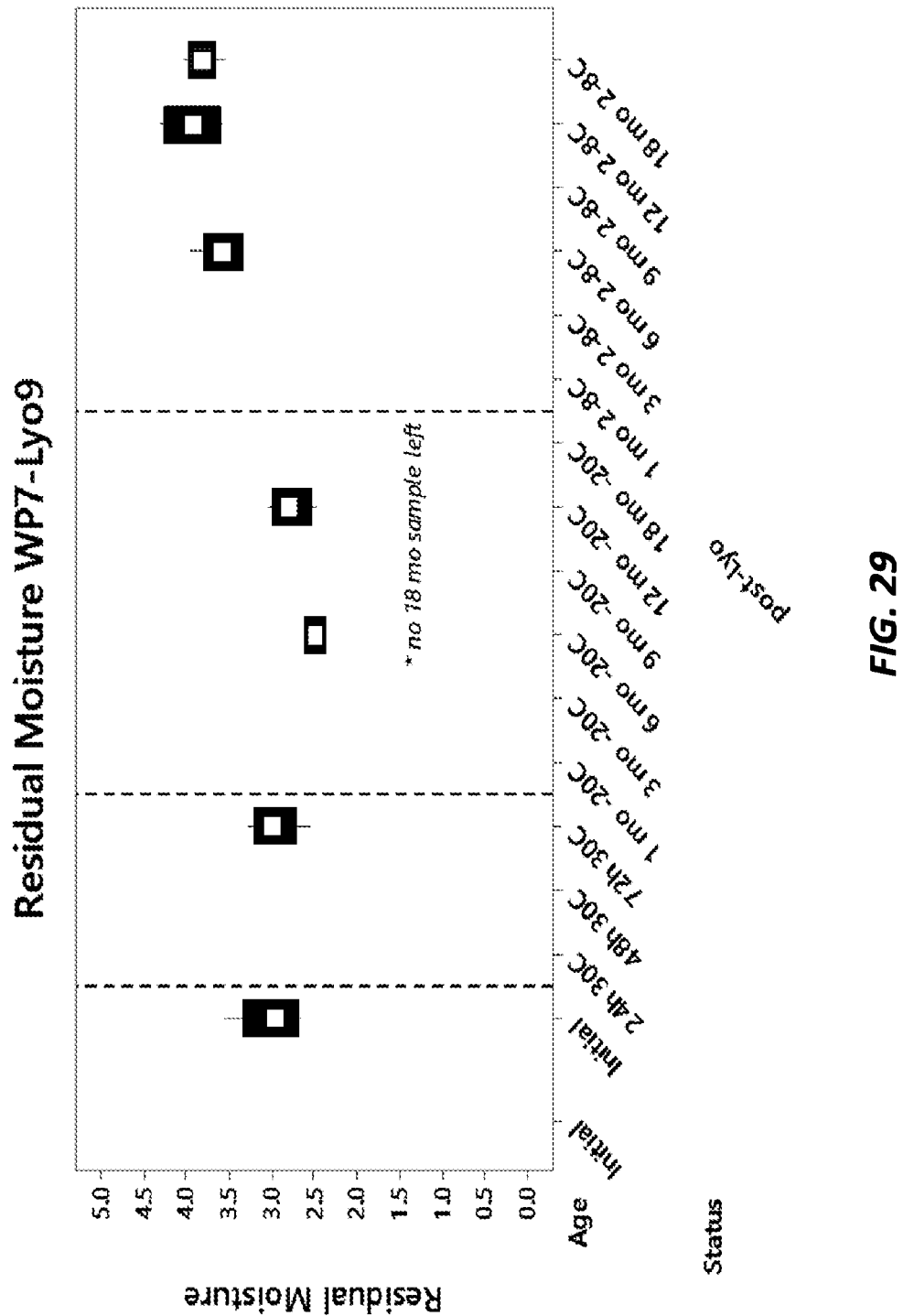

FIG. 29 shows residual moisture after storage at different temperatures for different amounts of time in the Lyo9 experiment.

Figure 30:
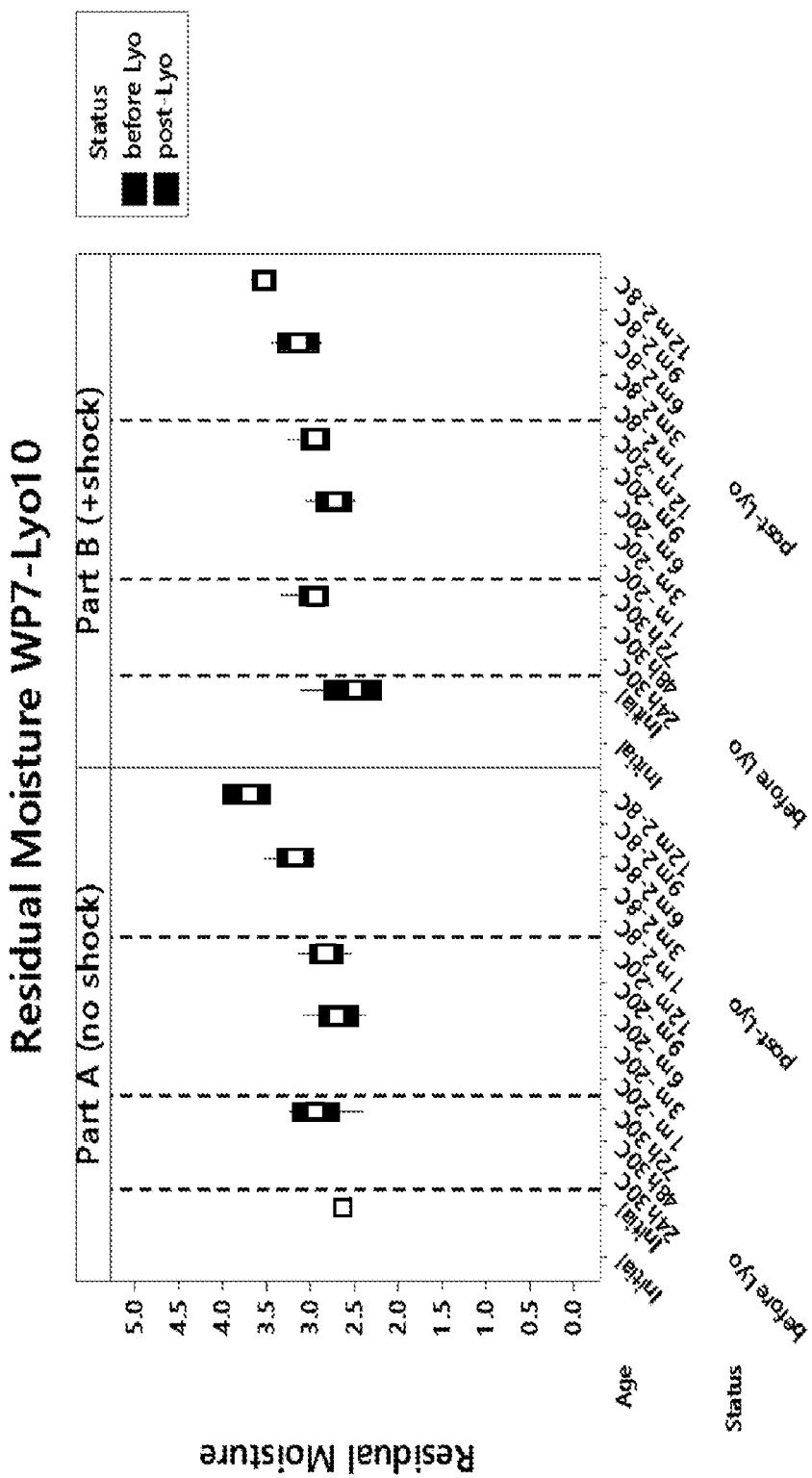

FIG. 30 shows residual moisture after storage at different temperatures for different amounts of time in the Lyo10 experiment.

Figure 31:
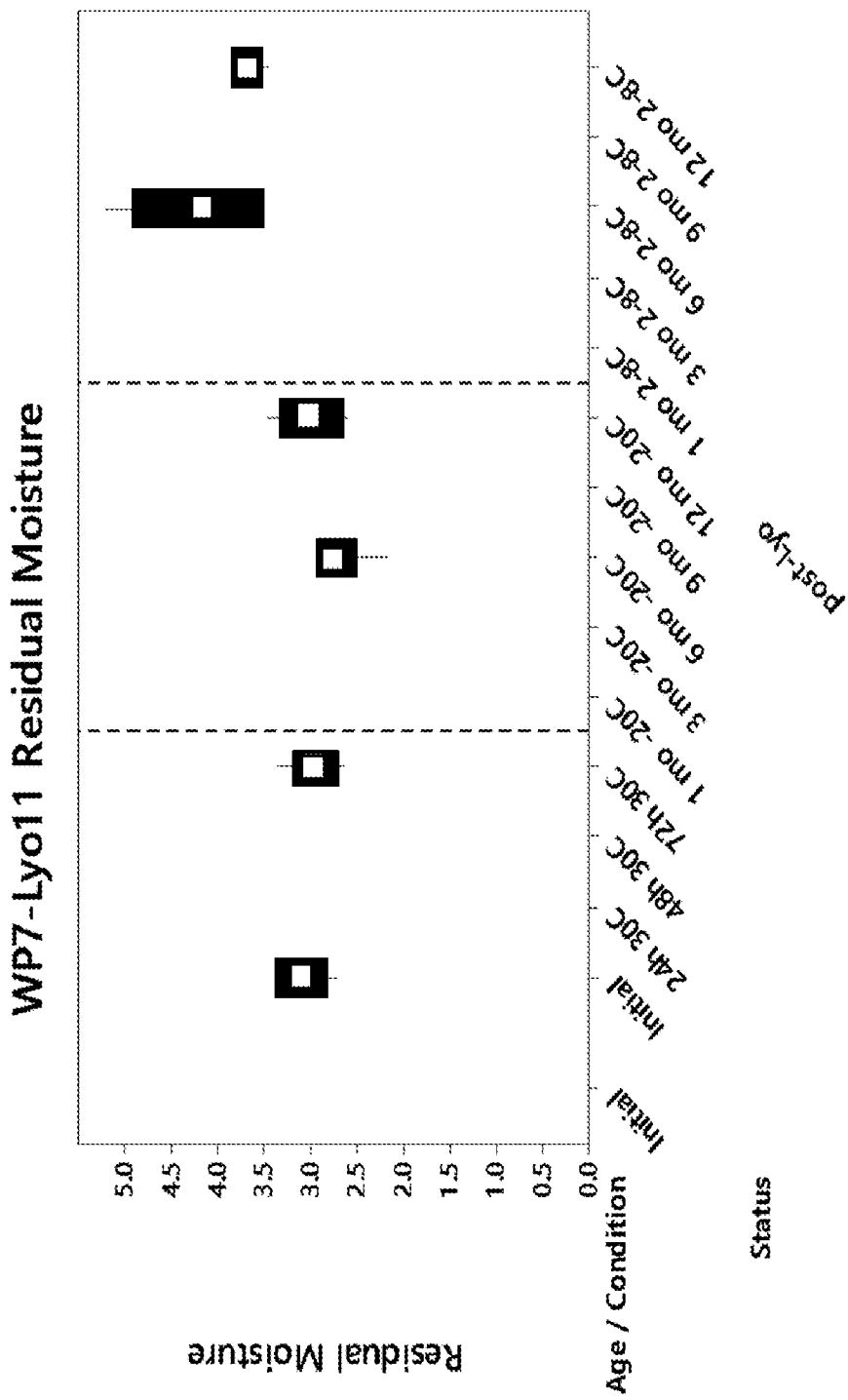

FIG. 31 shows residual moisture after storage at different temperatures for different amounts of time in the Lyo11 experiment.

Figure 32:
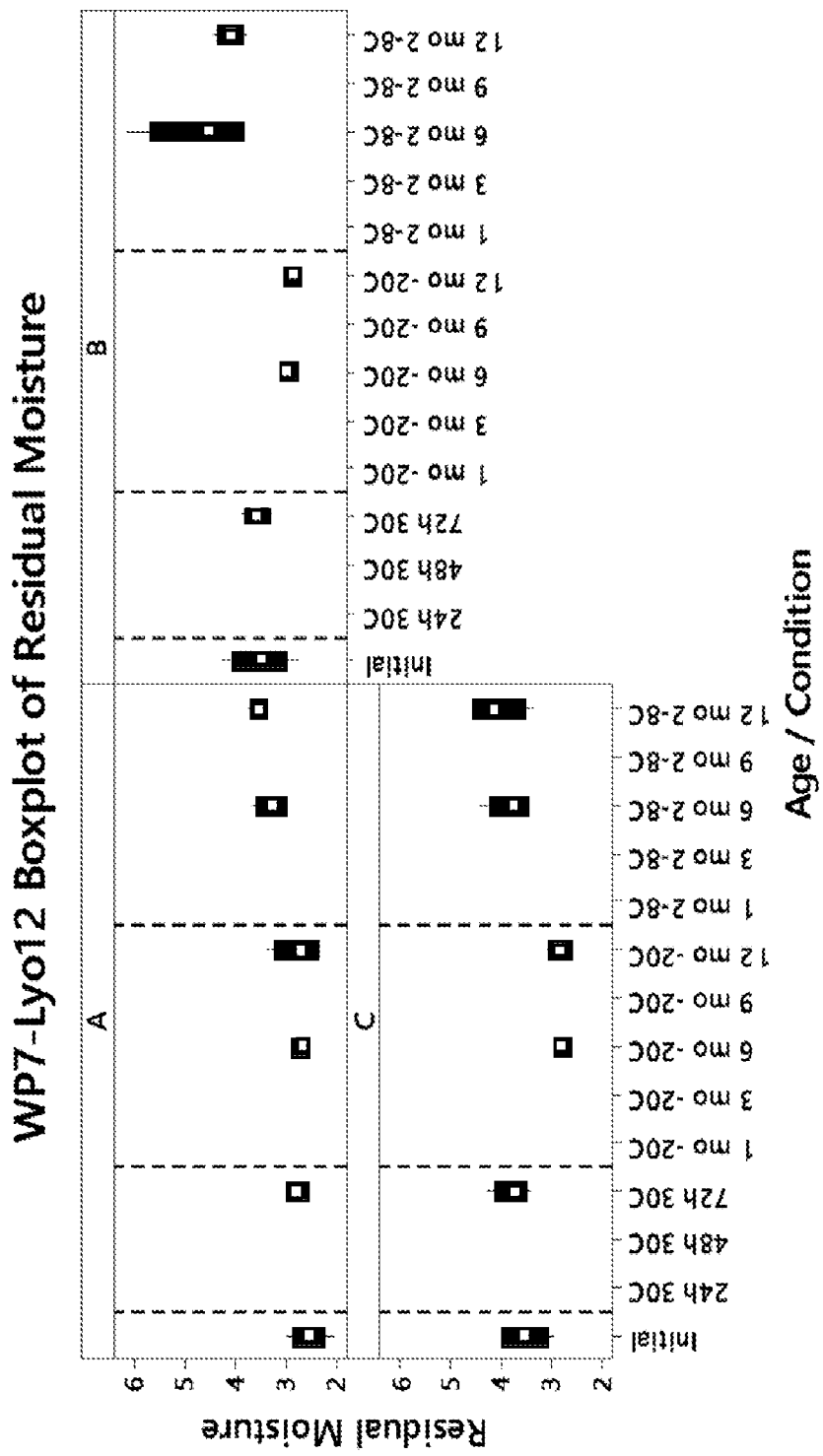

FIG. 32 shows residual moisture after storage at different temperatures for different amounts of time in the Lyo12 experiment.

Figure 33:
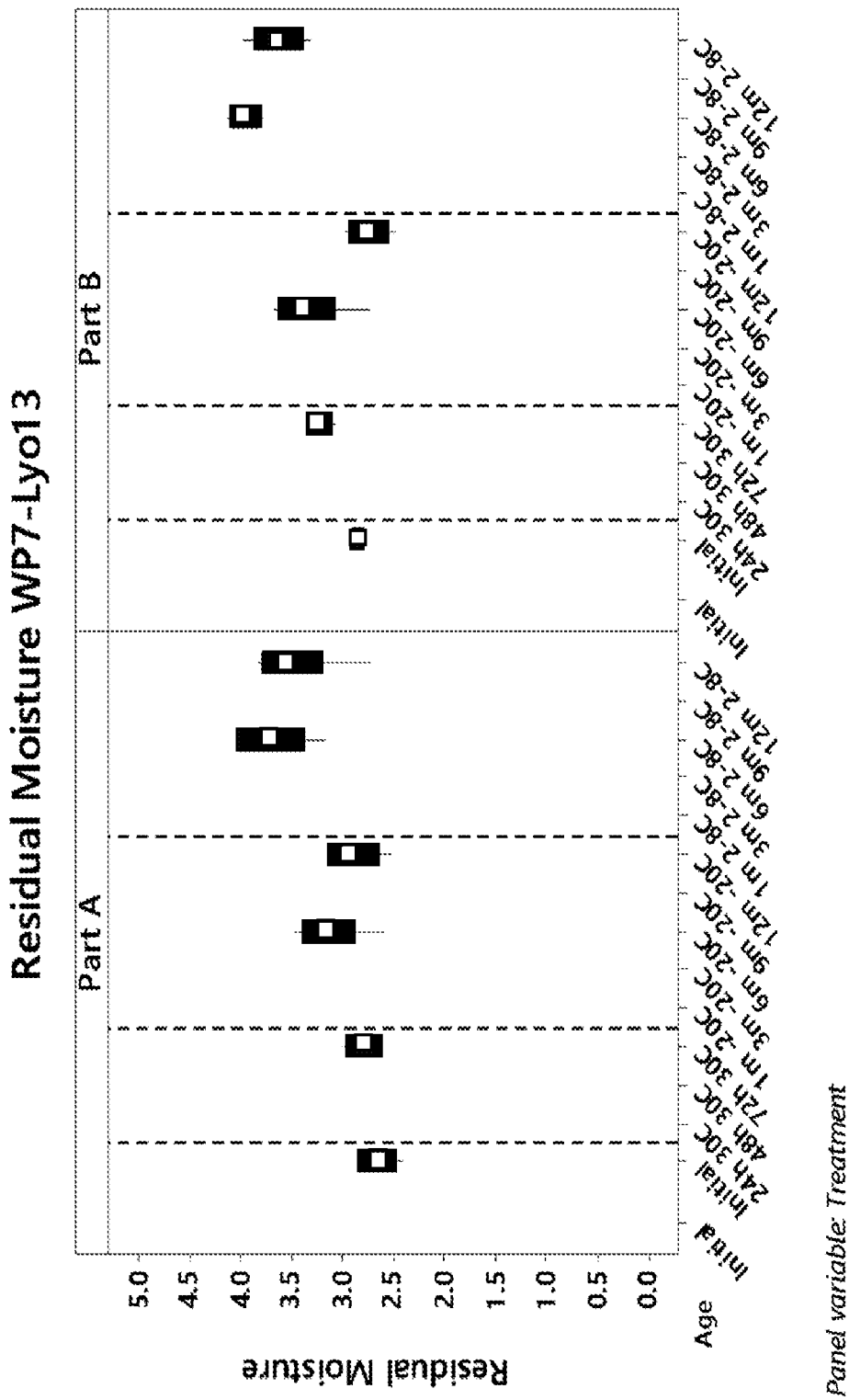

FIG. 33 shows residual moisture after storage at different temperatures for different amounts of time in the Lyo13 experiment.

Figure 34:
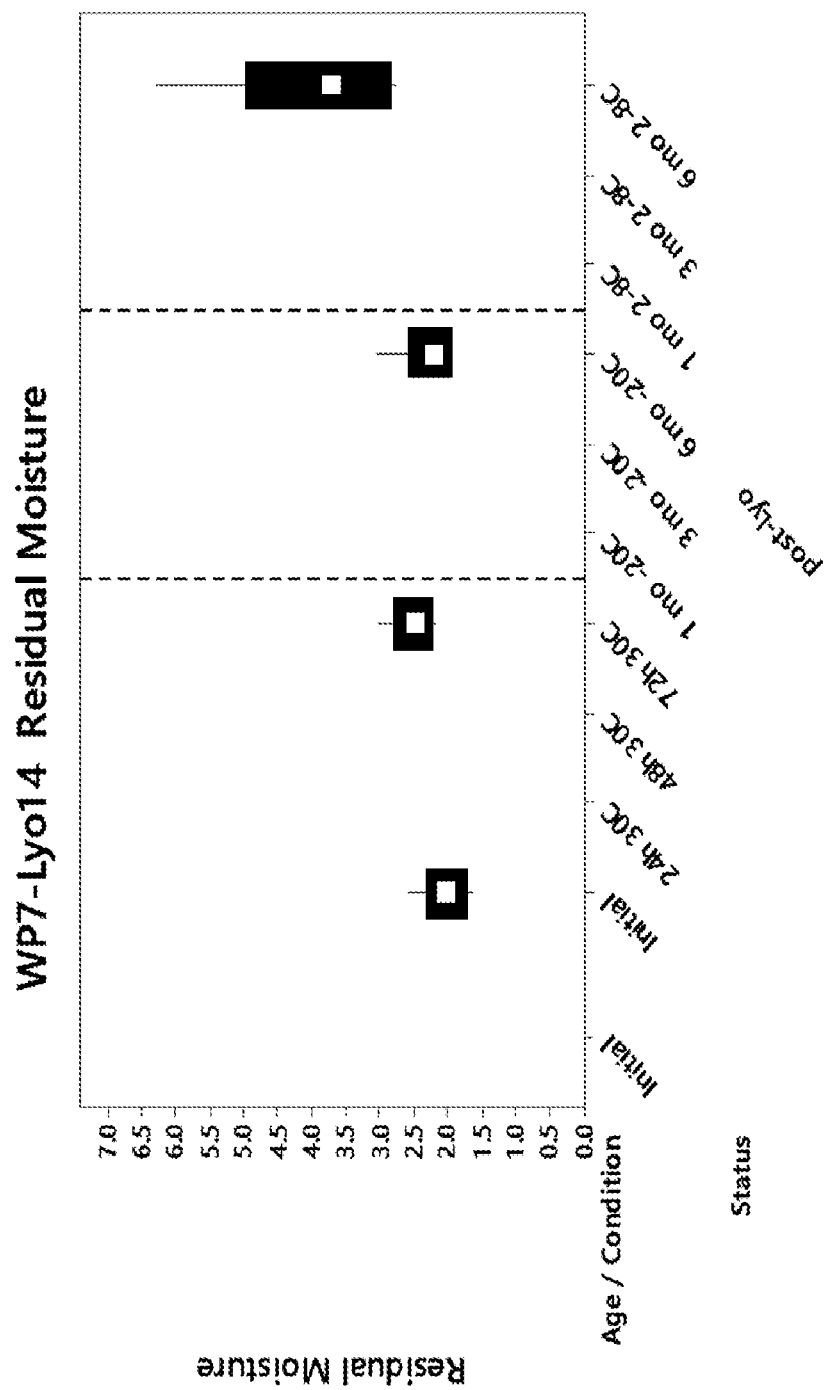

FIG. 34 shows residual moisture after storage at different temperatures for different amounts of time in the Lyo14 experiment.

Figure 35:
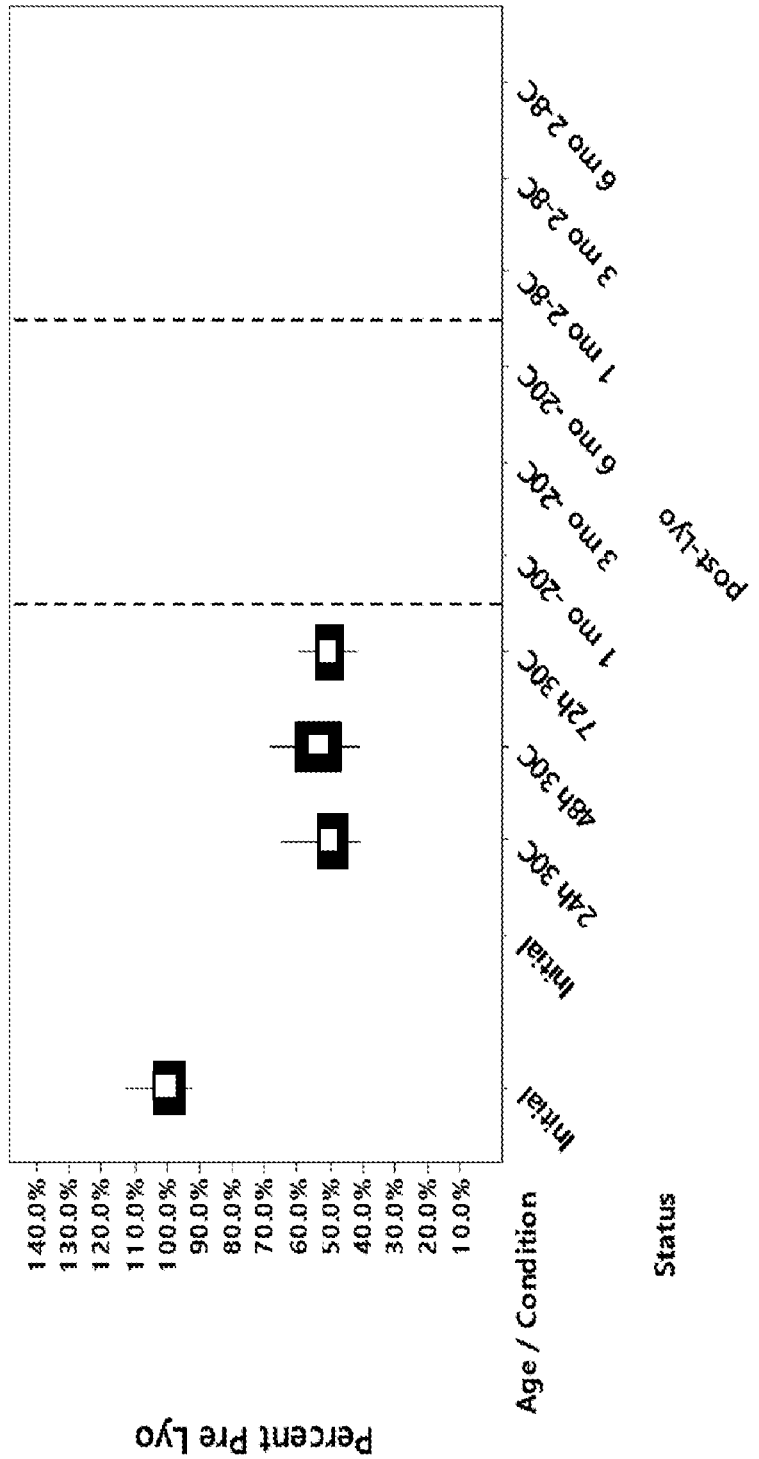

FIG. 35 shows VCC data post-lyophilization as a percent of pre-lyophilization after storage at 30° C. for different amounts of time in the batch scale experiment.

Figure 36:
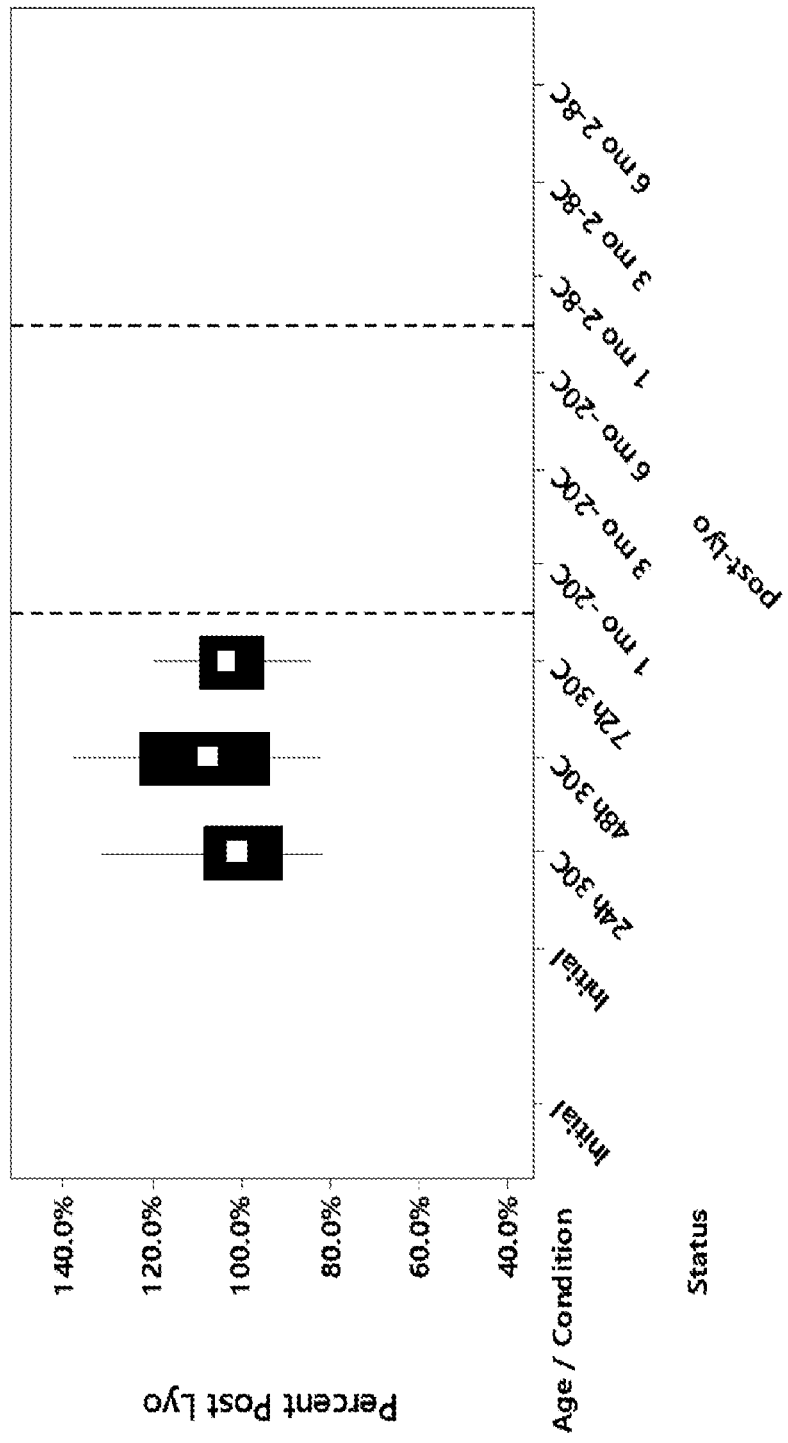

FIG. 36 shows VCC data post-lyophilization as a percent of post-lyophilization after storage at 30° C. for different amounts of time in the batch scale experiment.

Figure 37:
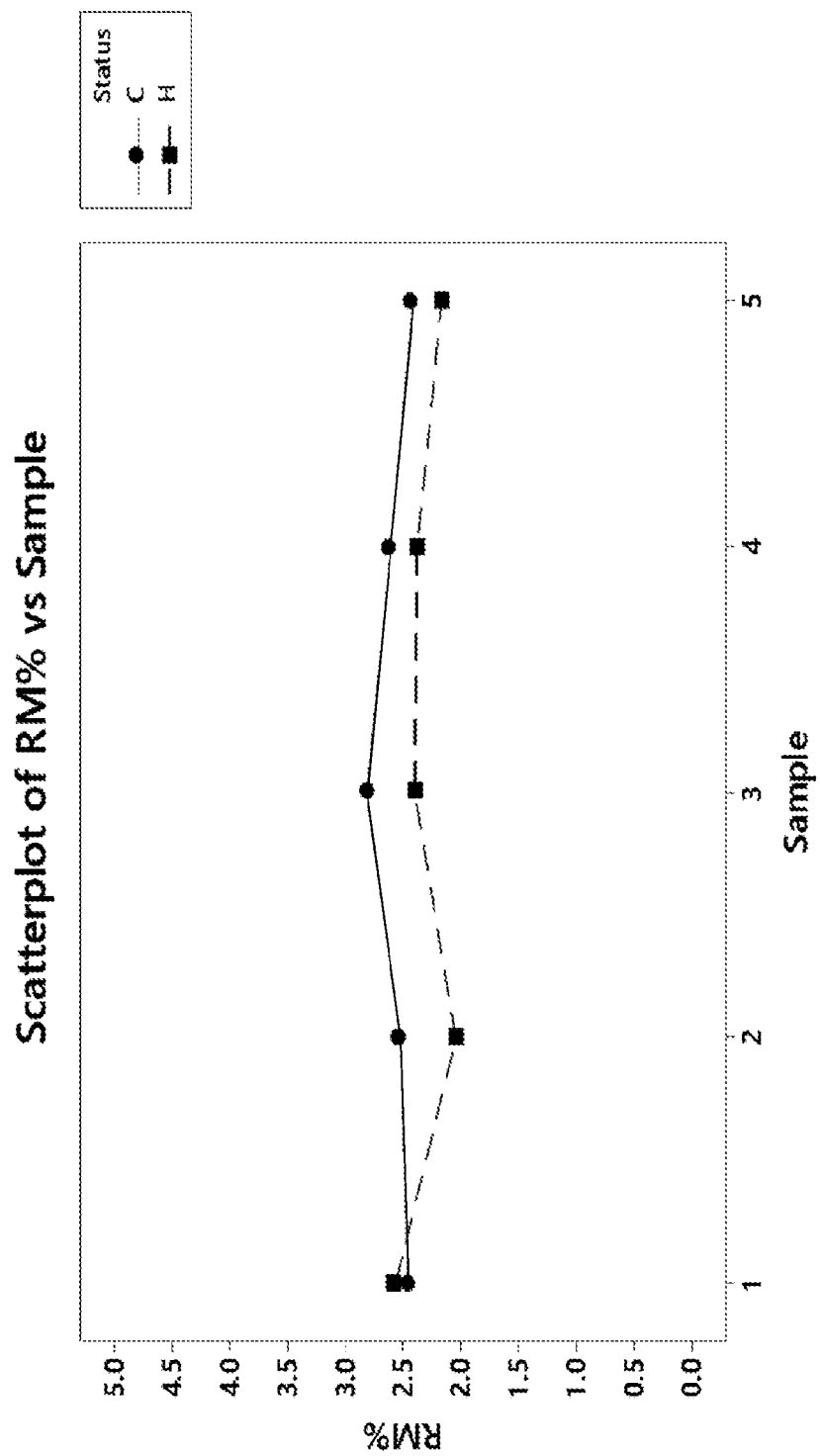

FIG. 37 shows residual moisture (RM) vs. sample in the batch scale experiment.

Figure 38:
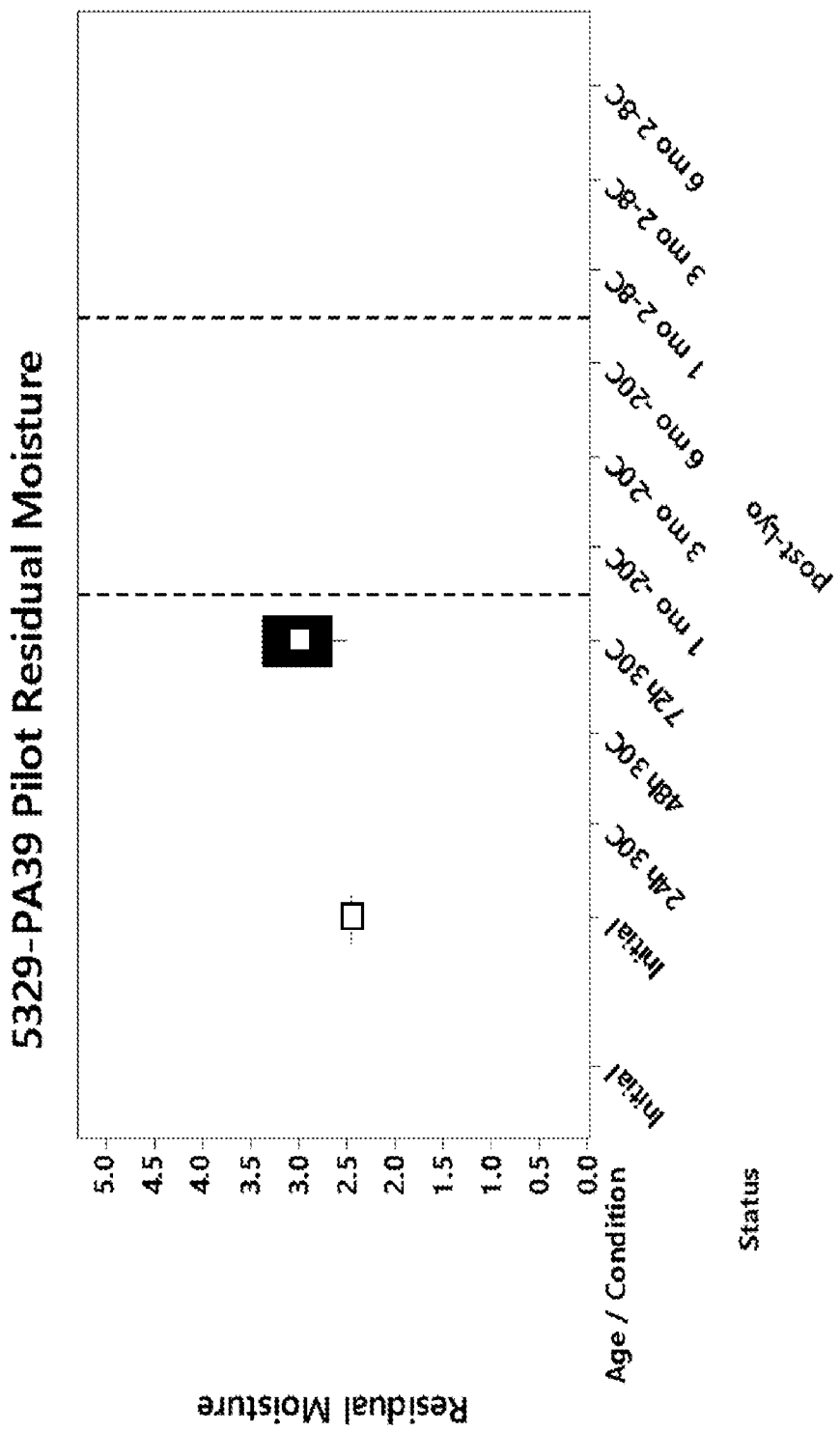

FIG. 38 shows residual moisture (RM) after lyophilization and storage for 72 hours at 30° C. in the batch scale experiment.

Figure 39:
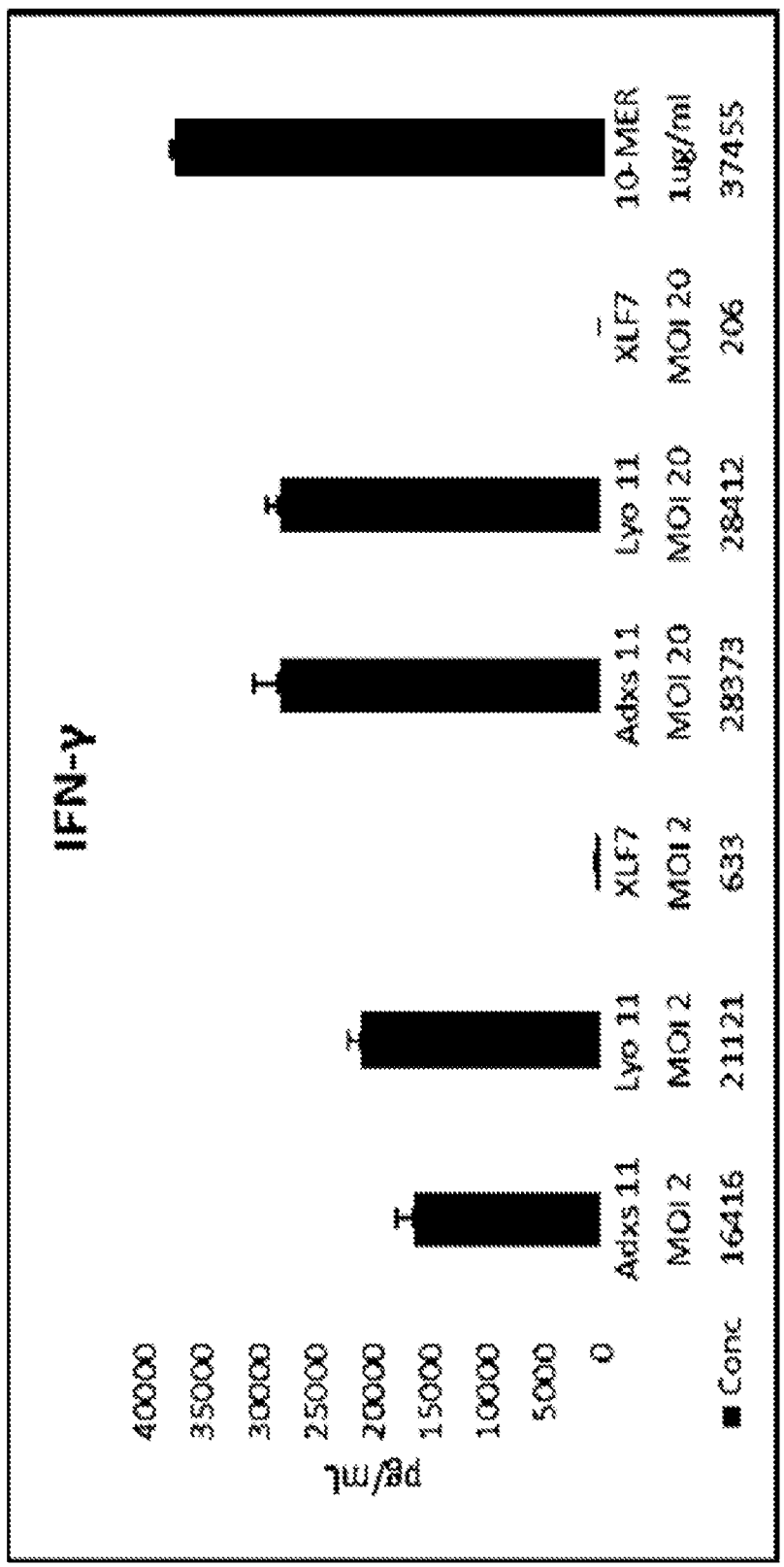

FIG. 39 shows bioactivity and INFγ induction of the lyophilized product compared to non-lyophilized bacteria and 10-mer control in the Lyo11 experiment.

Figure 40A:
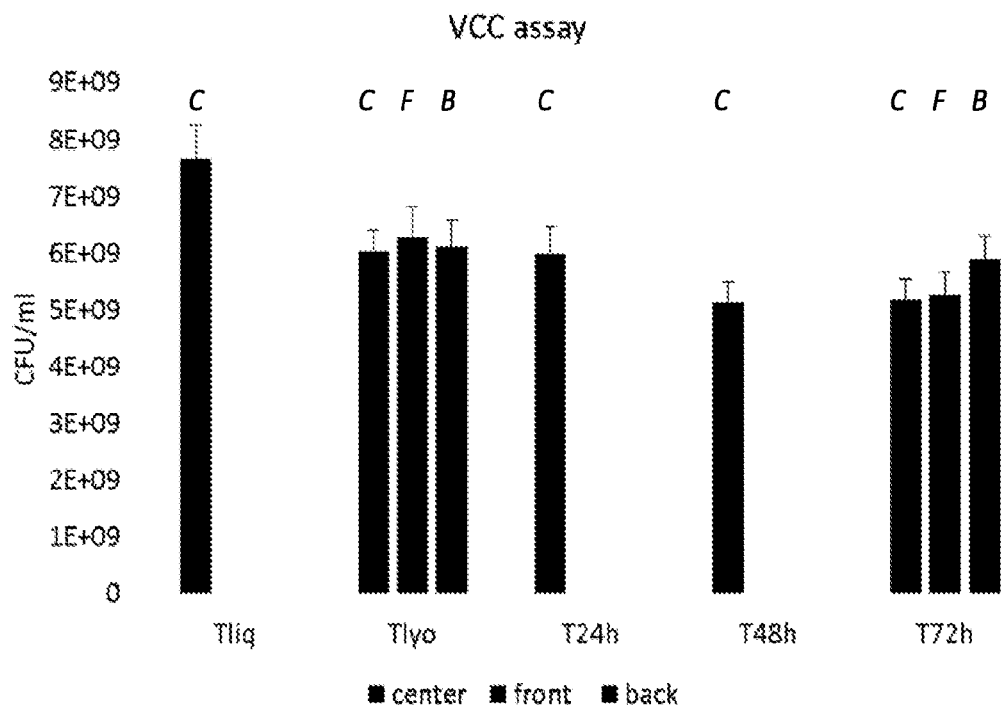
Figure 40B:
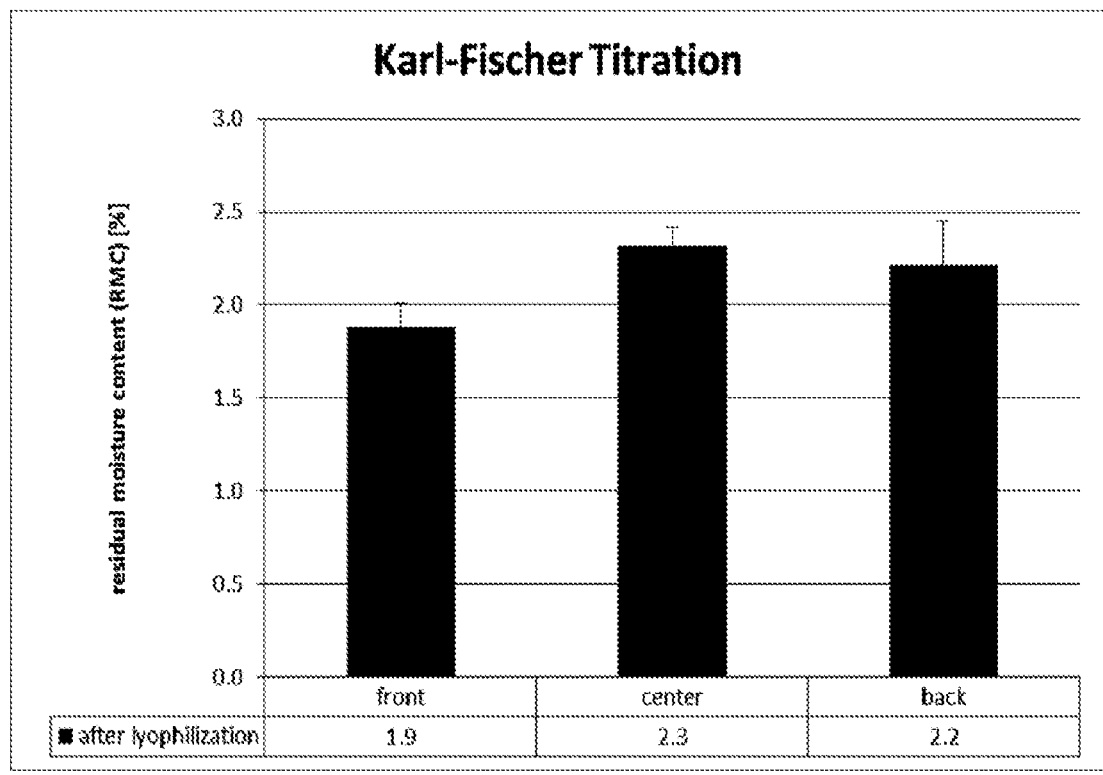

FIGS. 40A-B show VCC data (A) before lyophilization and post-lyophilization immediately after lyophilization and after storage at 30° C. for 24, 48, or 72 hours, and residual moisture (B) in the WP3 experiment.

Figure 41A:
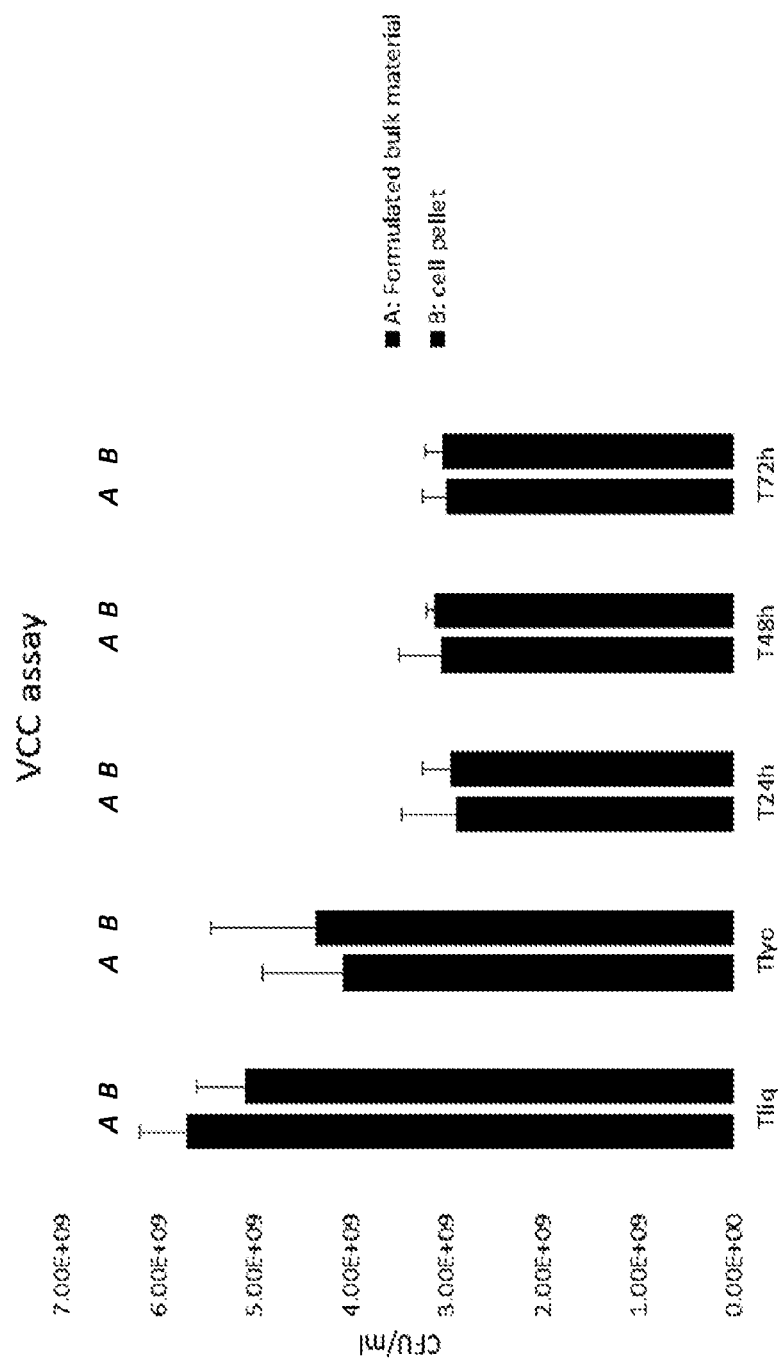
Figure 41B:
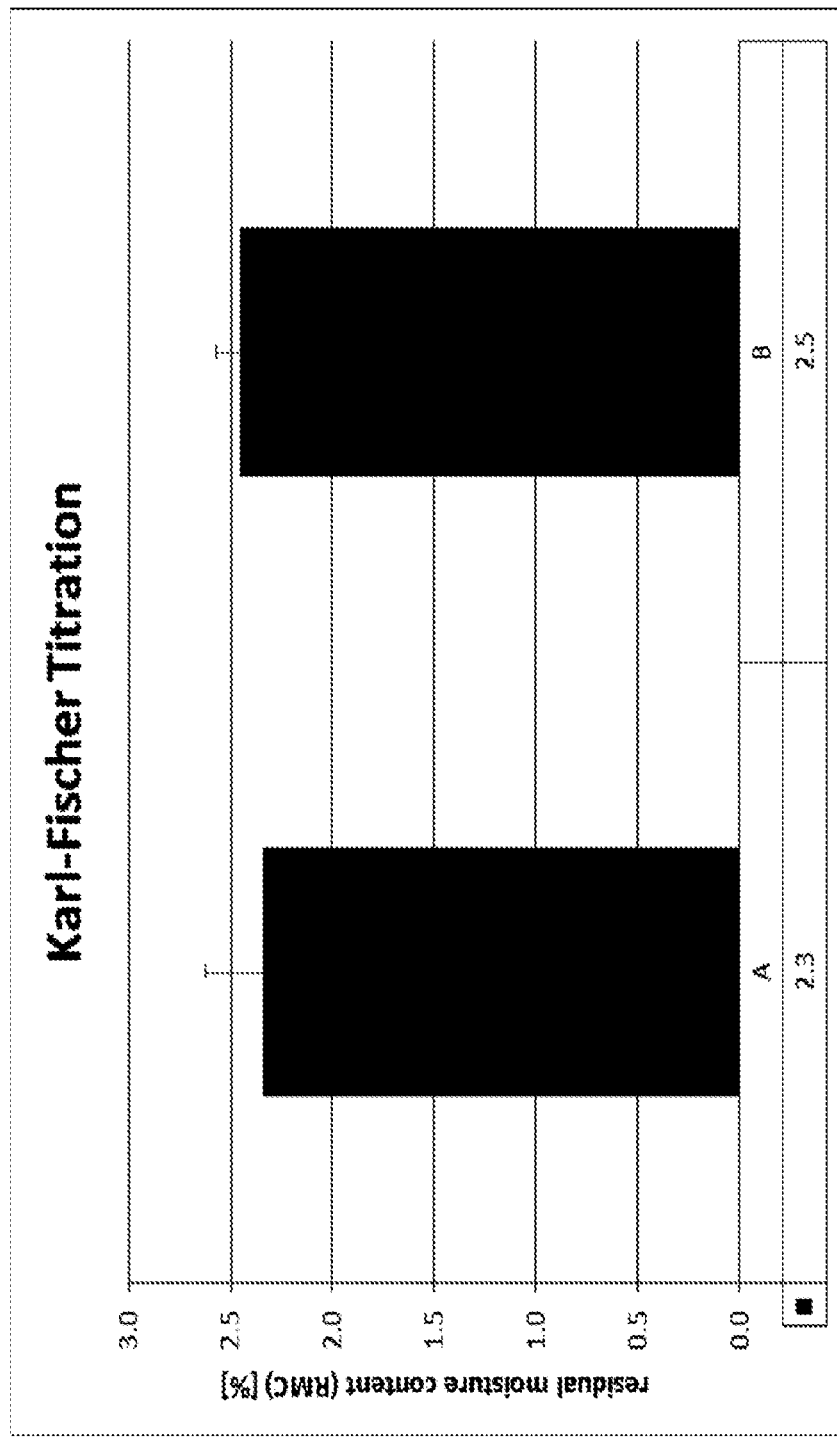

FIGS. 41A-B shows VCC data (A) before lyophilization and post-lyophilization immediately after lyophilization and after storage at 30° C. for 24, 48, or 72 hours, and residual moisture (B) in the WP6 experiment.

Figure 42A:
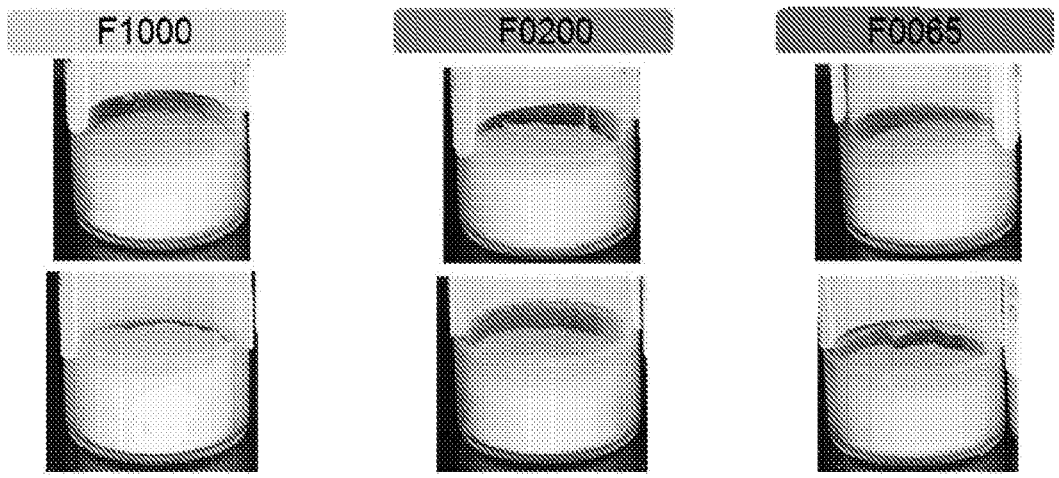
Figure 42B:
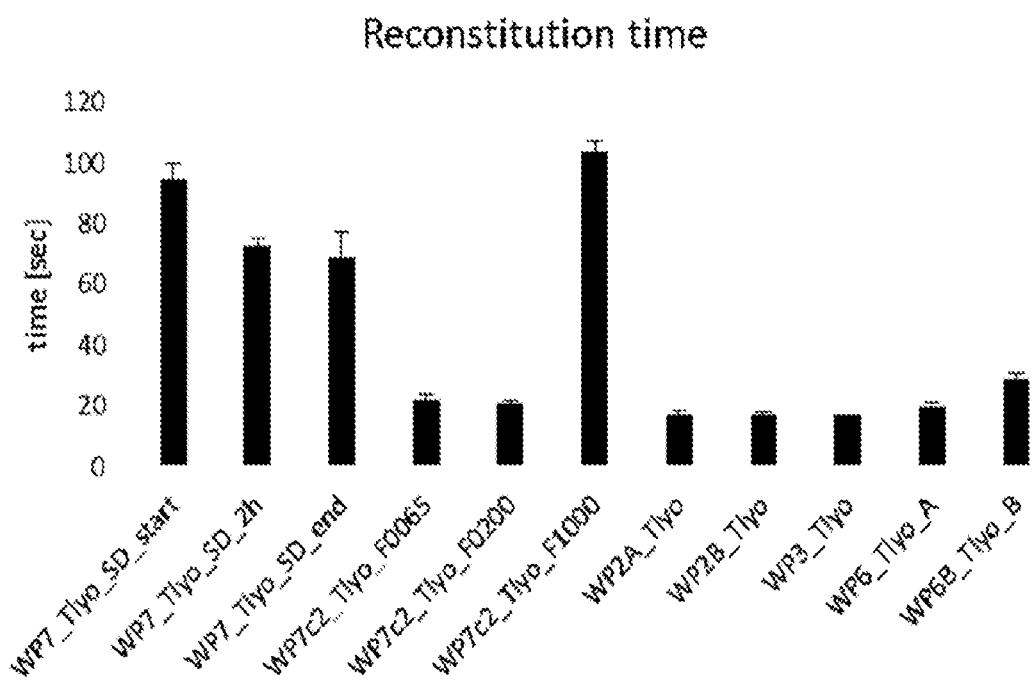

FIGS. 42A-B show lyophilization cakes (A) and reconstitution times (B) post-lyophilization immediately after lyophilization and after storage at 30° C. for 24, 48, or 72 hours in the WP7 experiment.

Figure 43:
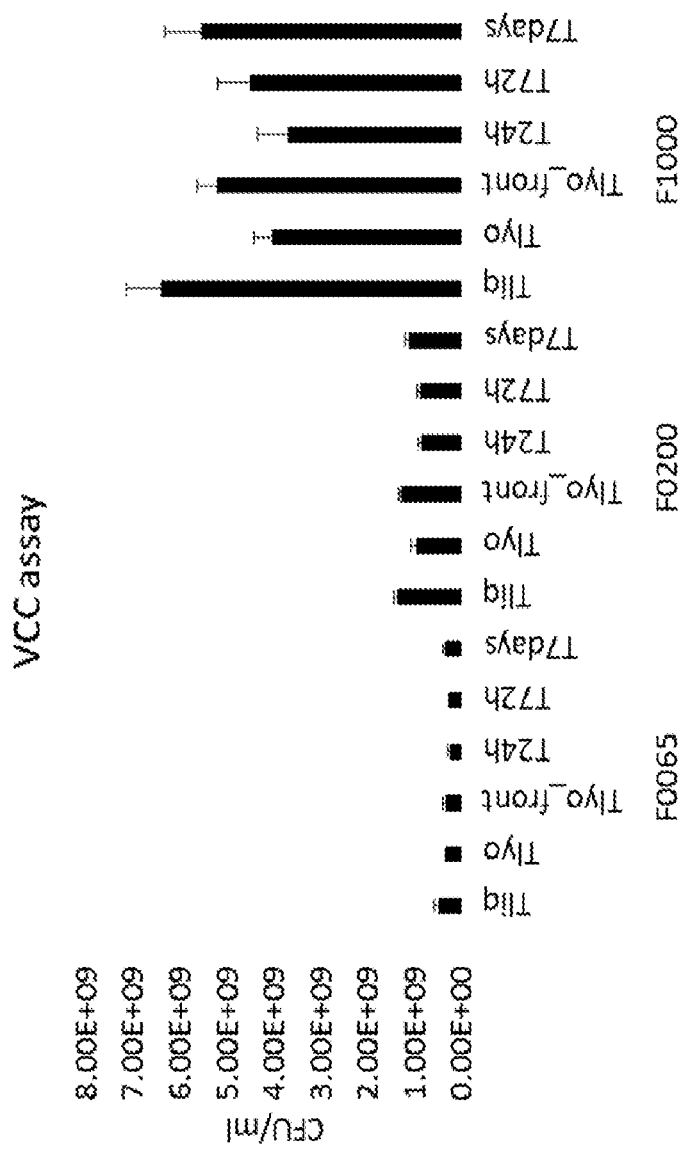

FIG. 43 shows VCC data before lyophilization and post-lyophilization immediately after lyophilization and after storage at 30° C. for 24 hours, 72 hours, and 7 days in the WP7 experiment.

Figure 44A:
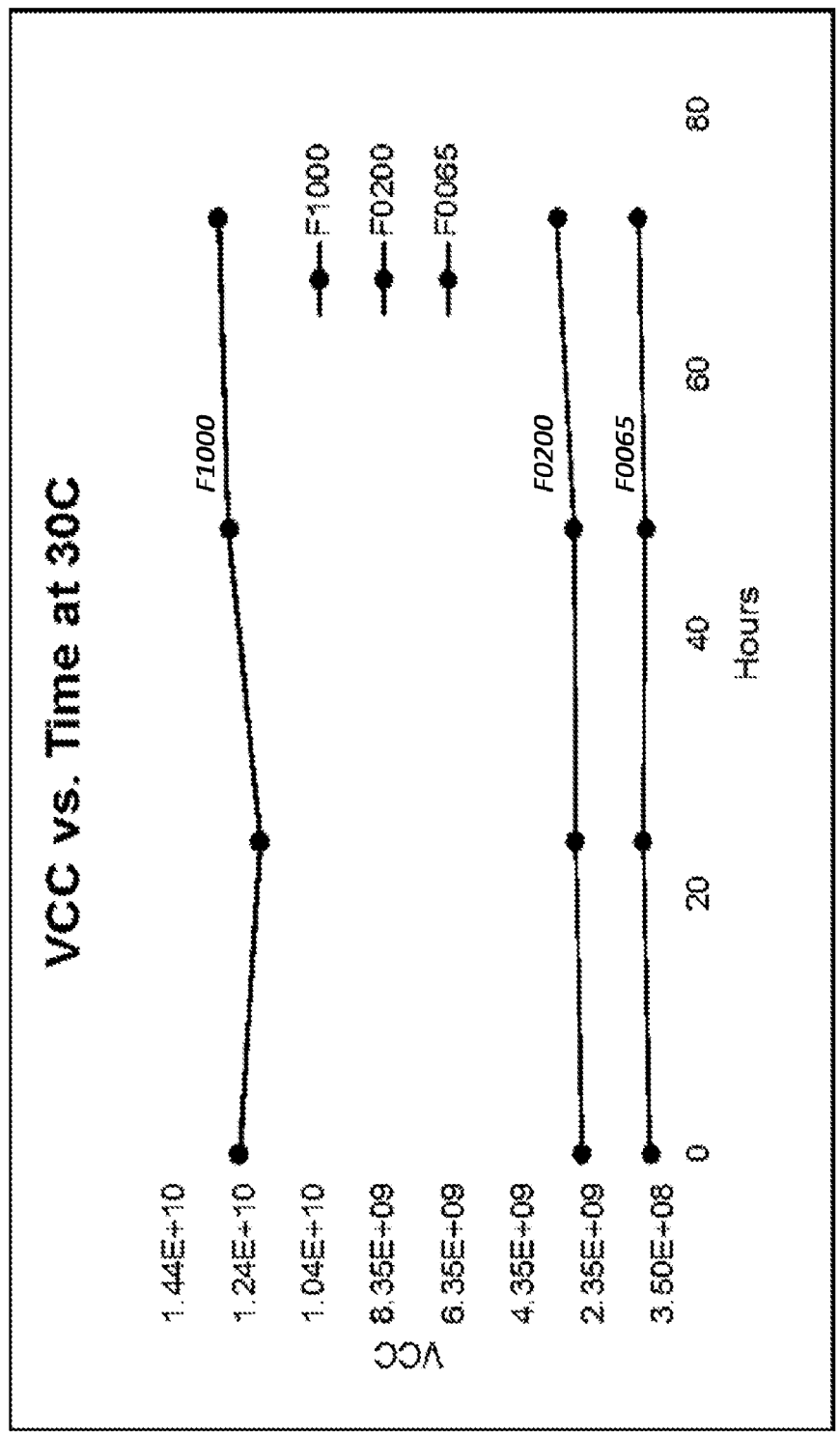
Figure 44B:
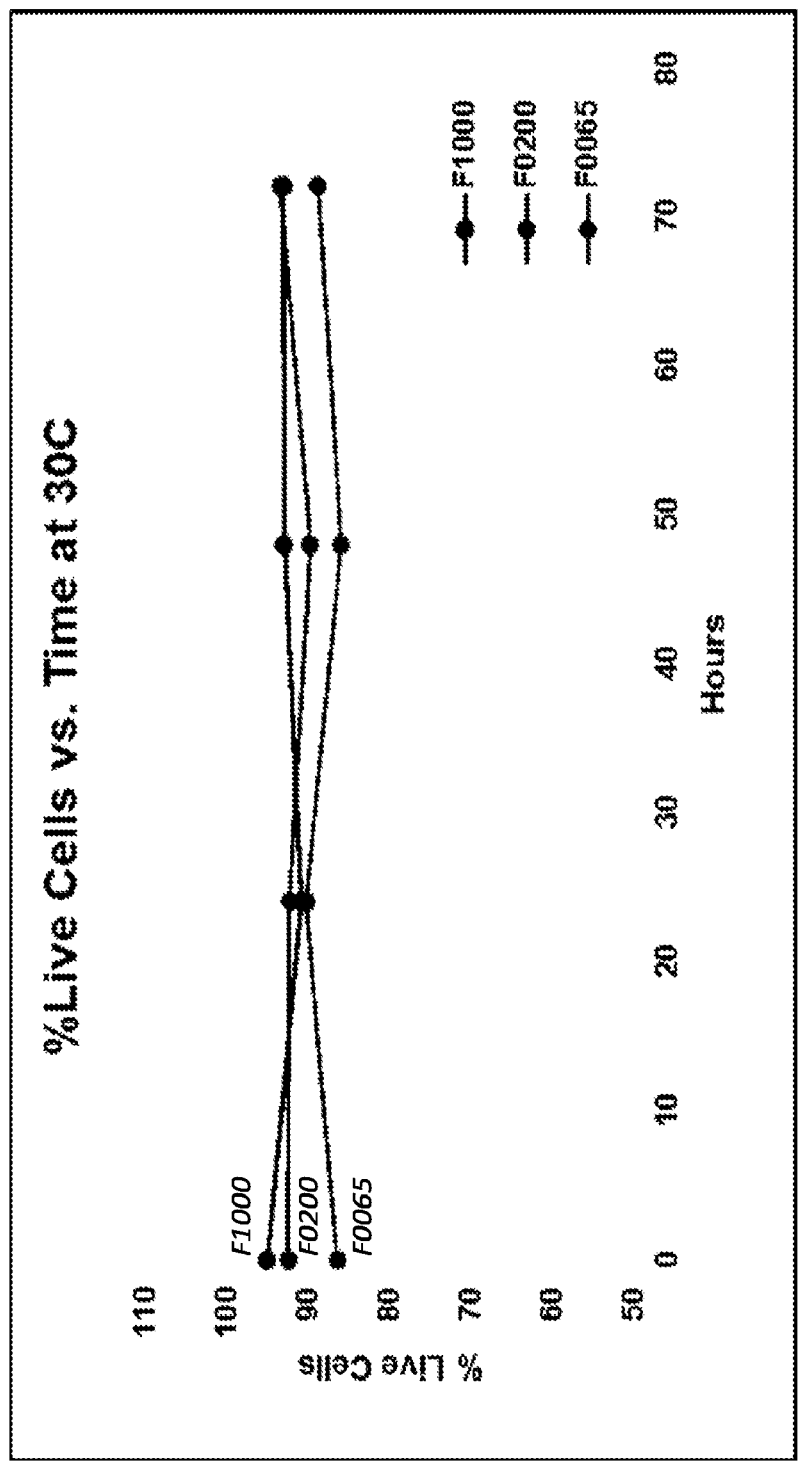

FIGS. 44A-B show VCC data (A) and percent live cells (B) vs. storage time at 30° C. in the WP7 experiment.

Figure 45A:
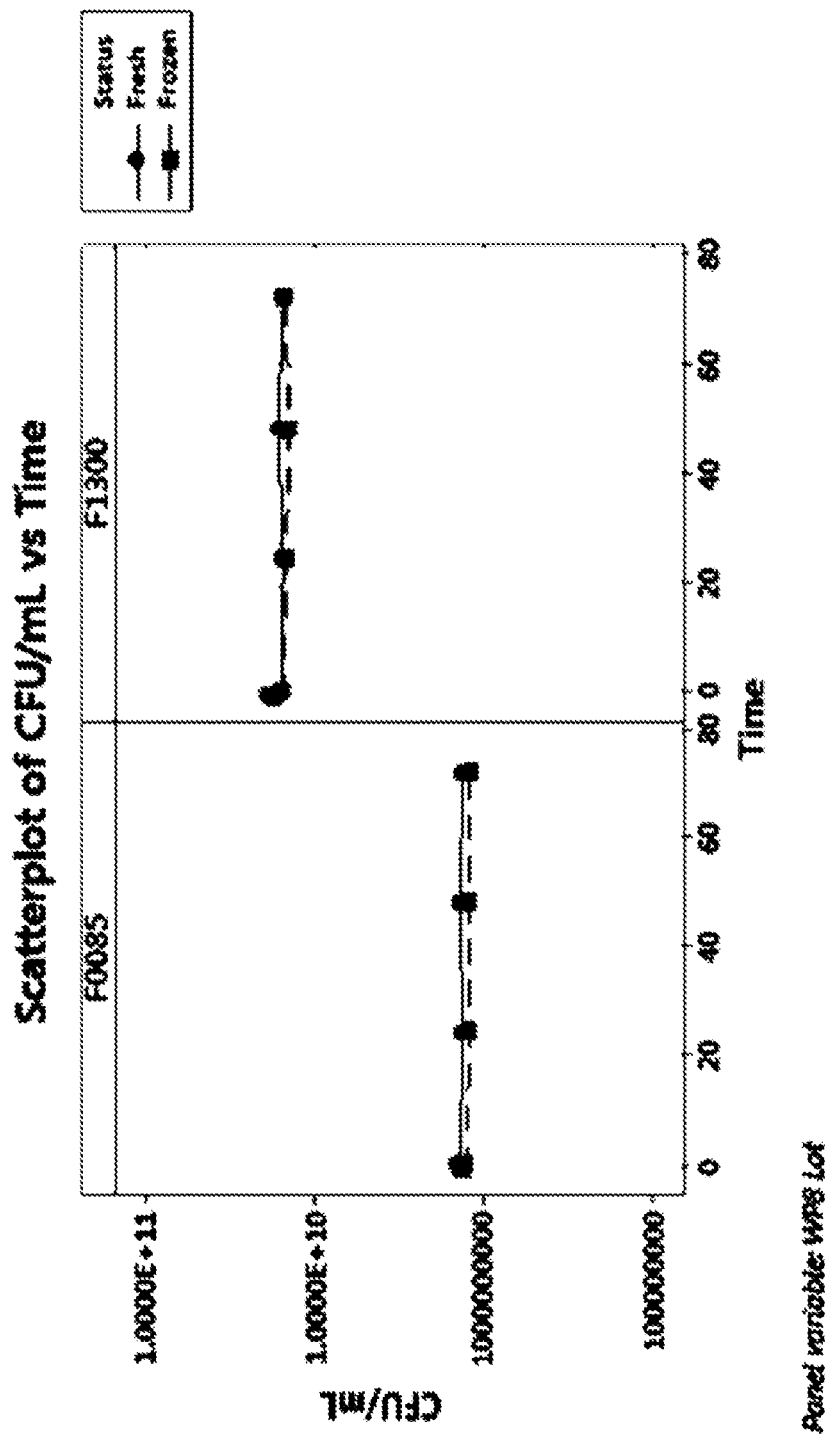
Figure 45B:
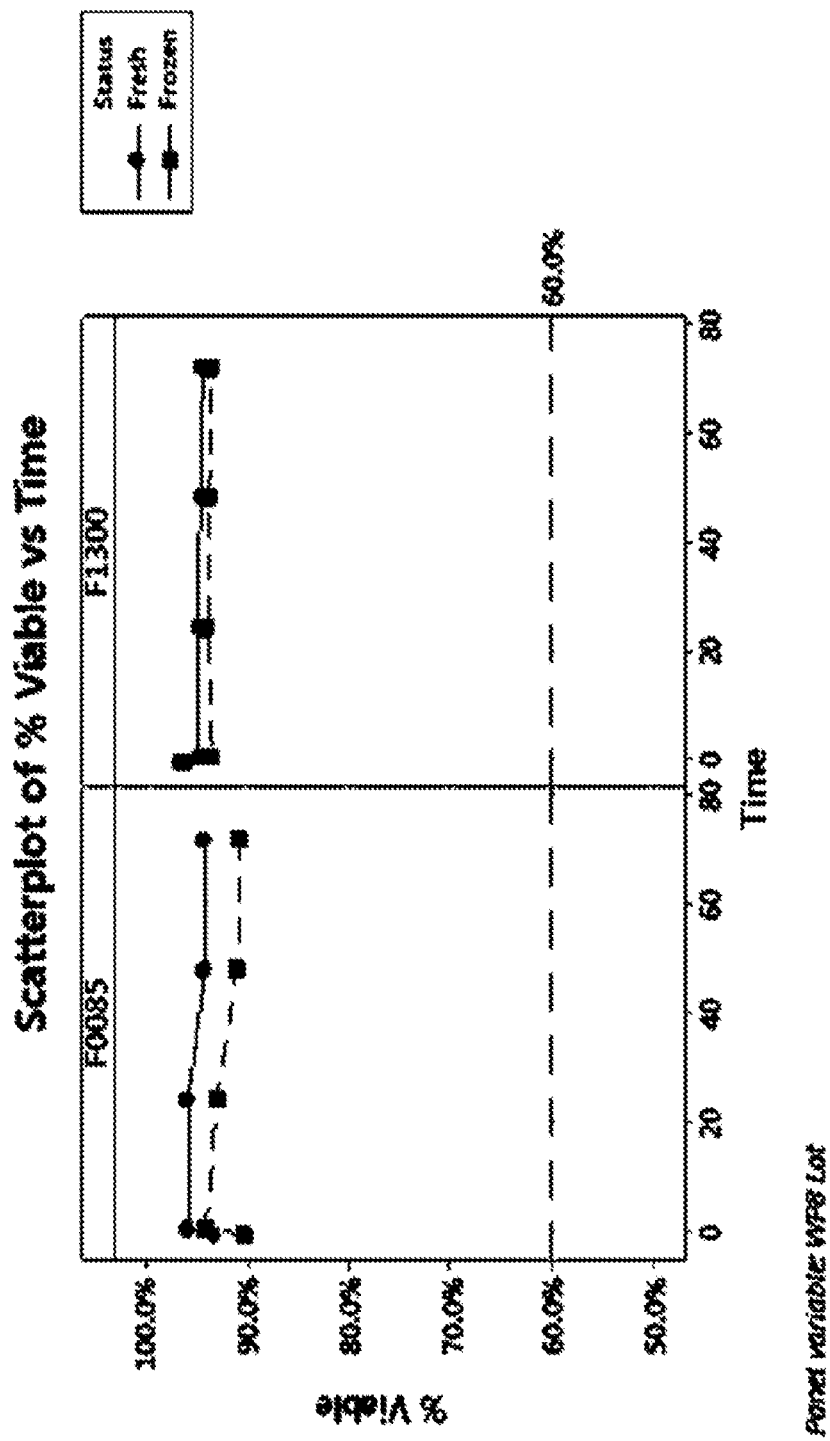

FIGS. 45A-B show CFU/mL (A) and percent viable cells (B) vs. time in the WP7 experiment.

Figure 46A:
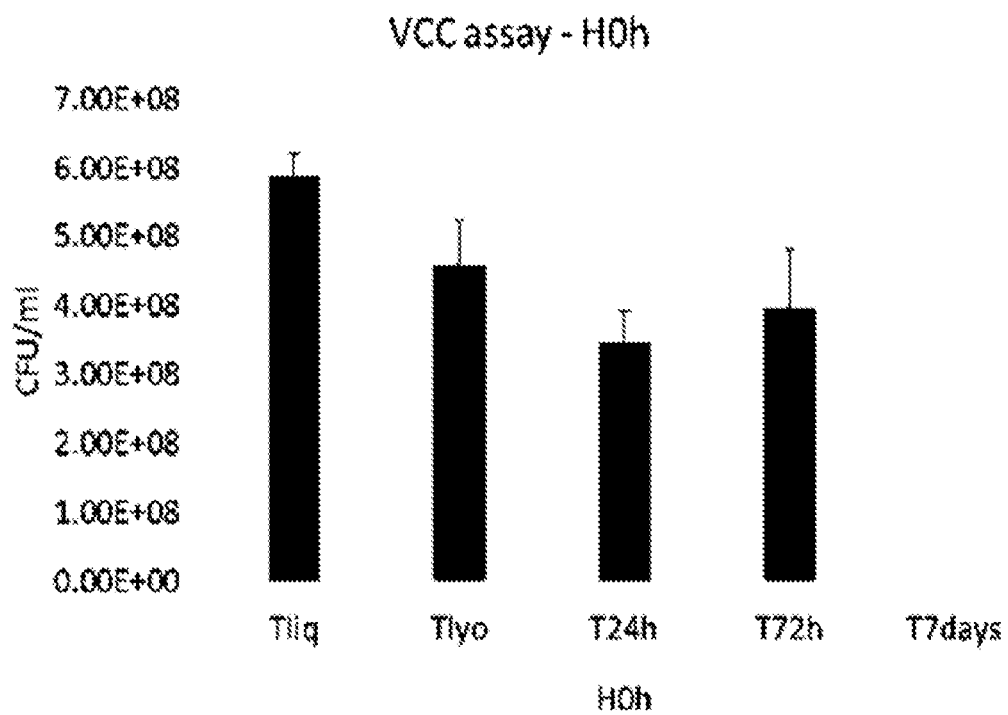
Figure 46B:
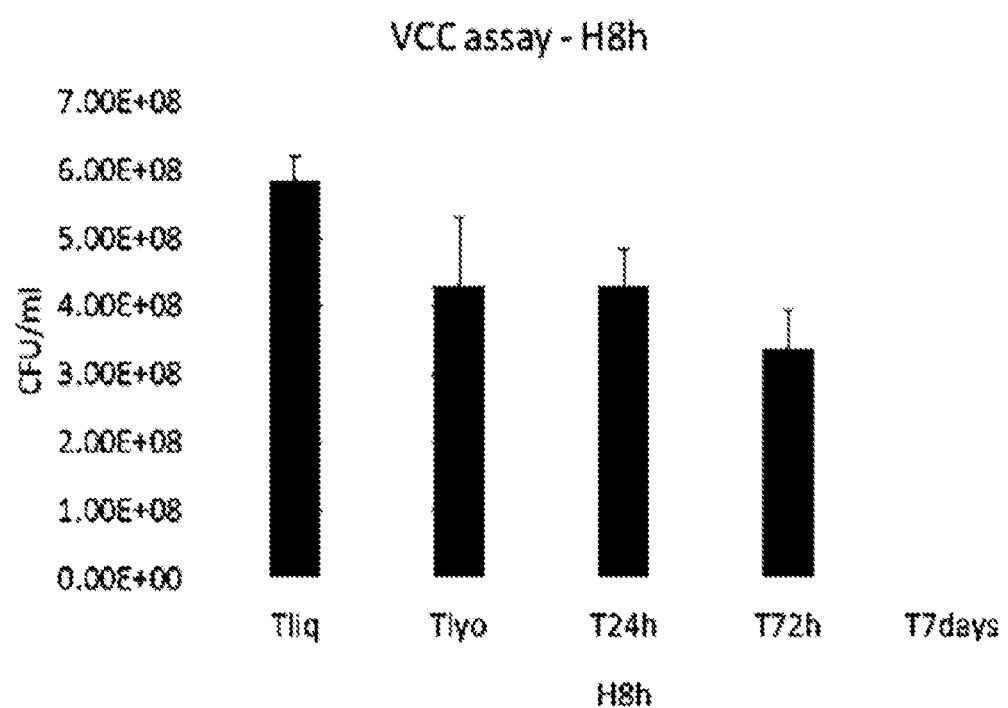

FIGS. 46A-B show VCC data before lyophilization and post-lyophilization immediately after lyophilization and after storage at 30° C. for 24 and 72 hours in the WP7 experiment.

Figure 47A:
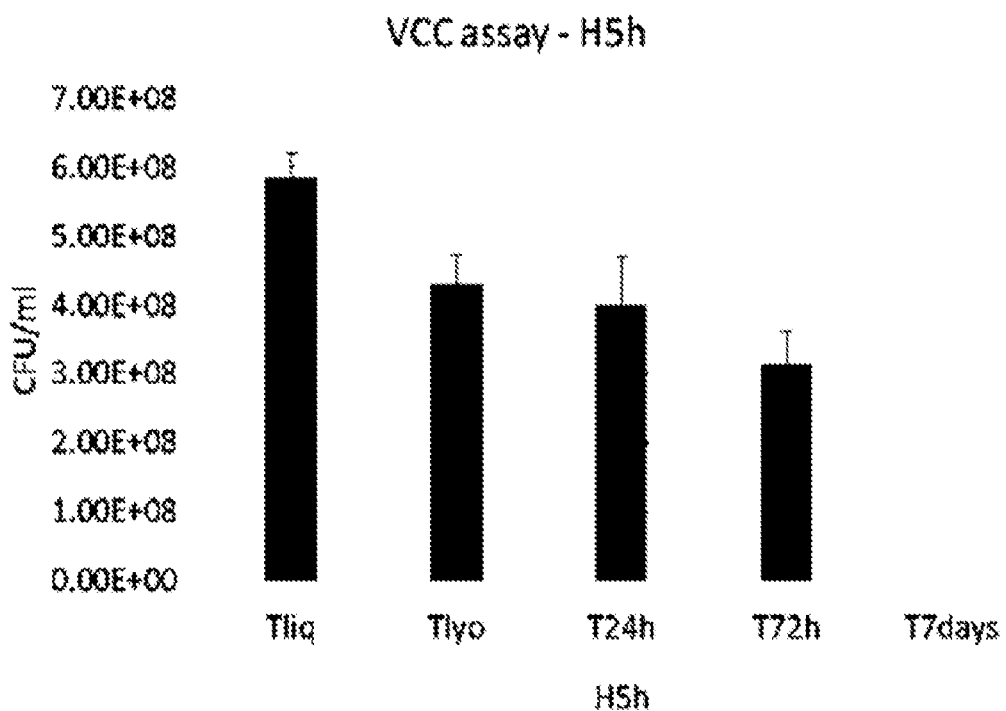
Figure 47B:
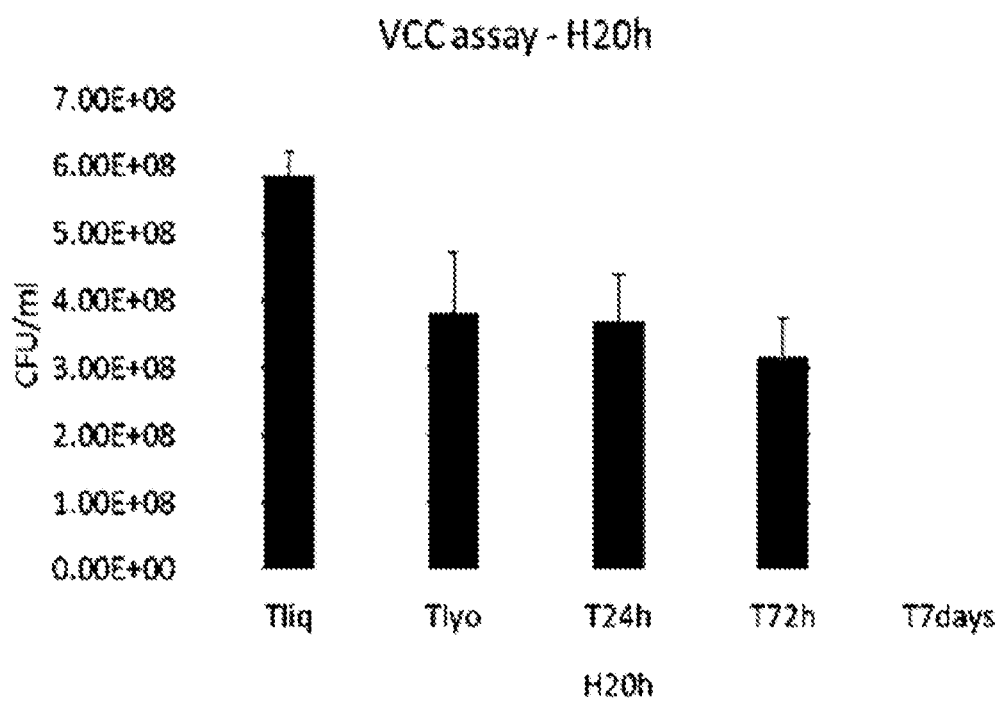

FIGS. 47A-B show VCC data before lyophilization and post-lyophilization immediately after lyophilization and after storage at 30° C. for 24 and 72 hours in the WP7 experiment.

Figure 48:
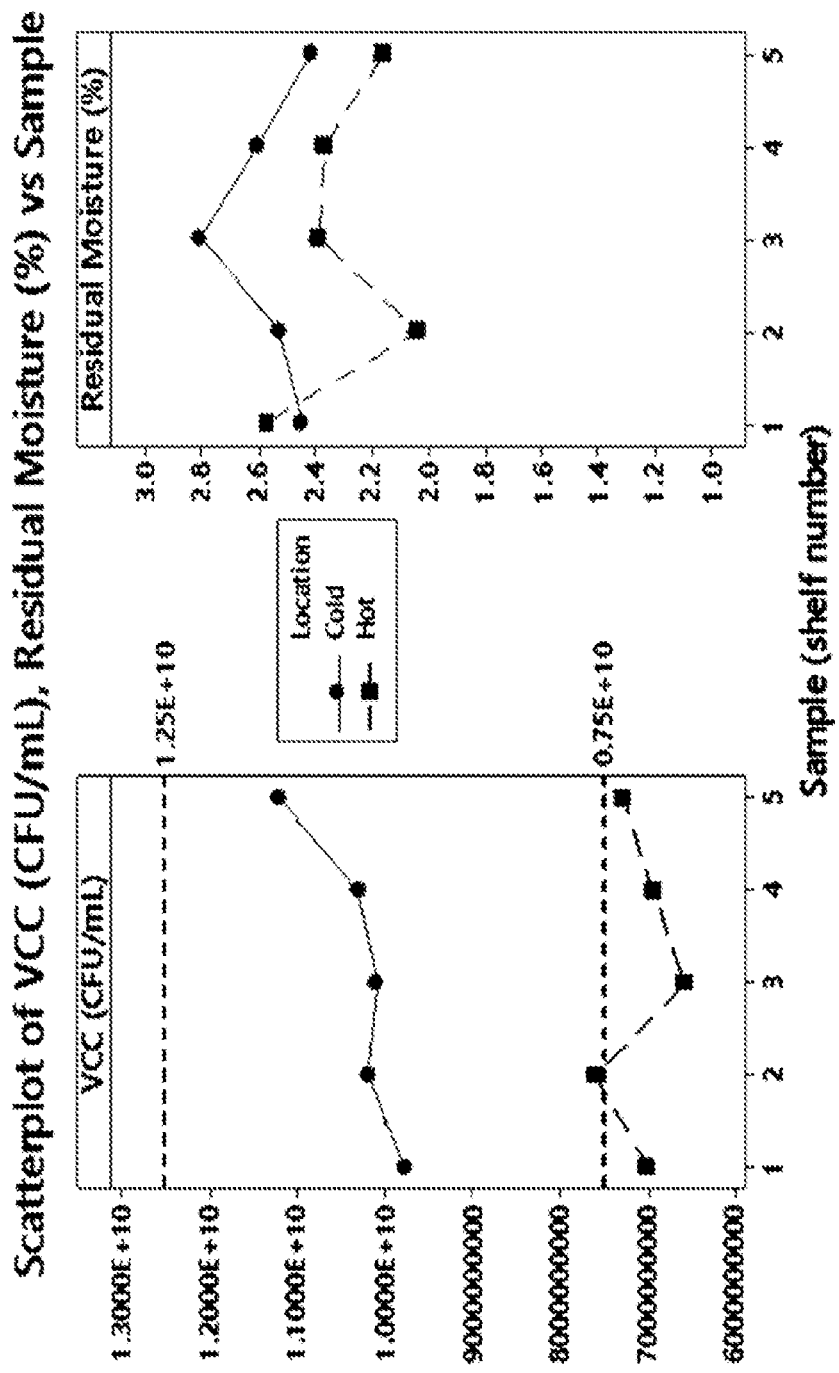

FIG. 48 shows a scatterplot of VCC and RM for ADXS11-001 Pilot Batch.

Figure 49:
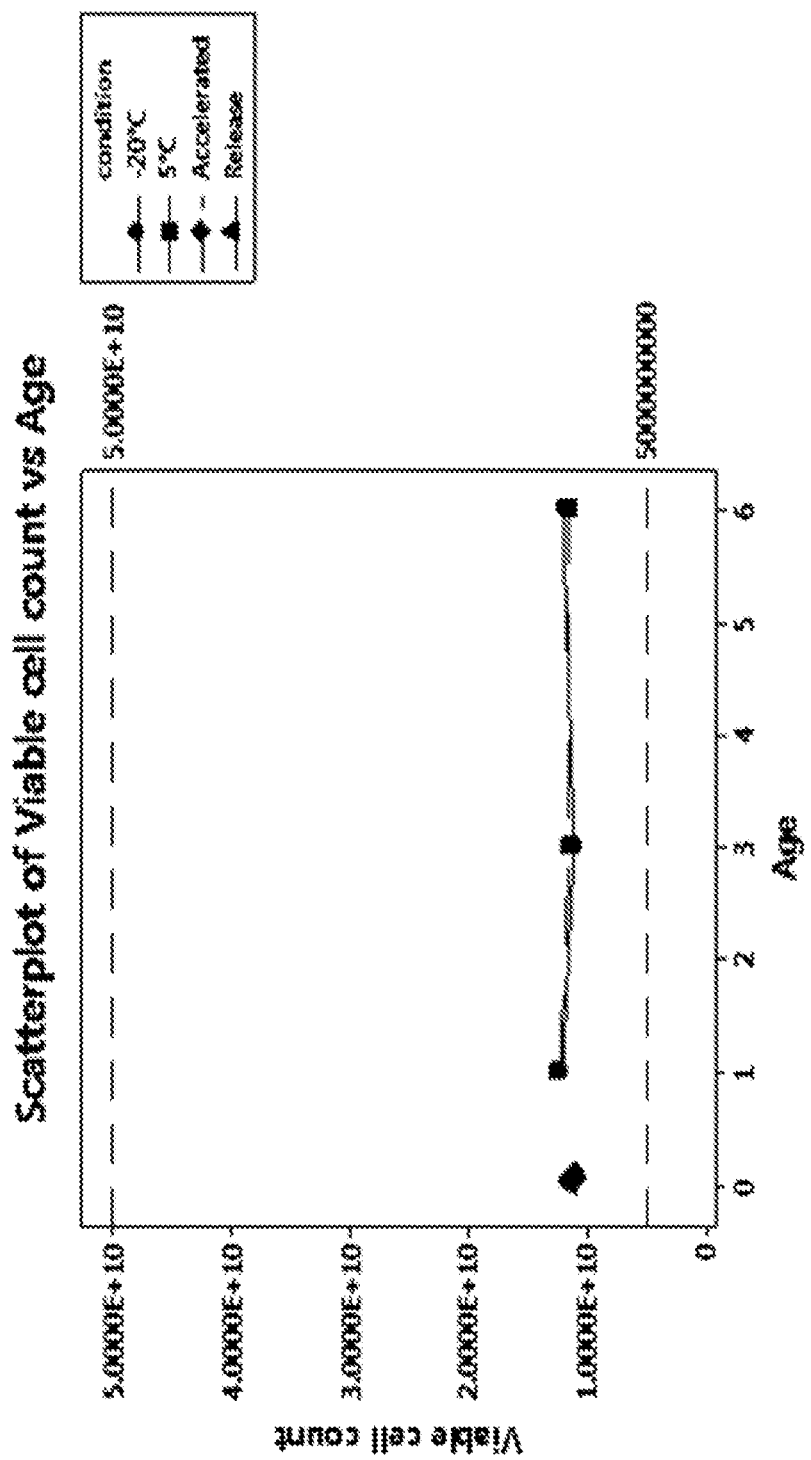

FIG. 49 shows a scatterplot of VCC for Lot #5329PD-17-01 (ADXS11-001 Pilot Batch).

Figure 50:
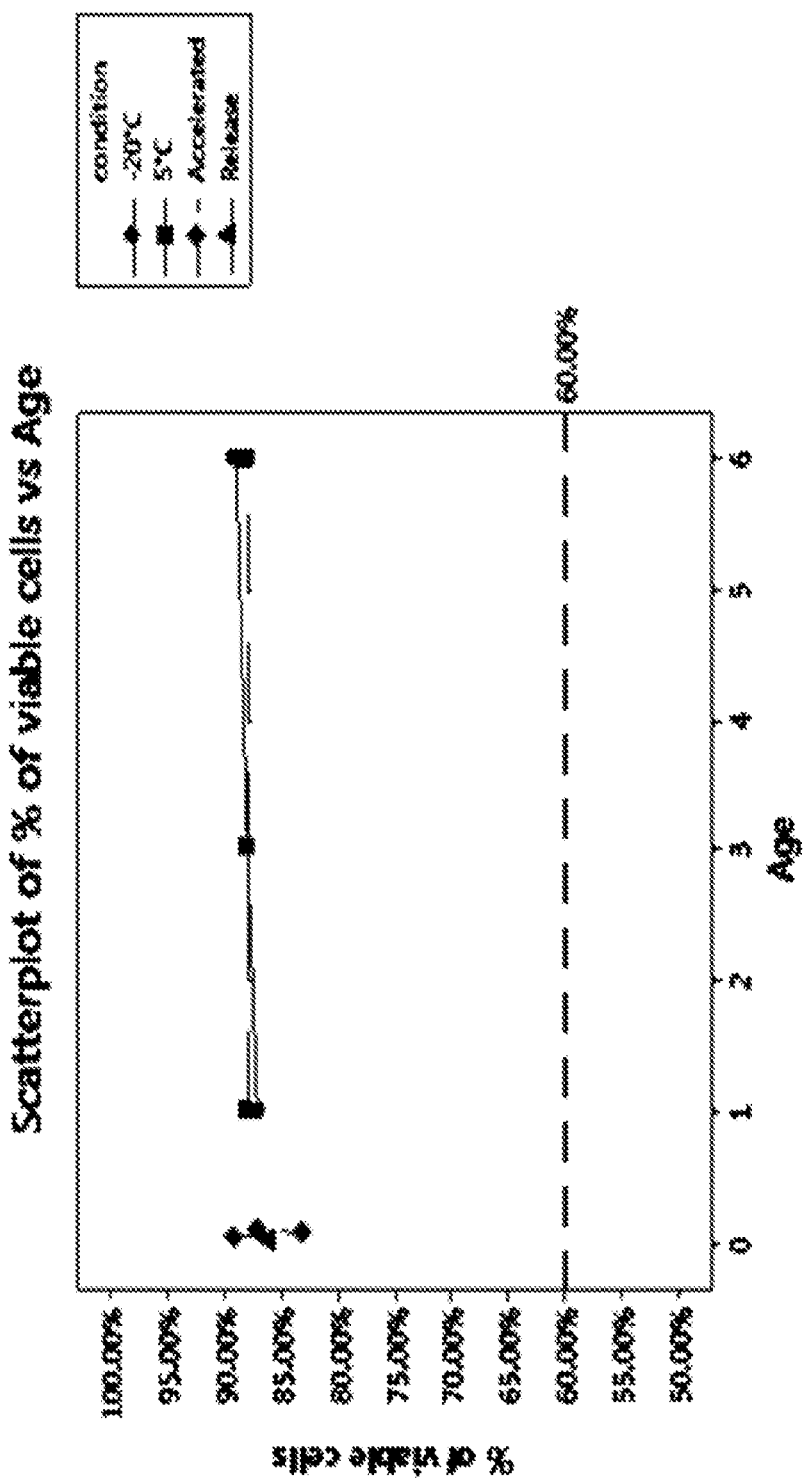

FIG. 50 show a scatterplot of % live for Lot #5329PD-17-01 (ADXS11-001 Pilot Batch).

Figure 51:
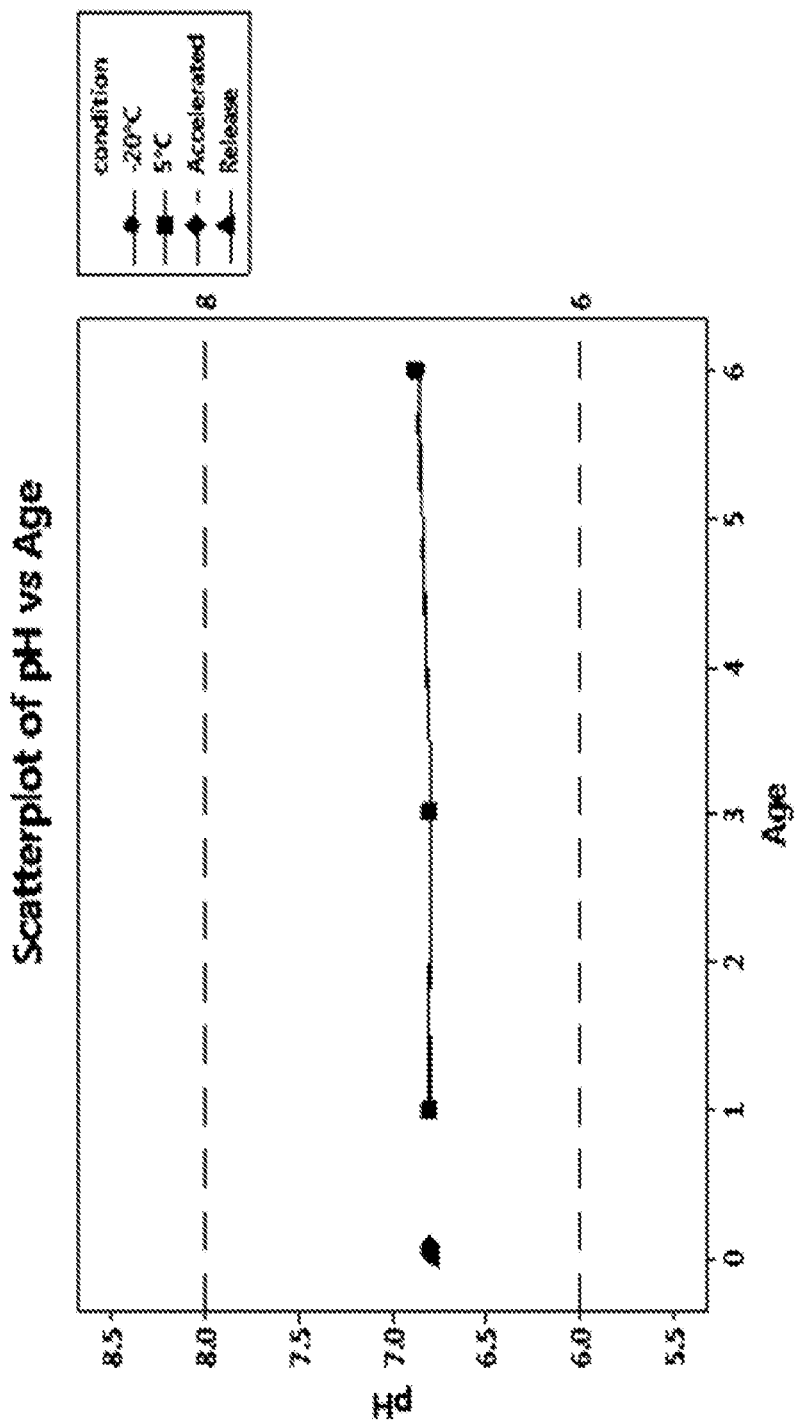

FIG. 51 show a scatterplot of pH for Lot #5329PD-17-01 (ADXS11-001 Pilot Batch).

Figure 52:
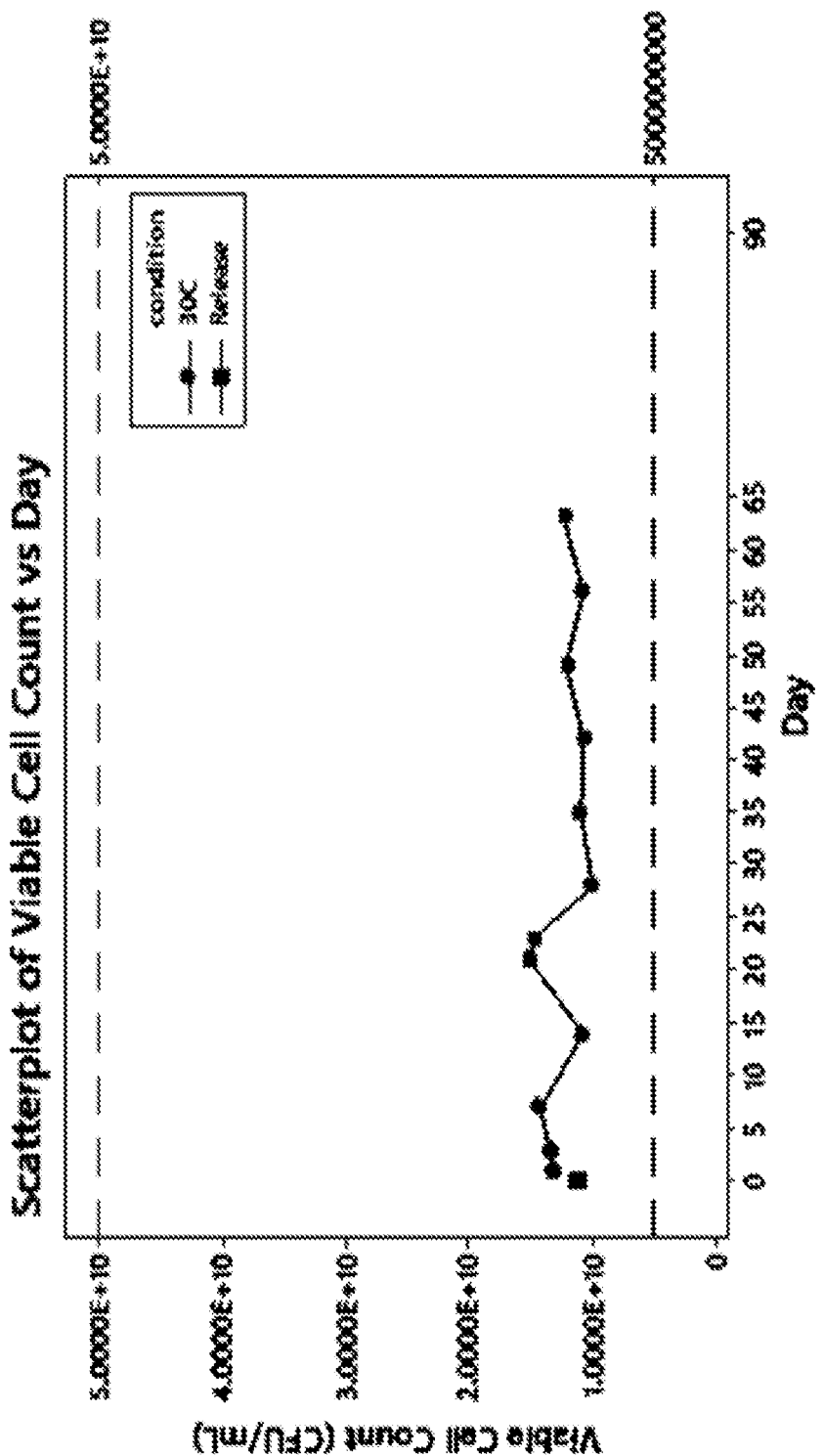

FIG. 52 shows a scatterplot of VCC for Lot #5329PD-17-01 stored at 30° C. (ADXS11-001 Pilot Batch).

Figure 53:
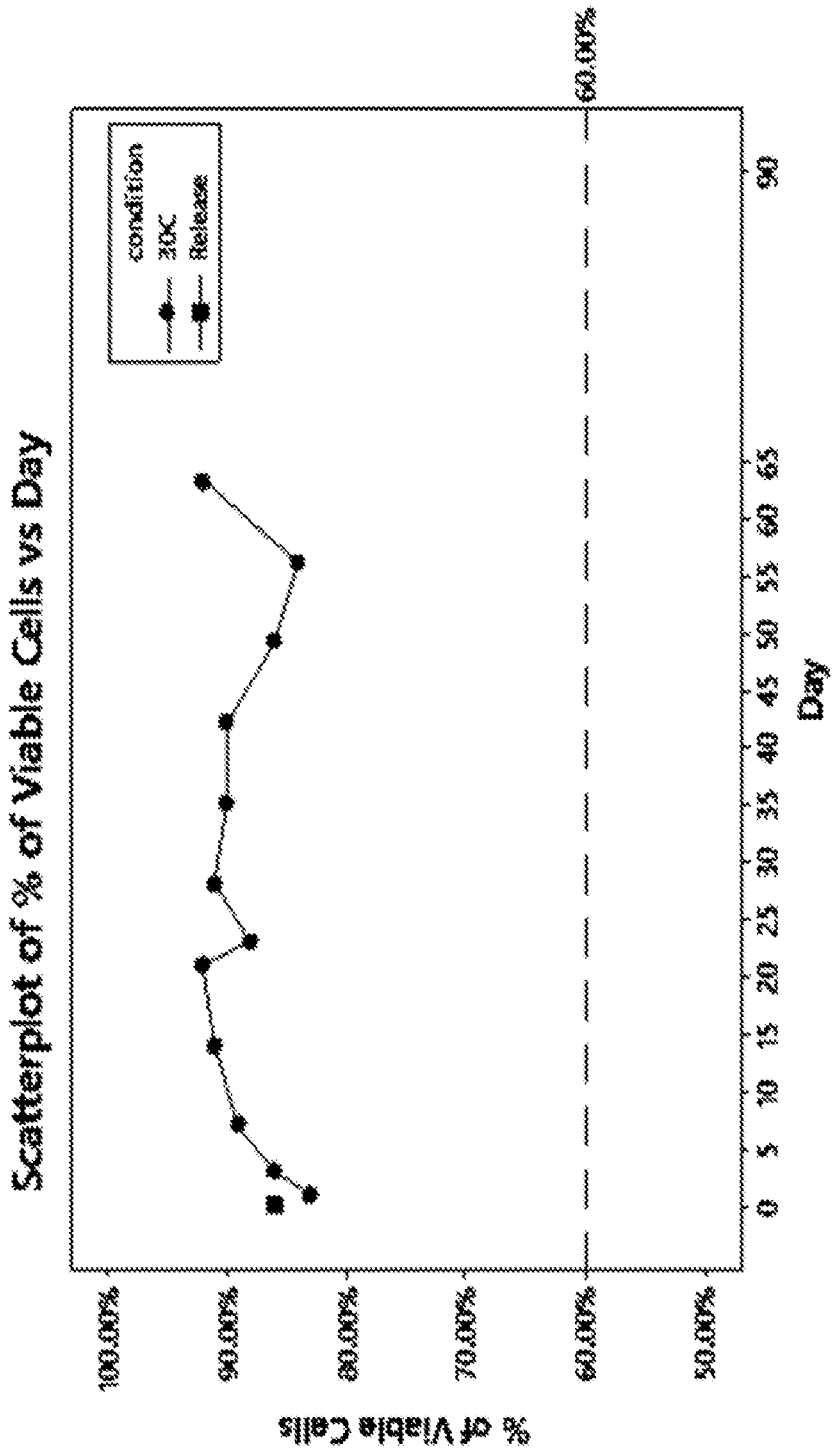

FIG. 53 shows a scatterplot of % live for Lot #5329PD-17-01 stored at 30° C. (ADXS11-001 Pilot Batch).

Figure 54:
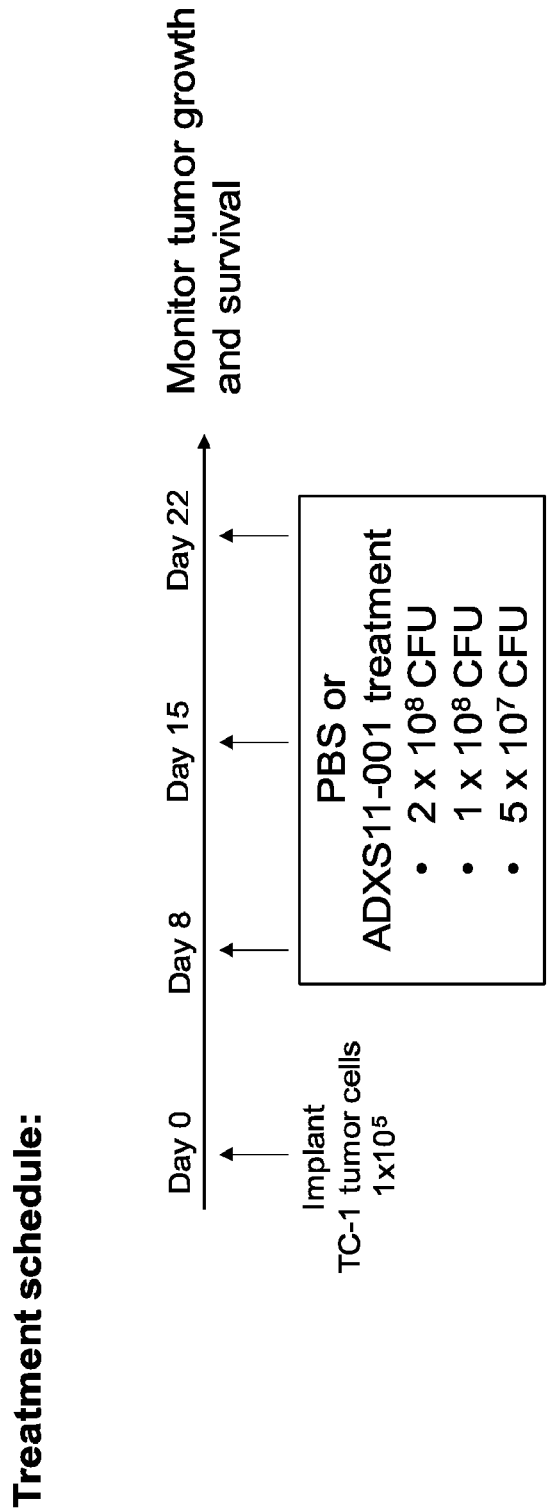

FIG. 54 shows a chart illustrating implantation and dosing schedule (ADXS11-001 Pilot Batch).

Figure 55:
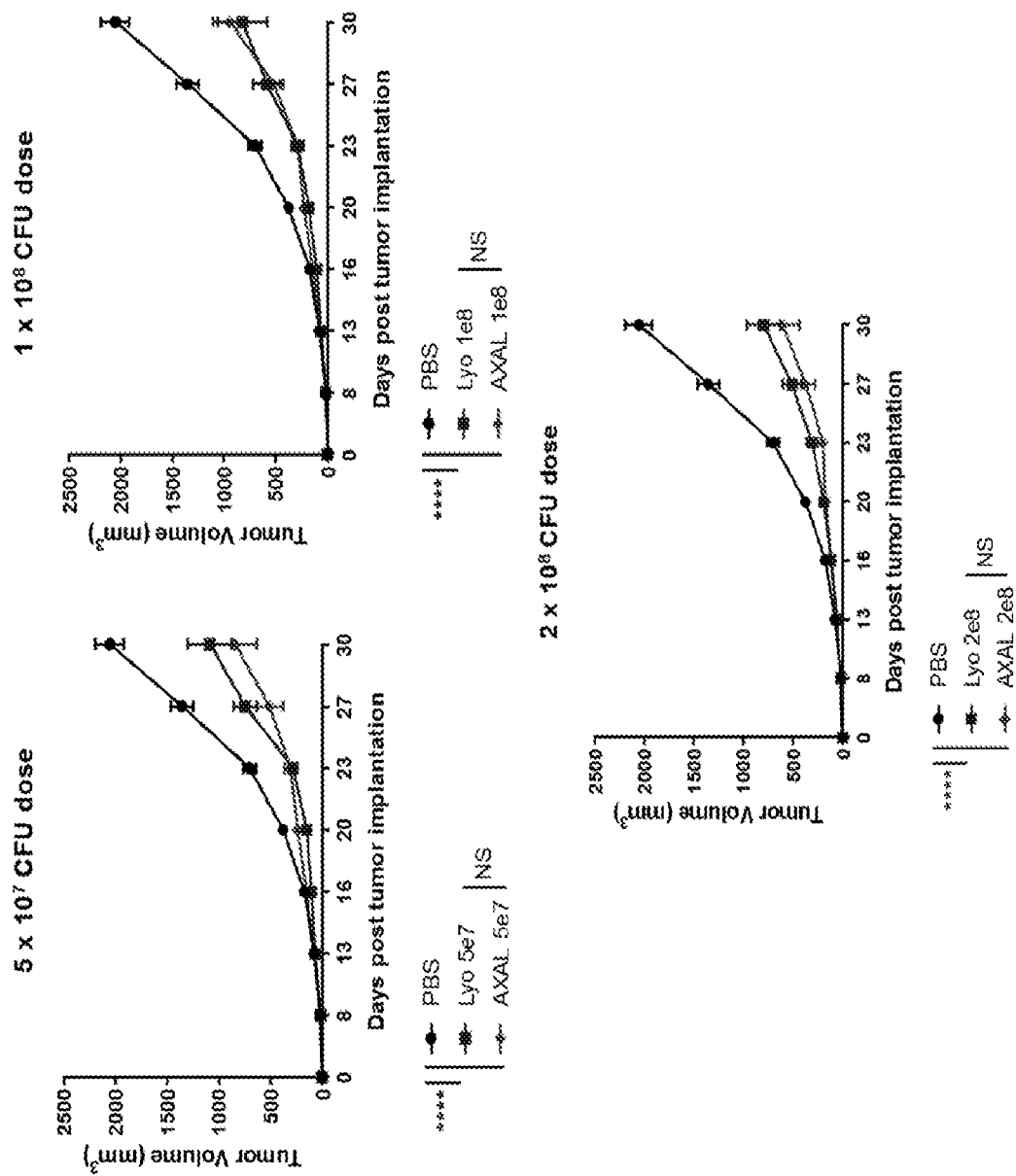

FIG. 55 shows graphs illustrating both lyophilized AXAL and clinical AXAL inhibit tumor growth in the TC-1 tumor model at different doses.

Figure 56:
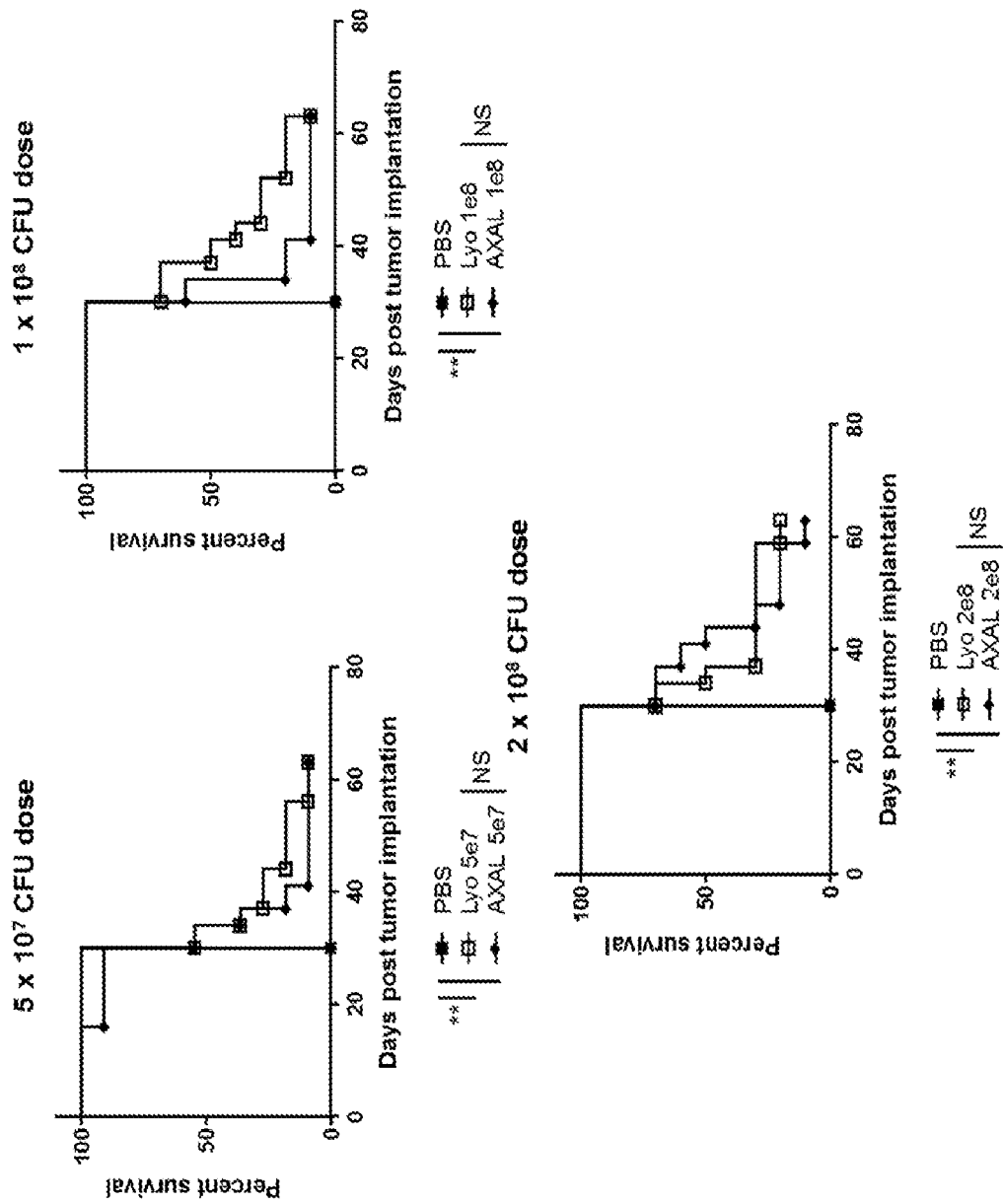

FIG. 56 shows graphs illustrating both lyophilized AXAL and clinical AXAL prolong animal survival in the TC-1 tumor model at different doses.

Figure 57:
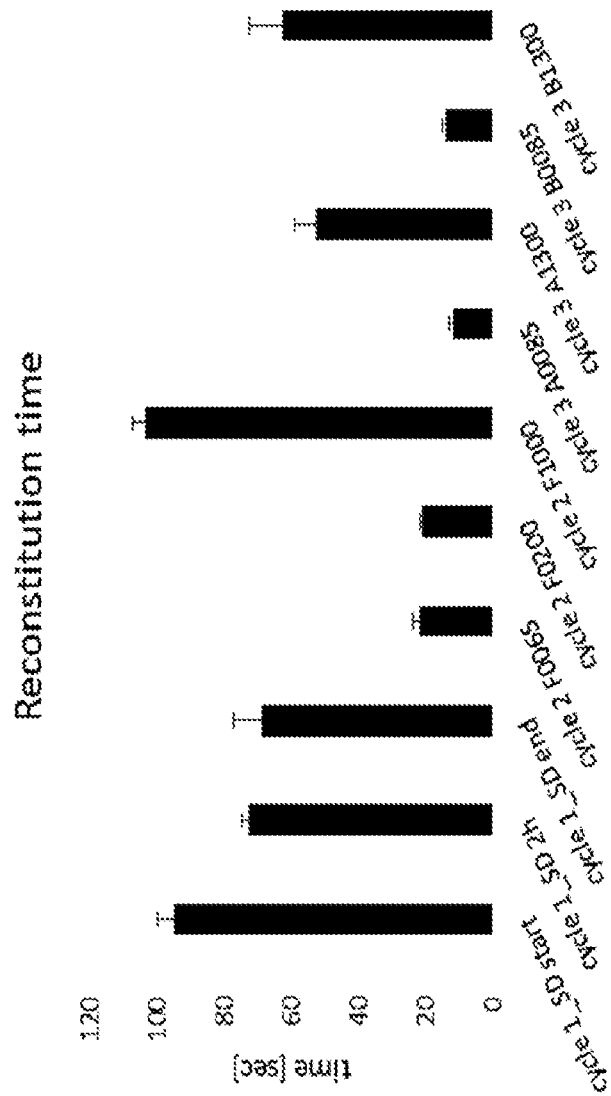

FIG. 57 shows a graph illustrating reconstitution time of WP7 cycle 3 compared to cycle 1 and cycle 2.

Figure 58A:
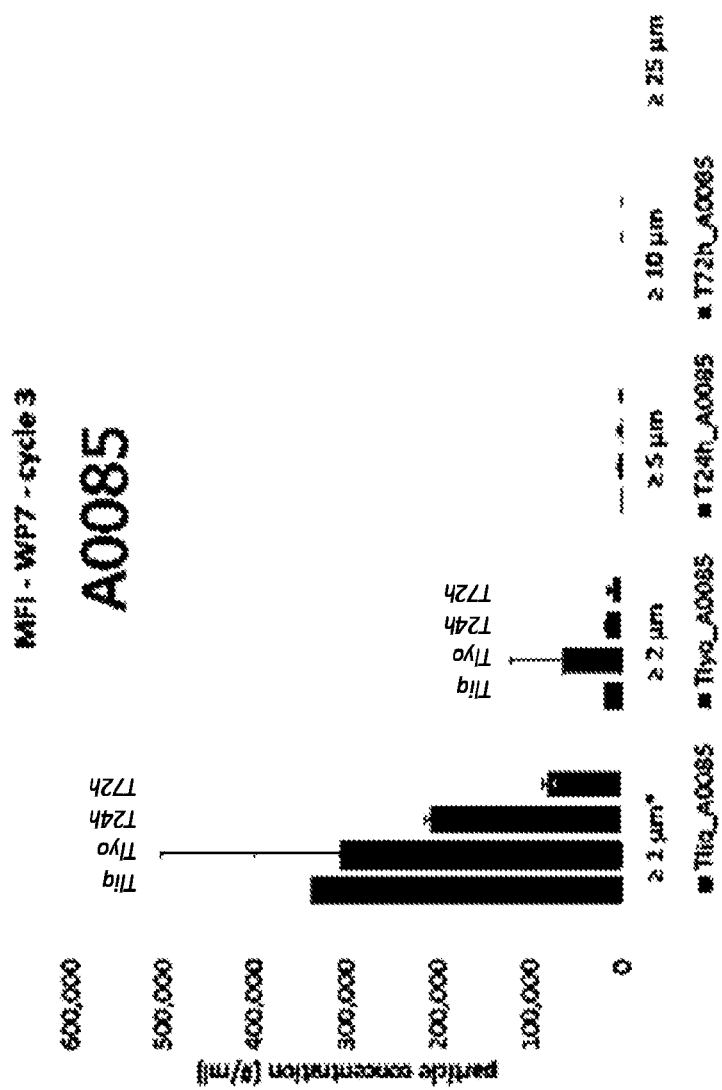
Figure 58B:
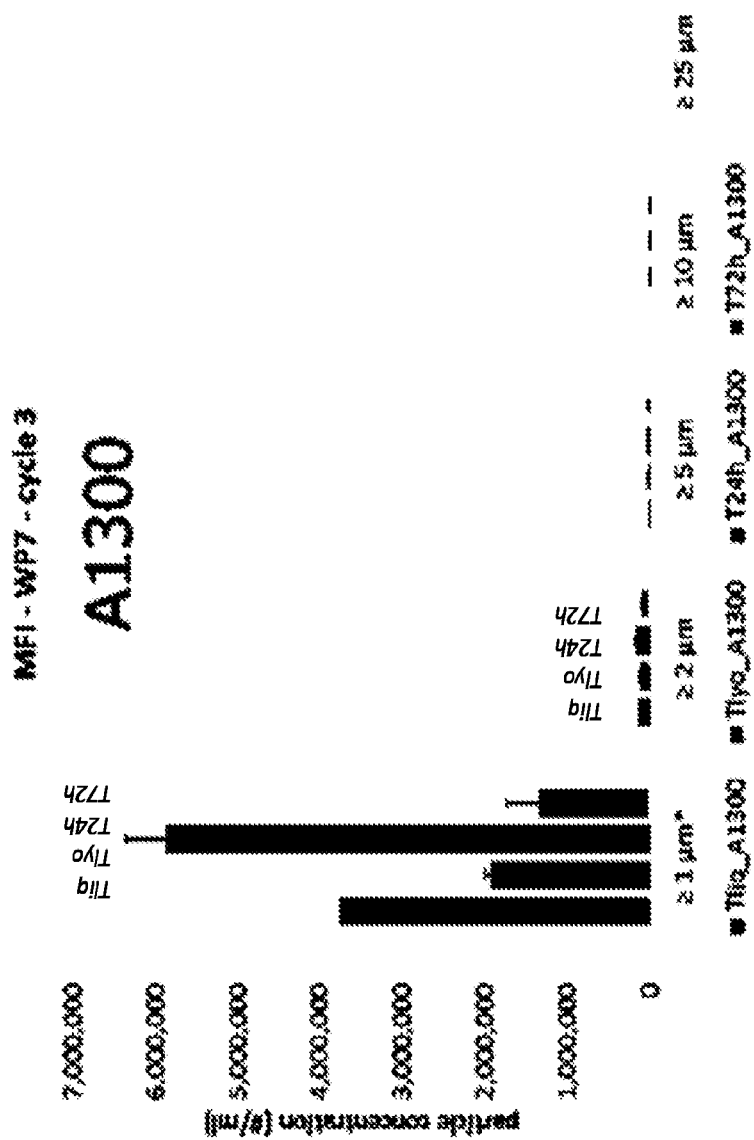

FIGS. 58A-B show graphs illustrating MFI analysis at Tliq, Tlyo, and after storage for 24 and 72 hours at 30° C. of A0085 (A) and A1300 (B).

Figure 58C:
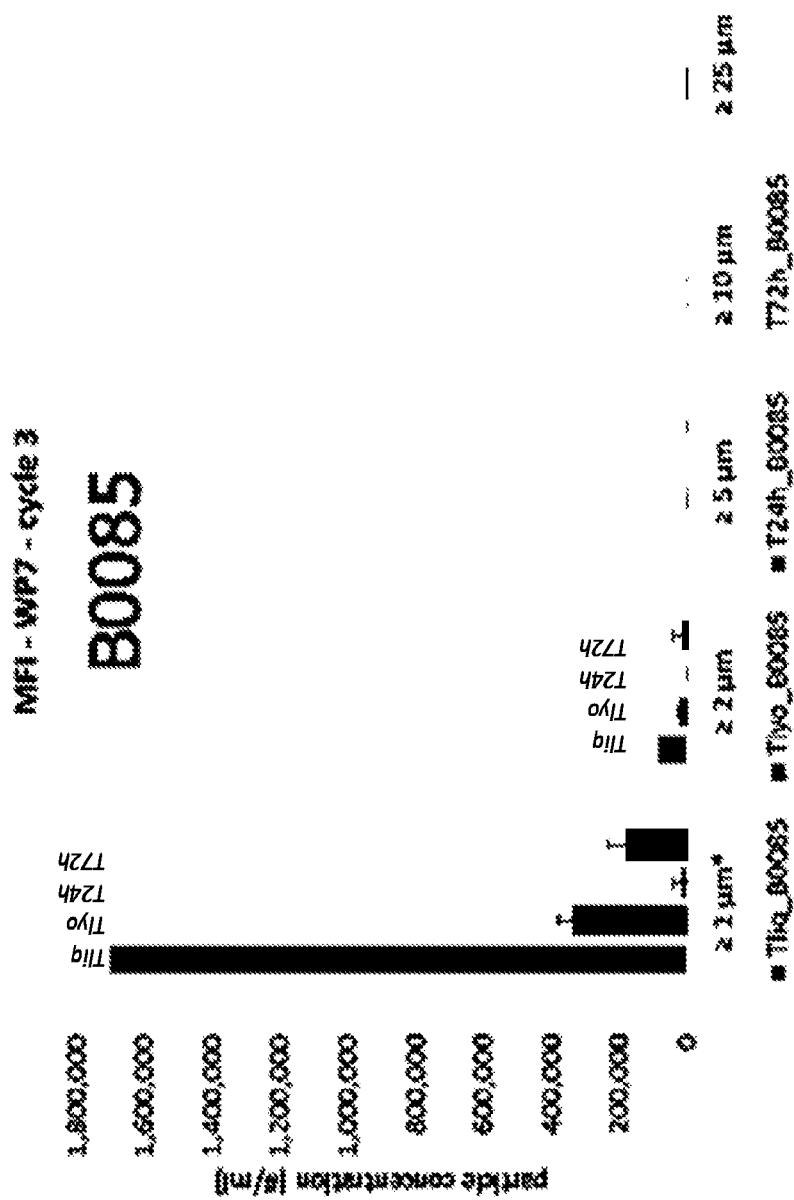
Figure 58D:
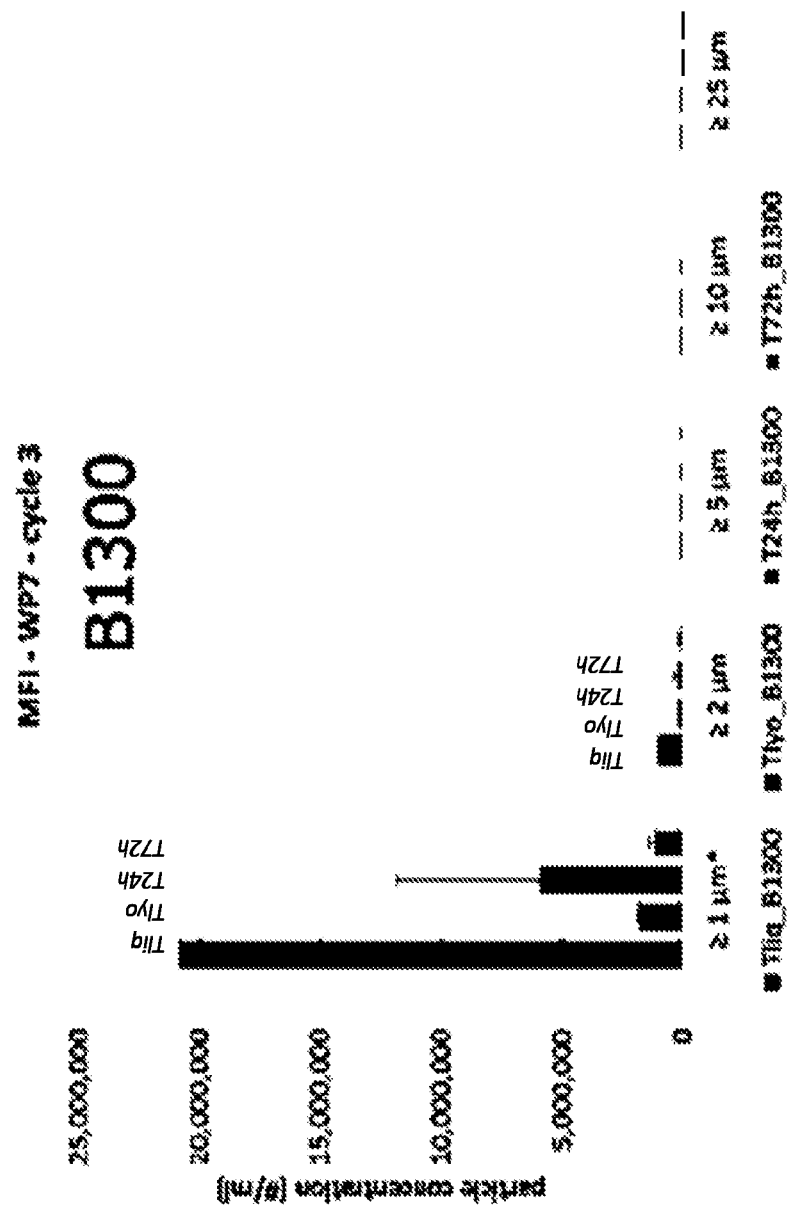

FIGS. 58C-D show graphs illustrating MFI analysis at Tliq, Tlyo, and after storage for 24 and 72 hours at 30° C. of B0085 (C) and B1300 (D).

Figure 59A:
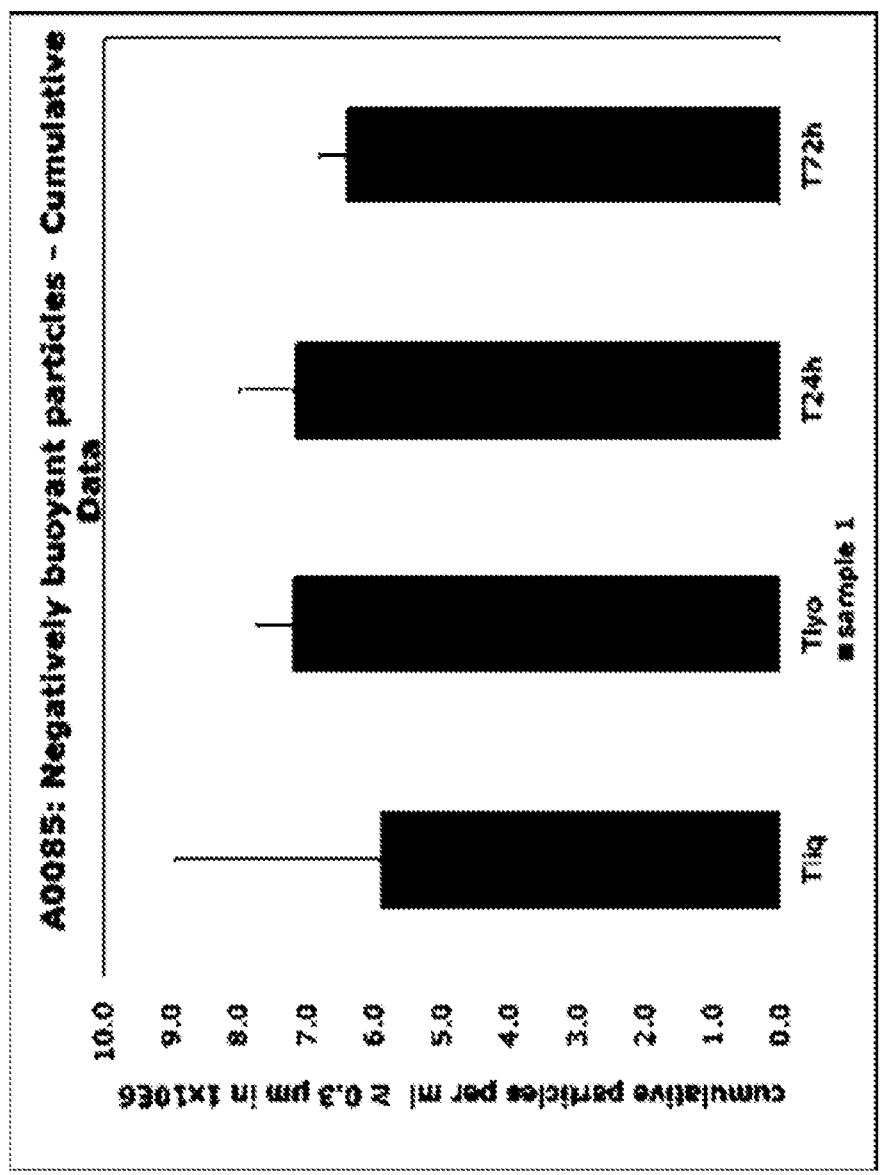
Figure 59B:
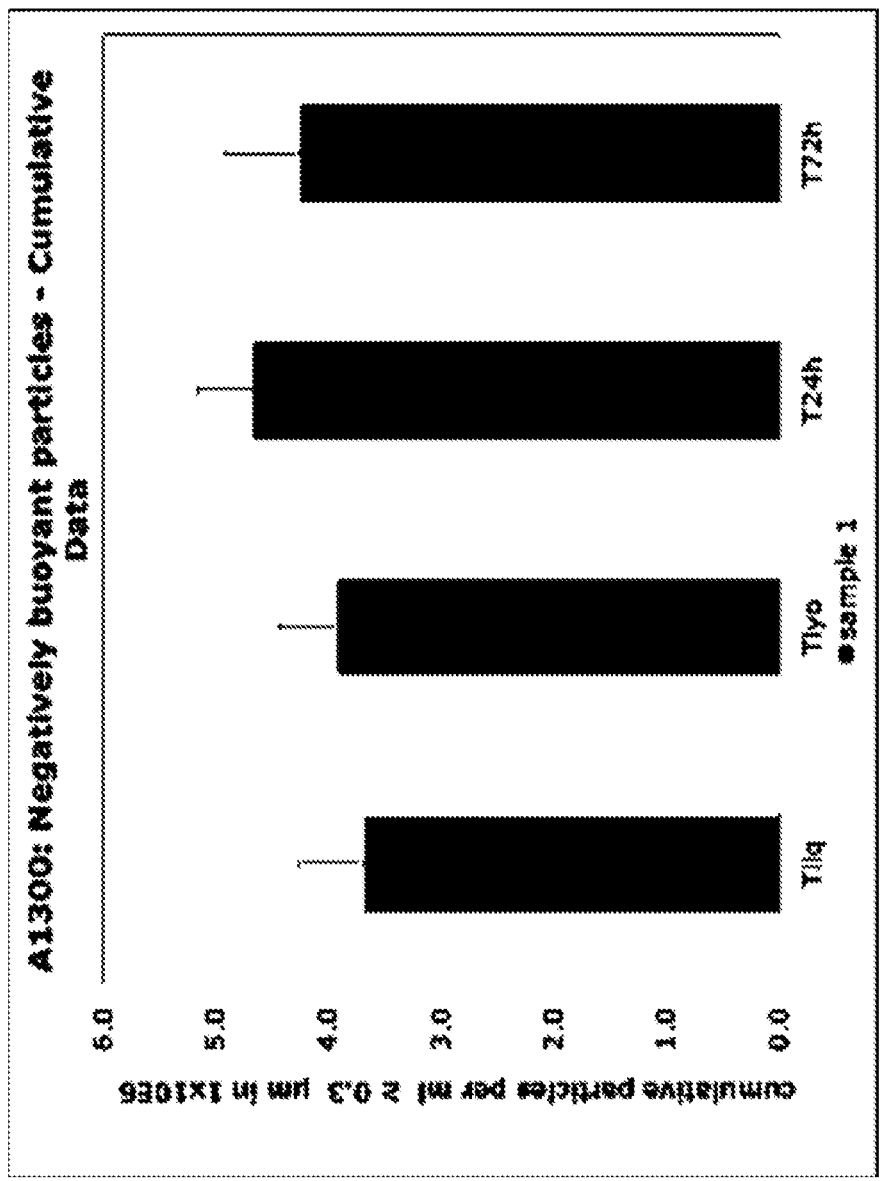

FIGS. 59A-B show graphs illustrating RRM results for A. A0085 (200 fold dilution) and B. A1300 (5,000-fold dilution).

Figure 59C:
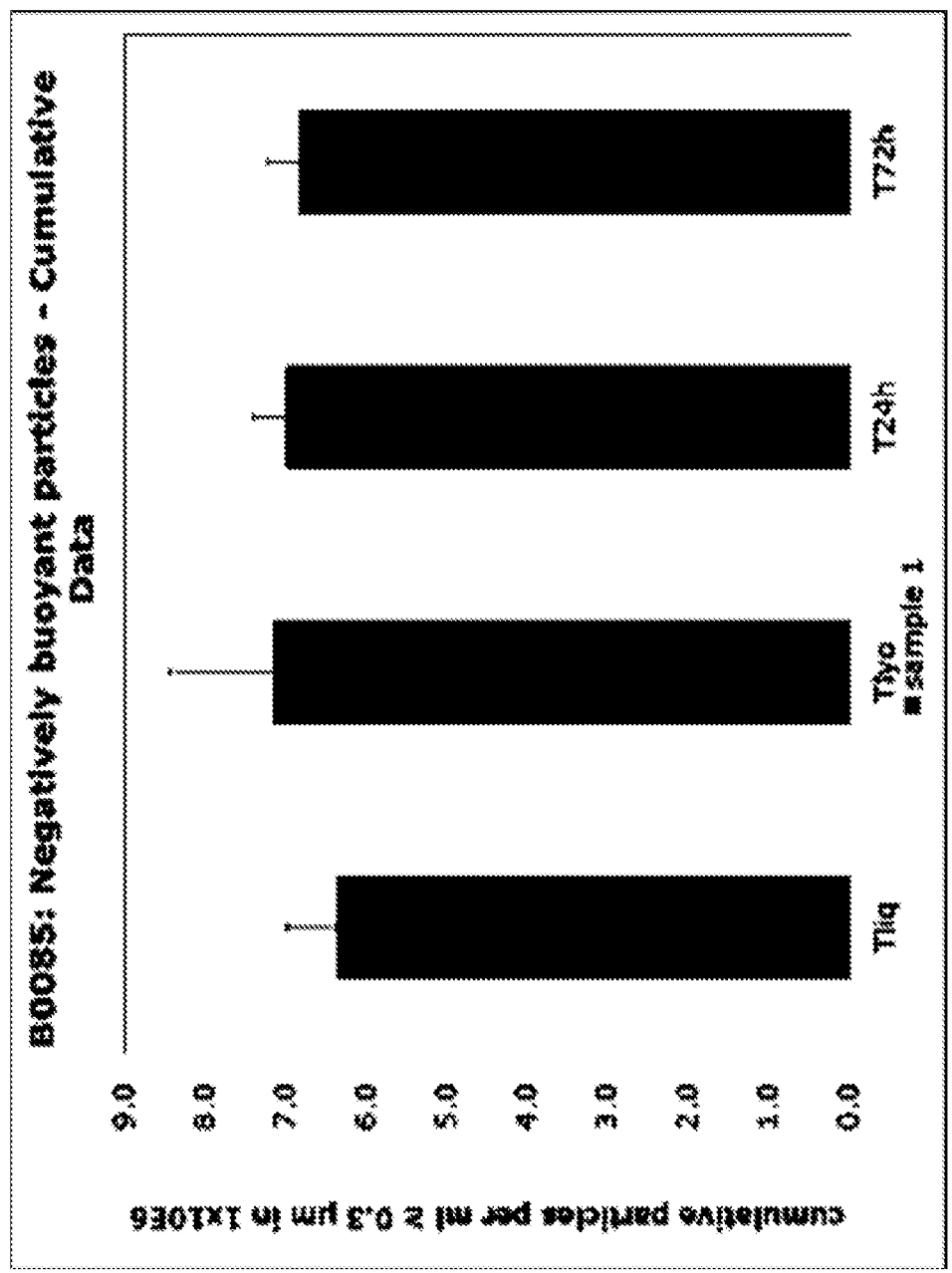
Figure 59D:
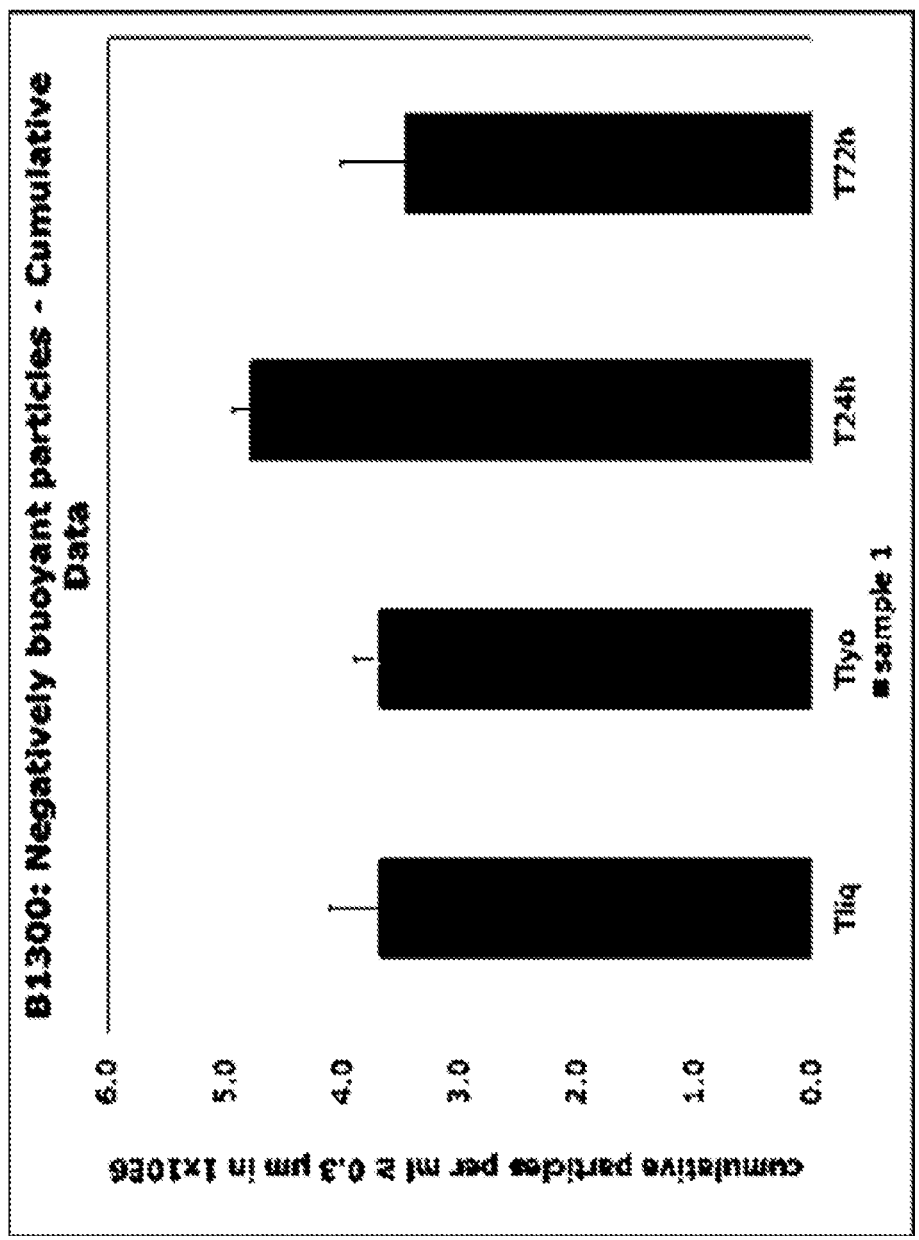

FIGS. 59C-D show graphs illustrating RRM results for C. B0085 (200 fold dilution) and D. B1300 (5,000-fold dilution).

Figure 60A:
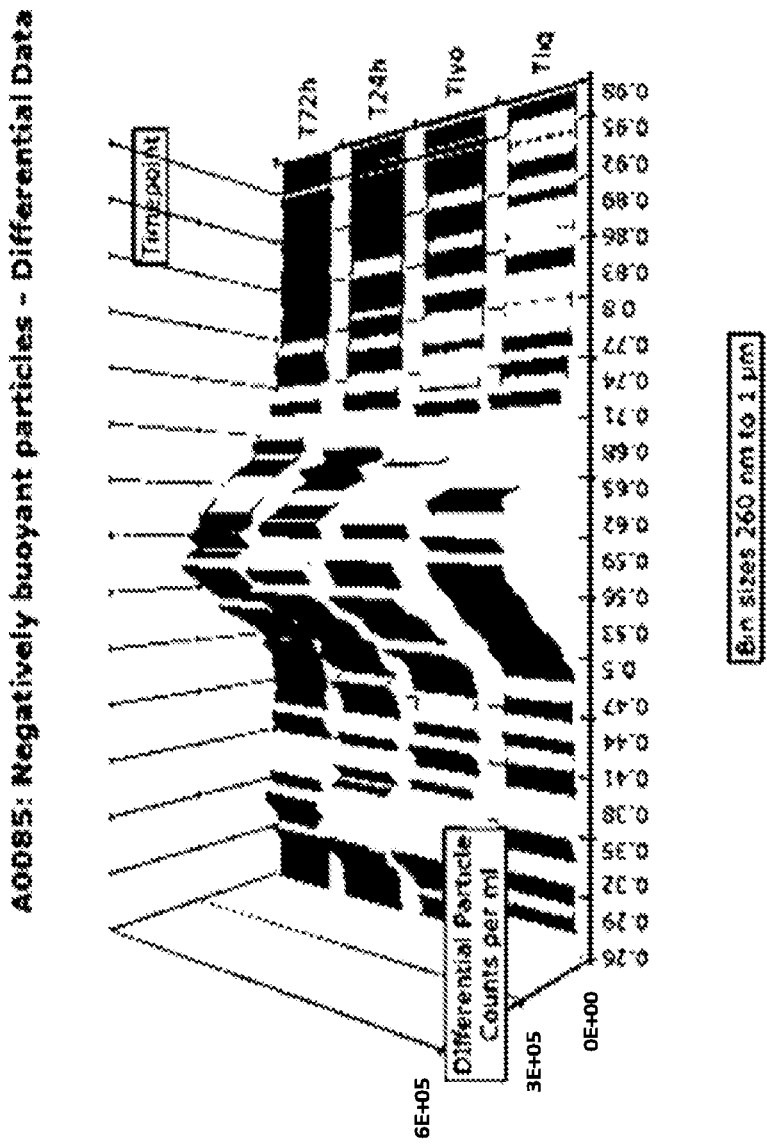
Figure 60B:
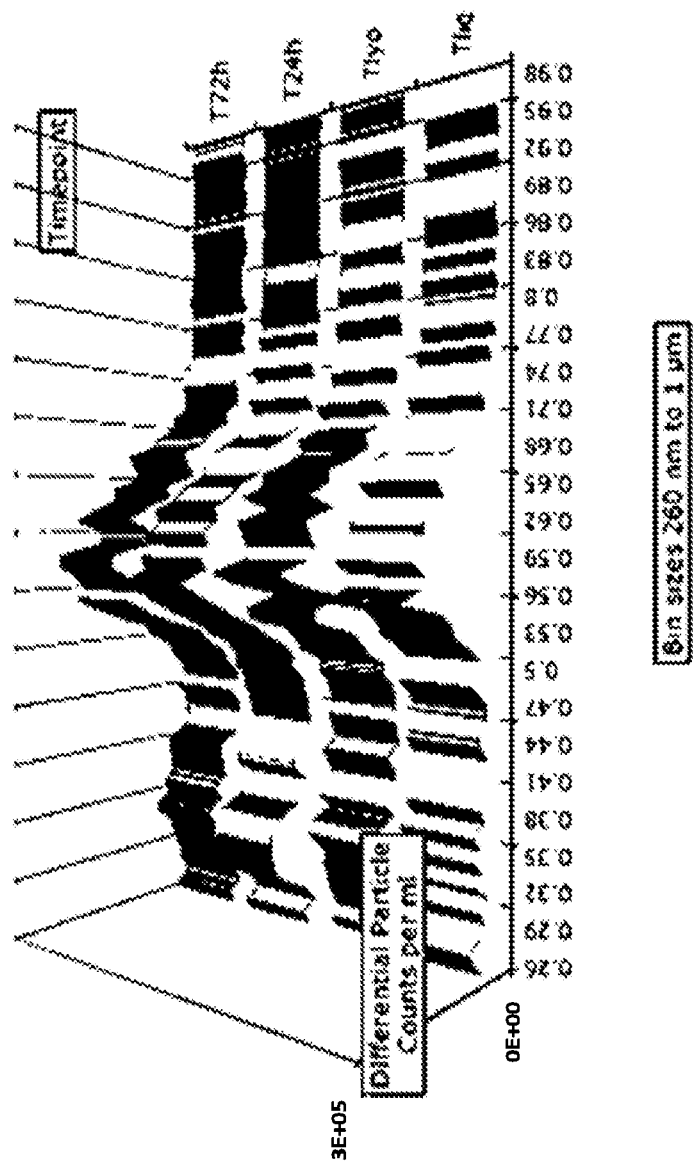

FIGS. 60A-B show graphs illustrating negatively buoyant particle distribution for A0085 (200 fold dilution) (A) and A1300 (5,000-fold dilution) (B).

Figure 60C:
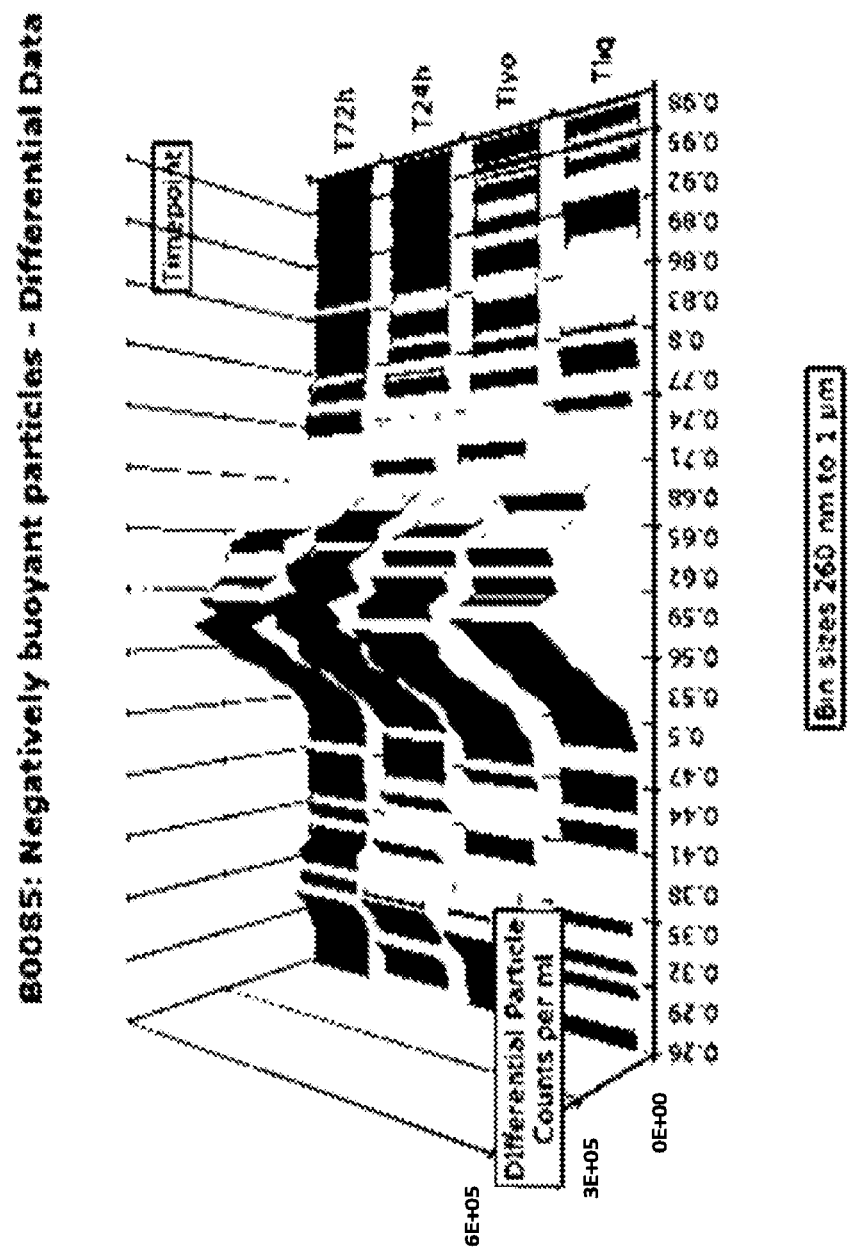
Figure 60D:
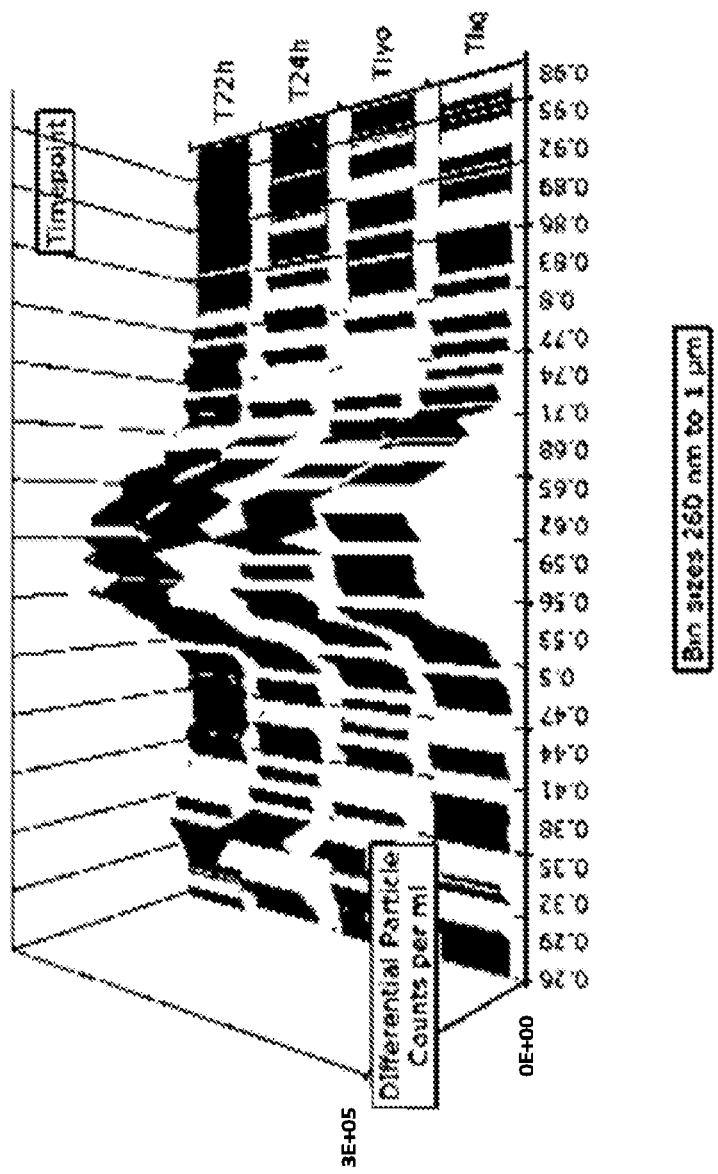

FIGS. 60C-D show graphs illustrating negatively buoyant particle distribution for B0085 (200 fold dilution) (C) and B1300 (5,000-fold dilution) (D).

Figure 61:
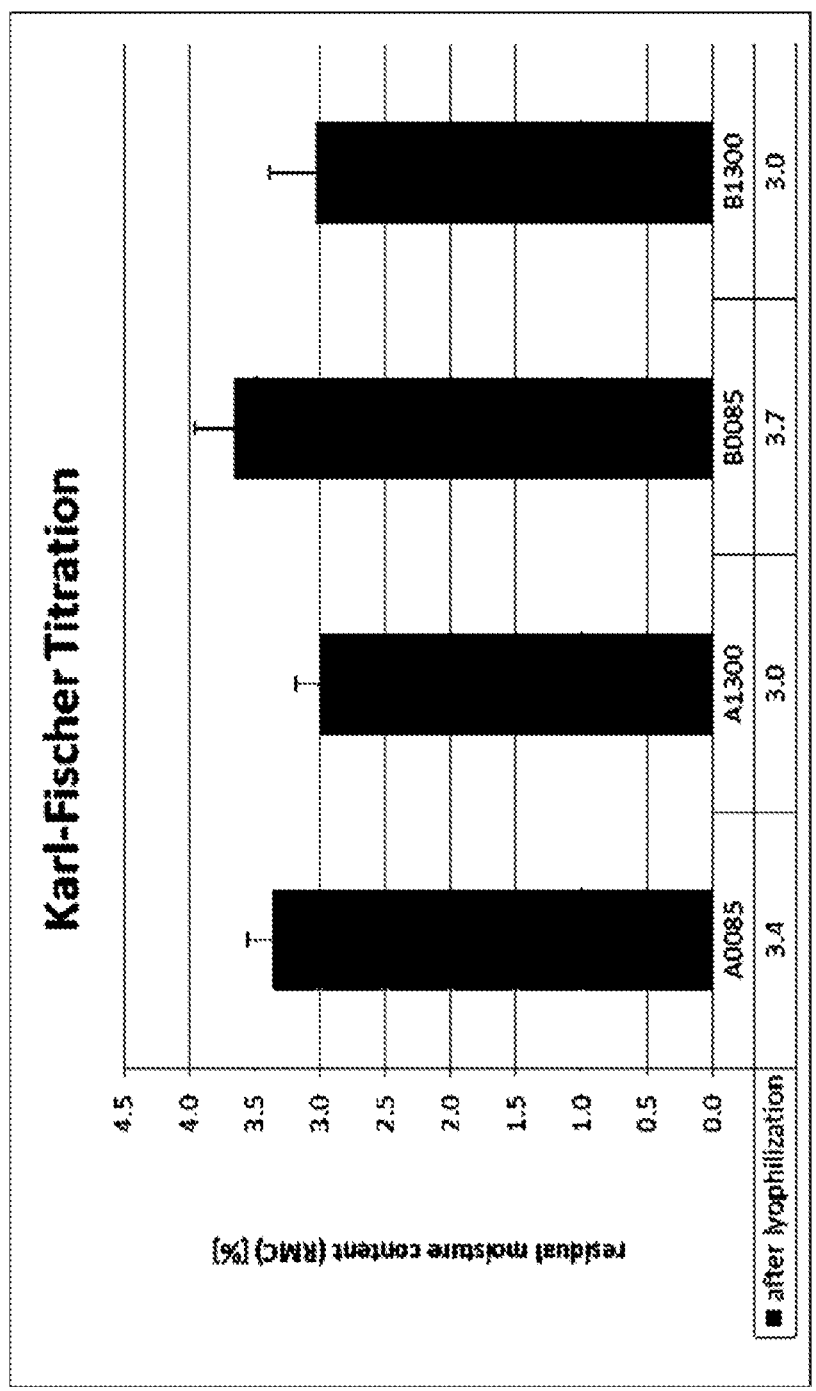

FIG. 61 shows a graph illustrating Karl-Fischer titration analysis of five vials at Tlyo of A0085, A1300, B0085, and B1300.

Figure 62:
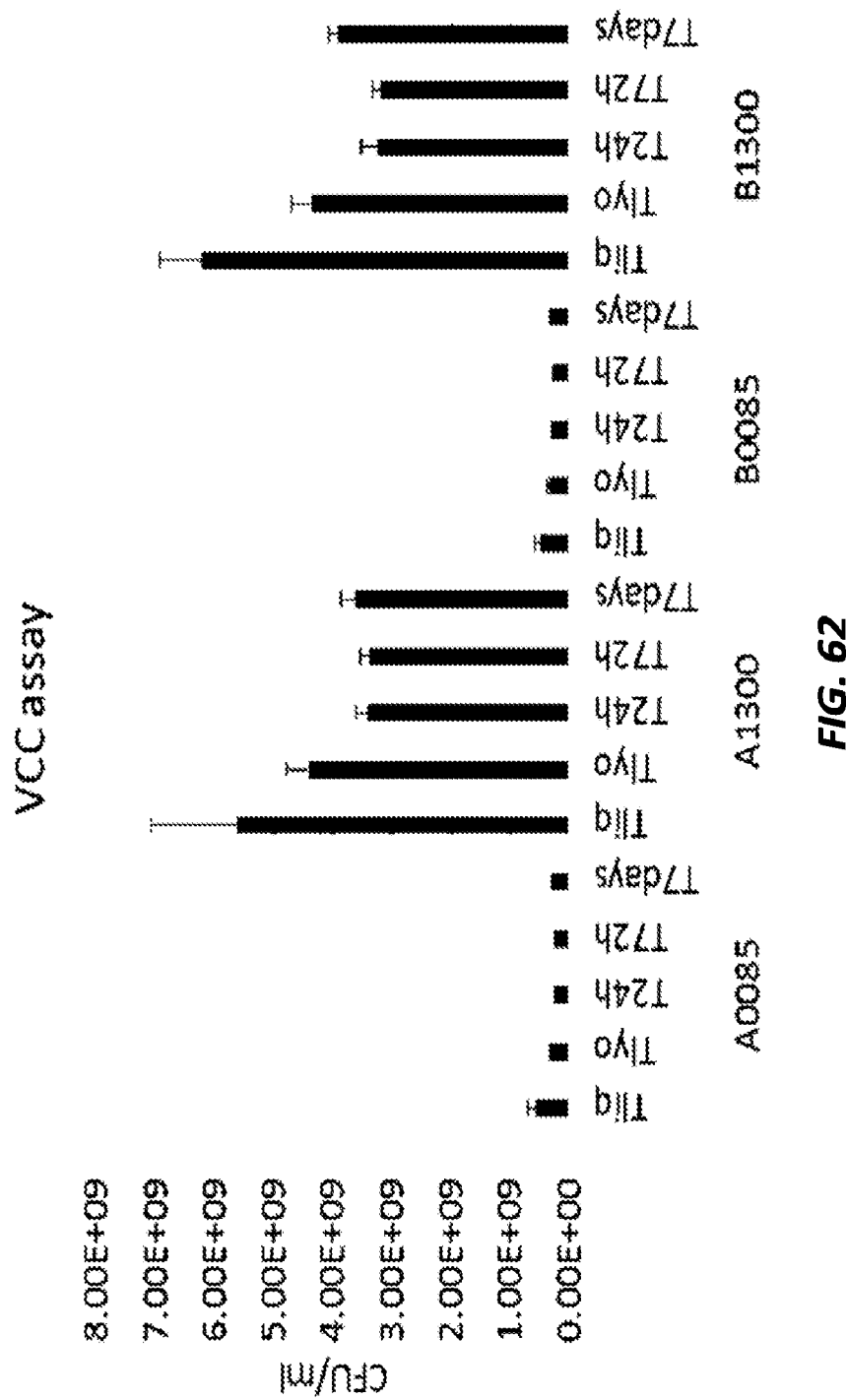

FIG. 62 shows a graph illustrating results of VCC assay performed at Tliq, Tlyo and after storage for 24 h, 48 h, and 72 h at 30° C. Front vials were stored at −20° C. for 7 days before analysis.

Figure 63A:
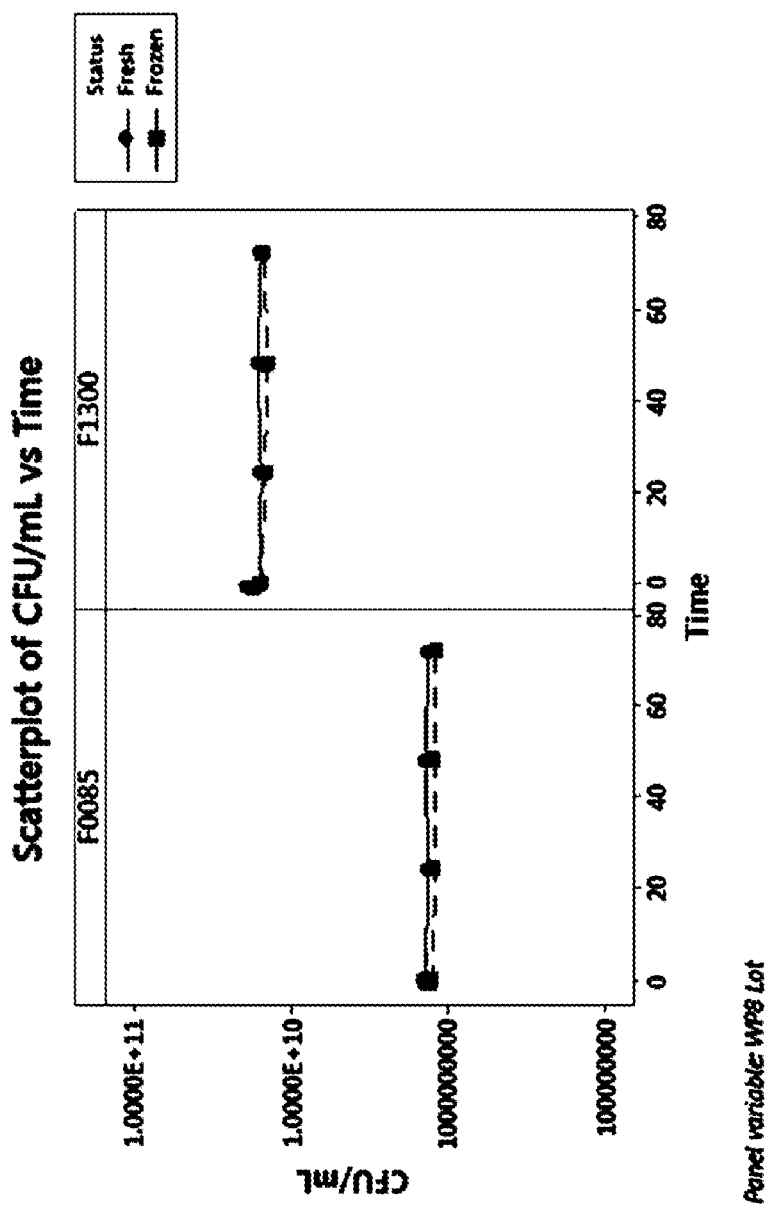

FIG. 63A shows a scatterplot illustrating VCC after WP7 Cycle 3 on accelerated stability.

Figure 63B:
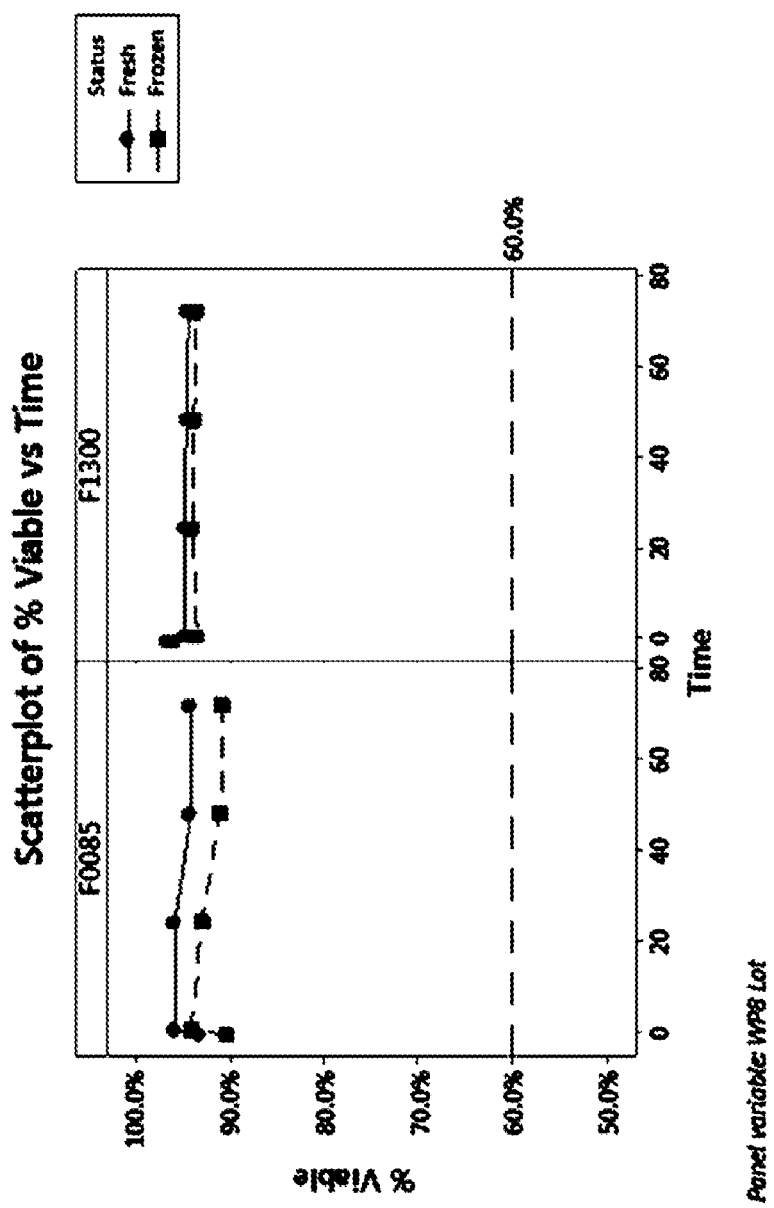

FIG. 63B shows a scatterplot illustrating % live after WP7 Cycle 3 on accelerated stability.

Figure 64:
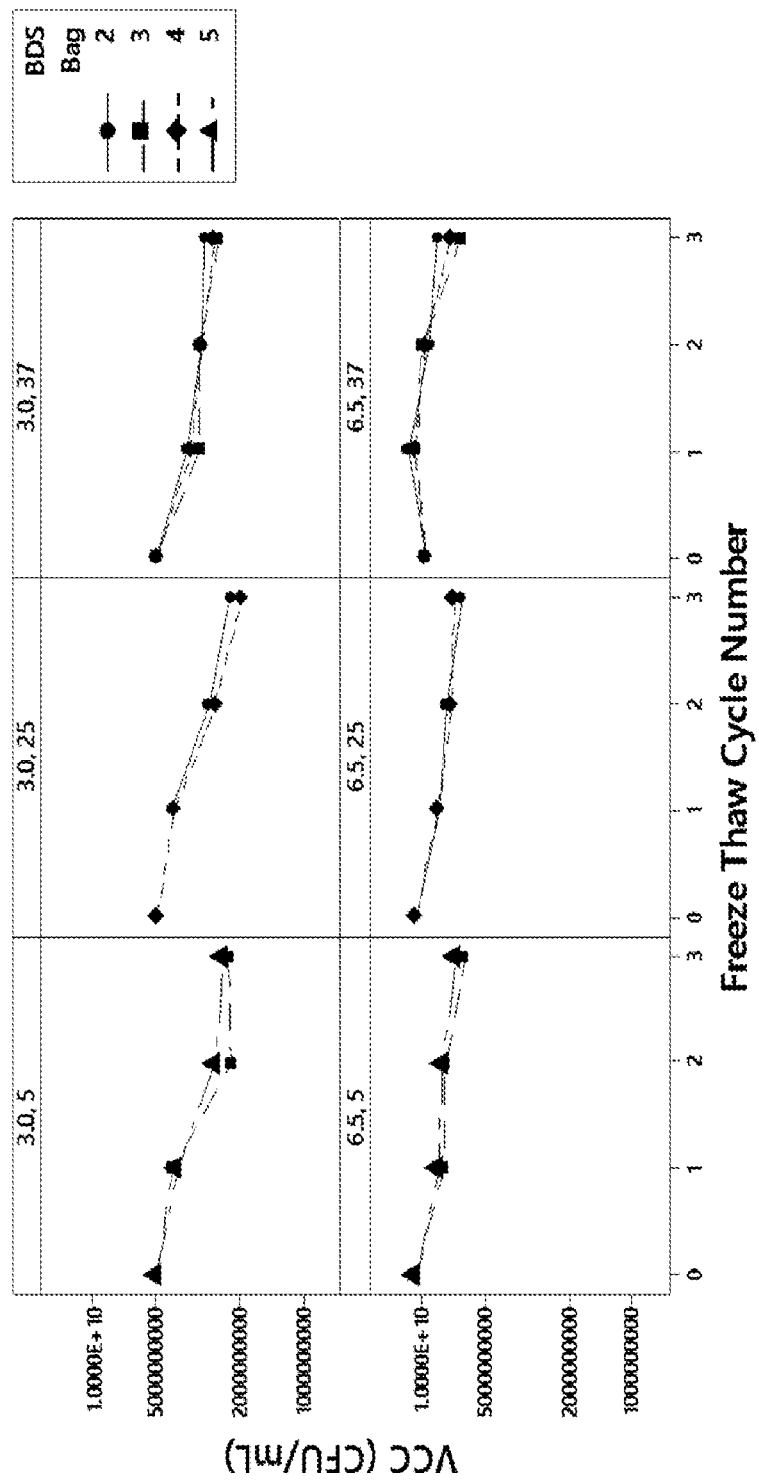

FIG. 64 shows a scatterplot illustrating impact on VCC of repeated freeze/thaw cycles on BDS (1 L Fill/1 L LDPE Bag) at various temperatures and VCC levels.

Figure 65:
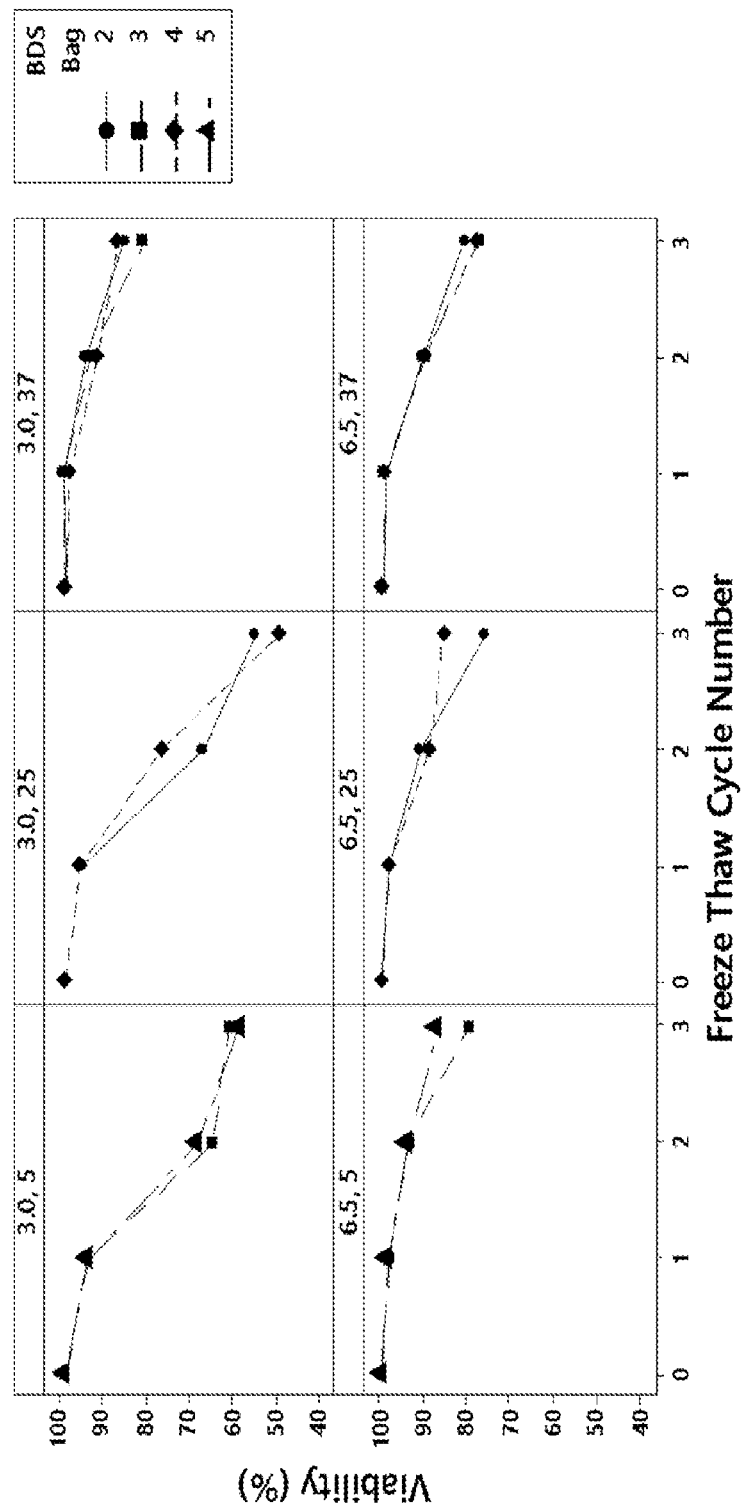

FIG. 65 shows a scatterplot illustrating impact on % live of repeated freeze/thaw cycles on BDS (1 L Fill/1 L LDPE Bag) at various temperatures and VCC levels.

DEFINITIONS

The terms "protein," "polypeptide," and "peptide," used interchangeably herein, refer to polymeric forms of amino acids of any length, including coded and non-coded amino acids and chemically or biochemically modified or derivatized amino acids. The terms include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The term "fusion protein" refers to a protein comprising two or more peptides linked together by peptide bonds or other chemical bonds. The peptides can be linked together directly by a peptide or other chemical bond. For example, a chimeric molecule can be recombinantly expressed as a single-chain fusion protein. Alternatively, the peptides can be linked together by a "linker" such as one or more amino acids or another suitable linker between the two or more peptides.

The terms "nucleic acid" and "polynucleotide," used interchangeably herein, refer to polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

"Codon optimization" refers to a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a fusion polypeptide can be modified to substitute codons having a higher frequency of usage in a given *Listeria* cell or any other host cell as compared to the naturally occurring nucleic acid sequence. Codon usage tables are readily available, for example, at the "Codon Usage Database." The optimal codons utilized by *L. monocytogenes* for each amino acid are shown US 2007/0207170, herein incorporated by reference in its entirety for all purposes. These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "plasmid" or "vector" includes any known delivery vector including a bacterial delivery vector, a viral vector delivery vector, a peptide immunotherapy delivery vector, a DNA immunotherapy delivery vector, an episomal plasmid, an integrative plasmid, or a phage vector. The term "vector" refers to a construct which is capable of delivering, and, optionally, expressing, one or more fusion polypeptides in a host cell.

The term "episomal plasmid" or "extrachromosomal plasmid" refers to a nucleic acid vector that is physically separate from chromosomal DNA (i.e., episomal or extra-chromosomal and does not integrated into a host cell's genome) and replicates independently of chromosomal DNA. A plasmid may be linear or circular, and it may be single-stranded or double-stranded. Episomal plasmids may optionally persist in multiple copies in a host cell's cytoplasm (e.g., Listeria), resulting in amplification of any genes of interest within the episomal plasmid.

The term "genomically integrated" refers to a nucleic acid that has been introduced into a cell such that the nucleotide sequence integrates into the genome of the cell and is capable of being inherited by progeny thereof. Any protocol may be used for the stable incorporation of a nucleic acid into the genome of a cell.

The term "stably maintained" refers to maintenance of a nucleic acid molecule or plasmid in the absence of selection (e.g., antibiotic selection) for at least 10 generations without detectable loss. For example, the period can be at least 15 generations, 20 generations, at least 25 generations, at least 30 generations, at least 40 generations, at least 50 generations, at least 60 generations, at least 80 generations, at least 100 generations, at least 150 generations, at least 200 generations, at least 300 generations, or at least 500 generations. Stably maintained can refer to a nucleic acid molecule or plasmid being maintained stably in cells in vitro (e.g., in culture), being maintained stably in vivo, or both.

An "open reading frame" or "ORF" is a portion of a DNA which contains a sequence of bases that could potentially encode a protein. As an example, an ORF can be located between the start-code sequence (initiation codon) and the stop-codon sequence (termination codon) of a gene.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety.

"Operable linkage" or being "operably linked" refers to the juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" refers to the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) refers to a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence.

The term "wild type" refers to entities having a structure and/or activity as found in a normal (as contrasted with mutant, diseased, altered, or so forth) state or context. Wild type gene and polypeptides often exist in multiple different forms (e.g., alleles).

The term "isolated" with respect to proteins and nucleic acid refers to proteins and nucleic acids that are relatively purified with respect to other bacterial, viral or cellular components that may normally be present in situ, up to and including a substantially pure preparation of the protein and the polynucleotide. The term "isolated" also includes proteins and nucleic acids that have no naturally occurring counterpart, have been chemically synthesized and are thus substantially uncontaminated by other proteins or nucleic acids, or has been separated or purified from most other cellular components with which they are naturally accompanied (e.g., other cellular proteins, polynucleotides, or cellular components).

"Exogenous" or "heterologous" molecules or sequences are molecules or sequences that are not normally expressed in a cell or are not normally present in a cell in that form. Normal presence includes presence with respect to the particular developmental stage and environmental conditions of the cell. An exogenous or heterologous molecule or sequence, for example, can include a mutated version of a corresponding endogenous sequence within the cell or can include a sequence corresponding to an endogenous sequence within the cell but in a different form (i.e., not within a chromosome). An exogenous or heterologous molecule or sequence in a particular cell can also be a molecule or sequence derived from a different species than a reference species of the cell or from a different organism within the same species. For example, in the case of a *Listeria* strain expressing a heterologous polypeptide, the heterologous polypeptide could be a polypeptide that is not native or endogenous to the *Listeria* strain, that is not normally expressed by the *Listeria* strain, from a source other than the *Listeria* strain, derived from a different organism within the same species.

In contrast, "endogenous" molecules or sequences or "native" molecules or sequences are molecules or sequences that are normally present in that form in a particular cell at a particular developmental stage under particular environmental conditions.

The term "variant" refers to an amino acid or nucleic acid sequence (or an organism or tissue) that is different from the majority of the population but is still sufficiently similar to the common mode to be considered to be one of them (e.g., splice variants).

The term "isoform" refers to a version of a molecule (e.g., a protein) with only slight differences compared to another isoform, or version (e.g., of the same protein). For example, protein isoforms may be produced from different but related genes, they may arise from the same gene by alternative splicing, or they may arise from single nucleotide polymorphisms.

The term "fragment" when referring to a protein means a protein that is shorter or has fewer amino acids than the full length protein. The term "fragment" when referring to a nucleic acid means a nucleic acid that is shorter or has fewer nucleotides than the full length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment. A fragment can also be, for example, a functional fragment or an immunogenic fragment.

The term "analog" when referring to a protein means a protein that differs from a naturally occurring protein by conservative amino acid differences, by modifications which do not affect amino acid sequence, or by both.

The term "functional" refers to the innate ability of a protein or nucleic acid (or a fragment, isoform, or variant thereof) to exhibit a biological activity or function. Such biological activities or functions can include, for example, the ability to elicit an immune response when administered to a subject. Such biological activities or functions can also include, for example, binding to an interaction partner. In the case of functional fragments, isoforms, or variants, these biological functions may in fact be changed (e.g., with respect to their specificity or selectivity), but with retention of the basic biological function.

The terms "immunogenicity" or "immunogenic" refer to the innate ability of a molecule (e.g., a protein, a nucleic acid, an antigen, or an organism) to elicit an immune response in a subject when administered to the subject. Immunogenicity can be measured, for example, by a greater number of antibodies to the molecule, a greater diversity of antibodies to the molecule, a greater number of T-cells specific for the molecule, a greater cytotoxic or helper T-cell response to the molecule, and the like.

The term "antigen" is used herein to refer to a substance that, when placed in contact with a subject or organism (e.g., when present in or when detected by the subject or organism), results in a detectable immune response from the subject or organism. An antigen may be, for example, a lipid, a protein, a carbohydrate, a nucleic acid, or combinations and variations thereof. For example, an "antigenic peptide" refers to a peptide that leads to the mounting of an immune response in a subject or organism when present in or detected by the subject or organism. For example, such an "antigenic peptide" may encompass proteins that are loaded onto and presented on MHC class I and/or class II molecules on a host cell's surface and can be recognized or detected by an immune cell of the host, thereby leading to the mounting of an immune response against the protein. Such an immune response may also extend to other cells within the host, such as diseased cells (e.g., tumor or cancer cells) that express the same protein.

The term "epitope" refers to a site on an antigen that is recognized by the immune system (e.g., to which an antibody binds). An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996), herein incorporated by reference in its entirety for all purposes.

The term "mutation" refers to the any change of the structure of a gene or a protein. For example, a mutation can result from a deletion, an insertion, a substitution, or a rearrangement of chromosome or a protein. An "insertion" changes the number of nucleotides in a gene or the number of amino acids in a protein by adding one or more additional nucleotides or amino acids. A "deletion" changes the number of nucleotides in a gene or the number of amino acids in a protein by reducing one or more additional nucleotides or amino acids.

A "frameshift" mutation in DNA occurs when the addition or loss of nucleotides changes a gene's reading frame. A reading frame consists of groups of 3 bases that each code for one amino acid. A frameshift mutation shifts the grouping of these bases and changes the code for amino acids. The resulting protein is usually nonfunctional. Insertions and deletions can each be frameshift mutations.

A "missense" mutation or substitution refers to a change in one amino acid of a protein or a point mutation in a single nucleotide resulting in a change in an encoded amino acid. A point mutation in a single nucleotide that results in a change in one amino acid is a "nonsynonymous" substitution in the DNA sequence. Nonsynonymous substitutions can also result in a "nonsense" mutation in which a codon is changed to a premature stop codon that results in truncation of the resulting protein. In contrast, a "synonymous" mutation in a DNA is one that does not alter the amino acid sequence of a protein (due to codon degeneracy).

The term "somatic mutation" includes genetic alterations acquired by a cell other than a germ cell (e.g., sperm or egg). Such mutations can be passed on to progeny of the mutated cell in the course of cell division but are not inheritable. In contrast, a germinal mutation occurs in the germ line and can be passed on to the next generation of offspring.

The term "in vitro" refers to artificial environments and to processes or reactions that occur within an artificial environment (e.g., a test tube).

The term "in vivo" refers to natural environments (e.g., a cell or organism or body) and to processes or reactions that occur within a natural environment.

The term "frozen state glass transition temperature" (Tg') refers to the following. When heated, solutions of sugar glasses undergo a second-order transition from a rigid state to a viscoelastic rubbery state. The temperature at which the vitreous transformation occurs is the glass-transition temperature in the frozen state.

The term "solid state glass transition temperature" (Tg) refers to the following. Similar to Tg', this is the temperature at which the freeze-dried glassy solid transforms to a viscoelastic rubbery state.

The term "collapse temperature" (Tc) refers to the maximum temperature that the product can withstand during primary drying without losing its physical structure.

The term "drug substance" (DS) refers to an active ingredient. It refers to any component of a drug product intended to furnish pharmacological activity or other direct effect in the diagnosis, cure, mitigation, treatment, or prevention of disease, or to affect the structure or any function of the body of humans or other animals. Active ingredients include those components of the product that may undergo chemical change during the manufacture of the drug product and be present in the drug product in a modified form intended to furnish the specified activity or effect. For example, Lm (e.g., ADXS-HPV or ADXS-HER2) is considered a drug substance.

The term "bulk drug substance" (BDS) refers to any substance that is represented for use in a drug and that, when used in the manufacturing, processing, or packaging of a drug, becomes an active ingredient or a finished dosage form of the drug, but the term does not include intermediates used in the synthesis of such substances.

The term "drug product" (DP) refers to a finished dosage form, for example, a tablet, capsule or solution that contains an active pharmaceutical ingredient, generally, but not necessarily, in association with inactive ingredients. For example, lyophilized Lm (e.g., ADXS-HPV or ADXS-HER2) is considered a drug product.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value or variations±0.5%, 1%, 5%, or 10% from a specified value.

The singular forms of the articles "a," "an," and "the" include plural references unless the context clearly dictates otherwise. For example, the term "an antigen" or "at least one antigen" can include a plurality of antigens, including mixtures thereof.

Statistically significant means $p \leq 0.05$.

DETAILED DESCRIPTION

I. Overview

Disclosed herein are compositions and methods directed to a stable lyophilized pharmaceutical formulation prepared by lyophilizing an aqueous formulation comprising a bacteria or *Listeria* strain, such as *Listeria monocytogenes*. In some embodiments, the lyophilized formulation is stable at 4° C. or −20° C. for at least 6 months, at least 1 year, or at least 2 years. In some embodiments, the lyophilized formulation is suitable for parenteral administration such as intravenous injection.

The frozen liquid formulations currently used for therapeutics comprising, for example, *L. monocytogenes*, are stored and shipped at −80° C. The low temperature presents supply chain challenges with both shipping and storage of the material at clinical sites, particularly in countries in South America and Africa. Therefore, it is desirable to have a refrigerated or −20° C. supply chain. Through optimization of the manufacturing process as described herein, it is possible to generate a stable drug product that is able to be maintained at higher temperatures. Counterintuitively, the working examples described herein show that higher residual moistures (e.g., higher than normal targeted residual moisture levels such as about 2.5%, 3.0%, or 3.5% in one embodiment) improved the stability of the lyophilized product. Similarly, counterintuitively, higher shelf temperatures during the primary drying step (e.g., about −17° C. to about −19° C. or about −18° C. in one embodiment, which is well above the Tg) improved the stability of the lyophilized product. In addition, preconditioning of the cells prior to lyophilization through heat shock improved the stability of the lyophilized product. In addition, use of a higher concentration of viable bacteria (viable cell count, or VCC) results in an improvement in the stability of the lyophilized drug product relative to lower VCC. In addition, counterintuitively, thawing of frozen drug substance at about 37° C. prior to lyophilization improved stability of the lyophilized drug product relative to thawing at room temperature or 2-8° C. These process enhancements improve stability at higher temperatures compared to a liquid frozen formulation allowing for a higher temperature supply chain. This allows for a more manageable supply chain and distribution to countries were −80° C. storage is not feasible.

The process of inducing a stress response within the *L. monocytogenes* cells through a temperature shift prior to lyophilization in addition to optimization of the residual moisture in the lyophilized cake (e.g., using higher than normal targeted residual moisture levels such as about 3.5% in one embodiment, which can be achieved by altering the secondary drying temperature and optionally the secondary drying time) improve stability of the lyophilized drug product at higher temperatures. Similarly, use of formulations comprising a phosphate buffer and lower than normal levels of sucrose (e.g., about 2.5% w/v sucrose in one embodiment) and using high primary drying step temperatures (e.g., about −18° C. in one embodiment) improve stability of the lyophilized drug product at higher temperatures, including −20° C., 2-8° C., and even room temperature (about 20° C. to about 25° C., or about 20° C., about 23° C., or about 25° C.). These process enhancements improve stability at higher temperatures compared to a liquid frozen formulation allowing for a higher temperature supply chain. This allows for a more manageable supply chain and distribution to countries were −80° C. storage is not feasible.

II. Lyophilization of Bacteria or *Listeria*

Lyophilization can be divided in three steps: freezing, primary drying, and secondary drying. As water freezes in the first step, the dissolved components in the formulation remain in the residual liquid (the freeze-concentrate). At the point of maximal ice formation, the freeze-concentrate solidifies between the ice crystals that make up the lattice. Under appropriate lyophilization conditions, the ice is removed by sublimation during primary drying, leaving the remaining freeze-concentrate in the same physical and chemical structure as when the ice was present. Residual water in the freeze-concentrate is removed in the secondary drying step.

Lyophilization involves manipulating the temperature and pressure of the solution so that the phase of the solvent can move directly from the frozen state to the gaseous state without moving through the liquid phase/state. This is achieved by cooling the solution and lowering the pressure to below the triple point of water. This allows for the removal of the solvent from the product without subjecting the product to intense heat. During the freezing stage, the formulation is cooled. Pure crystalline ice forms from the liquid, thereby resulting in a freeze concentration of the remainder of the liquid to a more viscous state that inhibits further crystallization. Ultimately, this highly concentrated and viscous solution solidifies, yielding an amorphous, crystalline, or combined amorphous-crystalline phase. During the primary drying stage, the ice formed during freezing is removed by sublimation at sub-ambient temperatures under vacuum. Throughout this stage, the product is maintained in the solid state below the collapse temperature of the product in order to dry the product with retention of the structure established in the freezing step. The collapse temperature is the glass transition temperature (Tg') in the case of amorphous products or the eutectic temperature (Te) for crystalline products. During the secondary drying stage, the relatively small amount of bound water remaining in the matrix is removed by desorption. During this stage, the temperature of the shelf and product are increased to promote adequate desorption rates and achieve the desired residual moisture.

The target profile for a lyophilized drug product is one that produces a well-defined cake at a target residual moisture that is stable at either 2-8° C. or −20° C. and retains the same potency and biological activity as the liquid-frozen formulation. Protection strategies that may enhance bacterial viability during freeze drying include, for example, adding excipients to the drying medium, controlling the process parameters, pre-stressing the bacterial sample prior to freeze drying, and changing the fermentation conditions of the bacteria. However, the efficiency of these strategies is strain-dependent, because the intrinsic tolerance to the drying process varies also from strain to strain. Even in highly related bacteria strains, one strain may be much more resistant to the freeze-drying process than the other. This strain dependency makes it difficult to draw general conclusions and guidelines.

Provided herein are methods for producing a lyophilized composition comprising a bacteria or *Listeria* strain. Such methods can comprise providing a composition comprising a bacteria or *Listeria* strain in a formulation comprising a buffer, cooling the composition in a freezing step, exposing the cooled composition to a vacuum and a first increased temperature in a primary drying step, and exposing the composition from the primary drying step to a vacuum and a second increased temperature in a secondary drying step, whereby the lyophilized composition is produced.

In some such methods, the bacteria or *Listeria* strain used in the composition is a frozen *Listeria* strain that is thawed prior to the freezing step. Examples of such preconditioning steps are described in more detail elsewhere herein. In a specific example, the frozen bacteria or *Listeria* strain can be thawed at a temperature of about 2° C. to about 37° C., about 20° C. to about 37° C., about 23° C. to about 37° C., about 25° C. to about 37° C., about 32° C. to about 37° C., or about 37° C. Optionally, the thawing is for no more than about 8 hours. Optionally, the thawed bacteria or *Listeria* strain is held at temperature of between about 2° C. and about 8° C. for no more than about 24 hours. In a specific example, the concentration of the bacteria or *Listeria* strain being thawed can be between about 1×10E9 and about 1×10E10 colony forming units (CFU) per milliliter.

In some such methods, the formulation comprises a buffer and sucrose. For example, the formulation buffer can comprise about 1% to about 5% w/v sucrose, about 2% to about 3% w/v sucrose, or about 2.5% w/v sucrose. Optionally, the formulation does not comprise other excipients such as trehalose, monosodium glutamate (MSG), or recombinant human serum albumin (rHSA).

In some such methods, the formulation comprises about 1×10E9 to about 1×10E10 colony forming units (CFU) of bacteria or *Listeria* per milliliter.

In some such methods, the holding temperature in the primary drying step is between about −10° C. and about −30° C., between about −12° C. and about −22° C., between about −17° C. and about −19° C., or about −18° C.

In some such methods, the residual moisture in the lyophilized composition is at least about 2.5%, at least about 3%, or at least about 3.5%. In some such methods, the residual moisture is between about 1% and about 5% or between about 2% and about 4%.

In some such methods, the lyophilized composition shows at least about 60%, 70%, 80%, or 90% viability after storage at between about −20° C. and about 4° C. or after storage at about −20° C. or about 4° C. for about 6 months, 12 months, 18 months, or 24 months.

Some such methods comprise: (a) providing a composition comprising a bacteria or *Listeria* strain in a formulation comprising a buffer and sucrose; (b) cooling the composition provided in step (a) at a holding temperature between about −32° C. and about −80° C. in a freezing step; (c) exposing the composition produced by step (b) to a vacuum at a holding temperature between about −10° C. and about −30° C. in a primary drying step; and (d) exposing the composition produced by step (c) to a vacuum at a holding temperature between about −5° C. and about 25° C. in a secondary drying step.

Additional embodiments for the preconditioning of cells, the formulations, the freezing step, the primary drying step, the secondary drying step, and the lyophilized product are provided below.

A. Pre-Conditioning of Bacteria or *Listeria*

A culture of a bacteria or *Listeria* strain that is used in a lyophilization method disclosed herein can be from a frozen stock, from a starter culture, or from a colony (e.g., freshly cultured bacteria or *Listeria*).

Methods are provided herein for preparing a frozen bacteria or *Listeria* strain for lyophilization, comprising thawing the frozen bacteria or *Listeria* strain. If the bacteria or *Listeria* strain is from a frozen stock, it can be thawed by any means. Temperature and the time for thawing can impact stability. Identifying appropriate conditions for thawing frozen drug substance allows freezing and holding of the drug substance prior to lyophilization. Ensuring high-quality healthy cells coming out of thaw ensures that the resulting lyophilized drug product is also of sufficient quality. In one example, it can be thawed at about −4° C., about 2-8° C., or about 4° C. and incubated, for example, for about 0.5, 1, 2, 3, 4, or more hours. In another example, it can be thawed at about 37° C. and incubated, for example, for about 0.5, 1, 2, 3, 4, or more hours.

In one example, the frozen bacteria or *Listeria* strain can be thawed a temperature between about 4° C. and about 37° C., about 10° C. and about 37° C., about 15° C. and about 37° C., about 20° C. and about 37° C., about 23° C. and about 37° C., about 25° C. and about 37° C., about 25° C. and about 37° C., about 30° C. and about 37° C., about 32° C. and about 37° C., about 32° C. and about 42° C., about 34° C. and about 40° C., about 35° C. and about 39° C., about 36° C. and 38° C., or about 37° C.

The frozen bacteria or *Listeria* strain can be thawed, for example, for about 0.5, 1, 2, 3, 4, 5, 6, 7, or 8 hours, for between about 0.5 and about 8 hours, between about 1 and about 8 hours, between about 2 and about 8 hours, between about 3 and about 8 hours, between about 4 and about 8 hours, between about 5 and about 8 hours, between about 6 and about 8 hours, or between about 7 and about 8 hours. Alternatively, the frozen bacteria or *Listeria* strain can be thawed, for example, for no more than about 0.5, 1, 2, 3, 4, 5, 6, 7, or 8 hours.

The frozen bacteria or *Listeria* strain being thawed can be in a bacteria or *Listeria* lyophilization formulation or can be thawed in a bacteria or *Listeria* lyophilization formulation. Such bacteria or *Listeria* lyophilization formulations are disclosed in more detail elsewhere herein.

The frozen bacteria or *Listeria* strain can be held at a temperature after thawing. For example, the frozen bacteria or *Listeria* strain can be held at a temperature of between about 2° C. to about 8° C. after thawing. The frozen bacteria or *Listeria* strain can be held, for example, for about 0.5 1, 2, 3, 4, 5, 6, 7, 8, 9, 10, 11, 12, 13, 14, 15, 16, 17, 18, 19, 20, 21, 22, 23, or 24 hours or between about 0.5 and about 24 hours, between about 1 and about 24 hours, between about 2 and about 24 hours, between about 5 and about 24 hours, between about 10 and about 24 hours, between about 12 and about 24 hours. Alternatively, the frozen bacteria or *Listeria* strain can be held, for example, for no more than about 0.5 1, 2, 3, 4, 5, 6, 7, 8, 9, 10, 11, 12, 13, 14, 15, 16, 17, 18, 19, 20, 21, 22, 23, or 24 hours. In a specific example, the frozen bacteria or *Listeria* strain is thawed at a temperature of about 37° C. for no more than about 8 hours and is held at temperature of between about 2° C. and about 8° C. for no more than about 24 hours.

The concentration of the bacteria or *Listeria* strain being thawed can be any suitable concentration. For example, the concentration can be between about 1×10E9 and about 1×10E10 colony forming units (CFU) per milliliter.

The culture used for lyophilization can be at any growth phase. The culture can be, for example, at mid-log growth phase, at approximately mid-log growth phase, or at another growth phase.

The nutrient medium utilized for growing a culture of a bacteria or *Listeria* strain can be any suitable nutrient medium. Examples of suitable media include, for example, Luria broth (LB; Luria-Bertani broth); Terrific Broth (TB); a modified, animal-product-free Terrific Broth; or a defined medium. The bacteria or *Listeria* strain can be cultured by any known means of growing bacteria. For example, the step of growing can be performed with a shake flask (such as a baffled shake flask), a batch fermenter, a stirred tank or flask, an airlift fermenter, a fed batch, a continuous cell reactor, an immobilized cell reactor, or any other means of growing bacteria.

Optionally, a constant pH is maintained during growth of the culture (e.g. in a batch fermenter). For example, the pH can be maintained at about 6.0, at about 6.5, at about 7.0, at about 7.5, or about 8.0. Likewise, the pH can be, for example, from about 6.5 to about 7.5, from about 6.0 to about 8.0, from about 6.0 to about 7.0, from about 6.0 to about 7.0, or about 6.5 to about 7.5. Alternatively, immediately after harvesting the cells from the bioreactor, the pH can be dropped by the addition of acid to induce a stress response, which can activate a set of genes that may better prepare the cells for lyophilization.

Optionally, a constant temperature can be maintained during growth of the culture. For example, the temperature can be maintained at about 37° C. Alternatively, the temperature can be maintained at about 25° C., about 27° C., about 28° C., about 30° C., about 32° C., about 34° C., about 35° C., about 36° C., about 38° C., or about 39° C. Alternatively, immediately after harvesting the cells from the bioreactor, the temperature can be dropped by placing the cells in an ice bath (e.g., about 0° C. or about 4° C.) to induce a stress response, which can activate a set of genes that may better prepare the cells for lyophilization.

Optionally, a constant dissolved oxygen concentration can be maintained during growth of the culture. For example, the dissolved oxygen concentration can be maintained at 20% of saturation, 15% of saturation, 16% of saturation, 18% of saturation, 22% of saturation, 25% of saturation, 30% of saturation, 35% of saturation, 40% of saturation, 45% of saturation, 50% of saturation, 55% of saturation, 60% of saturation, 65% of saturation, 70% of saturation, 75% of saturation, 80% of saturation, 85% of saturation, 90% of saturation, 95% of saturation, 100% of saturation, or near 100% of saturation.

The bacteria strain or *Listeria* strain can optionally be passaged through an animal host prior to lyophilization. Such passaging can maximize efficacy of the *Listeria* strain as a vaccine vector, can stabilize the immunogenicity of the *Listeria* strain, can stabilize the virulence of the *Listeria* strain, can increase the immunogenicity of the *Listeria* strain, can increase the virulence of the *Listeria* strain, can remove unstable sub-strains of the *Listeria* strain, or can reduce the prevalence of unstable sub-strains of the *Listeria* strain. Methods for passaging a *Listeria* strain through an animal host are well-known and are described, for example, in US 2006/0233835, herein incorporated by reference in its entirety for all purposes.

B. Bacteria or *Listeria* Lyophilization Formulations

Prior to the lyophilization, the bacteria or *Listeria* strain can be provided in a suspension (formulation) comprising a buffer and an excipient. The design of a lyophilized formulation can depend on the requirements of the active pharmaceutical ingredient and the intended route of administration. A formulation may consist of a buffer and one or more excipients that perform one or more functions. Such excipients can be, for example, pH adjusters, bulking agents (e.g., sucrose, mannitol, maltose, trehalose, dextrose, and lactose), stabilizers such as cryoprotectants (e.g., PEG) and lyoprotectants (e.g., disaccharides), or tonicity modifiers (e.g., NaCl, mannitol, sucrose, glycine, and glycerol).

The buffer can be any suitable buffer. Buffers can stabilize pH in the formulation. For example, the buffer can be a phosphate buffer, a Tris buffer, a histidine buffer, a citrate buffer, or a MOPS (3-(N-morpholino)propanesulfonic acid) buffer. In a specific example, the buffer is a phosphate buffer. Phosphate buffers are often avoided in the development of lyophilized formulations because phosphate buffers, such as sodium phosphate, can undergo drastic pH changes during freezing. Because of this, low concentrations of buffers that undergo minimal pH changes during freezing, such as Tris, citrate, and histidine buffers are often used. However, as shown elsewhere herein, suitable viability levels of *Listeria monocytogenes* are achieved using phosphate buffers. In some such buffers, the concentration of $KH_2PO_4$ (anhydrous) is between about 0.1-0.3 g/L, 0.12-0.28 g/L, 0.14-0.26 g/L, 0.16-0.24 g/L, 0.18-0.22 g/L, 0.19-0.21 g/L, or 0.2 g/L. In some such buffers, the concentration of $Na_2HPO_4$ (anhydrous) is between about 1.0-1.3 g/L, 1.02-1.28 g/L, 1.04-1.26 g/L, 1.06-1.24 g/L, 1.08-1.22 g/L, 1.1-1.2 g/L, 1.12-1.18 g/L, 1.14-1.16 g/L, or 1.15 g/L. Some such buffers are about 5-20, 6-18, 7-16, 8-14, 9-12, 9-11, or 10 mM. Some such buffers have a pH of about 6.8-7.6, 6.9-7.5, 7.0-7.4, 7.1-7.3, or 7.2. As one example, the phosphate buffer can have between about 0.19-0.21 g/L (e.g., 0.2 g/L) of $KH_2PO_4$ (anhydrous), between about 1.14-1.16 g/L (e.g., 1.15 g/L) of $Na_2HPO_4$ (anhydrous), and can have a pH of about 7.1-7.3 (e.g., 7.2).

Excipients such as cryoprotectants and lyoprotectants can be added to the formulation to protect the bacteria or *Listeria* strain during the lyophilization process. Cryoprotectants are water-soluble chemicals that lower the melting point of water. As ice crystals are formed, bacterial cells are compressed in the unfrozen fraction. Adding cryoprotectants can enlarge the unfrozen section, giving more space to the bacterial cells, which can lead to less cellular damage by mechanical stress or osmotic stress. Lyoprotectants can protect bacterial cells during the drying steps when water is removed. Some sugars, such as sucrose and trehalose, can act as both cryoprotectants and lyoprotectants. Use of skim milk can also provide protective effects. Other examples of excipients include glucose, maltose, lactose, mannitol, glycine, glycerol, sodium chloride, yeast extract, dextran, dextrose, polydextrose, monosodium glutamate, maltodextrin, antioxidants (e.g., ascorbic acid), saccharides, disaccharides, sugars, and others. In one example, excipients used in a formulation include various combinations of sucrose, trehalose, monosodium glutamate (MSG), recombinant human serum albumin (rHSA), and amino acid mix. In a specific example, the excipients comprise, consist essentially of, or consist of sucrose, such as about 5% w/v (weight per volume) sucrose or about 2.5% w/v sucrose. For example, the formulation buffer can comprise about 1% to about 5% w/v sucrose, about 2% to about 3% w/v sucrose, or about 2.5% w/v sucrose.

Optionally, the excipients do not include one or more or all of trehalose, MSG, rHSA, amino acid mix, skim milk, glucose, maltose, lactose, mannitol, glycine, glycerol, sodium chloride, yeast extract, dextran, dextrose, polydextrose, monosodium glutamate, maltodextrin, ascorbic acid, saccharides other than sucrose, disaccharides other than sucrose, sugars other than sucrose, or antioxidants. Optionally, the excipients do not include one or more or all of trehalose, MSG, and rHSA.

The concentration of the bacteria or *Listeria* in the formulation can be any suitable concentration. For example, the concentration can be between about 1×10E9 and about 1×10E10 colony forming units (CFU) per milliliter.

C. Freezing Step

The first step in lyophilization is the freezing step. During this stage, the formulation is cooled. This can be accomplished, for example, in a shelf freeze dryer by reducing the temperature of the lyophilizer shelves (i.e., reducing the shelf temperature). During freezing, ice crystals are formed that can damage bacteria. The growth of the ice crystals is dependent on the freezing rate and temperature. In some embodiments, a higher freezing rate is utilized. A higher freezing rater can lead to the formation of smaller ice crystals thus reducing cellular damage as compared to a slower freezing rate. The formation of ice crystals can be detrimental to bacteria. As water crystallizes, the solutes in the remaining unfrozen fraction concentrate, which can lead to chemical and osmotic damage. Although freezing bacteria at lower temperatures corresponds to higher freezing rates and will result in smaller ice crystals, which should limit the cellular damage, a higher freezing rate does not always corresponds with the best viability results. Optimal freezing conditions can vary depending on protectants used in the formulation and the strain of bacteria.

The holding temperature (e.g., the shelf temperature) for the freezing step can be reached by reducing the temperature (e.g., the shelf temperature) at a rate of, for example, about 0.2° C. to about 2.0° C. per minute. Alternatively, the holding temperature (e.g., the shelf temperature) for the freezing step can be reached by reducing the temperature (e.g., the shelf temperature) at a rate of, for example, about 0.2° C. to about 1.8° C. per minute, about 0.4° C. to about 1.6° C. per minute, about 0.6° C. to about 1.4° C. per minute, about 0.8° C. to about 1.2° C. per minute, or about 0.9° C. to about 1.1° C. per minute. For example, the temperature can be reduced to the freezing temperature at a rate of about 0.2° C., about 0.3° C., about 0.4° C., about 0.5° C., about 0.6° C., about 0.7° C., about 0.8° C., about 0.9° C., about 1.0° C., about 1.1° C., about 1.2° C., about 1.3° C., about 1.4° C., about 1.5° C., about 1.6° C., about 1.7° C., about 1.8° C., about 1.9° C., or about 2.0° C. per minute. In a specific example, the holding temperature for the freezing step is reached by decreasing the temperature to the holding temperature at a rate of about 1° C. per minute.

The freezing step can be for any suitable time for freezing the bacteria or *Listeria* strain. Likewise, the temperature can be held at the freezing temperature for any suitable time for freezing the bacteria or *Listeria* strain. For example, the freezing step can be, or the temperature can be held at the freezing temperature, for about 2 to about 6, about 2.5 to about 6, about 1 to about 6, about 1 to about 5, about 1 to about 4, about 1 to about 3, about 1 to about 2, about 1.5 to about 2.5, about 1.5 to about 5.5, about 2 to about 5, about 2.5 to about 4.5, about 3 to about 4, about 1, about 1.5, about 2, about 2.5, about 3, about 3.5, about 4, about 4.5, about 5, about 5.5, or about 6 hours. In a specific example, the freezing step can be or the temperature can be held at the freezing temperature for 3.5 hours. In another specific example, freezing step can be or the temperature can be held at the freezing temperature for 2 hours. In another specific example, freezing step can be or the temperature can be held at the freezing temperature for 1.5 hours. In another specific example, the time of the entire freezing step (e.g., ramping the temperature to the freezing temperature and then holding at the freezing temperature) is about 3.5-4.5 hours or about 3.5 hours.

The freezing temperature (i.e., the holding temperature) can be any temperature suitable for freezing the bacteria or *Listeria* strain. In some embodiments, the freezing temperature (e.g., the shelf temperature) is such that the temperature of the formulation is below the glass transition temperature of the solution, which in the case of sucrose formulations can be, for example, about −32° C. Temperatures above this temperature may not truly freeze the solution, which may then undergo collapse during lyophilization, potentially leading to loss of viability. For example, the temperature (e.g., the shelf temperature) can be between about −49° C. to about −25° C., about −47° C. to about −40° C., about −45° C. to about −35° C., about −10° C. to about −80° C., about −15° C. to about −75° C., about −20° C. to about −70° C., about −25° C. to about −65° C., about −30° C. to about −60° C., about −35° C. to about −55° C., about −40° C. to about −50° C., about −41° C. to about −49° C., about −42° C. to about −48° C., about −43° C. to about −47° C., or about −44° C. to about −46° C. In a specific example, the freezing temperature can be about −45° C. In another example, the temperature can be between about −49° C. to about −32° C., about −47° C. to about −40° C., about −45° C. to about −35° C., about −32° C. to about −80° C., about −32° C. to about −75° C., about −32° C. to about −70° C., about −32° C. to about −65° C., about −32° C. to about −60° C., −49° C. to about −33° C., about −33° C. to about −80° C., about −33° C. to about −75° C., about −33° C. to about −70° C., about −33° C. to about −65° C., about −33° C. to about −60° C., about −35° C. to about −55° C., about −40° C. to about −50° C., about −41° C. to about −49° C., about −42° C. to about −48° C., about −43° C. to about −47° C., or about −44° C. to about −46° C. In one example, the freezing temperature can be about −39° C. In another example, the freezing temperature can be about −45° C. In a specific example, the holding temperature in the freezing step is between about −40° C. and about −50° C. (e.g., about −45° C.), the freezing step comprises decreasing the temperature to the holding temperature at a rate of about 1° C. per minute, and the cooling in the freezing step is from about 2 hours to about 4 hours (e.g., the freezing step comprises holding the composition at the holding temperature for about 2 hours).

D. Primary Drying Step

The second step in lyophilization is the primary drying step. In the primary drying step, exposing the composition comprising the bacteria or *Listeria* strain produced by the freezing step to a vacuum at an increased temperature. In this step, the frozen water is removed by sublimation under vacuum.

The temperature for the primary drying step can be reached by increasing the temperature (e.g., the shelf temperature) at a rate of, for example, about 0.2° C. to about 2.0° C. per minute. Alternatively, the holding temperature (e.g., the shelf temperature) for the primary drying step can be reached by increasing the temperature (e.g., the shelf temperature) at a rate of, for example, about 0.2° C. to about 1.8° C. per minute, about 0.4° C. to about 1.6° C. per minute, about 0.6° C. to about 1.4° C. per minute, about 0.8° C. to about 1.2° C. per minute, or about 0.9° C. to about 1.1° C. per minute. For example, the temperature can be increased to the primary drying temperature at a rate of about 0.2° C., about 0.3° C., about 0.4° C., about 0.5° C., about 0.6° C., about 0.7° C., about 0.8° C., about 0.9° C., about 1.0° C., about 1.1° C., about 1.2° C., about 1.3° C., about 1.4° C., about 1.5° C., about 1.6° C., about 1.7° C., about 1.8° C., about 1.9° C., or about 2.0° C. per minute. In a specific example, the holding temperature for the primary drying step is reached by increasing the temperature to the holding temperature at a rate of about 1° C. per minute.

The primary drying step can be for any suitable time. Likewise, the holding temperature (e.g., the shelf temperature) can be held at the primary drying temperature for any suitable time. The temperature should be held at the primary drying temperature until primary drying is completed. This time can vary depending on the lyophilizer, the vial size, the fill volume, the number of vials, the pressure, and other variables. The end of primary drying can be determined, for example, when the product temperature rises to a value at or above the shelf temperature. It can also be determined, for example, by a pressure rise test in which the freeze drying chamber is isolated from the vacuum pump to determine how much the pressure rises due to continued water sublimation. For example, the primary drying step can be or the temperature can be held at the primary drying temperature for about 10 to about 29, about 29 to about 42, about 36, about 10 to about 80, about 10 to about 70, about 10 to about 60, about 10 to about 50, about 10 to about 40, about 10 to about 30, or about 20 to about 30 hours. In a specific example, primary drying step can be or the temperature can be held at the primary drying temperature for about 25 to about 35, about 26 to about 34, about 27 to about 33, about 28 to about 32, about 29 to about 31, or about 30 hours. In another specific example, primary drying step can be or the temperature can be held at the primary drying temperature for about 20 to about 30, about 21 to about 30, about 22 to about 30, about 23 to about 29, about 24 to about 28, about 25 to about 27, or about 26 hours.

The primary drying step can be or the temperature can be held at the primary drying holding temperature for a time period defined as about 8 to about 20, about 9 to about 19, about 10 to about 18, about 11 to about 17, about 12 to about 16, about 13 to about 15, or about 14 hours after a probe in the lyophilizer (e.g., a probe for cold spots in the lyophilizer, such as in the center of the lyophilizer) has crossed the primary drying holding temperature or the $T_s$ set point (e.g., of about −18° C.). Alternatively, the drying step can be or the temperature can be held at the primary drying holding temperature for a time period defined as about 8 to about 20, about 9 to about 19, about 10 to about 18, about 11 to about 17, about 12 to about 16, about 13 to about 15, or about 14 hours after the composition being lyophilized (e.g., the samples of the compositions in the cold spots of the lyophilizer, or all samples of the compositions in the lyophilizer) has reached the primary drying holding temperature or the $T_s$ set point (e.g., about −18° C.). In a specific example, the primary drying step can be or the temperature can be held at the primary drying holding temperature for a time period defined as about 14 hours after a probe in the lyophilizer (e.g., a probe for cold spots in the lyophilizer, such as in the center of the lyophilizer) has crossed the primary drying holding temperature or the $T_s$ set point (e.g., about −18° C.) or after the composition being lyophilized (e.g., the samples of the compositions in the cold spots of the lyophilizer, or all samples of the compositions in the lyophilizer) has reached the primary drying holding temperature or the $T_s$ set point (e.g., about −18° C.), which can be, for example, about 30 hours.

The end of the primary drying step can be about 8 to about 20, about 9 to about 19, about 10 to about 18, about 11 to about 17, about 12 to about 16, about 13 to about 15, or about 14 hours after a probe in the lyophilizer (e.g., a probe for cold spots in the lyophilizer, such as in the center of the lyophilizer) has crossed the primary drying holding temperature or the $T_s$ set point (e.g., about −18° C.). Alternatively, the end of the primary drying step can be about 8 to about 20, about 9 to about 19, about 10 to about 18, about 11 to about 17, about 12 to about 16, about 13 to about 15, or about 14 hours after the composition being lyophilized (e.g., the samples of the compositions in the cold spots of the lyophilizer, or all samples of the compositions in the lyophilizer) has reached the primary drying holding temperature or the $T_s$ set point (e.g., of about −18° C.). In a specific example, the end of the primary drying step can be about 14 hours after a probe in the lyophilizer (e.g., a probe for cold spots in the lyophilizer, such as in the center of the lyophilizer) has crossed the primary drying holding temperature or the $T_s$ set point (e.g., about −18° C.) or after the composition being lyophilized (e.g., the samples of the compositions in the cold spots of the lyophilizer, or all samples of the compositions in the lyophilizer) has reached the primary drying holding temperature or the $T_s$ set point (e.g., of about −18° C.), which can be, for example, about 30 hours.

The primary drying temperature (e.g., the shelf temperature or the holding temperature) can be any temperature suitable for drying the bacteria or *Listeria* strain. For example, the holding temperature can be between about 0° C. to about −30° C., 0° C. to about −19° C., about −5° C. to about −30° C., about −10° C. to about −25° C., about −15° C. to about −20° C., about −17° C. to about −19° C., about −12° C. to about −30° C., about −12° C. to about −24° C., about −12° C. to about −22° C., about −14° C. to about −22° C., about −15° C. to about −21° C., about −16° C. to about −20° C., about −17° C. to about −19° C., about −18° C. to about −22° C., about −30°, about −29°, about −28°, about −27°, about −26°, about −25°, about −24°, about −23°, about −22°, about −21°, about −20°, about −19°, about −18°, about −17°, about −16°, about −15°, about −14°, about −13°, about −12°, about −11°, about −10°, about −9°, about −8°, about −7°, about −6°, about −5°, about −4°, about −3°, about −2°, about −1°, or about 0°. For example, the temperature can be no more than about −30°, about −29°, about −28°, about −27°, about −26°, about −25°, about −24°, about −23°, about −22°, about −21°, about −20°, about −19°, about −18°, about −17°, about −16°, about −15°, about −14°, about −13°, about −12°, about −11°, or about −10° C. In a specific example, the primary drying temperature can be about −25° C. to about −35° C., about −26° C. to about −37° C., about −27° C. to about −33° C., about −28° C. to about −32° C., about −29° C. to about −31° C., or about −30° C. In a specific example, the primary drying temperature can be about −17° C. to about −27° C., about −18° C. to about −26° C., about −19° C. to about −25° C., about −20° C. to about −24° C., about −21° C. to about −23° C., or about −22° C. In another specific example, the primary drying temperature can be about −7° C. to about −17° C., about −8° C. to about −16° C., about −9° C. to about −15° C., about −10° C. to about −14° C., about −11° C. to about −13° C., or about −12° C. In another specific example, the primary drying temperature can be about −13° C. to about −23° C., about −14° C. to about −22° C., about −15° C. to about −21° C., about −16° C. to about −20° C., about −17° C. to about −19° C., or about −18° C. In a specific example, the holding temperature in the primary drying step is between about −17° C. to about −19° C., or about −18° C.

The pressure (vacuum conditions) can be any suitable pressure. In some cases, the pressure should be no more than 50% of vapor pressure of ice at the glass transition temperature of the formulation (e.g., about 0.270 mbar). It should also not be too low. For example, the pressure can be from about 0.140 to about 0.050, about 0.100 to about 0.060, about 0.100 to about 0.070, about 0.100 to about 0.080, about 0.099 to about 0.081, about 0.098 to about 0.082, about 0.097 to about 0.083, about 0.096 to about 0.084, about 0.095 to about 0.085, about 0.094 to about 0.086, about 0.093 to about 0.087, about 0.092 to about 0.088, about 0.091 to about 0.089, about 0.090 mbar, or about 0.120 mbar. In a specific example, the pressure is about 0.090 mbar.

In a specific example, the holding temperature in the primary drying step is between about −17° C. and about −19° C. (e.g., about −18° C.), the primary drying step comprises increasing the temperature to the holding temperature at a rate of about 1° C. per minute, and the primary drying step is from about 10 hours to about 40 hours (e.g., about 20 to about 40 hours, or about 25-35 hours, such as about 30 hours or about 32 hours).

E. Secondary Drying Step

The third step in lyophilization is the secondary drying step. In the secondary drying step, exposing the composition comprising the bacteria or *Listeria* strain produced by the primary drying step to a vacuum at an increased temperature. In this step, the unfrozen water is removed by desorption.

The temperature for the secondary drying step can be reached by increasing the temperature (e.g., the shelf temperature) at a rate of, for example, about 0.2° C. to about 2.0° C. per minute. Alternatively, the holding temperature (e.g., the shelf temperature) for the secondary drying step can be reached by increasing the temperature (e.g., the shelf temperature) at a rate of, for example, about 0.2° C. to about 1.8° C. per minute, about 0.2° C. to about 1.6° C. per minute, about 0.2° C. to about 1.4° C. per minute, about 0.2° C. to about 1.2° C. per minute, about 0.2° C. to about 1.0° C. per minute, about 0.2° C. to about 0.8° C. per minute, about 0.2° C. to about 0.6° C. per minute, about 0.2° C. to about 0.4° C. per minute. For example, the temperature can be increased to the secondary drying temperature at a rate of about 0.2° C., about 0.3° C., about 0.4° C., about 0.5° C., about 0.6° C., about 0.7° C., about 0.8° C., about 0.9° C., about 1.0° C., about 1.1° C., about 1.2° C., about 1.3° C., about 1.4° C., about 1.5° C., about 1.6° C., about 1.7° C., about 1.8° C., about 1.9° C., or about 2.0° C. per minute. In a specific example, the holding temperature for the secondary drying step is reached by increasing the temperature to the holding temperature at a rate of about 0.2° C. per minute.

The secondary drying step can be for any suitable time. Likewise, the temperature (e.g., the shelf temperature or the holding temperature) can be held at the secondary drying temperature for any suitable time. For example, the temperature can be held at the secondary drying temperature for any suitable time to achieve the desired residual moisture levels in the lyophilized product. For example, the secondary drying step can be or the temperature can be held at the secondary drying temperature for about 5 to about 40, about 10 to about 30, about 15 to about 25, about 2 to about 25, about 2 to about 20, about 2 to about 10, about 2 to about 4, about 1 to about 25, about 1 to about 20, about 1 to about 10, about 1 to about 9, about 1 to about 8, about 1 to about 7, about 1 to about 6, about 1 to about 5, about 1 to about 4, about 1 to about 3, about 1 to about 2, about 1.5 to about 2.5, about 2.5 to about 3.5, about 15, about 14, about 13, about 12, about 11, about 10, about 9, about 8, about 7, about 6, about 5, about 4, about 3, about 2, or about 1 hours. In a specific example, secondary drying step can be or the secondary drying hold time is no more than about 10 hours. In another specific example, the secondary drying hold time is no more than 6 hours. In another specific example, the temperature can be held at the secondary drying temperature for about 3 hours. In another specific example, the temperature can be held at the secondary drying temperature for about 2 hours. In one example, the secondary drying step is for about 1 hour to about 10 hours. In another example, the secondary drying step comprises holding the composition at the holding temperature for about 2 hours to about 6 hours, for about 5 hours to about 6 hours, or for about 5 hours or about 6 hours.

The secondary drying temperature (e.g., the shelf temperature or the holding temperature) can be any temperature suitable for drying the bacteria or *Listeria* strain to achieve the desired residual moisture levels in the lyophilized product. For example, the temperature can be between about 5° C. to about 40° C., about 5° C. to about 30° C., about 10° C. to about 30° C., about 20° C. to about 30° C., or about 15° C. to about 25° C. In a specific example, the secondary drying temperature can be about 25° C. In another specific example, the secondary drying temperature can be about 20° C. In another specific example, the secondary drying temperature is no more than about 20° C. In another example, the temperature can be between about 5° C. to about 20° C., about 9° C. to about 15° C., about 10° C. to about 15° C., about 11° C. to about 14° C., about 11° C. to about 13° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., or about 20° C. In a specific example, the secondary drying temperature can be about 12° C. Alternatively, the holding temperature can be between about −10° C. and about 30° C., between about −10° C. and about 25° C., between about −10° C. and about 20° C., between about −10° C. and about 10° C., between about −5° C. and about 30° C., between about −5° C. and about 25° C., between about −5° C. and about 20° C., between about −5° C. and about 15° C., between about −5° C. and about 10° C., between about −5° C. and about 5° C., between about −4° C. and about 4° C., between about −3° C. and about 3° C., between about −2° C. and about 2° C., between about −1° C. and about 1° C., or about 0° C. In a specific example, the holding temperature can be between about −5° C. and about 5° C. or about 0° C.

The pressure (vacuum conditions) can be any suitable pressure. In some cases, the pressure is in the same range as for the primary drying step. However, some cycles during secondary drying may have full vacuum. For example, the pressure can be from about 0.140 to about 0.020, 0.140 to about 0.030, 0.140 to about 0.040, 0.140 to about 0.050, about 0.100 to about 0.060, about 0.100 to about 0.070, about 0.100 to about 0.080, about 0.099 to about 0.081, about 0.098 to about 0.082, about 0.097 to about 0.083, about 0.096 to about 0.084, about 0.095 to about 0.085, about 0.094 to about 0.086, about 0.093 to about 0.087, about 0.092 to about 0.088, about 0.091 to about 0.089, about 0.090 mbar, or about 0.120 mbar. In a specific example, the pressure is about 0.090 mbar.

In a specific example, the holding temperature in the secondary drying step is between about −5° C. and about 5° C. (e.g., about 0° C.), the secondary drying step comprises increasing the temperature to the holding temperature at a rate of about 0.2° C. per minute, and the secondary drying step secondary drying step comprises holding the composition at the holding temperature for about 5 hours to about 6 hours.

The secondary drying step can result in a lyophilized product having any desired residual moisture. For example, the residual moisture can be no more than about 7.0%, about 6.9%, about 6.8%, about 6.7%, about 6.6%, about 6.5%, about 6.4%, about 6.3%, about 6.2%, about 6.1%, about 6.0%, about 5.9%, about 5.8%, about 5.7%, about 5.6%, about 5.5%, about 5.4%, about 5.3%, about 5.2%, about 5.1%, about 5.0%, about 4.9%, about 4.8%, about 4.7%, about 4.6%, about 4.5%, about 4.4%, about 4.3%, about 4.2%, about 4.1%, about 4.0%, about 3.9%, about 3.8%, about 3.7%, about 3.6%, about 3.5%, about 3.4%, about 3.3%, about 3.2%, about 3.1%, about 3.0%, about 2.9%, about 2.8%, about 2.7%, about 2.6%, about 2.5%, about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, or about 1.0%. Alternatively, the residual moisture can be at least about 7.0%, about 6.9%, about 6.8%, about 6.7%, about 6.6%, about 6.5%, about 6.4%, about 6.3%, about 6.2%, about 6.1%, about 6.0%, about 5.9%, about 5.8%, about 5.7%, about 5.6%, about 5.5%, about 5.4%, about 5.3%, about 5.2%, about 5.1%, about 5.0%, about 4.9%, about 4.8%, about 4.7%, about 4.6%, about 4.5%, about 4.4%, about 4.3%, about 4.2%, about 4.1%, about 4.0%, about 3.9%, about 3.8%, about 3.7%, about 3.6%, about 3.5%, about 3.4%, about 3.3%, about 3.2%, about 3.1%, about 3.0%, about 2.9%, about 2.8%, about 2.7%, about 2.6%, about 2.5%, about 2.4%, about 2.3%, about 2.2%, about 2.1%, about 2.0%, about 1.9%, about 1.8%, about 1.7%, about 1.6%, about 1.5%, about 1.4%, about 1.3%, about 1.2%, about 1.1%, or about 1.0%. In a specific example, the residual moisture can be at least about 1%, at least about 1.5%, or at about least 2% and no more than about 7%. Alternatively, the residual moisture can be between about 1% to about 7%, about 1% to about 6.5%, about 1% to about 6%, about 1% to about 5.5%, about 1% to about 5%, about 1.5% to about 7%, about 1.5% to about 6.5%, about 1.5% to about 6%, about 1.5% to about 5.5%, about 1.5% to about 5%, about 1.5% to about 4.5%, about 2% to about 7%, about 2% to about 6.5%, about 2% to about 6%, about 2% to about 5.5%, about 2% to about 5%, about 2% to about 4.5%, about 2% to about 4%, about 2% to about 3%, or about 3% to about 4%. In a specific example, the residual moisture can be about 3% to about 4%, about 3.1% to about 3.9%, about 3.2% to about 3.8%, about 3.3% to about 3.7%, about 3.4% to about 3.6%, or about 3.5%. In a specific example, the residual moisture is at least about 2%, at least about 2.5%, or at least about 3%. In another specific example, the residual moisture is between about 1% and about 5%, between about 2% and about 4%, between about 2.5% and about 3.5%, between about 2.5% and about 4%, between about 3% and about 4%, or between about 3% and about 3.5%.

F. Storage and Reconstitution of Lyophilized Bacteria or Listeria

The resulting lyophilized bacteria or Listeria can be a lyophilized composition comprising any combination of the components listed in the formulation section. In one example, the lyophilized composition comprises a Listeria strain, a buffer (e.g., a phosphate), and an excipient (e.g., sucrose). Optionally, the lyophilized composition does not comprise one or more or all of trehalose, monosodium glutamate (MSG), and recombinant human serum albumin (rHSA). Optionally, the lyophilized composition does not comprise one or more or all of the optional components listed in the formulation section.

The resulting lyophilized bacteria or Listeria can be a lyophilized composition with any of the residual moisture levels listed elsewhere herein. As one example, the residual moisture level can be between about 1% and about 5%, between about 2% and about 4%, or between about 3% and about 4%.

The lyophilized bacteria can be stored under any suitable conditions, including any suitable temperature, relative humidity, and atmospheric oxygen level, which are well-known. The lyophilized bacteria or Listeria can exhibit viability upon reconstitution of at least about 50%, about 55%, about 60%, about 65%, about 70%, about 75%, about 80%, about 85%, about 90%, or about 95% after storage for a defined amount of time. The reconstitution can follow storage of the lyophilized bacteria or Listeria for example, for 2 days, 3 days, 4 days, 1 week, 2 weeks, 3 weeks, 1 month, 2 months, 3 months, 5 months, 6 months, 9 months, 12 months (1 year), 15 months, 18 months, 21 months, or 24 months (2 years).

The storage temperature of the lyophilized bacteria or Listeria can be for example, between about 0° C. and about 10° C., about 1° C. and about 9° C., about 2° C. and about 8° C., about 2° C. and about 6° C., or about 3° C. and about 5° C. In a specific example, the storage temperature of can be between about 2° C. and about 8° C., or the storage temperature can be about 4° C. In another example, the storage temperature can be between about −15° C. and about −25° C., about −16° C. and about −24° C., about −17° C. and about −23° C., about −18° C. and about −22° C., or about −19° C. and about −21° C. In a specific example, the storage temperature of can be about −20° C.

For example, the lyophilized bacteria or Listeria can show at least about 60%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% viability after storage at about 2-8° C. (e.g., 4° C.) or about −20° C. for about 6 months, about 9 months, about 12 months, about 18 months, or about 24 months. The lyophilized bacteria or Listeria can show at least about 60%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% viability after storage at about 30° C., at about room temperature (i.e., about 20-25° C. (e.g., 20° C., 21° C., 22° C., 23° C., 24° C., or 25° C.)), at about 2-8° C. (e.g., 4° C.) or about −20° C. for about 1 month, about 2 months, about 3 months, about 4 months, about 5 months, about 6 months, about 9 months, about 12 months, about 18 months, or about 24 months. As one example, the lyophilized bacteria or Listeria can show at least about 75% to about 80% viability at 2-8° C. after 6 months. As another example, the lyophilized bacteria or Listeria can show at least about 95% to about 100% viability at −20° C. after 9 months. As another example, the lyophilized bacteria or Listeria can show at least about 80% to about 90% viability at room temperature or at 30° C. after 2 months. As another example, the lyophilized bacteria or Listeria can show at least about 60%, 65%, 70%, 75%, 80%, 85%, or 90% viability at about −20° C. after about 12 months, 18 months, or 24 months. As another example, the lyophilized bacteria or Listeria can show at least about 60%, 65%, 70%, 75%, 80% viability at about 2-8° C. after about 12 months, 18 months, or 24 months. As another example, the lyophilized bacteria or Listeria can show at least about 60%, 65%, 70%, 75%, or 80% viability at about 2-8° C. after about 12 months, 18 months, or 24 months.

After storage, the lyophilized bacteria or Listeria strain can optionally be reconstituted with a solvent or diluent (e.g., water). As one example, the solvent or diluent can be appropriate media for culturing the bacteria or Listeria strain. Methods for reconstitution and rehydration of lyophilized bacteria or Listeria strains are well-known. In one example, the volume of solvent used is the volume of pre-lyophilization solution used to make the lyophilized bacteria or Listeria strain. In another example, the volume of solvent used is more than the volume of pre-lyophilization solution used to make the lyophilized bacteria or Listeria strain. In another example, the volume of solvent used is less than the volume of pre-lyophilization solution used to make the lyophilized bacteria or Listeria strain.

The reconstitution time can be any suitable reconstitution time. For example, the reconstitution time can be less than about 1, 2, 3, 4, 5, 6, 7, 8, 9, 10, 20, or 30 minutes. In a specific example, the reconstitution time is less than about 2 minutes.

III. Recombinant Bacteria or Listeria Strains

The lyophilized compositions disclosed herein and the compositions that undergo the lyophilization methods disclosed herein comprise bacteria strains, such as a *Listeria* strain. Such bacteria strains can be recombinant bacteria strains. Such recombinant bacteria strains can comprise a recombinant fusion polypeptide disclosed herein or a nucleic acid encoding the recombinant fusion polypeptide as disclosed elsewhere herein. In some embodiments, the bacteria strain is a *Listeria* strain, such as a *Listeria monocytogenes* (Lm) strain. Lm has a number of inherent advantages as a vaccine vector. The bacterium grows very efficiently in vitro without special requirements, and it lacks LPS, which is a major toxicity factor in gram-negative bacteria, such as *Salmonella*. Genetically attenuated Lm vectors also offer additional safety as they can be readily eliminated with antibiotics, in case of serious adverse effects, and unlike some viral vectors, no integration of genetic material into the host genome occurs.

The recombinant *Listeria* strain can be any *Listeria* strain. Examples of suitable *Listeria* strains include *Listeria seeligeri, Listeria grayi, Listeria ivanovii, Listeria murrayi, Listeria welshimeri, Listeria monocytogenes* (Lm), or any other known *Listeria* species. In some embodiments, the recombinant listeria strain is a strain of the species *Listeria monocytogenes*. Examples of *Listeria monocytogenes* strains include the following: *L. monocytogenes* 10403S wild type (see, e.g., Bishop and Hinrichs (1987) *J Immunol* 139:2005-2009; Lauer et al. (2002) *J Bact* 184:4177-4186); *L. monocytogenes* DP-L4056, which is phage cured (see, e.g., Lauer et al. (2002) *J Bact* 184:4177-4186); *L. monocytogenes* DP-L4027, which is phage cured and has an hly gene deletion (see, e.g., Lauer et al. (2002) *J Bact* 184:4177-4186; Jones and Portnoy (1994) *Infect Immunity* 65:5608-5613); *L. monocytogenes* DP-L4029, which is phage cured and has an actA gene deletion (see, e.g., Lauer et al. (2002) *J Bact* 184:4177-4186; Skoble et al. (2000) *J Cell Biol* 150:527-538); *L. monocytogenes* DP-L4042 (delta PEST) (see, e.g., Brockstedt et al. (2004) *Proc Natl Acad Sci. USA* 101:13832-13837 and supporting information); *L. monocytogenes* DP-L4097 (LLO-S44A) (see, e.g., Brockstedt et al. (2004) *Proc Natl Acad Sci USA* 101:13832-13837 and supporting information); *L. monocytogenes* DP-L4364 (delta lplA; lipoate protein ligase) (see, e.g., Brockstedt et al. (2004) *Proc Natl Acad Sci USA* 101:13832-13837 and supporting information); *L. monocytogenes* DP-L4405 (delta inlA) (see, e.g., Brockstedt et al. (2004) *Proc Natl Acad Sci USA* 101:13832-13837 and supporting information); *L. monocytogenes* DP-L4406 (delta inlB) (see, e.g., Brockstedt et al. (2004) *Proc Natl Acad Sci USA* 101:13832-13837 and supporting information); *L. monocytogenes* CS-L0001 (delta actA; delta inlB) (see, e.g., Brockstedt et al. (2004) *Proc Natl Acad Sci USA* 101:13832-13837 and supporting information); *L. monocytogenes* CS-L0002 (delta actA; delta lplA) (see, e.g., Brockstedt et al. (2004) *Proc Natl Acad Sci USA* 101:13832-13837 and supporting information); *L. monocytogenes* CS-L0003 (LLO L461T; delta lplA) (see, e.g., Brockstedt et al. (2004) *Proc Natl Acad Sci USA* 101:13832-13837 and supporting information); *L. monocytogenes* DP-L4038 (delta actA; LLO L461T) (see, e.g., Brockstedt et al. (2004) *Proc Natl Acad Sci USA* 101:13832-13837 and supporting information); *L. monocytogenes* DP-L4384 (LLO S44A; LLO L461T) (see, e.g., Brockstedt et al. (2004) *Proc Natl Acad Sci USA* 101:13832-13837 and supporting information); a *L. monocytogenes* strain with an lplA1 deletion (encoding lipoate protein ligase LplA1) (see, e.g., O'Riordan et al. (2003) *Science* 302:462-464); *L. monocytogenes* DP-L4017 (10403S with LLO L461T) (see, e.g., U.S. Pat. No. 7,691,393); *L. monocytogenes* EGD (see, e.g., GenBank Accession No. AL591824).

In another embodiment, the *Listeria* strain is *L. monocytogenes* EGD-e (see GenBank Accession No. NC_003210; ATCC Accession No. BAA-679); *L. monocytogenes* DP-L4029 (actA deletion, optionally in combination with uvrAB deletion (DP-L4029uvrAB) (see, e.g., U.S. Pat. No. 7,691,393); *L. monocytogenes* actA-linlB—double mutant (see, e.g., ATCC Accession No. PTA-5562); *L. monocytogenes* lplA mutant or hly mutant (see, e.g., US 2004/0013690); *L. monocytogenes* dal/dat double mutant (see, e.g., US 2005/0048081). Other *L. monocytogenes* strains includes those that are modified (e.g., by a plasmid and/or by genomic integration) to contain a nucleic acid encoding one of, or any combination of, the following genes: hly (LLO; listeriolysin); iap (p60); inlA; inlB; inlC; dal (alanine racemase); dat (D-amino acid aminotransferase); plcA; plcB; actA; or any nucleic acid that mediates growth, spread, breakdown of a single walled vesicle, breakdown of a double walled vesicle, binding to a host cell, or uptake by a host cell. Each of the above references is herein incorporated by reference in its entirety for all purposes.

The recombinant bacteria or *Listeria* can have wild-type virulence, can have attenuated virulence, or can be avirulent. For example, a recombinant *Listeria* of can be sufficiently virulent to escape the phagosome or phagolysosome and enter the cytosol. Such *Listeria* strains can also be live-attenuated *Listeria* strains, which comprise at least one attenuating mutation, deletion, or inactivation as disclosed elsewhere herein. In some embodiments, the recombinant *Listeria* is an attenuated auxotrophic strain. An auxotrophic strain is one that is unable to synthesize a particular organic compound required for its growth. Examples of such strains are described in U.S. Pat. No. 8,114,414, herein incorporated by reference in its entirety for all purposes.

In some embodiments, the recombinant *Listeria* strain lacks antibiotic resistance genes. For example, such recombinant *Listeria* strains can comprise a plasmid that does not encode an antibiotic resistance gene. However, some recombinant *Listeria* strains provided herein comprise a plasmid comprising a nucleic acid encoding an antibiotic resistance gene. Antibiotic resistance genes may be used in the conventional selection and cloning processes commonly employed in molecular biology and vaccine preparation. Exemplary antibiotic resistance genes include gene products that confer resistance to ampicillin, penicillin, methicillin, streptomycin, erythromycin, kanamycin, tetracycline, chloramphenicol (CAT), neomycin, hygromycin, and gentamicin.

A. Bacteria or *Listeria* Strains Comprising Recombinant Fusion Polypeptides or Nucleic Acids Encoding Recombinant Fusion Polypeptides The recombinant bacteria strains (e.g., *Listeria* strains) disclosed herein comprise a recombinant fusion polypeptide disclosed herein or a nucleic acid encoding the recombinant fusion polypeptide as disclosed elsewhere herein.

In bacteria or *Listeria* strains comprising a nucleic acid encoding a recombinant fusion protein, the nucleic acid can be codon optimized. Examples of optimal codons utilized by *L. monocytogenes* for each amino acid are shown US 2007/0207170, herein incorporated by reference in its entirety for all purposes. A nucleic acid is codon-optimized if at least one codon in the nucleic acid is replaced with a codon that is more frequently used by *L. monocytogenes* for that amino acid than the codon in the original sequence.

The nucleic acid can be present in an episomal plasmid within the bacteria or *Listeria* strain and/or the nucleic acid can be genomically integrated in the bacteria or *Listeria* strain. Some recombinant bacteria or *Listeria* strains comprise two separate nucleic acids encoding two recombinant fusion polypeptides as disclosed herein: one nucleic acid in an episomal plasmid, and one genomically integrated in the bacteria or *Listeria* strain.

The episomal plasmid can be one that is stably maintained in vitro (in cell culture), in vivo (in a host), or both in vitro and in vivo. If in an episomal plasmid, the open reading frame encoding the recombinant fusion polypeptide can be operably linked to a promoter/regulatory sequence in the plasmid. If genomically integrated in the bacteria or *Listeria* strain, the open reading frame encoding the recombinant fusion polypeptide can be operably linked to an exogenous promoter/regulatory sequence or to an endogenous promoter/regulatory sequence. Examples of promoters/regulatory sequences useful for driving constitutive expression of a gene are well-known and include, for example, an hly, hlyA, actA, prfA, and p60 promoters of *Listeria*, the *Streptococcus* bac promoter, the *Streptomyces griseus* sgiA promoter, and the *B. thuringiensis* phaZ promoter. In some cases, an inserted gene of interest is not interrupted or subjected to regulatory constraints which often occur from integration into genomic DNA, and in some cases, the presence of the inserted heterologous gene does not lead to rearrangement or interruption of the cell's own important regions.

Such recombinant bacteria or *Listeria* strains can be made by transforming a bacteria or *Listeria* strain or an attenuated bacteria or *Listeria* strain described elsewhere herein with a plasmid or vector comprising a nucleic acid encoding the recombinant fusion polypeptide. The plasmid can be an episomal plasmid that does not integrate into a host chromosome. Alternatively, the plasmid can be an integrative plasmid that integrates into a chromosome of the bacteria or *Listeria* strain. The plasmids used herein can also be multicopy plasmids. Methods for transforming bacteria are well-known, and include calcium-chloride competent cell-based methods, electroporation methods, bacteriophage-mediated transduction, chemical transformation techniques, and physical transformation techniques. See, e.g., de Boer et al. (1989) *Cell* 56:641-649; Miller et al. (1995) *FASEB J.* 9:190-199; Sambrook et al. (1989) Molecular Cloning: A Laboratory Manual, Cold Spring Harbor Laboratory, New York; Ausubel et al. (1997) Current Protocols in Molecular Biology, John Wiley & Sons, New York; Gerhardt et al., eds., 1994, Methods for General and Molecular Bacteriology, American Society for Microbiology, Washington, D.C.; and Miller, 1992, A Short Course in Bacterial Genetics, Cold Spring Harbor Laboratory Press, Cold Spring Harbor, N.Y., each of which is herein incorporated by reference in its entirety for all purposes.

Bacteria or *Listeria* strains with genomically integrated heterologous nucleic acids can be made, for example, by using a site-specific integration vector, whereby the bacteria or *Listeria* comprising the integrated gene is created using homologous recombination. The integration vector can be any site-specific integration vector that is capable of infecting a bacteria or *Listeria* strain. Such an integration vector can comprise, for example, a PSA attPP' site, a gene encoding a PSA integrase, a U153 attPP' site, a gene encoding a U153 integrase, an A118 attPP' site, a gene encoding an A118 integrase, or any other known attPP' site or any other phage integrase.

Such bacteria or *Listeria* strains comprising an integrated gene can also be created using any other known method for integrating a heterologous nucleic acid into a bacteria or *Listeria* chromosome. Techniques for homologous recombination are well-known, and are described, for example, in Baloglu et al. (2005) *Vet Microbiol* 109(1-2):11-17); Jiang et al. 2005) *Acta Biochim Biophys Sin (Shanghai)* 37(1):19-24), and U.S. Pat. No. 6,855,320, each of which is herein incorporated by reference in its entirety for all purposes.

Integration into a bacteria or Listerial chromosome can also be achieved using transposon insertion. Techniques for transposon insertion are well-known, and are described, for example, for the construction of DP-L967 by Sun et al. (1990) *Infection and Immunity* 58: 3770-3778, herein incorporated by reference in its entirety for all purposes. Transposon mutagenesis can achieve stable genomic insertion, but the position in the genome where the heterologous nucleic acids has been inserted is unknown.

Integration into a bacterial or Listerial chromosome can also be achieved using phage integration sites (see, e.g., Lauer et al. (2002) *J Bacteriol* 184(15):4177-4186, herein incorporated by reference in its entirety for all purposes). For example, an integrase gene and attachment site of a bacteriophage (e.g., U153 or PSA listeriophage) can be used to insert a heterologous gene into the corresponding attachment site, which may be any appropriate site in the genome (e.g. comK or the 3' end of the arg tRNA gene). Endogenous prophages can be cured from the utilized attachment site prior to integration of the heterologous nucleic acid. Such methods can result, for example, in single-copy integrants. In order to avoid a "phage curing step," a phage integration system based on PSA phage can be used (see, e.g., Lauer et al. (2002) *J Bacteriol* 184:4177-4186, herein incorporated by reference in its entirety for all purposes). Maintaining the integrated gene can require, for example, continuous selection by antibiotics. Alternatively, a phage-based chromosomal integration system can be established that does not require selection with antibiotics. Instead, an auxotrophic host strain can be complemented. For example, a phage-based chromosomal integration system for clinical applications can be used, where a host strain that is auxotrophic for essential enzymes, including, for example, D-alanine racemase is used (e.g., Lm dal(−)dat(−)).

Conjugation can also be used to introduce genetic material and/or plasmids into bacteria. Methods for conjugation are well-known, and are described, for example, in Nikodinovic et al. (2006) *Plasmid* 56(3):223-227 and Auchtung et al. (2005) *Proc Natl Acad Sci USA* 102(35):12554-12559, each of which is herein incorporated by reference in its entirety for all purposes.

In a specific example, a recombinant bacteria or *Listeria* strain can comprise a nucleic acid encoding a recombinant fusion polypeptide genomically integrated into the bacteria or *Listeria* genome as an open reading frame with an endogenous actA sequence (encoding an ActA protein) or an endogenous hly sequence (encoding an LLO protein). For example, the expression and secretion of the fusion polypeptide can be under the control of the endogenous actA promoter and ActA signal sequence or can be under the control of the endogenous hly promoter and LLO signal sequence. As another example, the nucleic acid encoding a recombinant fusion polypeptide can replace an actA sequence encoding an ActA protein or an hly sequence encoding an LLO protein.

Selection of recombinant bacteria or *Listeria* strains can be achieved by any means. For example, antibiotic selection can be used. Antibiotic resistance genes may be used in the conventional selection and cloning processes commonly employed in molecular biology and vaccine preparation. Exemplary antibiotic resistance genes include gene products that confer resistance to ampicillin, penicillin, methicillin, streptomycin, erythromycin, kanamycin, tetracycline, chloramphenicol (CAT), neomycin, hygromycin, and gentamicin. Alternatively, auxotrophic strains can be used, and an exogenous metabolic gene can be used for selection instead of or in addition to an antibiotic resistance gene. As an example, in order to select for auxotrophic bacteria comprising a plasmid encoding a metabolic enzyme or a complementing gene provided herein, transformed auxotrophic bacteria can be grown in a medium that will select for expression of the gene encoding the metabolic enzyme (e.g., amino acid metabolism gene) or the complementing gene. Alternatively, a temperature-sensitive plasmid can be used to select recombinants or any other known means for selecting recombinants.

B. Attenuation of Bacteria or *Listeria* Strains

The recombinant bacteria strains (e.g., recombinant *Listeria* strains) disclosed herein can be attenuated. The term "attenuation" encompasses a diminution in the ability of the bacterium to cause disease in a host animal. For example, the pathogenic characteristics of an attenuated *Listeria* strain may be lessened compared with wild-type *Listeria*, although the attenuated *Listeria* is capable of growth and maintenance in culture. In some embodiments, using as an example the intravenous inoculation of BALB/c mice with an attenuated *Listeria*, the lethal dose at which 50% of inoculated animals survive ($LD_{50}$) is increased above the $LD_{50}$ of wild-type *Listeria* by at least about 10-fold, by at least about 100-fold, by at least about 1,000 fold, by at least about 10,000 fold, or by at least about 100,000-fold. An attenuated strain of *Listeria* is thus one that does not kill an animal to which it is administered, or is one that kills the animal only when the number of bacteria administered is vastly greater than the number of wild-type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. Attenuated strains are environmentally safe in that they are incapable of uncontrolled replication (I) Methods of Attenuating Bacteria and *Listeria* Strains Attenuation can be accomplished by any known means. For example, such attenuated strains can be deficient in one or more endogenous virulence genes or one or more endogenous metabolic genes. Examples of such genes are disclosed herein, and attenuation can be achieved by inactivation of any one of or any combination of the genes disclosed herein. Inactivation can be achieved, for example, through deletion or through mutation (e.g., an inactivating mutation). The term "mutation" includes any type of mutation or modification to the sequence (nucleic acid or amino acid sequence) and may encompass a deletion, a truncation, an insertion, a substitution, a disruption, or a translocation. For example, a mutation can include a frameshift mutation, a mutation which causes premature termination of a protein, or a mutation of regulatory sequences which affect gene expression. Mutagenesis can be accomplished using recombinant DNA techniques or using traditional mutagenesis technology using mutagenic chemicals or radiation and subsequent selection of mutants. In some embodiments, deletion mutants are used because of the accompanying low probability of reversion. The term "metabolic gene" refers to a gene encoding an enzyme involved in or required for synthesis of a nutrient utilized or required by a host bacteria. For example, the enzyme can be involved in or required for the synthesis of a nutrient required for sustained growth of the host bacteria. The term "virulence" gene includes a gene whose presence or activity in an organism's genome that contributes to the pathogenicity of the organism (e.g., enabling the organism to achieve colonization of a niche in the host (including attachment to cells), immunoevasion (evasion of host's immune response), immunosuppression (inhibition of host's immune response), entry into and exit out of cells, or obtaining nutrition from the host).

A specific example of such an attenuated strain is *Listeria monocytogenes* (Lm) dal(−)dat(−) (Lmdd). Another example of such an attenuated strain is Lm dal(−)dat(−)ΔactA (LmddA). See, e.g., US 2011/0142791, herein incorporated by references in its entirety for all purposes. LmddA is based on a *Listeria* strain which is attenuated due to the deletion of the endogenous virulence gene actA. Such strains can retain a plasmid for antigen expression in vivo and in vitro by complementation of the dal gene. Alternatively, the LmddA can be a dal/dat/actA *Listeria* having mutations in the endogenous dal, dat, and actA genes. Such mutations can be, for example, a deletion or other inactivating mutation.

Another specific example of an attenuated strain is Lm prfA(−) or a strain having a partial deletion or inactivating mutation in the prfA gene. The PrfA protein controls the expression of a regulon comprising essential virulence genes required by Lm to colonize its vertebrate hosts; hence the prfA mutation strongly impairs PrfA ability to activate expression of PrfA-dependent virulence genes.

Yet another specific example of an attenuated strain is Lm inlB(−)actA(−) in which two genes critical to the bacterium's natural virulence—internalin B and act A—are deleted.

Other examples of attenuated bacteria or *Listeria* strains include bacteria or *Listeria* strains deficient in one or more endogenous virulence genes. Examples of such genes include actA, prfA, plcB, plcA, inlA, inlB, inlC, inlJ, and bsh in *Listeria*. Attenuated *Listeria* strains can also be the double mutant or triple mutant of any of the above-mentioned strains. Attenuated *Listeria* strains can comprise a mutation or deletion of each one of the genes, or comprise a mutation or deletion of, for example, up to ten of any of the genes provided herein (e.g., including the actA, prfA, and dal/dat genes). For example, an attenuated *Listeria* strain can comprise a mutation or deletion of an endogenous internalin C (inlC) gene and/or a mutation or deletion of an endogenous actA gene. Alternatively, an attenuated *Listeria* strain can comprise a mutation or deletion of an endogenous internalin B (inlB) gene and/or a mutation or deletion of an endogenous actA gene. Alternatively, an attenuated *Listeria* strain can comprise a mutation or deletion of endogenous inlB, inlC, and actA genes. Translocation of *Listeria* to adjacent cells is inhibited by the deletion of the endogenous actA gene and/or the endogenous inlC gene or endogenous inlB gene, which are involved in the process, thereby resulting in high levels of attenuation with increased immunogenicity and utility as a strain backbone. An attenuated *Listeria* strain can also be a double mutant comprising mutations or deletions of both plcA and plcB. In some cases, the strain can be constructed from the EGD *Listeria* backbone.

A bacteria or *Listeria* strain can also be an auxotrophic strain having a mutation in a metabolic gene. As one example, the strain can be deficient in one or more endogenous amino acid metabolism genes. For example, the generation of auxotrophic strains of *Listeria* deficient in D-alanine, for example, may be accomplished in a number of ways that are well-known, including deletion mutations, insertion mutations, frameshift mutations, mutations which cause premature termination of a protein, or mutation of regulatory sequences which affect gene expression. In some embodiments, deletion mutants are used because of the accompanying low probability of reversion of the auxotrophic phenotype. As an example, mutants of D-alanine which are generated according to the protocols presented herein may be tested for the ability to grow in the absence of D-alanine in a simple laboratory culture assay. Those mutants which are unable to grow in the absence of this compound can be selected.

Examples of endogenous amino acid metabolism genes include a vitamin synthesis gene, a gene encoding pantothenic acid synthase, a D-glutamic acid synthase gene, a D-alanine amino transferase (dat) gene, a D-alanine racemase (dal) gene, dga, a gene involved in the synthesis of diaminopimelic acid (DAP), a gene involved in the synthesis of Cysteine synthase A (cysK), a vitamin-B12 independent methionine synthase, trpA, trpB, trpE, asnB, gltD, gltB, leuA, argG, and thrC. The Listeria strain can be deficient in two or more such genes (e.g., dat and dal). D-glutamic acid synthesis is controlled in part by the dal gene, which is involved in the conversion of D-glu+pyr to alpha-ketoglutarate+D-ala, and the reverse reaction.

As another example, an attenuated Listeria strain can be deficient in an endogenous synthase gene, such as an amino acid synthesis gene. Examples of such genes include folP, a gene encoding a dihydrouridine synthase family protein, ispD, ispF, a gene encoding a phosphoenolpyruvate synthase, hisF, hisH, fliI, a gene encoding a ribosomal large subunit pseudouridine synthase, ispD, a gene encoding a bifunctional GMP synthase/glutamine amidotransferase protein, cobS, cobB, cbiD, a gene encoding a uroporphyrin-III C-methyltransferase/uroporphyrinogen-III synthase, cobQ, uppS, truB, dxs, mvaS, dapA, ispG, folC, a gene encoding a citrate synthase, argJ, a gene encoding a 3-deoxy-7-phosphoheptulonate synthase, a gene encoding an indole-3-glycerol-phosphate synthase, a gene encoding an anthranilate synthase/glutamine amidotransferase component, menB, a gene encoding a menaquinone-specific isochorismate synthase, a gene encoding a phosphoribosylformylglycinamidine synthase I or II, a gene encoding a phosphoribosylaminoimidazole-succinocarboxamide synthase, carB, carA, thyA, mgsA, aroB, hepB, rluB, ilvB, ilvN, alsS, fabF, fabH, a gene encoding a pseudouridine synthase, pyrG, truA, pabB, and an ATP synthase gene (e.g., atpC, atpD-2, aptG, atpA-2, and so forth).

Attenuated Listeria strains can be deficient in endogenous phoP, aroA, aroC, aroD, or plcB. As yet another example, an attenuated Listeria strain can be deficient in an endogenous peptide transporter. Examples include genes encoding an ABC transporter/ATP-binding/permease protein, an oligopeptide ABC transporter/oligopeptide-binding protein, an oligopeptide ABC transporter/permease protein, a zinc ABC transporter/zinc-binding protein, a sugar ABC transporter, a phosphate transporter, a ZIP zinc transporter, a drug resistance transporter of the EmrB/QacA family, a sulfate transporter, a proton-dependent oligopeptide transporter, a magnesium transporter, a formate/nitrite transporter, a spermidine/putrescine ABC transporter, a Na/Pi-cotransporter, a sugar phosphate transporter, a glutamine ABC transporter, a major facilitator family transporter, a glycine betaine/L-proline ABC transporter, a molybdenum ABC transporter, a techoic acid ABC transporter, a cobalt ABC transporter, an ammonium transporter, an amino acid ABC transporter, a cell division ABC transporter, a manganese ABC transporter, an iron compound ABC transporter, a maltose/maltodextrin ABC transporter, a drug resistance transporter of the Bcr/CflA family, and a subunit of one of the above proteins.

Other attenuated bacteria and Listeria strains can be deficient in an endogenous metabolic enzyme that metabolizes an amino acid that is used for a bacterial growth process, a replication process, cell wall synthesis, protein synthesis, metabolism of a fatty acid, or for any other growth or replication process. Likewise, an attenuated strain can be deficient in an endogenous metabolic enzyme that can catalyze the formation of an amino acid used in cell wall synthesis, can catalyze the synthesis of an amino acid used in cell wall synthesis, or can be involved in synthesis of an amino acid used in cell wall synthesis. Alternatively, the amino acid can be used in cell wall biogenesis. Alternatively, the metabolic enzyme is a synthetic enzyme for D-glutamic acid, a cell wall component.

Other attenuated Listeria strains can be deficient in metabolic enzymes encoded by a D-glutamic acid synthesis gene, dga, an alr (alanine racemase) gene, or any other enzymes that are involved in alanine synthesis. Yet other examples of metabolic enzymes for which the Listeria strain can be deficient include enzymes encoded by serC (a phosphoserine aminotransferase), asd (aspartate betasemialdehyde dehydrogenase; involved in synthesis of the cell wall constituent diaminopimelic acid), the gene encoding gsaB—glutamate-1-semialdehyde aminotransferase (catalyzes the formation of 5-aminolevulinate from (S)-4-amino-5-oxopentanoate), hemL (catalyzes the formation of 5-aminolevulinate from (S)-4-amino-5-oxopentanoate), aspB (an aspartate aminotransferase that catalyzes the formation of oxalozcetate and L-glutamate from L-aspartate and 2-oxoglutarate), argF-1 (involved in arginine biosynthesis), aroE (involved in amino acid biosynthesis), aroB (involved in 3-dehydroquinate biosynthesis), aroD (involved in amino acid biosynthesis), aroC (involved in amino acid biosynthesis), hisB (involved in histidine biosynthesis), hisD (involved in histidine biosynthesis), hisG (involved in histidine biosynthesis), metX (involved in methionine biosynthesis), proB (involved in proline biosynthesis), argR (involved in arginine biosynthesis), argJ (involved in arginine biosynthesis), thiI (involved in thiamine biosynthesis), LMOf2365_1652 (involved in tryptophan biosynthesis), aroA (involved in tryptophan biosynthesis), ilvD (involved in valine and isoleucine biosynthesis), ilvC (involved in valine and isoleucine biosynthesis), leuA (involved in leucine biosynthesis), dapF (involved in lysine biosynthesis), and thrB (involved in threonine biosynthesis) (all GenBank Accession No. NC_002973).

An attenuated Listeria strain can be generated by mutation of other metabolic enzymes, such as a tRNA synthetase. For example, the metabolic enzyme can be encoded by the trpS gene, encoding tryptophanyl-tRNA synthetase. For example, the host strain bacteria can be Δ(trpS aroA), and both markers can be contained in an integration vector.

Other examples of metabolic enzymes that can be mutated to generate an attenuated Listeria strain include an enzyme encoded by murE (involved in synthesis of diaminopimelic acid; GenBank Accession No: NC_003485), LMOf2365_2494 (involved in teichoic acid biosynthesis), WecE (Lipopolysaccharide biosynthesis protein rffA; GenBank Accession No: AE014075.1), or amiA (an N-acetyl-muramoyl-L-alanine amidase). Yet other examples of metabolic enzymes include aspartate aminotransferase, histidinol-phosphate aminotransferase (GenBank Accession No. NP_466347), or the cell wall teichoic acid glycosylation protein GtcA.

Other examples of metabolic enzymes that can be mutated to generate an attenuated *Listeria* strain include a synthetic enzyme for a peptidoglycan component or precursor. The component can be, for example, UDP-N-acetylmuramylpentapeptide, UDP-N-acetylglucosamine, MurNAc-(pentapeptide)-pyrophosphoryl-undecaprenol, GlcNAc-p-(1,4)-MurNAc-(pentapeptide)-pyrophosphorylundecaprenol, or any other peptidoglycan component or precursor.

Yet other examples of metabolic enzymes that can be mutated to generate an attenuated *Listeria* strain include metabolic enzymes encoded by murG, murD, murA-1, or murA-2 (all set forth in GenBank Accession No. NC_002973). Alternatively, the metabolic enzyme can be any other synthetic enzyme for a peptidoglycan component or precursor. The metabolic enzyme can also be a transglycosylase, a trans-peptidase, a carboxy-peptidase, any other class of metabolic enzyme, or any other metabolic enzyme. For example, the metabolic enzyme can be any other *Listeria* metabolic enzyme or any other *Listeria monocytogenes* metabolic enzyme.

Other bacteria strains can be attenuated as described above for *Listeria* by mutating the corresponding orthologous genes in the other bacteria strains.

(2) Methods of Complementing Attenuated Bacteria and *Listeria* Strains

The attenuated bacteria or *Listeria* strains disclosed herein can further comprise a nucleic acid comprising a complementing gene or encoding a metabolic enzyme that complements an attenuating mutation (e.g., complements the auxotrophy of the auxotrophic *Listeria* strain). For example, a nucleic acid having a first open reading frame encoding a fusion polypeptide as disclosed herein can further comprise a second open reading frame comprising the complementing gene or encoding the complementing metabolic enzyme. Alternatively, a first nucleic acid can encode the fusion polypeptide and a separate second nucleic acid can comprise the complementing gene or encode the complementing metabolic enzyme.

The complementing gene can be extrachromosomal or can be integrated into the bacteria or *Listeria* genome. For example, the auxotrophic *Listeria* strain can comprise an episomal plasmid comprising a nucleic acid encoding a metabolic enzyme. Such plasmids will be contained in the *Listeria* in an episomal or extrachromosomal fashion. Alternatively, the auxotrophic *Listeria* strain can comprise an integrative plasmid (i.e., integration vector) comprising a nucleic acid encoding a metabolic enzyme. Such integrative plasmids can be used for integration into a *Listeria* chromosome. In some embodiments, the episomal plasmid or the integrative plasmid lacks an antibiotic resistance marker.

The metabolic gene can be used for selection instead of or in addition to an antibiotic resistance gene. As an example, in order to select for auxotrophic bacteria comprising a plasmid encoding a metabolic enzyme or a complementing gene provided herein, transformed auxotrophic bacteria can be grown in a medium that will select for expression of the gene encoding the metabolic enzyme (e.g., amino acid metabolism gene) or the complementing gene. For example, a bacteria auxotrophic for D-glutamic acid synthesis can be transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. Similarly, a bacterium auxotrophic for D-alanine synthesis will grow in the absence of D-alanine when transformed and expressing a plasmid comprising a nucleic acid encoding an amino acid metabolism enzyme for D-alanine synthesis. Such methods for making appropriate media comprising or lacking necessary growth factors, supplements, amino acids, vitamins, antibiotics, and the like are well-known and are available commercially.

Once the auxotrophic bacteria comprising the plasmid encoding a metabolic enzyme or a complementing gene provided herein have been selected in appropriate medium, the bacteria can be propagated in the presence of a selective pressure. Such propagation can comprise growing the bacteria in media without the auxotrophic factor. The presence of the plasmid expressing the metabolic enzyme or the complementing gene in the auxotrophic bacteria ensures that the plasmid will replicate along with the bacteria, thus continually selecting for bacteria harboring the plasmid. Production of the bacteria or *Listeria* strain can be readily scaled up by adjusting the volume of the medium in which the auxotrophic bacteria comprising the plasmid are growing.

In one specific example, the attenuated strain is a strain having a deletion of or an inactivating mutation in dal and dat (e.g., *Listeria monocytogenes* (Lm) dal(−)dat(−) (Lmdd) or Lm dal(−)dat(−)ΔactA (LmddA)), and the complementing gene encodes an alanine racemase enzyme (e.g., encoded by dal gene) or a D-amino acid aminotransferase enzyme (e.g., encoded by dat gene). An exemplary alanine racemase protein can have the sequence set forth in SEQ ID NO: 76 (encoded by SEQ ID NO: 78; GenBank Accession No: AF038438) or can be a homologue, variant, isoform, analog, fragment, fragment of a homologue, fragment of a variant, fragment of an analog, or fragment of an isoform of SEQ ID NO: 76. The alanine racemase protein can also be any other *Listeria* alanine racemase protein. Alternatively, the alanine racemase protein can be any other gram-positive alanine racemase protein or any other alanine racemase protein. An exemplary D-amino acid aminotransferase protein can have the sequence set forth in SEQ ID NO: 77 (encoded by SEQ ID NO: 79; GenBank Accession No: AF038439) or can be a homologue, variant, isoform, analog, fragment, fragment of a homologue, fragment of a variant, fragment of an analog, or fragment of an isoform of SEQ ID NO: 77. The D-amino acid aminotransferase protein can also be any other *Listeria* D-amino acid aminotransferase protein. Alternatively, the D-amino acid aminotransferase protein can be any other gram-positive D-amino acid aminotransferase protein or any other D-amino acid aminotransferase protein.

In another specific example, the attenuated strain is a strain having a deletion of or an inactivating mutation in prfA (e.g., Lm prfA(−)), and the complementing gene encodes a PrfA protein. For example, the complementing gene can encode a mutant PrfA (D133V) protein that restores partial PrfA function. An example of a wild type PrfA protein is set forth in SEQ ID NO: 80 (encoded by nucleic acid set forth in SEQ ID NO: 81), and an example of a D133V mutant PrfA protein is set forth in SEQ ID NO: 82 (encoded by nucleic acid set forth in SEQ ID NO: 83). The complementing PrfA protein can be a homologue, variant, isoform, analog, fragment, fragment of a homologue, fragment of a variant, fragment of an analog, or fragment of an isoform of SEQ ID NO: 80 or 82. The PrfA protein can also be any other *Listeria* PrfA protein. Alternatively, the PrfA protein can be any other gram-positive PrfA protein or any other PrfA protein.

In another example, the bacteria strain or *Listeria* strain can comprise a deletion of or an inactivating mutation in an actA gene, and the complementing gene can comprise an actA gene to complement the mutation and restore function to the *Listeria* strain.

Other auxotroph strains and complementation systems can also be adopted for the use with the methods and compositions provided herein.

IV. Recombinant Fusion Polypeptides

The recombinant fusion polypeptides in the recombinant bacteria or *Listeria* strains disclosed herein can be in any form. Some such fusion polypeptides can comprise a PEST-containing peptide fused to one or more disease-associated antigenic peptides. Other such recombinant fusion polypeptides can comprise one or more disease-associated antigenic peptides, and wherein the fusion polypeptide does not comprise a PEST-containing peptide.

Another example of a recombinant fusion polypeptides comprises from N-terminal end to C-terminal end a bacterial secretion sequence, a ubiquitin (Ub) protein, and one or more disease-associated antigenic peptides (i.e., in tandem, such as Ub-peptide1-peptide2). Alternatively, if two or more disease-associated antigenic peptides are used, a combination of separate fusion polypeptides can be used in which each antigenic peptide is fused to its own secretion sequence and Ub protein (e.g., Ub1-peptide1; Ub2-peptide2).

Nucleic acids (termed minigene constructs) encoding such recombinant fusion polypeptides are also disclosed. Such minigene nucleic acid constructs can further comprise two or more open reading frames linked by a Shine-Dalgarno ribosome binding site nucleic acid sequence between each open reading frame. For example, a minigene nucleic acid construct can further comprise two to four open reading frames linked by a Shine-Dalgarno ribosome binding site nucleic acid sequence between each open reading frame. Each open reading frame can encode a different polypeptide. In some nucleic acid constructs, the codon encoding the carboxy terminus of the fusion polypeptide is followed by two stop codons to ensure termination of protein synthesis.

The bacterial signal sequence can be a Listerial signal sequence, such as an Hly or an ActA signal sequence, or any other known signal sequence. In other cases, the signal sequence can be an LLO signal sequence. An exemplary LLO signal sequence is set forth in SEQ ID NO: 97. The signal sequence can be bacterial, can be native to a host bacterium (e.g., *Listeria monocytogenes*, such as a secA1 signal peptide), or can be foreign to a host bacterium. Specific examples of signal peptides include an Usp45 signal peptide from *Lactococcus lactis*, a Protective Antigen signal peptide from *Bacillus anthracis*, a secA2 signal peptide such the p60 signal peptide from *Listeria monocytogenes*, and a Tat signal peptide such as a *B. subtilis* Tat signal peptide (e.g., PhoD). In specific examples, the secretion signal sequence is from a *Listeria* protein, such as an ActA$_{300}$ secretion signal or an ActA$_{100}$ secretion signal. An exemplary ActA signal sequence is set forth in SEQ ID NO: 98.

The ubiquitin can be, for example, a full-length protein. The ubiquitin expressed from the nucleic acid construct provided herein can be cleaved at the carboxy terminus from the rest of the recombinant fusion polypeptide expressed from the nucleic acid construct through the action of hydrolases upon entry to the host cell cytosol. This liberates the amino terminus of the fusion polypeptide, producing a peptide in the host cell cytosol.

Selection of, variations of, and arrangement of antigenic peptides within a fusion polypeptide are discussed in detail elsewhere herein, and examples of disease-associated antigenic peptides are discussed in more detail elsewhere herein.

The recombinant fusion polypeptides can comprise one or more tags. For example, the recombinant fusion polypeptides can comprise one or more peptide tags N-terminal and/or C-terminal to one or more antigenic peptides. A tag can be fused directly to an antigenic peptide or linked to an antigenic peptide via a linker (examples of which are disclosed elsewhere herein). Examples of tags include the following: FLAG tag; 2×FLAG tag; 3×FLAG tag; His tag, 6×His tag; and SIINFEKL tag. An exemplary SIINFEKL tag is set forth in SEQ ID NO: 16 (encoded by any one of the nucleic acids set forth in SEQ ID NOS: 1-15). An exemplary 3×FLAG tag is set forth in SEQ ID NO: 32 (encoded by any one of the nucleic acids set forth in SEQ ID NOS: 17-31). An exemplary variant 3×FLAG tag is set forth in SEQ ID NO: 99. Two or more tags can be used together, such as a 2×FLAG tag and a SIINFEKL tag, a 3×FLAG tag and a SIINFEKL tag, or a 6×His tag and a SIINFEKL tag. If two or more tags are used, they can be located anywhere within the recombinant fusion polypeptide and in any order. For example, the two tags can be at the C-terminus of the recombinant fusion polypeptide, the two tags can be at the N-terminus of the recombinant fusion polypeptide, the two tags can be located internally within the recombinant fusion polypeptide, one tag can be at the C-terminus and one tag at the N-terminus of the recombinant fusion polypeptide, one tag can be at the C-terminus and one internally within the recombinant fusion polypeptide, or one tag can be at the N-terminus and one internally within the recombinant fusion polypeptide. Other tags include chitin binding protein (CBP), maltose binding protein (MBP), glutathione-S-transferase (GST), thioredoxin (TRX), and poly(NANP). Particular recombinant fusion polypeptides comprise a C-terminal SIINFEKL tag. Such tags can allow for easy detection of the recombinant fusion protein, confirmation of secretion of the recombinant fusion protein, or for following the immunogenicity of the secreted fusion polypeptide by following immune responses to these "tag" sequence peptides. Such immune response can be monitored using a number of reagents including, for example, monoclonal antibodies and DNA or RNA probes specific for these tags.

The recombinant fusion polypeptides disclosed herein can be expressed by recombinant *Listeria* strains or can be expressed and isolated from other vectors and cell systems used for protein expression and isolation. Recombinant *Listeria* strains comprising expressing such antigenic peptides can be used, for example in immunogenic compositions comprising such recombinant *Listeria* and in vaccines comprising the recombinant *Listeria* strain and an adjuvant. Expression of one or more antigenic peptides as a fusion polypeptides with a nonhemolytic truncated form of LLO, ActA, or a PEST-like sequence in host cell systems in *Listeria* strains and host cell systems other than *Listeria* can result in enhanced immunogenicity of the antigenic peptides.

Nucleic acids encoding such recombinant fusion polypeptides are also disclosed. The nucleic acid can be in any form. The nucleic acid can comprise or consist of DNA or RNA, and can be single-stranded or double-stranded. The nucleic acid can be in the form of a plasmid, such as an episomal plasmid, a multicopy episomal plasmid, or an integrative plasmid. Alternatively, the nucleic acid can be in the form of a viral vector, a phage vector, or in a bacterial artificial chromosome. Such nucleic acids can have one open reading frame or can have two or more open reading frames (e.g., an open reading frame encoding the recombinant fusion polypeptide and a second open reading frame encoding a metabolic enzyme). In one example, such nucleic acids can comprise two or more open reading frames linked by a Shine-Dalgarno ribosome binding site nucleic acid sequence between each open reading frame. For example, a nucleic acid can comprise two to four open reading frames linked by a Shine-Dalgarno ribosome binding site nucleic acid sequence between each open reading frame. Each open reading frame can encode a different polypeptide. In some nucleic acids, the codon encoding the carboxy terminus of the fusion polypeptide is followed by two stop codons to ensure termination of protein synthesis.

A. Antigenic Peptides

Disease-associated peptides include peptides from proteins that are expressed in a particular disease. For example, such peptides may be from proteins that are expressed in a disease tissue but not in a corresponding normal tissue, or that are expressed at abnormally high levels in a disease tissue. The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life. Examples of disease-associated antigenic peptides can include Human Papilloma Virus (HPV) E7 or E6, a Prostate Specific Antigen (PSA), a chimeric Her2 antigen, Her2/neu chimeric antigen. Another example of a disease-associated antigenic peptide is a WT1 antigenic peptide. The Human Papilloma Virus can be HPV 16 or HPV 18. The antigenic peptide can also include HPV16 E6, HPV16 E7, HPV18 E6, HPV18 E7 antigens operably linked in tandem or HPV16 antigenic peptide operably linked in tandem to an HPV antigenic peptide.

The fusion polypeptide can include a single antigenic peptide or can includes two or more antigenic peptides. Each antigenic peptide can be of any length sufficient to induce an immune response, and each antigenic peptide can be the same length or the antigenic peptides can have different lengths. For example, an antigenic peptide disclosed herein can be 5-100, 15-50, or 21-27 amino acids in length, or 15-100, 15-95, 15-90, 15-85, 15-80, 15-75, 15-70, 15-65, 15-60, 15-55, 15-50, 15-45, 15-40, 15-35, 15-30, 20-100, 20-95, 20-90, 20-85, 20-80, 20-75, 20-70, 20-65, 20-60, 20-55, 20-50, 20-45, 20-40, 20-35, 20-30, 11-21, 15-21, 21-31, 31-41, 41-51, 51-61, 61-71, 71-81, 81-91, 91-101, 101-121, 121-141, 141-161, 161-181, 181-201, 8-27, 10-30, 10-40, 15-30, 15-40, 15-25, 1-10, 10-20, 20-30, 30-40, 1-100, 5-75, 5-50, 5-40, 5-30, 5-20, 5-15, 5-10, 1-75, 1-50, 1-40, 1-30, 1-20, 1-15, 1-10, 8-11, or 11-16 amino acids in length. For example, an antigenic peptide can be at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids in length. Some specific examples of antigenic peptides are 21 or 27 amino acids in length. Other antigenic peptides can be full-length proteins or fragments thereof.

As one example, an antigenic peptide can comprise a neoepitope. These neoepitopes can be, for example, patient-specific (i.e., subject-specific) cancer mutations. Antigenic peptides comprising neoepitopes can be generated in a process for creating a personalized immunotherapy comprising comparing nucleic acids extracted from a cancer sample from a subject to nucleic acids extracted from a normal or healthy reference sample in order to identify somatic mutations or sequence differences present in the cancer sample compared with the normal or healthy sample. For examples, these mutations or sequence differences can be somatic, nonsynonymous missense mutations, or somatic frameshift mutations, and can encode an expressed amino acid sequence. A peptide expressing such somatic mutations or sequence differences can be referred to as a "neoepitope." A cancer-specific neoepitope may refer to an epitope that is not present in a reference sample (such as a normal non-cancerous or germline cell or tissue) but is found in a cancer sample. This includes, for example, situations in which in a normal non-cancerous or germline cell a corresponding epitope is found, but due to one or more mutations in a cancer cell, the sequence of the epitope is changed so as to result in the neoepitope. A neoepitope can comprise a mutated epitope, and can comprise non-mutated sequence on either or both sides of the mutation.

As another example, antigenic peptides can comprise recurrent cancer mutations. Each antigenic peptide can comprise a single recurrent cancer mutation or can comprise two or more recurrent cancer mutations (e.g., two recurrent cancer mutations). For example, an antigenic peptide can comprise more than one recurrent cancer mutation (e.g., 2 or 3 recurrent cancer mutations) because of the close proximity of the mutated residues to each other in the cancer-associated protein. The recurrent cancer mutations can be any type of mutation (e.g., somatic missense mutation or frameshift mutation). For example, a recombinant fusion polypeptide disclosed herein can comprise a PEST-containing peptide fused to two or more antigenic peptides (i.e., in tandem, such as PEST-peptide1-peptide2) or can comprise two or more antigenic peptides not fused to a PEST-containing peptide, wherein each antigenic peptide comprises a single, recurrent cancer mutation (i.e., a single, recurrent change in the amino acid sequence of a protein, or a sequence encoded by a single, different, nonsynonymous, recurrent cancer mutation in a gene), and wherein at least two of the antigenic peptides comprise different recurrent cancer mutations and are fragments of the same cancer-associated protein. Alternatively, each of the antigenic peptides can comprise a different recurrent cancer mutation from a different cancer-associated protein. Alternatively, a combination of separate fusion polypeptides can be used in which each antigenic peptide is fused (or is not fused) to its own PEST-containing peptide (e.g., PEST1-peptide1; PEST2-peptide2). Optionally, some or all of the fragments are non-contiguous fragments of the same cancer-associated protein. Non-contiguous fragments are fragments that do not occur sequentially in a protein sequence (e.g., the first fragment consists of residues 10-30, and the second fragment consists of residues 100-120; or the first fragment consists of residues 10-30, and the second fragment consists of residues 20-40). Optionally, each of the antigenic peptides comprises a different recurrent cancer mutation from a single type of cancer.

Recurrent cancer mutations can be from cancer-associated proteins. The term "cancer-associated protein" includes proteins having mutations that occur in multiple types of cancer, that occur in multiple subjects having a particular type of cancer, or that are correlated with the occurrence or progression of one or more types of cancer. For example, a cancer-associated protein can be an oncogenic protein (i.e., a protein with activity that can contribute to cancer progression, such as proteins that regulate cell growth), or it can be a tumor-suppressor protein (i.e., a protein that typically acts to alleviate the potential for cancer formation, such as through negative regulation of the cell cycle or by promoting apoptosis). In some embodiments, a cancer-associated protein has a "mutational hotspot." A mutational hotspot is an amino acid position in a protein-coding gene that is mutated (such as by somatic substitutions rather than other somatic abnormalities, such as translocations, amplifications, and deletions) more frequently than would be expected in the absence of selection. Such hotspot mutations can occur across multiple types of cancer and/or can be shared among multiple cancer patients. Mutational hotspots indicate selective pressure across a population of tumor samples. Tumor genomes contain recurrent cancer mutations that "drive" tumorigenesis by affecting genes (i.e., tumor driver genes) that confer selective growth advantages to the tumor cells upon alteration. Such tumor driver genes can be identified, for example, by identifying genes that are mutated more frequently than expected from the background mutation rate (i.e., recurrence); by identifying genes that exhibit other signals of positive selection across tumor samples (e.g., a high rate of non-silent mutations compared to silent mutations, or a bias towards the accumulation of functional mutations); by exploiting the tendency to sustain mutations in certain regions of the protein sequence based on the knowledge that whereas inactivating mutations are distributed along the sequence of the protein, gain-of-function mutations tend to occur specifically in particular residues or domains; or by exploiting the overrepresentation of mutations in specific functional residues, such as phosphorylation sites. Many of these mutations frequently occur in the functional regions of biologically active proteins (for example, kinase domains or binding domains) or interrupt active sites (for example, phosphorylation sites) resulting in loss-of-function or gain-of-function mutations, or they can occur in such a way that the three-dimensional structure and/or charge balance of the protein is perturbed sufficiently to interfere with normal function. Genomic analysis of large numbers of tumors reveals that mutations often occur at a limited number of amino acid positions. Therefore, a majority of the common mutations can be represented by a relatively small number of potential tumor-associated antigens or T cell epitopes.

A "recurrent cancer mutation" is a change in the amino acid sequence of a protein that occurs in multiple types of cancer and/or in multiple subjects having a particular types of cancer. Such mutations associated with a cancer can result in tumor-associated antigens that are not normally present in corresponding healthy tissue.

Tumor-driver genes and cancer-associated proteins having common mutations that occur across multiple cancers or among multiple cancer patients are known, and sequencing data across multiple tumor samples and multiple tumor types exists. See, e.g., Chang et al. (2016) *Nat Biotechnol* 34(2): 155-163; Tamborero et al. (2013) *Sci Rep* 3:2650, each of which is herein incorporated by reference in its entirety.

As another example, an antigenic peptide can be a heteroclitic antigenic peptide. For example, a heteroclitic antigenic peptide can be a fragment of a cancer-associated protein (i.e., a contiguous sequence of amino acids from a cancer-associated protein) comprising a heteroclitic mutation. A heteroclitic antigenic peptide can comprise a single heteroclitic mutation or can comprise two or more heteroclitic mutations (e.g., two heteroclitic mutations). The term "heteroclitic" refers to a peptide that generates an immune response that recognizes the native peptide from which the heteroclitic peptide was derived (e.g., the peptide not containing the anchor residue mutations).

Some recombinant fusion polypeptides disclosed herein can comprise any combination of antigenic peptides comprising recurrent cancer mutations, antigenic peptides (e.g., from cancer-associated proteins) comprising heteroclitic mutations, and antigenic peptides (e.g., from cancer-associated proteins) expressed from minigene constructs (i.e., antigenic peptides such as a heteroclitic antigenic peptide fused to ubiquitin). For example, such a recombinant fusion polypeptide can comprise a PEST-containing peptide fused to two or more antigenic peptides, wherein at least one antigenic peptide is from a cancer-associated protein and comprises a recurrent cancer mutation, and at least one antigenic peptide is from a cancer-associated protein and comprises a heteroclitic mutation. Optionally, the PEST-containing peptide comprises a bacterial secretion signal sequence, and the fusion polypeptide further comprises a ubiquitin protein fused to a carboxy-terminal antigenic peptide, wherein the PEST-containing peptide, the two or more antigenic peptides, the ubiquitin, and the carboxy-terminal antigenic peptide are arranged in tandem from the amino-terminal end to the carboxy-terminal end of the fusion polypeptide.

Each antigenic peptide can also be hydrophilic or can score up to or below a certain hydropathy threshold, which can be predictive of secretability in *Listeria monocytogenes* or another bacteria of interest. For example, antigenic peptides can be scored by a Kyte and Doolittle hydropathy index 21 amino acid window, and all scoring above a cutoff (around 1.6) can be excluded as they are unlikely to be secretable by *Listeria monocytogenes*. Likewise, the combination of antigenic peptides or the fusion polypeptide can be hydrophilic or can score up to or below a certain hydropathy threshold, which can be predictive of secretability in *Listeria monocytogenes* or another bacteria of interest.

The antigenic peptides can be linked together in any manner. For example, the antigenic peptides can be fused directly to each other with no intervening sequence. Alternatively, the antigenic peptides can be linked to each other indirectly via one or more linkers, such as peptide linkers. In some cases, some pairs of adjacent antigenic peptides can be fused directly to each other, and other pairs of antigenic peptides can be linked to each other indirectly via one or more linkers. The same linker can be used between each pair of adjacent antigenic peptides, or any number of different linkers can be used between different pairs of adjacent antigenic peptides. In addition, one linker can be used between a pair of adjacent antigenic peptides, or multiple linkers can be used between a pair of adjacent antigenic peptides.

Any suitable sequence can be used for a peptide linker. As an example, a linker sequence may be, for example, from 1 to about 50 amino acids in length. Some linkers may be hydrophilic. The linkers can serve varying purposes. For example, the linkers can serve to increase bacterial secretion, to facilitate antigen processing, to increase flexibility of the fusion polypeptide, to increase rigidity of the fusion polypeptide, or any other purpose. In some cases, different amino acid linker sequences are distributed between the antigenic peptides or different nucleic acids encoding the same amino acid linker sequence are distributed between the antigenic peptides (e.g., SEQ ID NOS: 84-94) in order to minimize repeats. This can also serve to reduce secondary structures, thereby allowing efficient transcription, translation, secretion, maintenance, or stabilization of the nucleic acid (e.g., plasmid) encoding the fusion polypeptide within a Lm recombinant vector strain population. Other suitable peptide linker sequences may be chosen, for example, based on one or more of the following factors: (1) their ability to adopt a flexible extended conformation; (2) their inability to adopt a secondary structure that could interact with functional epitopes on the antigenic peptides; and (3) the lack of hydrophobic or charged residues that might react with the functional epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in Maratea et al. (1985) *Gene* 40:39-46; Murphy et al. (1986) *Proc Natl Acad Sci USA* 83:8258-8262; U.S. Pat. Nos. 4,935,233; and 4,751,180, each of which is herein incorporated by reference in its entirety for all purposes. Specific examples of linkers include those in Table 2 (each of which can be used by itself as a linker, in a linker comprising repeats of the sequence, or in a linker further comprising one or more of the other sequences in the table), although others can also be envisioned (see, e.g., Reddy Chichili et al. (2013) *Protein Science* 22:153-167, herein incorporated by reference in its entirety for all purposes). Unless specified, "n" represents an undetermined number of repeats in the listed linker.

TABLE 2

Linkers.

| Peptide Linker | Example | SEQ ID NO: | Hypothetical Purpose |
|---|---|---|---|
| (GAS)$_n$ | GASGAS | 33 | Flexibility |
| (GSA)$_n$ | GSAGSA | 34 | Flexibility |
| (G)$_n$; n = 4-8 | GGGG | 35 | Flexibility |
| (GGGGS)$_n$; n = 1-3 | GGGGS | 36 | Flexibility |
| VGKGGSGG | VGKGGSGG | 37 | Flexibility |
| (PAPAP)$_n$ | PAPAP | 38 | Rigidity |
| (EAAAK)$_n$; n = 1-3 | EAAAK | 39 | Rigidity |
| (AYL)$_n$ | AYLAYL | 40 | Antigen Processing |
| (LRA)$_n$ | LRALRA | 41 | Antigen Processing |
| (RLRA)$_n$ | RLRA | 42 | Antigen Processing |

B. PEST-Containing Peptides

The recombinant fusion proteins disclosed herein comprise a PEST-containing peptide. The PEST-containing peptide may at the amino terminal (N-terminal) end of the fusion polypeptide (i.e., N-terminal to the antigenic peptides), may be at the carboxy terminal (C-terminal) end of the fusion polypeptide (i.e., C-terminal to the antigenic peptides), or may be embedded within the antigenic peptides. In some recombinant *Listeria* strains and methods, a PEST containing peptide is not part of and is separate from the fusion polypeptide. Fusion of an antigenic peptides to a PEST-like sequence, such as an LLO peptide, can enhance the immunogenicity of the antigenic peptides and can increase cell-mediated and antitumor immune responses (i.e., increase cell-mediated and anti-tumor immunity). See, e.g., Singh et al. (2005) *J Immunol* 175(6):3663-3673, herein incorporated by reference in its entirety for all purposes.

A PEST-containing peptide is one that comprises a PEST sequence or a PEST-like sequence. PEST sequences in eukaryotic proteins have long been identified. For example, proteins containing amino acid sequences that are rich in prolines (P), glutamic acids (E), serines (S) and threonines (T) (PEST), generally, but not always, flanked by clusters containing several positively charged amino acids, have rapid intracellular half-lives (Rogers et al. (1986) *Science* 234:364-369, herein incorporated by reference in its entirety for all purposes). Further, it has been reported that these sequences target the protein to the ubiquitin-proteasome pathway for degradation (Rechsteiner and Rogers (1996) *Trends Biochem. Sci.* 21:267-271, herein incorporated by reference in its entirety for all purposes). This pathway is also used by eukaryotic cells to generate immunogenic peptides that bind to MHC class I and it has been hypothesized that PEST sequences are abundant among eukaryotic proteins that give rise to immunogenic peptides (Realini et al. (1994) *FEBS Lett.* 348:109-113, herein incorporated by reference in its entirety for all purposes). Prokaryotic proteins do not normally contain PEST sequences because they do not have this enzymatic pathway. However, a PEST-like sequence rich in the amino acids proline (P), glutamic acid (E), serine (S) and threonine (T) has been reported at the amino terminus of LLO and has been reported to be essential for *L. monocytogenes* pathogenicity (Decatur and Portnoy (2000) *Science* 290:992-995, herein incorporated by reference in its entirety for all purposes). The presence of this PEST-like sequence in LLO targets the protein for destruction by proteolytic machinery of the host cell so that once the LLO has served its function and facilitated the escape of *L. monocytogenes* from the phagosomal or phagolysosomal vacuole, it is destroyed before it can damage the cells.

Identification of PEST and PEST-like sequences is well-known and is described, for example, in Rogers et al. (1986) *Science* 234(4774):364-378 and in Rechsteiner and Rogers (1996) *Trends Biochem. Sci.* 21:267-271, each of which is herein incorporated by reference in its entirety for all purposes. A PEST or PEST-like sequence can be identified using the PEST-find program. For example, a PEST-like sequence can be a region rich in proline (P), glutamic acid (E), serine (S), and threonine (T) residues. Optionally, the PEST-like sequence can be flanked by one or more clusters containing several positively charged amino acids. For example, a PEST-like sequence can be defined as a hydrophilic stretch of at least 12 amino acids in length with a high local concentration of proline (P), aspartate (D), glutamate (E), serine (S), and/or threonine (T) residues. In some cases, a PEST-like sequence contains no positively charged amino acids, namely arginine (R), histidine (H), and lysine (K). Some PEST-like sequences can contain one or more internal phosphorylation sites, and phosphorylation at these sites precedes protein degradation.

In one example, the PEST-like sequence fits an algorithm disclosed in Rogers et al. In another example, the PEST-like sequence fits an algorithm disclosed in Rechsteiner and Rogers. PEST-like sequences can also be identified by an initial scan for positively charged amino acids R, H, and K within the specified protein sequence. All amino acids between the positively charged flanks are counted, and only those motifs containing a number of amino acids equal to or higher than the window-size parameter are considered further. Optionally, a PEST-like sequence must contain at least one P, at least one D or E, and at least one S or T.

The quality of a PEST motif can be refined by means of a scoring parameter based on the local enrichment of critical amino acids as well as the motifs hydrophobicity. Enrichment of D, E, P, S, and T is expressed in mass percent (w/w) and corrected for one equivalent of D or E, one1 of P, and one of S or T. Calculation of hydrophobicity can also follow in principle the method of Kyte and Doolittle (1982) *J. Mol. Biol.* 157:105, herein incorporated by reference in its entirety for all purposes. For simplified calculations, Kyte-Doolittle hydropathy indices, which originally ranged from −4.5 for arginine to +4.5 for isoleucine, are converted to positive integers, using the following linear transformation, which yielded values from 0 for arginine to 90 for isoleucine: Hydropathy index=10*Kyte-Doolittle hydropathy index+45.

A potential PEST motif's hydrophobicity can also be calculated as the sum over the products of mole percent and hydrophobicity index for each amino acid species. The desired PEST score is obtained as combination of local enrichment term and hydrophobicity term as expressed by the following equation: PEST score=0.55*DEPST−0.5*hydrophobicity index.

Thus, a PEST-containing peptide can refer to a peptide having a score of at least +5 using the above algorithm. Alternatively, it can refer to a peptide having a score of at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 32, at least 35, at least 38, at least 40, or at least 45.

Any other known available methods or algorithms can also be used to identify PEST-like sequences. See, e.g., the CaSPredictor (Garay-Malpartida et al. (2005) *Bioinformatics* 21 Suppl 1:i169-76, herein incorporated by reference in its entirety for all purposes). Another method that can be used is the following: a PEST index is calculated for each stretch of appropriate length (e.g. a 30-35 amino acid stretch) by assigning a value of one to the amino acids Ser, Thr, Pro, Glu, Asp, Asn, or Gln. The coefficient value (CV) for each of the PEST residues is one and the CV for each of the other AA (non-PEST) is zero.

Examples of PEST-like amino acid sequences are those set forth in SEQ ID NOS: 43-51. One example of a PEST-like sequence is KENSISSMAPPASPPASPKT-PIEKKHADEIDK (SEQ ID NO: 43). Another example of a PEST-like sequence is KENSISSMAPPASPPASPK (SEQ ID NO: 44). However, any PEST or PEST-like amino acid sequence can be used. PEST sequence peptides are known and are described, for example, in U.S. Pat. Nos. 7,635,479; 7,665,238; and US 2014/0186387, each of which is herein incorporated by reference in its entirety for all purposes.

The PEST-like sequence can be from a *Listeria* species, such as from *Listeria monocytogenes*. For example, the *Listeria monocytogenes* ActA protein contains at least four such sequences (SEQ ID NOS: 45-48), any of which are suitable for use in the compositions and methods disclosed herein. Other similar PEST-like sequences include SEQ ID NOS: 52-54. Streptolysin O proteins from *Streptococcus* sp. also contain a PEST sequence. For example, *Streptococcus pyogenes* streptolysin O comprises the PEST sequence KQNTASTETTTTNEQPK (SEQ ID NO: 49) at amino acids 35-51 and *Streptococcus equisimilis* streptolysin O comprises the PEST-like sequence KQNTANTETTTTNEQPK (SEQ ID NO: 50) at amino acids 38-54. Another example of a PEST-like sequence is from *Listeria seeligeri* cytolysin, encoded by the lso gene: RSEVTISPAETPESPPATP (e.g., SEQ ID NO: 51).

Alternatively, the PEST-like sequence can be derived from other prokaryotic organisms. Other prokaryotic organisms wherein PEST-like amino acid sequences would be expected include, for example, other *Listeria* species.

(1) Listeriolysin O (LLO)

One example of a PEST-containing peptide that can be utilized in the compositions and methods disclosed herein is a listeriolysin O (LLO) peptide. An example of an LLO protein is the protein assigned GenBank Accession No. P13128 (SEQ ID NO: 55; nucleic acid sequence is set forth in GenBank Accession No. X15127). SEQ ID NO: 55 is a proprotein including a signal sequence. The first 25 amino acids of the proprotein is the signal sequence and is cleaved from LLO when it is secreted by the bacterium, thereby resulting in the full-length active LLO protein of 504 amino acids without the signal sequence. An LLO peptide disclosed herein can comprise the signal sequence or can comprise a peptide that does not include the signal sequence. Exemplary LLO proteins that can be used comprise, consist essentially of, or consist of the sequence set forth in SEQ ID NO: 55 or homologues, variants, isoforms, analogs, fragments, fragments of homologues, fragments of variants, fragments of analogs, and fragments of isoforms of SEQ ID NO: 55. Any sequence that encodes a fragment of an LLO protein or a homologue, variant, isoform, analog, fragment of a homologue, fragment of a variant, or fragment of an analog of an LLO protein can be used. A homologous LLO protein can have a sequence identity with a reference LLO protein, for example, of greater than 70%, 72%, 75%, 78%, 80%, 82%, 83%, 85%, 87%, 88%, 90%, 92%, 93%, 95%, 96%, 97%, 98%, or 99%.

Another example of an LLO protein is set forth in SEQ ID NO: 56. LLO proteins that can be used can comprise, consist essentially of, or consist of the sequence set forth in SEQ ID NO: 56 or homologues, variants, isoforms, analogs, fragments, fragments of homologues, fragments of variants, fragments of analogs, and fragments of isoforms of SEQ ID NO: 56.

Another example of an LLO protein is an LLO protein from the *Listeria monocytogenes* 10403S strain, as set forth in GenBank Accession No.: ZP_01942330 or EBA21833, or as encoded by the nucleic acid sequence as set forth in GenBank Accession No.: NZ_AARZ01000015 or AARZ01000015.1. Another example of an LLO protein is an LLO protein from the *Listeria monocytogenes* 4b F2365 strain (see, e.g., GenBank Accession No.: YP_012823), EGD-e strain (see, e.g., GenBank Accession No.: NP_463733), or any other strain of *Listeria monocytogenes*. Yet another example of an LLO protein is an LLO protein from Flavobacteriales bacterium HTCC2170 (see, e.g., GenBank Accession No.: ZP_01106747 or EAR01433, or encoded by GenBank Accession No.: NZ_AAOC01000003). LLO proteins that can be used can comprise, consist essentially of, or consist of any of the above LLO proteins or homologues, variants, isoforms, analogs, fragments, fragments of homologues, fragments of variants, fragments of analogs, and fragments of isoforms of the above LLO proteins.

Proteins that are homologous to LLO, or homologues, variants, isoforms, analogs, fragments, fragments of homologues, fragments of variants, fragments of analogs, and fragments of isoforms thereof, can also be used. One such example is alveolysin, which can be found, for example, in *Paenibacillus alvei* (see, e.g., GenBank Accession No.: P23564 or AAA22224, or encoded by GenBank Accession No.: M62709). Other such homologous proteins are known.

The LLO peptide can be a full-length LLO protein or a truncated LLO protein or LLO fragment. Likewise, the LLO peptide can be one that retains one or more functionalities of a native LLO protein or lacks one or more functionalities of a native LLO protein. For example, the retained LLO functionality can be allowing a bacteria (e.g., *Listeria*) to escape from a phagosome or phagolysosome, or enhancing the immunogenicity of a peptide to which it is fused. The retained functionality can also be hemolytic function or antigenic function. Alternatively, the LLO peptide can be a non-hemolytic LLO. Other functions of LLO are known, as are methods and assays for evaluating LLO functionality.

An LLO fragment can be a PEST-like sequence or can comprise a PEST-like sequence. LLO fragments can comprise one or more of an internal deletion, a truncation from the C-terminal end, and a truncation from the N-terminal end. In some cases, an LLO fragment can comprise more than one internal deletion. Other LLO peptides can be full-length LLO proteins with one or more mutations.

Some LLO proteins or fragments have reduced hemolytic activity relative to wild type LLO or are non-hemolytic fragments. For example, an LLO protein can be rendered non-hemolytic by deletion or mutation of the activation domain at the carboxy terminus, by deletion or mutation of cysteine 484, or by deletion or mutation at another location.

Other LLO proteins are rendered non-hemolytic by a deletion or mutation of the cholesterol binding domain (CBD) as detailed in U.S. Pat. No. 8,771,702, herein incorporated by reference in its entirety for all purposes. The mutations can comprise, for example, a substitution or a deletion. The entire CBD can be mutated, portions of the CBD can be mutated, or specific residues within the CBD can be mutated. For example, the LLO protein can comprise a mutation of one or more of residues C484, W491, and W492 (e.g., C484, W491, W492, C484 and W491, C484 and W492, W491 and W492, or all three residues) of SEQ ID NO: 55 or corresponding residues when optimally aligned with SEQ ID NO: 55 (e.g., a corresponding cysteine or tryptophan residue). As an example, a mutant LLO protein can be created wherein residues C484, W491, and W492 of LLO are substituted with alanine residues, which will substantially reduce hemolytic activity relative to wild type LLO. The mutant LLO protein with C484A, W491A, and W492A mutations is termed "mutLLO."

As another example, a mutant LLO protein can be created with an internal deletion comprising the cholesterol-binding domain. The sequence of the cholesterol-binding domain of SEQ ID NO: 55 set forth in SEQ ID NO: 74. For example, the internal deletion can be a 1-11 amino acid deletion, an 11-50 amino acid deletion, or longer. Likewise, the mutated region can be 1-11 amino acids, 11-50 amino acids, or longer (e.g., 1-50, 1-11, 2-11, 3-11, 4-11, 5-11, 6-11, 7-11, 8-11, 9-11, 10-11, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 12-50, 11-15, 11-20, 11-25, 11-30, 11-35, 11-40, 11-50, 11-60, 11-70, 11-80, 11-90, 11-100, 11-150, 15-20, 15-25, 15-30, 15-35, 15-40, 15-50, 15-60, 15-70, 15-80, 15-90, 15-100, 15-150, 20-25, 20-30, 20-35, 20-40, 20-50, 20-60, 20-70, 20-80, 20-90, 20-100, 20-150, 30-35, 30-40, 30-60, 30-70, 30-80, 30-90, 30-100, or 30-150 amino acids). For example, a mutated region consisting of residues 470-500, 470-510, or 480-500 of SEQ ID NO: 55 will result in a deleted sequence comprising the CBD (residues 483-493 of SEQ ID NO: 55). However, the mutated region can also be a fragment of the CBD or can overlap with a portion of the CBD. For example, the mutated region can consist of residues 470-490, 480-488, 485-490, 486-488, 490-500, or 486-510 of SEQ ID NO: 55. For example, a fragment of the CBD (residues 484-492) can be replaced with a heterologous sequence, which will substantially reduce hemolytic activity relative to wild type LLO. For example, the CBD (ECTGLAWEWWR; SEQ ID NO: 74) can be replaced with a CTL epitope from the antigen NY-ESO-1 (ESLLMWITQCR; SEQ ID NO: 75), which contains the HLA-A2 restricted epitope 157-165 from NY-ESO-1. The resulting LLO is termed "ctLLO."

In some mutated LLO proteins, the mutated region can be replaced by a heterologous sequence. For example, the mutated region can be replaced by an equal number of heterologous amino acids, a smaller number of heterologous amino acids, or a larger number of amino acids (e.g., 1-50, 1-11, 2-11, 3-11, 4-11, 5-11, 6-11, 7-11, 8-11, 9-11, 10-11, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 12-50, 11-15, 11-20, 11-25, 11-30, 11-35, 11-40, 11-50, 11-60, 11-70, 11-80, 11-90, 11-100, 11-150, 15-20, 15-25, 15-30, 15-35, 15-40, 15-50, 15-60, 15-70, 15-80, 15-90, 15-100, 15-150, 20-25, 20-30, 20-35, 20-40, 20-50, 20-60, 20-70, 20-80, 20-90, 20-100, 20-150, 30-35, 30-40, 30-60, 30-70, 30-80, 30-90, 30-100, or 30-150 amino acids). Other mutated LLO proteins have one or more point mutations (e.g., a point mutation of 1 residue, 2 residues, 3 residues, or more). The mutated residues can be contiguous or not contiguous.

In one example embodiment, an LLO peptide may have a deletion in the signal sequence and a mutation or substitution in the CBD.

Some LLO peptides are N-terminal LLO fragments (i.e., LLO proteins with a C-terminal deletion). Some LLO peptides are at least 494, 489, 492, 493, 500, 505, 510, 515, 520, or 525 amino acids in length or 492-528 amino acids in length. For example, the LLO fragment can consist of about the first 440 or 441 amino acids of an LLO protein (e.g., the first 441 amino acids of SEQ ID NO: 55 or 56, or a corresponding fragment of another LLO protein when optimally aligned with SEQ ID NO: 55 or 56). Other N-terminal LLO fragments can consist of the first 420 amino acids of an LLO protein (e.g., the first 420 amino acids of SEQ ID NO: 55 or 56, or a corresponding fragment of another LLO protein when optimally aligned with SEQ ID NO: 55 or 56). Other N-terminal fragments can consist of about amino acids 20-442 of an LLO protein (e.g., amino acids 20-442 of SEQ ID NO: 55 or 56, or a corresponding fragment of another LLO protein when optimally aligned with SEQ ID NO: 55 or 56). Other N-terminal LLO fragments comprise any ΔLLO without the activation domain comprising cysteine 484, and in particular without cysteine 484. For example, the N-terminal LLO fragment can correspond to the first 425, 400, 375, 350, 325, 300, 275, 250, 225, 200, 175, 150, 125, 100, 75, 50, or 25 amino acids of an LLO protein (e.g., the first 425, 400, 375, 350, 325, 300, 275, 250, 225, 200, 175, 150, 125, 100, 75, 50, or 25 amino acids of SEQ ID NO: 55 or 56, or a corresponding fragment of another LLO protein when optimally aligned with SEQ ID NO: 55 or 56). In some embodiments, the fragment comprises one or more PEST-like sequences. LLO fragments and truncated LLO proteins can contain residues of a homologous LLO protein that correspond to any one of the above specific amino acid ranges. The residue numbers need not correspond exactly with the residue numbers enumerated above (e.g., if the homologous LLO protein has an insertion or deletion relative to a specific LLO protein disclosed herein). Examples of N-terminal LLO fragments include SEQ ID NOS: 57, 58, and 59. LLO proteins that can be used comprise, consist essentially of, or consist of the sequence set forth in SEQ ID NO: 57, 58, or 59 or homologues, variants, isoforms, analogs, fragments, fragments of homologues, fragments of variants, fragments of analogs, and fragments of isoforms of SEQ ID NO: 57, 58, or 59. In some compositions and methods, the N-terminal LLO fragment set forth in SEQ ID NO: 59 is used. An example of a nucleic acid encoding the N-terminal LLO fragment set forth in SEQ ID NO: 59 is SEQ ID NO: 60.

(2) ActA

Another example of a PEST-containing peptide that can be utilized in the compositions and methods disclosed herein is an ActA peptide. ActA is a surface-associated protein and acts as a scaffold in infected host cells to facilitate the polymerization, assembly, and activation of host actin polymers in order to propel a *Listeria monocytogenes* through the cytoplasm. Shortly after entry into the mammalian cell cytosol, *L. monocytogenes* induces the polymerization of host actin filaments and uses the force generated by actin polymerization to move, first intracellularly and then from cell to cell. ActA is responsible for mediating actin nucleation and actin-based motility. The ActA protein provides multiple binding sites for host cytoskeletal components, thereby acting as a scaffold to assemble the cellular actin polymerization machinery. The N-terminus of ActA binds to monomeric actin and acts as a constitutively active nucleation promoting factor by stimulating the intrinsic actin nucleation activity. The actA and hly genes are both members of the 10-kb gene cluster regulated by the transcriptional activator PrfA, and actA is upregulated approximately 226-fold in the mammalian cytosol. Any sequence that encodes an ActA protein or a homologue, variant, isoform, analog, fragment of a homologue, fragment of a variant, or fragment of an analog of an ActA protein can be used. A homologous ActA protein can have a sequence identity with a reference ActA protein, for example, of greater than 70%, 72%, 75%, 78%, 80%, 82%, 83%, 85%, 87%, 88%, 90%, 92%, 93%, 95%, 96%, 97%, 98%, or 99%.

One example of an ActA protein comprises, consists essentially of, or consists of the sequence set forth in SEQ ID NO: 61. Another example of an ActA protein comprises, consists essentially of, or consists of the sequence set forth in SEQ ID NO: 62. The first 29 amino acid of the proprotein corresponding to either of these sequences are the signal sequence and are cleaved from ActA protein when it is secreted by the bacterium. An ActA peptide can comprise the signal sequence (e.g., amino acids 1-29 of SEQ ID NO: 61 or 62), or can comprise a peptide that does not include the signal sequence. Other examples of ActA proteins comprise, consist essentially of, or consist of homologues, variants, isoforms, analogs, fragments, fragments of homologues, fragments of isoforms, or fragments of analogs of SEQ ID NO: 61 or 62.

Another example of an ActA protein is an ActA protein from the *Listeria monocytogenes* 10403S strain (GenBank Accession No.: DQ054585) the NICPBP 54002 strain (GenBank Accession No.: EU394959), the S3 strain (GenBank Accession No.: EU394960), NCTC 5348 strain (GenBank Accession No.: EU394961), NICPBP 54006 strain (GenBank Accession No.: EU394962), M7 strain (GenBank Accession No.: EU394963), S19 strain (GenBank Accession No.: EU394964), or any other strain of *Listeria monocytogenes*. LLO proteins that can be used can comprise, consist essentially of, or consist of any of the above LLO proteins or homologues, variants, isoforms, analogs, fragments, fragments of homologues, fragments of variants, fragments of analogs, and fragments of isoforms of the above LLO proteins.

ActA peptides can be full-length ActA proteins or truncated ActA proteins or ActA fragments (e.g., N-terminal ActA fragments in which a C-terminal portion is removed). In some embodiments, truncated ActA proteins comprise at least one PEST sequence (e.g., more than one PEST sequence). In addition, truncated ActA proteins can optionally comprise an ActA signal peptide. Examples of PEST-like sequences contained in truncated ActA proteins include SEQ ID NOS: 45-48. Some such truncated ActA proteins comprise at least two of the PEST-like sequences set forth in SEQ ID NOS: 45-48 or homologs thereof, at least three of the PEST-like sequences set forth in SEQ ID NOS: 45-48 or homologs thereof, or all four of the PEST-like sequences set forth in SEQ ID NOS: 45-48 or homologs thereof. Examples of truncated ActA proteins include those comprising, consisting essentially of, or consisting of about residues 30-122, about residues 30-229, about residues 30-332, about residues 30-200, or about residues 30-399 of a full length ActA protein sequence (e.g., SEQ ID NO: 62). Other examples of truncated ActA proteins include those comprising, consisting essentially of, or consisting of about the first 50, 100, 150, 200, 233, 250, 300, 390, 400, or 418 residues of a full length ActA protein sequence (e.g., SEQ ID NO: 62). Other examples of truncated ActA proteins include those comprising, consisting essentially of, or consisting of about residues 200-300 or residues 300-400 of a full length ActA protein sequence (e.g., SEQ ID NO: 62). For example, the truncated ActA consists of the first 390 amino acids of the wild type ActA protein as described in U.S. Pat. No. 7,655,238, herein incorporated by reference in its entirety for all purposes. As another example, the truncated ActA can be an ActA-N100 or a modified version thereof (referred to as ActA-N100*) in which a PEST motif has been deleted and containing the nonconservative QDNKR (SEQ ID NO: 73) substitution as described in US 2014/0186387, herein incorporated by references in its entirety for all purposes. Alternatively, truncated ActA proteins can contain residues of a homologous ActA protein that corresponds to one of the above amino acid ranges or the amino acid ranges of any of the ActA peptides disclosed herein. The residue numbers need not correspond exactly with the residue numbers enumerated herein (e.g., if the homologous ActA protein has an insertion or deletion, relative to an ActA protein utilized herein, then the residue numbers can be adjusted accordingly).

Examples of truncated ActA proteins include, for example, proteins comprising, consisting essentially of, or consisting of the sequence set forth in SEQ ID NO: 63, 64, 65, or 66 or homologues, variants, isoforms, analogs, fragments of variants, fragments of isoforms, or fragments of analogs of SEQ ID NO: 63, 64, 65, or 66. SEQ ID NO: 63 referred to as ActA/PEST1 and consists of amino acids 30-122 of the full length ActA sequence set forth in SEQ ID NO: 62. SEQ ID NO: 64 is referred to as ActA/PEST2 or LA229 and consists of amino acids 30-229 of the full length ActA sequence set forth in the full-length ActA sequence set forth in SEQ ID NO: 62. SEQ ID NO: 65 is referred to as ActA/PEST3 and consists of amino acids 30-332 of the full-length ActA sequence set forth in SEQ ID NO: 62. SEQ ID NO: 66 is referred to as ActA/PEST4 and consists of amino acids 30-399 of the full-length ActA sequence set forth in SEQ ID NO: 62. As a specific example, the truncated ActA protein consisting of the sequence set forth in SEQ ID NO: 64 can be used.

Examples of truncated ActA proteins include, for example, proteins comprising, consisting essentially of, or consisting of the sequence set forth in SEQ ID NO: 67, 69, 70, or 72 or homologues, variants, isoforms, analogs, fragments of variants, fragments of isoforms, or fragments of analogs of SEQ ID NO: 67, 69, 70, or 72. As a specific example, the truncated ActA protein consisting of the sequence set forth in SEQ ID NO: 67 (encoded by the nucleic acid set forth in SEQ ID NO: 68) can be used. As another specific example, the truncated ActA protein consisting of the sequence set forth in SEQ ID NO: 70 (encoded by the nucleic acid set forth in SEQ ID NO: 71) can be used. SEQ ID NO: 71 is the first 1170 nucleotides encoding ActA in the *Listeria monocytogenes* 10403S strain. In some cases, the ActA fragment can be fused to a heterologous signal peptide. For example, SEQ ID NO: 72 sets forth an ActA fragment fused to an Hly signal peptide.

C. Generating Immunotherapy Constructs Encoding Recombinant Fusion Polypeptides

Also provided herein are methods for generating immunotherapy constructs encoding or compositions comprising the recombinant fusion polypeptides disclosed herein. For example, such methods can comprise selecting and designing antigenic peptides to include in the immunotherapy construct (and, for example, testing the hydropathy of the each antigenic peptide, and modifying or deselecting an antigenic peptide if it scores above a selected hydropathy index threshold value), designing one or more fusion polypeptides comprising each of the selected antigenic peptides, and generating a nucleic acid construct encoding the fusion polypeptide.

The antigenic peptides can be screened for hydrophobicity or hydrophilicity. Antigenic peptides can be selected, for example, if they are hydrophilic or if they score up to or below a certain hydropathy threshold, which can be predictive of secretability in a particular bacteria of interest (e.g., *Listeria monocytogenes*). For example, antigenic peptides can be scored by Kyte and Doolittle hydropathy index with a 21 amino acid window, all scoring above cutoff (around 1.6) are excluded as they are unlikely to be secretable by *Listeria monocytogenes*. See, e.g., Kyte-Doolittle (1982) *J Mol Biol* 157(1):105-132; herein incorporated by reference in its entirety for all purposes. Alternatively, an antigenic peptide scoring about a selected cutoff can be altered (e.g., changing the length of the antigenic peptide). Other sliding window sizes that can be used include, for example, 9, 11, 13, 15, 17, 19, 21, 23, 25, 27 or more amino acids. For example, the sliding window size can be 9-11 amino acids, 11-13 amino acids, 13-15 amino acids, 15-17 amino acids, 17-19 amino acids, 19-21 amino acids, 21-23 amino acids, 23-25 amino acids, or 25-27 amino acids. Other cutoffs that can be used include, for example, the following ranges 1.2-1.4, 1.4-1.6, 1.6-1.8, 1.8-2.0, 2.0-2.2 2.2-2.5, 2.5-3.0, 3.0-3.5, 3.5-4.0, or 4.0-4.5, or the cutoff can be 1.4, 1.5, 1.7, 1.8, 1.9, 2.0, 2.1, 2.2, 2.3, 2.3, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5. The cutoff can vary, for example, depending on the genus or species of the bacteria being used to deliver the fusion polypeptide.

Other suitable hydropathy plots or other appropriate scales include, for example, those reported in Rose et al. (1993) *Annu Rev Biomol Struct* 22:381-415; Biswas et al. (2003) *Journal of Chromatography A* 1000:637-655; Eisenberg (1984) *Ann Rev Biochem* 53:595-623; Abraham and Leo (1987) *Proteins: Structure, Function and Genetics* 2:130-152; Sweet and Eisenberg (1983) *Mol Biol* 171:479-488; Bull and Breese (1974) *Arch Biochem Biophys* 161: 665-670; Guy (1985) *Biophys J* 47:61-70; Miyazawa et al. (1985) *Macromolecules* 18:534-552; Roseman (1988) *J Mol Biol* 200:513-522; Wolfenden et al. (1981) *Biochemistry* 20:849-855; Wilson (1981) *Biochem J* 199:31-41; Cowan and Whittaker (1990) *Peptide Research* 3:75-80; Aboderin (1971) *Int J Biochem* 2:537-544; Eisenberg et al. (1984) *J Mol Biol* 179:125-142; Hopp and Woods (1981) *Proc Natl Acad Sci USA* 78:3824-3828; Manavalan and Ponnuswamy (1978) *Nature* 275:673-674; Black and Mould (1991) *Anal Biochem* 193:72-82; Fauchere and Pliska (1983) *Eur J Med Chem* 18:369-375; Janin (1979) *Nature* 277:491-492; Rao and Argos (1986) *Biochim Biophys Acta* 869:197-214; Tanford (1962) *Am Chem Soc* 84:4240-4274; Welling et al. (1985) *FEBS Lett* 188:215-218; Parker et al. (1986) *Biochemistry* 25:5425-5431; and Cowan and Whittaker (1990) *Peptide Research* 3:75-80, each of which is herein incorporated by reference in its entirety for all purposes.

Optionally, the antigenic peptides can be scored for their ability to bind to the subject human leukocyte antigen (HLA) type (for example by using the Immune Epitope Database (IED) available at www.iedb.org, which includes netMHCpan, ANN, SMMPMBEC. SMM, CombLib_Sidney2008, PickPocket, and netMHCcons) and ranked by best MHC binding score from each antigenic peptide. Other sources include TEpredict (tepredict.sourceforge.net/help.html) or other available MHC binding measurement scales. Cutoffs may be different for different expression vectors such as *Salmonella*.

Optionally, the antigenic peptides can be screened for immunosuppressive epitopes (e.g., T-reg epitopes, IL-10-inducing T helper epitopes, and so forth) to deselect antigenic peptides or to avoid immunosuppressive influences.

Optionally, a predicative algorithm for immunogenicity of the epitopes can be used to screen the antigenic peptides. However, these algorithms are at best 20% accurate in predicting which peptide will generate a T cell response. Alternatively, no screening/predictive algorithms are used. Alternatively, the antigenic peptides can be screened for immunogenicity. For example, this can comprise contacting one or more T cells with an antigenic peptide, and analyzing for an immunogenic T cell response, wherein an immunogenic T cell response identifies the peptide as an immunogenic peptide. This can also comprise using an immunogenic assay to measure secretion of at least one of CD25, CD44, or CD69 or to measure secretion of a cytokine selected from the group comprising IFN-γ, TNF-α, IL-1, and IL-2 upon contacting the one or more T cells with the peptide, wherein increased secretion identifies the peptide as comprising one or more T cell epitopes.

The selected antigenic peptides can be arranged into one or more candidate orders for a potential fusion polypeptide. If there are more usable antigenic peptides than can fit into a single plasmid, different antigenic peptides can be assigned priority ranks as needed/desired and/or split up into different fusion polypeptides (e.g., for inclusion in different recombinant *Listeria* strains). Priority rank can be determined by factors such as relative size, priority of transcription, and/or overall hydrophobicity of the translated polypeptide. The antigenic peptides can be arranged so that they are joined directly together without linkers, or any combination of linkers between any number of pairs of antigenic peptides, as disclosed in more detail elsewhere herein. The number of linear antigenic peptides to be included can be determined based on consideration of the number of constructs needed versus the mutational burden, the efficiency of translation and secretion of multiple epitopes from a single plasmid, and the MOI needed for each bacteria or Lm comprising a plasmid.

The combination of antigenic peptides or the entire fusion polypeptide (i.e., comprising the antigenic peptides and the PEST-containing peptide and any tags) also be scored for hydrophobicity. For example, the entirety of the fused antigenic peptides or the entire fusion polypeptide can be scored for hydropathy by a Kyte and Doolittle hydropathy index with a sliding 21 amino acid window. If any region scores above a cutoff (e.g., around 1.6), the antigenic peptides can be reordered or shuffled within the fusion polypeptide until an acceptable order of antigenic peptides is found (i.e., one in which no region scores above the cutoff). Alternatively, any problematic antigenic peptides can be removed or redesigned to be of a different size. Alternatively or additionally, one or more linkers between antigenic peptides as disclosed elsewhere herein can be added or modified to change the hydrophobicity. As with hydropathy testing for the individual antigenic peptides, other window sizes can be used, or other cutoffs can be used (e.g., depending on the genus or species of the bacteria being used to deliver the fusion polypeptide). In addition, other suitable hydropathy plots or other appropriate scales could be used.

Optionally, the combination of antigenic peptides or the entire fusion polypeptide can be further screened for immunosuppressive epitopes (e.g., T-reg epitopes, IL-10-inducing T helper epitopes, and so forth) to deselect antigenic peptides or to avoid immunosuppressive influences.

A nucleic acid encoding a candidate combination of antigenic peptides or fusion polypeptide can then be designed and optimized. For example, the sequence can be optimized for increased levels of translation, duration of expression, levels of secretion, levels of transcription, and any combination thereof. For example, the increase can be 2-fold to 1000-fold, 2-fold to 500-fold, 2-fold to 100-fold, 2-fold to 50-fold, 2-fold to 20-fold, 2-fold to 10-fold, or 3-fold to 5-fold relative to a control, non-optimized sequence.

For example, the fusion polypeptide or nucleic acid encoding the fusion polypeptide can be optimized for decreased levels of secondary structures possibly formed in the oligonucleotide sequence, or alternatively optimized to prevent attachment of any enzyme that may modify the sequence. Expression in bacterial cells can be hampered, for example, by transcriptional silencing, low mRNA half-life, secondary structure formation, attachment sites of oligonucleotide binding molecules such as repressors and inhibitors, and availability of rare tRNAs pools. The source of many problems in bacterial expressions is found within the original sequence. The optimization of RNAs may include modification of cis acting elements, adaptation of its GC-content, modifying codon bias with respect to non-limiting tRNAs pools of the bacterial cell, and avoiding internal homologous regions. Thus, optimizing a sequence can entail, for example, adjusting regions of very high (>80%) or very low (<30%) GC content. Optimizing a sequence can also entail, for example, avoiding one or more of the following cis-acting sequence motifs: internal TATA-boxes, chi-sites, and ribosomal entry sites; AT-rich or GC-rich sequence stretches; repeat sequences and RNA secondary structures; (cryptic) splice donor and acceptor sites; branch points; or a combination thereof. Optimizing expression can also entail adding sequence elements to flanking regions of a gene and/or elsewhere in the plasmid.

Optimizing a sequence can also entail, for example, adapting the codon usage to the codon bias of host genes (e.g., *Listeria monocytogenes* genes). For example, the codons that can be used for *Listeria monocytogenes* include A=GCA, G=GGT, L=TTA, Q=CAA, V=GTT, C=TGT, H=CAT, M=ATG, R=CGT, W=TGG, D=GAT, I=ATT, N=AAC, S=TCT, Y=TAT, E=GAA, K=AAA, P=CCA, T=ACA, F=TTC, and STOP=TAA.

A nucleic acid encoding a fusion polypeptide can be generated and introduced into a delivery vehicle such as a bacteria strain or *Listeria* strain. Other delivery vehicles may be suitable for DNA immunotherapy or peptide immunotherapy, such as a vaccinia virus or virus-like particle. Once a plasmid encoding a fusion polypeptide is generated and introduced into a bacteria strain or *Listeria* strain, the bacteria or *Listeria* strain can be cultured and characterized to confirm expression and secretion of the fusion polypeptide comprising the antigenic peptides.

V. Immunogenic Compositions, Pharmaceutical Compositions, and Vaccines

Also provided are immunogenic compositions, pharmaceutical compositions, or vaccines comprising a lyophilized recombinant bacteria or *Listeria* strain as disclosed herein, optionally wherein the lyophilized recombinant bacteria or *Listeria* strain is reconstituted by dissolving in an amount of solvent. An immunogenic composition comprising a *Listeria* strain can be inherently immunogenic by virtue of its comprising a *Listeria* strain and/or the composition can also further comprise an adjuvant. Other immunogenic compositions comprise DNA immunotherapy or peptide immunotherapy compositions.

The term "immunogenic composition" refers to any composition containing an antigen that elicits an immune response against the antigen in a subject upon exposure to the composition. The immune response elicited by an immunogenic composition can be to a particular antigen or to a particular epitope on the antigen.

An immunogenic composition can comprise a single lyophilized or reconstituted recombinant bacteria or *Listeria* strain as disclosed herein, or it can comprise multiple different lyophilized or reconstituted recombinant bacteria or *Listeria* strains as disclosed herein. A bacteria or *Listeria* strain comprising a first recombinant fusion polypeptide is different from a bacteria or *Listeria* strain comprising a second recombinant fusion polypeptide, for example, if the first recombinant fusion polypeptide includes one antigenic peptide that the second recombinant fusion polypeptide does not. The two recombinant fusion polypeptides can include some of the same antigenic peptides and still be considered different. Such different lyophilized or reconstituted recombinant bacteria or *Listeria* strains can be administered concomitantly to a subject or sequentially to a subject. Sequential administration can be particularly useful when a drug substance comprising a lyophilized or reconstituted recombinant *Listeria* strain (or recombinant fusion polypeptide or nucleic acid) disclosed herein is in different dosage forms and/or is administered on different dosing schedules (e.g., one composition from the mixture is administered at least daily and another is administered less frequently, such as once weekly, once every two weeks, or once every three weeks). The multiple lyophilized or reconstituted recombinant bacteria or *Listeria* strains can each comprise a different set of antigenic peptides. Alternatively, two or more of the lyophilized or reconstituted recombinant bacteria or *Listeria* strains can comprise the same set of antigenic peptides (e.g., the same set of antigenic peptides in a different order).

An immunogenic composition can additionally comprise an adjuvant (e.g., two or more adjuvants), a cytokine, a chemokine, or combination thereof. Optionally, an immunogenic composition can additionally comprises antigen presenting cells (APCs), which can be autologous or can be allogeneic to the subject.

The term adjuvant includes compounds or mixtures that enhance the immune response to an antigen. For example, an adjuvant can be a non-specific stimulator of an immune response or substances that allow generation of a depot in a subject which when combined with an immunogenic composition disclosed herein provides for an even more enhanced and/or prolonged immune response. An adjuvant can favor, for example, a predominantly Th1-mediated immune response, a Th1-type immune response, or a Th1-mediated immune response. Likewise, an adjuvant can favor a cell-mediated immune response over an antibody-mediated response. Alternatively, an adjuvant can favor an antibody-mediated response. Some adjuvants can enhance the immune response by slowly releasing the antigen, while other adjuvants can mediate their effects by any of the following mechanisms: increasing cellular infiltration, inflammation, and trafficking to the injection site, particularly for antigen-presenting cells (APC); promoting the activation state of APCs by upregulating costimulatory signals or major histocompatibility complex (MHC) expression; enhancing antigen presentation; or inducing cytokine release for indirect effect.

Examples of adjuvants include saponin QS21, CpG oligonucleotides, unmethylated CpG-containing oligonucleotides, MPL, TLR agonists, TLR4 agonists, TLR9 agonists, Resiquimod®, imiquimod, cytokines or nucleic acids encoding the same, chemokines or nucleic acids encoding same, IL-12 or a nucleic acid encoding the same, IL-6 or a nucleic acid encoding the same, and lipopolysaccharides. Another example of a suitable adjuvant is Montanide ISA 51. Montanide ISA 51 contains a natural metabolizable oil and a refined emulsifier. Other examples of a suitable adjuvant include granulocyte/macrophage colony-stimulating factor (GM-CSF) or a nucleic acid encoding the same and keyhole limpet hemocyanin (KLH) proteins or nucleic acids encoding the same. The GM-CSF can be, for example, a human protein grown in a yeast (S. cerevisiae) vector. GM-CSF promotes clonal expansion and differentiation of hematopoietic progenitor cells, antigen presenting cells (APCs), dendritic cells, and T cells.

Yet another example of a suitable adjuvant is detoxified listeriolysin O (dtLLO) protein. Detoxification can be accomplished by introducing point mutations for three selected amino acids important for binding of LLO to cholesterol and for eventual membrane pore formation. The three targeted amino acids are present in the cholesterol binding domain of LLO (ECTGLAWEWWR; SEQ ID NO: 74) and can be modified in the sequence (EATGLAWEAAR; SEQ ID NO: 96) by point mutations introduced into the DNA sequence by PCR. One example of a dtLLO suitable for use as an adjuvant is encoded by SEQ ID NO: 95. The detoxified, nonhemolytic form of LLO (dtLLO) is an effective adjuvant in tumor immunotherapy and may activate innate and cellular immune responses by acting as a PAMP. A dtLLO encoded by a sequence at least 90%, 95%, 96%, 97%, 98%, or 99% identical to SEQ ID NO: 95 is also suitable for use as an adjuvant.

Yet other examples of adjuvants include growth factors or nucleic acids encoding the same, cell populations, Freund's incomplete adjuvant, aluminum phosphate, aluminum hydroxide, BCG (bacille Calmette-Guerin), alum, interleukins or nucleic acids encoding the same, quill glycosides, monophosphoryl lipid A, liposomes, bacterial mitogens, bacterial toxins, or any other type of known adjuvant (see, e.g., Fundamental Immunology, 5th ed. (August 2003): William E. Paul (Editor); Lippincott Williams & Wilkins Publishers; Chapter 43: Vaccines, GJV Nossal, which is herein incorporated by reference in its entirety for all purposes).

An immunogenic composition can further comprise one or more immunomodulatory molecules. Examples include interferon gamma, a cytokine, a chemokine, and a T cell stimulant.

An immunogenic composition can be in the form of a vaccine or pharmaceutical composition. The terms "vaccine" and "pharmaceutical composition" are interchangeable and refer to an immunogenic composition in a pharmaceutically acceptable carrier for in vivo administration to a subject. A vaccine may be, for example, a vaccine contained within and delivered by a cell (e.g., a recombinant Listeria as disclosed herein). A vaccine may prevent a subject from contracting or developing a disease and/or a vaccine may be therapeutic to a subject having a disease.

A "pharmaceutically acceptable carrier" refers to a vehicle for containing an immunogenic composition that can be introduced into a subject without significant adverse effects and without having deleterious effects on the immunogenic composition. That is, "pharmaceutically acceptable" refers to any formulation which is safe, and provides the appropriate delivery for the desired route of administration of an effective amount of at least one immunogenic composition for use in the methods disclosed herein. Pharmaceutically acceptable carriers or vehicles or excipients are well-known. Descriptions of suitable pharmaceutically acceptable carriers, and factors involved in their selection, are found in a variety of readily available sources such as, for example, *Remington's Pharmaceutical Sciences*, 18th ed., 1990, herein incorporated by reference in its entirety for all purposes. Such carriers can be suitable for any route of administration (e.g., parenteral, enteral (e.g., oral), or topical application). Such pharmaceutical compositions can be buffered, for example, wherein the pH is maintained at a particular desired value, ranging from pH 4.0 to pH 9.0, in accordance with the stability of the immunogenic compositions and route of administration.

Suitable pharmaceutically acceptable carriers include, for example, sterile water, salt solutions such as saline, glucose, buffered solutions such as phosphate buffered solutions or bicarbonate buffered solutions, alcohols, gum arabic, vegetable oils, benzyl alcohols, polyethylene glycols, gelatine, carbohydrates (e.g., lactose, amylose or starch), magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, and the like. Pharmaceutical compositions or vaccines may also include auxiliary agents including, for example, diluents, stabilizers (e.g., sugars and amino acids), preservatives, wetting agents, emulsifiers, pH buffering agents, viscosity enhancing additives, lubricants, salts for influencing osmotic pressure, buffers, vitamins, coloring, flavoring, aromatic substances, and the like which do not deleteriously react with the immunogenic composition.

For liquid formulations (e.g., in embodiments wherein the lyophilized recombinant bacteria or Listeria strain is reconstituted by dissolving in an amount of solvent), for example, pharmaceutically acceptable carriers may be aqueous or non-aqueous solutions, suspensions, emulsions, or oils. Non-aqueous solvents include, for example, propylene glycol, polyethylene glycol, and injectable organic esters such as ethyl oleate. Aqueous carriers include, for example, water, alcoholic/aqueous solutions, emulsions or suspensions, including saline and buffered media. Examples of oils include those of petroleum, animal, vegetable, or synthetic origin, such as peanut oil, soybean oil, mineral oil, olive oil, sunflower oil, and fish-liver oil. Solid carriers/diluents include, for example, a gum, a starch (e.g., corn starch, pregelatinized starch), a sugar (e.g., lactose, mannitol, sucrose, or dextrose), a cellulosic material (e.g., microcrystalline cellulose), an acrylate (e.g., polymethylacrylate), calcium carbonate, magnesium oxide, talc, or mixtures thereof.

Optionally, sustained or directed release pharmaceutical compositions or vaccines can be formulated. This can be accomplished, for example, through use of liposomes or compositions wherein the active compound is protected with differentially degradable coatings (e.g., by microencapsulation, multiple coatings, and so forth). Such compositions may be formulated for immediate or slow release. It is also possible to freeze-dry the compositions and use the lyophilisates obtained (e.g., for the preparation of products for injection).

An immunogenic composition, pharmaceutical composition, or vaccine disclosed herein may also comprise one or more additional compounds effective in preventing or treating cancer. For example, the additional compound may comprise a compound useful in chemotherapy, such as amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil (5-FU), gemcitabine, gliadelimplants, hydroxycarbamide, idarubicin, ifosfamide, irinotecan, leucovorin, liposomaldoxorubicin, liposomaldaunorubicin, lomustine, melphalan, mercaptopurine, mesna, methotrexate, mitomycin, mitoxantrone, oxaliplatin, paclitaxel (Taxol), pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. The additional compound can also comprise other biologics, including Herceptin® (trastuzumab) against the HER2 antigen, Avastin® (bevacizumab) against VEGF, or antibodies to the EGF receptor, such as Erbitux® (cetuximab), and Vectibix® (panitumumab). The additional compound can also comprise, for example, an additional immunotherapy.

An additional compound can also comprise an immune checkpoint inhibitor antagonist, such as a PD-1 signaling pathway inhibitor, a CD-80/86 and CTLA-4 signaling pathway inhibitor, a T cell membrane protein 3 (TIM3) signaling pathway inhibitor, an adenosine A2a receptor (A2aR) signaling pathway inhibitor, a lymphocyte activation gene 3 (LAG3) signaling pathway inhibitor, a killer immunoglobulin receptor (KIR) signaling pathway inhibitor, a CD40 signaling pathway inhibitor, or any other antigen-presenting cell/T cell signaling pathway inhibitor. Examples of immune checkpoint inhibitor antagonists include an anti-PD-L1/PD-L2 antibody or fragment thereof, an anti-PD-1 antibody or fragment thereof, an anti-CTLA-4 antibody or fragment thereof, or an anti-B7-H4 antibody or fragment thereof. An additional compound can also comprise a T cell stimulator, such as an antibody or functional fragment thereof binding to a T-cell receptor co-stimulatory molecule, an antigen presenting cell receptor binding co-stimulatory molecule, or a member of the TNF receptor superfamily. The T-cell receptor co-stimulatory molecule can comprise, for example, CD28 or ICOS. The antigen presenting cell receptor binding co-stimulatory molecule can comprise, for example, a CD80 receptor, a CD86 receptor, or a CD46 receptor. The TNF receptor superfamily member can comprise, for example, glucocorticoid-induced TNF receptor (GITR), OX40 (CD134 receptor), 4-1BB (CD137 receptor), or TNFR25. See, e.g., WO2016100929, WO2016011362, and WO2016011357, each of which is incorporated by reference in its entirety for all purposes.

VI. Therapeutic Methods

The lyophilized bacteria or *Listeria* strains (optionally wherein the lyophilized recombinant bacteria or *Listeria* strain is reconstituted by dissolving in an amount of solvent), immunogenic compositions, pharmaceutical compositions, and vaccines disclosed herein can be used in various methods. For example, they can be used in methods of inducing or enhancing an anti-disease-associated-antigen (e.g., cancer-associated antigen or tumor-associated antigen) immune response in a subject, in methods of inducing or enhancing an anti-disease (e.g., anti-tumor or anti-cancer) immune response in a subject, in methods of treating a disease (e.g., a tumor or cancer) in a subject, in methods of preventing a disease (e.g., tumor or cancer) in a subject, or in methods of protecting a subject against a disease (e.g., tumor or cancer). They can also be used in methods of increasing the ratio of T effector cells to regulatory T cells (Tregs) in the spleen and tumor of a subject, wherein the T effector cells are targeted to a disease-associated antigen. They can also be used in methods for increasing disease-associated-antigen antigen T cells in a subject, increasing survival time of a subject having a disease, delaying the onset of a disease in a subject, or alleviating symptoms of a disease in a subject.

A method of inducing or enhancing an anti-disease-associated antigen immune response in a subject can comprise, for example, administering to the subject a lyophilized or reconstituted recombinant bacteria or *Listeria* strain, an immunogenic composition, a pharmaceutical composition, or a vaccine disclosed herein. An anti-disease-associated antigen immune response can thereby be induced or enhanced in the subject. For example, in the case of a lyophilized or reconstituted recombinant *Listeria* strain, the *Listeria* strain can express the fusion polypeptide, thereby eliciting an immune response in the subject. The immune response can comprise, for example, a T-cell response, such as a CD4+FoxP3− T cell response, a CD8+ T cell response, or a CD4+FoxP3− and CD8+ T cell response. Such methods can also increase the ratio of T effector cells to regulatory T cells (Tregs) in the spleen and tumor microenvironments of the subject, allowing for a more profound anti-tumor response in the subject.

A method of inducing or enhancing an anti-disease (e.g., anti-cancer or anti-tumor) immune response in a subject can comprise, for example, administering to the subject a lyophilized or reconstituted recombinant bacteria or *Listeria* strain, an immunogenic composition, a pharmaceutical composition, or a vaccine disclosed herein. An anti-disease immune response can thereby be induced or enhanced in the subject. For example, in the case of a recombinant *Listeria* strain, the *Listeria* strain can express the fusion polypeptide, thereby eliciting an anti-disease response in the subject.

A method of treating a disease (e.g., cancer or tumor) in a subject, can comprise, for example, administering to the subject a lyophilized or reconstituted recombinant bacteria or *Listeria* strain, an immunogenic composition, a pharmaceutical composition, or a vaccine disclosed herein. The subject can then mount an immune response against the disease expressing the disease-associated antigen, thereby treating the disease in the subject.

A method of preventing a disease (e.g., tumor or cancer) in a subject or protecting a subject against developing a disease, can comprise, for example, administering to the subject a lyophilized or reconstituted recombinant bacteria or *Listeria* strain, an immunogenic composition, a pharmaceutical composition, or a vaccine disclosed herein. The subject can then mount an immune response against the disease-associated antigen, thereby preventing a disease or protecting the subject against developing a disease.

In some of the above methods, two or more lyophilized or reconstituted recombinant bacteria or *Listeria* strains, immunogenic compositions, pharmaceutical compositions, or vaccines are administered. The multiple recombinant bacteria or *Listeria* strains, immunogenic compositions, pharmaceutical compositions, or vaccines can be administered sequentially in any order or combination, or can be administered simultaneously in any combination. As an example, if four different *Listeria* strains are being administered, they can be administered sequentially, they can be administered simultaneously, or they can be administered in any combination (e.g., administering the first and second strains simultaneously and subsequently administering the third and fourth strains simultaneously). Optionally, in the case of sequential administration, the compositions can be administered during the same immune response. In some embodiments the compositions are administered within 0-10 or 3-7 days of each other. The multiple recombinant bacteria or *Listeria* strains, immunogenic compositions, pharmaceutical compositions, or vaccines can each comprise a different set of antigenic peptides. Alternatively, two or more can comprise the same set of antigenic peptides (e.g., the same set of antigenic peptides in a different order).

In some methods, the disease is a cancer or tumor. Cancer is a physiological condition in mammals that is typically characterized by unregulated cell growth and proliferation. Cancers can be hematopoietic malignancies or solid tumors (i.e., masses of cells that result from excessive cell growth or proliferation, including pre-cancerous legions). Metastatic cancer refers to a cancer that has spread from the place where it first started to another place in the body. Tumors formed by metastatic cancer cells are called a metastatic tumor or a metastasis, which is a term also used to refer to the process by which cancer cells spread to other parts of the body. In general, metastatic cancer has the same name and same type of cancer cells as the original, or primary, cancer. Examples of solid tumors include melanoma, carcinoma, blastoma, and sarcoma. Hematologic malignancies include, for example, leukemia or lymphoid malignancies, such as lymphoma. Exemplary categories of cancers include brain, breast, gastrointestinal, genitourinary, gynecologic, head and neck, heme, skin and thoracic. Brain malignancies include, for example, glioblastoma, high-grade pontine glioma, low-grade glioma, medulloblastoma, neuroblastoma, and pilocytic astrocytoma. Gastrointestinal cancers include, for example, colorectal, gallbladder, hepatocellular, pancreas, PNET, gastric, and esophageal. Genitourinary cancers include, for example, adrenocortical, bladder, kidney chromophobe, renal (clear cell), renal (papillary), rhabdoid cancers, and prostate. Gynecologic cancers include, for example, uterine carcinosarcoma, uterine endometrial, serous ovarian, and cervical. Head and neck cancers include, for example, thyroid, nasopharyngeal, head and neck, and adenoid cystic. Heme cancers include, for example, multiple myeloma, myelodysplasia, mantle-cell lymphoma, acute lymphoblastic leukemia (ALL), non-lymphoma, chronic lymphocytic leukemia (CLL), and acute myeloid leukemia (AML). Skin cancers includes, for example, cutaneous melanoma and squamous cell carcinoma. Thoracic cancers include, for example, squamous lung, small-cell lung, and lung adenocarcinoma.

More particular examples of such cancers include squamous cell cancer or carcinoma (e.g., oral squamous cell carcinoma), myeloma, oral cancer, juvenile nasopharyngeal angiofibroma, neuroendocrine tumors, lung cancer, cancer of the peritoneum, hepatocellular cancer, gastric or stomach cancer including gastrointestinal cancer, pancreatic cancer, glioma, glioblastoma, glial tumors, cervical cancer, ovarian cancer, liver cancer, bladder cancer, hepatoma, hepatocellular carcinoma, breast cancer, triple-negative breast cancer, colon cancer, rectal cancer, colorectal cancer, endometrial cancer or uterine cancer or carcinoma, salivary gland carcinoma, kidney or renal cancer (e.g., renal cell carcinoma), prostate cancer, vulval cancer, thyroid cancer, hepatic carcinoma, anal carcinoma, penile carcinoma, fibrosarcoma, gallbladder cancer, osteosarcoma, mesothelioma, as well as head and neck cancer. A cancer can also be a brain cancer or another type of CNS or intracranial tumor. For example, a subject can have an astrocytic tumor (e.g., astrocytoma, anaplastic astrocytoma, glioblastoma, pilocytic astrocytoma, subependymal giant cell astrocytoma, pleomorphic xanthoastrocytoma), oligodendroglial tumor (e.g., oligodendroglioma, anaplastic oligodendroglioma), ependymal cell tumor (e.g., ependymoma, anaplastic ependymoma, myxopapillary ependymoma, subependymoma), mixed glioma (e.g., mixed oligoastrocytoma, anaplastic oligoastrocytoma), neuroepithelial tumor of uncertain origin (e.g., polar spongioblastoma, astroblastoma, gliomatosis cerebri), tumor of the choroid plexus (e.g., choroid plexus papilloma, choroid plexus carcinoma), neuronal or mixed neuronal-glial tumor (e.g., gangliocytoma, dyplastic gangliocytoma of cerebellum, ganglioglioma, anaplastic ganglioglioma, desmoplastic infantile ganglioma, central neurocytoma, dysembryoplastic neuroepthelial tumor, olfactory neuroblastoma), pineal parenchyma tumor (e.g., pineocytoma, pineoblastoma, mixed pineocytoma/pineoblastoma), or tumor with mixed neuroblastic or glioblastic elements (e.g., medulloepithelioma, medulloblastoma, neuroblastoma, retinoblastoma, ependymoblastoma).

The term "treat" or "treating" refers to both therapeutic treatment and prophylactic or preventative measures, wherein the object is to prevent or lessen the symptoms of the targeted disease. Treating may include one or more of directly affecting or curing, suppressing, inhibiting, preventing, reducing the severity of, delaying the onset of, slowing the progression of, stabilizing the progression of, inducing remission of, preventing or delaying the metastasis of, reducing/ameliorating symptoms associated with the disease, or a combination thereof. For example, treating may include increasing expected survival time. The effect (e.g., suppressing, inhibiting, preventing, reducing the severity of, delaying the onset of, slowing the progression of, stabilizing the progression of, inducing remission of, preventing or delaying, reducing/ameliorating symptoms of, and so forth, can be relative to a control subject not receiving a treatment or receiving a placebo treatment. The term "treat" or "treating" can also refer to increasing percent chance of survival or increasing expected time of survival for a subject with the disease (e.g., relative to a control subject not receiving a treatment or receiving a placebo treatment). In one example, "treating" refers to delaying progression, expediting remission, inducing remission, augmenting remission, speeding recovery, increasing efficacy of alternative therapeutics, decreasing resistance to alternative therapeutics, or a combination thereof (e.g., relative to a control subject not receiving a treatment or receiving a placebo treatment). The terms "preventing" or "impeding" can refer, for example to delaying the onset of symptoms, preventing relapse of a disease, decreasing the number or frequency of relapse episodes, increasing latency between symptomatic episodes, or a combination thereof. The terms "suppressing" or "inhibiting" can refer, for example, to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

The term "subject" refers to a mammal (e.g., a human) in need of therapy for, or susceptible to developing, a disease. The term subject also refers to a mammal (e.g., a human) that receives either prophylactic or therapeutic treatment. The subject may include dogs, cats, pigs, cows, sheep, goats, horses, rats, mice, non-human mammals, and humans. The term "subject" does not necessarily exclude an individual that is healthy in all respects and does not have or show signs of the disease.

An individual is at increased risk of developing a disease if the subject has at least one known risk-factor (e.g., genetic, biochemical, family history, and situational exposure) placing individuals with that risk factor at a statistically significant greater risk of developing the disease than individuals without the risk factor.

A "symptom" or "sign" refers to objective evidence of a disease as observed by a physician or subjective evidence of a disease, such as altered gait, as perceived by the subject. A symptom or sign may be any manifestation of a disease. Symptoms can be primary or secondary. The term "primary" refers to a symptom that is a direct result of a particular disease or disorder (e.g., a tumor or cancer), while the term "secondary" refers to a symptom that is derived from or consequent to a primary cause. The lyophilized or reconstituted recombinant bacteria or *Listeria* strains, the immunogenic compositions, the pharmaceutical compositions, and the vaccines disclosed herein can treat primary or secondary symptoms or secondary complications.

The lyophilized or reconstituted recombinant bacteria or *Listeria* strains, immunogenic compositions, pharmaceutical compositions, or vaccines are administered in an effective regime, meaning a dosage, route of administration, and frequency of administration that delays the onset, reduces the severity, inhibits further deterioration, and/or ameliorates at least one sign or symptom of the disease. Alternatively, the lyophilized or reconstituted recombinant bacteria or *Listeria* strains, immunogenic compositions, pharmaceutical compositions, or vaccines are administered in an effective regime, meaning a dosage, route of administration, and frequency of administration that induces an immune response to a disease-associated antigen in the lyophilized or reconstituted recombinant bacteria or *Listeria* strain, the immunogenic composition, the pharmaceutical composition, or the vaccine, or that induces an immune response to the bacteria or *Listeria* strain itself. If a subject is already suffering from the disease, the regime can be referred to as a therapeutically effective regime. If the subject is at elevated risk of developing the disease relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients. For example, a regime can be considered therapeutically or prophylactically effective if an individual treated patient achieves an outcome more favorable than the mean outcome in a control population of comparable patients not treated by methods described herein, or if a more favorable outcome is demonstrated in treated patients versus control patients in a controlled clinical trial (e.g., a phase II, phase II/III or phase III trial) at the p<0.05 or 0.01 or even 0.001 level.

Exemplary dosages for a recombinant *Listeria* strain are, for example, $1 \times 10^6$-$1 \times 10^7$ CFU, $1 \times 10^7$-$1 \times 10^8$ CFU, $1 \times 10^8$-$3.31 \times 10^{10}$ CFU, $1 \times 10^9$-$3.31 \times 10^{10}$ CFU, 5-500$\times 10^8$ CFU, 7-500$\times 10^8$ CFU, 10-500$\times 10^8$ CFU, 20-500$\times 10^8$ CFU, 30-500$\times 10^8$ CFU, 50-500$\times 10^8$ CFU, 70-500$\times 10^8$ CFU, 100-500$\times 10^8$ CFU, 150-500$\times 10^8$ CFU, 5-300$\times 10^8$ CFU, 5-200$\times 10^8$ CFU, 5-15$\times 10^8$ CFU, 5-100$\times 10^8$ CFU, 5-70$\times 10^8$ CFU, 5-50$\times 10^8$ CFU, 5-30$\times 10^8$ CFU, 5-20$\times 10^8$ CFU, 1-30$\times 10^9$ CFU, 1-20$\times 10^9$ CFU, 2-30$\times 10^9$ CFU, 1-10$\times 10^9$ CFU, 2-10$\times 10^9$ CFU, 3-10$\times 10^9$ CFU, 2-7$\times 10^9$ CFU, 2-5$\times 10^9$ CFU, and 3-5$\times 10^9$ CFU. Other exemplary dosages for a recombinant *Listeria* strain are, for example, $1 \times 10^7$ organisms, $1.5 \times 10^7$ organisms, $2 \times 10^8$ organisms, $3 \times 10^7$ organisms, $4 \times 10^7$ organisms, $5 \times 10^7$ organisms, $6 \times 10^7$ organisms, $7 \times 10^7$ organisms, $8 \times 10^7$ organisms, $10 \times 10^7$ organisms, $1.5 \times 10^8$ organisms, $2 \times 10^8$ organisms, $2.5 \times 10^8$ organisms, $3 \times 10^8$ organisms, $3.3 \times 10^8$ organisms, $4 \times 10^8$ organisms, $5 \times 10^8$ organisms, $1 \times 10^9$ organisms, $1.5 \times 10^9$ organisms, $2 \times 10^9$ organisms, $3 \times 10^9$ organisms, $4 \times 10^9$ organisms, $5 \times 10^9$ organisms, $6 \times 10^9$ organisms, $7 \times 10^9$ organisms, $8 \times 10^9$ organisms, $10 \times 10^9$ organisms, $1.5 \times 10^{10}$ organisms, $2 \times 10^{10}$ organisms, $2.5 \times 10^{10}$ organisms, $3 \times 10^{10}$ organisms, $3.3 \times 10^{10}$ organisms, $4 \times 10^{10}$ organisms, and $5 \times 10^{10}$ organisms. The dosage can depend on the condition of the patient and response to prior treatment, if any, whether the treatment is prophylactic or therapeutic, and other factors.

Administration can be by any suitable means. For example, administration can be parenteral, intravenous, oral, subcutaneous, intra-arterial, intracranial, intrathecal, intracerebroventricular, intraperitoneal, topical, intranasal, intramuscular, intra-ocular, intrarectal, conjunctival, transdermal, intradermal, vaginal, rectal, intratumoral, parcanceral, transmucosal, intravascular, intraventricular, inhalation (aerosol), nasal aspiration (spray), sublingual, aerosol, suppository, or a combination thereof. For intranasal administration or application by inhalation, solutions or suspensions of the recombinant fusion polypeptides, nucleic acids encoding recombinant fusion polypeptides, recombinant bacteria or *Listeria* strains, immunogenic compositions, pharmaceutical compositions, or vaccines mixed and aerosolized or nebulized in the presence of the appropriate carrier are suitable. Such an aerosol may comprise any lyophilized or reconstituted recombinant bacteria or *Listeria* strain, immunogenic composition, pharmaceutical composition, or vaccine described herein. Administration may also be in the form of a suppository (e.g., rectal suppository or urethral suppository), in the form of a pellet for subcutaneous implantation (e.g., providing for controlled release over a period of time), or in the form of a capsule. Administration may also be via injection into a disease site. Regimens of administration can be readily determined based on factors such as exact nature and type of the disease being treated, the severity of the disease, the age and general physical condition of the subject, body weight of the subject, response of the individual subject, and the like.

The frequency of administration can depend on the half-life of the lyophilized or reconstituted recombinant bacteria or *Listeria* strains, immunogenic compositions, pharmaceutical compositions, or vaccines in the subject, the condition of the subject, and the route of administration, among other factors. The frequency can be, for example, daily, weekly, monthly, quarterly, or at irregular intervals in response to changes in the subject's condition or progression of the tumor or cancer being treated. The course of treatment can depend on the condition of the subject and other factors. For example, the course of treatment can be several weeks, several months, or several years (e.g., up to 2 years). For example, repeat administrations (doses) may be undertaken immediately following the first course of treatment or after an interval of days, weeks or months to achieve disease regression or suppression. Assessment may be determined by any known technique, including diagnostic methods such as imaging techniques, analysis of serum biomarkers, biopsy, or the presence, absence, or amelioration of disease-associated symptoms. As a specific example, the lyophilized or reconstituted recombinant bacteria or *Listeria* strains, immunogenic compositions, pharmaceutical compositions, or vaccines can be administered every 3 weeks for up to 2 years. In one example, a lyophilized or reconstituted recombinant bacteria or *Listeria* strain, an immunogenic composition, a pharmaceutical composition, or a vaccine disclosed herein is administered in increasing doses in order to increase the T-effector cell to regulatory T cell ratio and generate a more potent anti-disease immune response. Anti-disease immune responses can be further strengthened by providing the subject with cytokines including, for example, IFN-γ, TNF-α, and other cytokines known to enhance cellular immune response. See, e.g., U.S. Pat. No. 6,991,785, herein incorporated by reference in its entirety for all purposes.

Some methods may further comprise "boosting" the subject with additional lyophilized or reconstituted recombinant bacteria or *Listeria* strains, immunogenic compositions, pharmaceutical compositions, or vaccines or administering the lyophilized or reconstituted recombinant bacteria or *Listeria* strains, immunogenic compositions, pharmaceutical compositions, or vaccines multiple times. "Boosting" refers to administering an additional dose to a subject. For example, in some methods, 2 boosts are administered (or a total of 3 inoculations) are administered, 3 boosts are administered, 4 boosts are administered, 5 boosts are administered, or 6 or more boosts are administered. The number of dosages administered can depend on, for example, the response of the disease to the treatment.

Optionally, the lyophilized or reconstituted recombinant bacteria or *Listeria* strain, immunogenic composition, pharmaceutical composition, or vaccine used in the booster inoculation is the same as the lyophilized or reconstituted recombinant bacteria or *Listeria* strain, immunogenic composition, pharmaceutical composition, or vaccine used in the initial "priming" inoculation. Alternatively, the booster is different from the priming recombinant bacteria or *Listeria* strain, immunogenic composition, pharmaceutical composition, or vaccine. Optionally, the same dosages are used in the priming and boosting inoculations. Alternatively, a larger dosage is used in the booster, or a smaller dosage is used in the booster. The period between priming and boosting inoculations can be experimentally determined. For example, the period between priming and boosting inoculations can be 1 week, 2 weeks, 3 weeks, 4 weeks, 5 weeks, 6-8 weeks, or 8-10 weeks.

Heterologous prime boost strategies have been effective for enhancing immune responses and protection against numerous pathogens. See, e.g., Schneider et al. (1999) *Immunol. Rev.* 170:29-38; Robinson (2002) *Nat. Rev. Immunol.* 2:239-250; Gonzalo et al. (2002) *Vaccine* 20:1226-1231; and Tanghe (2001) *Infect. Immun.* 69:3041-3047, each of which is herein incorporated by reference in its entirety for all purposes. Providing antigen in different forms in the prime and the boost injections can maximize the immune response to the antigen. DNA vaccine priming followed by boosting with protein in adjuvant or by viral vector delivery of DNA encoding antigen is one effective way of improving antigen-specific antibody and CD4$^+$ T-cell responses or CD8$^+$ T-cell responses. See, e.g., Shiver et al. (2002) *Nature* 415: 331-335; Gilbert et al. (2002) *Vaccine* 20:1039-1045; Billaut-Mulot et al. (2000) *Vaccine* 19:95-102; and Sin et al. (1999) *DNA Cell Biol.* 18:771-779, each of which is herein incorporated by reference in its entirety for all purposes. As one example, adding CRL1005 poloxamer (12 kDa, 5% POE) to DNA encoding an antigen can enhance T-cell responses when subjects are vaccinated with a DNA prime followed by a boost with an adenoviral vector expressing the antigen. See, e.g., Shiver et al. (2002) *Nature* 415:331-335, herein incorporated by reference in its entirety for all purposes. As another example, a vector construct encoding an immunogenic portion of an antigen and a protein comprising the immunogenic portion of the antigen can be administered. See, e.g., US 2002/0165172, herein incorporated by reference in its entirety for all purposes. Similarly, an immune response of nucleic acid vaccination can be enhanced by simultaneous administration of (e.g., during the same immune response, in some embodiments within 0-10 or 3-7 days of each other) a polynucleotide and polypeptide of interest. See, e.g., U.S. Pat. No. 6,500,432, herein incorporated by reference in its entirety for all purposes.

The therapeutic methods disclosed herein can also comprise administering one or more additional compounds effective in preventing or treating a disease (e.g., a tumor or cancer). For example, an additional compound may comprise a compound useful in chemotherapy, such as amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil (5-FU), gemcitabine, gliadelimplants, hydroxycarbamide, idarubicin, ifosfamide, irinotecan, leucovorin, liposomaldoxorubicin, liposomaldaunorubicin, lomustine, melphalan, mercaptopurine, mesna, methotrexate, mitomycin, mitoxantrone, oxaliplatin, paclitaxel (Taxol), pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Alternatively, an additional compound can also comprise other biologics, including Herceptin® (trastuzumab) against the HER2 antigen, Avastin® (bevacizumab) against VEGF, or antibodies to the EGF receptor, such as Erbitux® (cetuximab), and Vectibix® (panitumumab). Alternatively, an additional compound can comprise other immunotherapies. Alternatively, the additional compound can be an indoleamine 2,3-dioxygenase (IDO) pathway inhibitor, such as 1-methyltryptophan (1MT), 1-methyltryptophan (1MT), Necrostatin-1, Pyridoxal Isonicotinoyl Hydrazone, Ebselen, 5-Methylindole-3-carboxaldehyde, CAY10581, an anti-IDO antibody, or a small molecule IDO inhibitor. IDO inhibition can enhance the efficacy of chemotherapeutic agents. The therapeutic methods disclosed herein can also be combined with radiation, stem cell treatment, surgery, or any other treatment.

Such additional compounds or treatments can precede the administration of a lyophilized or reconstituted recombinant bacteria or *Listeria* strain, an immunogenic composition, a pharmaceutical composition, or a vaccine disclosed herein, follow the administration of a lyophilized or reconstituted recombinant bacteria or *Listeria* strain, an immunogenic composition, a pharmaceutical composition, or a vaccine disclosed herein, or be simultaneous to the administration of a lyophilized or reconstituted recombinant bacteria or *Listeria* strain, an immunogenic composition, a pharmaceutical composition, or a vaccine disclosed herein.

Targeted immunomodulatory therapy is focused primarily on the activation of costimulatory receptors, for example by using agonist antibodies that target members of the tumor necrosis factor receptor superfamily, including 4-1BB, OX40, and GITR (glucocorticoid-induced TNF receptor-related). The modulation of GITR has demonstrated potential in both antitumor and vaccine settings. Another target for agonist antibodies are co-stimulatory signal molecules for T cell activation. Targeting costimulatory signal molecules may lead to enhanced activation of T cells and facilitation of a more potent immune response. Co-stimulation may also help prevent inhibitory influences from checkpoint inhibition and increase antigen-specific T cell proliferation.

Listeria-based immunotherapy acts by inducing the de novo generation of tumor antigen-specific T cells that infiltrate and destroy the tumor and by reducing the numbers and activities of immunosuppressive regulatory T cells (Tregs) and myeloid-derived suppressor cells (MDSCs) in the tumor microenvironment. Antibodies (or functional fragments thereof) for T cell co-inhibitory or co-stimulatory receptors (e.g., checkpoint inhibitors CTLA-4, PD-1, TIM-3, LAG3 and co-stimulators CD137, OX40, GITR, and CD40) can have synergy with Listeria-based immunotherapy.

Thus, some methods can comprise further administering a composition comprising an immune checkpoint inhibitor antagonist, such as a PD-1 signaling pathway inhibitor, a CD-80/86 and CTLA-4 signaling pathway inhibitor, a T cell membrane protein 3 (TIM3) signaling pathway inhibitor, an adenosine A2a receptor (A2aR) signaling pathway inhibitor, a lymphocyte activation gene 3 (LAG3) signaling pathway inhibitor, a killer immunoglobulin receptor (KIR) signaling pathway inhibitor, a CD40 signaling pathway inhibitor, or any other antigen-presenting cell/T cell signaling pathway inhibitor. Examples of immune checkpoint inhibitor antagonists include an anti-PD-L1/PD-L2 antibody or fragment thereof, an anti-PD-1 antibody or fragment thereof, an anti-CTLA-4 antibody or fragment thereof, or an anti-B7-H4 antibody or fragment thereof. For example, an anti PD-1 antibody can be administered to a subject at 5-10 mg/kg every 2 weeks, 5-10 mg/kg every 3 weeks, 1-2 mg/kg every 3 weeks, 1-10 mg/kg every week, 1-10 mg/kg every 2 weeks, 1-10 mg/kg every 3 weeks, or 1-10 mg/kg every 4 weeks.

Likewise, some methods can further comprise administering a T cell stimulator, such as an antibody or functional fragment thereof binding to a T-cell receptor co-stimulatory molecule, an antigen presenting cell receptor binding co-stimulatory molecule, or a member of the TNF receptor superfamily. The T-cell receptor co-stimulatory molecule can comprise, for example, CD28 or ICOS. The antigen presenting cell receptor binding co-stimulatory molecule can comprise, for example, a CD80 receptor, a CD86 receptor, or a CD46 receptor. The TNF receptor superfamily member can comprise, for example, glucocorticoid-induced TNF receptor (GITR), OX40 (CD134 receptor), 4-1BB (CD137 receptor), or TNFR25.

For example, some methods can further comprise administering an effective amount of a composition comprising an antibody or functional fragment thereof binding to a T-cell receptor co-stimulatory molecule or an antibody or functional fragment thereof binding to an antigen presenting cell receptor binding a co-stimulatory molecule. The antibody can be, for example, an anti-TNF receptor antibody or antigen-binding fragment thereof (e.g., TNF receptor superfamily member glucocorticoid-induced TNF receptor (GITR), OX40 (CD134 receptor), 4-1BB (CD137 receptor), or TNFR25), an anti-OX40 antibody or antigen-binding fragment thereof, or an anti-GITR antibody or antigen binding fragment thereof. Alternatively, other agonistic molecules can be administered (e.g., GITRL, an active fragment of GITRL, a fusion protein containing GITRL, a fusion protein containing an active fragment of GITRL, an antigen presenting cell (APC)/T cell agonist, CD134 or a ligand or fragment thereof, CD137 or a ligand or fragment thereof, or an inducible T cell costimulatory (ICOS) or a ligand or fragment thereof, or an agonistic small molecule).

In a specific example, some methods can further comprise administering an anti-CTLA-4 antibody or a functional fragment thereof and/or an anti-CD137 antibody or functional fragment thereof. For example, the anti-CTLA-4 antibody or a functional fragment thereof or the anti-CD137 antibody or functional fragment thereof can be administered about 72 hours after the first dose of recombinant fusion polypeptide, nucleic acids encoding a recombinant fusion polypeptide, recombinant bacteria or Listeria strain, immunogenic composition, pharmaceutical composition, or vaccine, or about 48 hours after the first dose of recombinant fusion polypeptide, nucleic acids encoding a recombinant fusion polypeptide, recombinant bacteria or Listeria strain, immunogenic composition, pharmaceutical composition, or vaccine. The anti-CTLA-4 antibody or a functional fragment thereof or anti-CD137 antibody or functional fragment thereof can be administered at a dose, for example, of about 0.05 mg/kg and about 5 mg/kg. A recombinant Listeria strain or immunogenic composition comprising a recombinant Listeria strain can be administered at a dose, for example, of about $1\times10^9$ CFU. Some such methods can further comprise administering an effective amount of an anti-PD-1 antibody or functional fragment thereof.

Methods for assessing efficacy of cancer immunotherapies are well-known and are described, for example, in Dzojic et al. (2006) *Prostate* 66(8):831-838; Naruishi et al. (2006) *Cancer Gene Ther.* 13(7):658-663, Sehgal et al. (2006) *Cancer Cell Int.* 6:21), and Heinrich et al. (2007) *Cancer Immunol Immunother* 56(5):725-730, each of which is herein incorporated by reference in its entirety for all purposes. As one example, for prostate cancer, a prostate cancer model can be to test methods and compositions disclosed herein, such as a TRAMP-C2 mouse model, a 178-2 BMA cell model, a PAIII adenocarcinoma cells model, a PC-3M model, or any other prostate cancer model.

Alternatively or additionally, the immunotherapy can be tested in human subjects, and efficacy can be monitored using known. Such methods can include, for example, directly measuring CD4+ and CD8+ T cell responses, or measuring disease progression (e.g., by determining the number or size of tumor metastases, or monitoring disease symptoms such as cough, chest pain, weight loss, and so forth). Methods for assessing the efficacy of a cancer immunotherapy in human subjects are well-known and are described, for example, in Uenaka et al. (2007) *Cancer Immun.* 7:9 and Thomas-Kaskel et al. (2006) *Int J Cancer* 119(10):2428-2434, each of which is herein incorporated by reference in its entirety for all purposes.

VII. Kits

Also provided are kits comprising a reagent utilized in performing a method disclosed herein or kits comprising a composition, tool, or instrument disclosed herein.

For example, such kits can comprise a lyophilized recombinant bacteria or Listeria strain disclosed herein, an immunogenic composition disclosed herein, a pharmaceutical composition disclosed herein, or a vaccine disclosed herein. Such kits can also comprise a solvent or diluent for reconstituting the lyophilized recombinant bacteria or Listeria strain. In addition, such kits can additionally comprise an instructional material which describes use of the lyophilized recombinant bacteria or Listeria strain, the immunogenic composition, the pharmaceutical composition, or the vaccine to perform the methods disclosed herein. Such kits can optionally further comprise an applicator. Although model kits are described below, the contents of other useful kits will be apparent in light of the present disclosure.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

Listing of Embodiments

The subject matter disclosed herein includes, but is not limited to, the following embodiments.

1. A method for producing a lyophilized composition comprising a *Listeria* strain, comprising: (a) providing a composition comprising a *Listeria* strain in a formulation comprising a buffer and sucrose; (b) cooling the composition provided in step (a) at a holding temperature between about −32° C. and about −80° C. in a freezing step; (c) exposing the composition produced by step (b) to a vacuum at a holding temperature between about −10° C. and about −30° C. in a primary drying step; and (d) exposing the composition produced by step (c) to a vacuum at a holding temperature between about −5° C. and about 25° C. in a secondary drying step, whereby the lyophilized composition is produced.

2. The method of embodiment 1, wherein prior to step (a), a stress response is induced in the *Listeria* strain by exposing the *Listeria* strain to a decreased temperature.

3. The method of embodiment 1, wherein prior to step (a), a stress response is not induced in the *Listeria* strain by exposing the *Listeria* strain to a decreased temperature.

4. The method of any preceding embodiment, wherein the *Listeria* strain used in the composition in step (a) is a frozen *Listeria* strain that is thawed prior to step (a).

5. The method of embodiment 4, wherein the concentration of the frozen *Listeria* strain being thawed is between about 1×10E9 to about 1×10E10 colony forming units (CFU) per milliliter.

6. The method of embodiment 4 or 5, wherein the frozen *Listeria* strain is thawed at about 2° C. to about 37° C.

7. The method of embodiment 6, wherein the frozen *Listeria* strain is thawed at about 20° C. to about 37° C.

8. The method of embodiment 7, wherein the frozen *Listeria* strain is thawed at about 32° C. and about 37° C.

9. The method of embodiment 8, wherein the frozen *Listeria* strain is thawed at about 37° C.

10. The method of any one of embodiments 4-9, wherein the frozen *Listeria* strain is thawed for no more than 8 hours.

11. The method of any one of embodiments 4-10, wherein the frozen *Listeria* strain is held at about 2° C. to about 8° C. for no more than 24 hours after thawing.

12. The method of any one of embodiments 1-3, wherein the *Listeria* strain used in the composition in step (a) is freshly cultured prior to step (a).

13. The method of any preceding embodiment, wherein the buffer is a phosphate buffer.

14. The method of any preceding embodiment, wherein the formulation comprises about 1% to about 5% w/v sucrose.

15. The method of embodiment 14, wherein the formulation comprises about 2% to about 3% w/v sucrose.

16. The method of embodiment 15, wherein the formulation comprises about 2.5% w/v sucrose.

17. The method of any preceding embodiment, wherein the formulation comprises about 1×10E9 to about 1×10E10 colony forming units (CFU) of *Listeria* per milliliter.

18. The method of any preceding embodiment, wherein the formulation does not comprise one or more of trehalose, monosodium glutamate (MSG), and recombinant human serum albumin (rHSA).

19. The method of embodiment 18, wherein the formulation does not comprise trehalose, MSG, or rHSA.

20. The method of any preceding embodiment, wherein the holding temperature in the freezing step (b) is between about −40° C. and about −50° C.

21. The method of embodiment 20, wherein the holding temperature in the freezing step (b) is about −45° C.

22. The method of any preceding embodiment, wherein the freezing step (b) comprises decreasing the temperature to the holding temperature at a rate of about 1° C. per minute.

23. The method of any preceding embodiment, wherein the cooling in the freezing step (b) is for about 2 hours to about 4 hours.

24. The method any preceding embodiment, wherein cooling in the freezing step (b) comprises holding the composition at the holding temperature for about 2 hours.

25. The method of any preceding embodiment, wherein the holding temperature in the primary drying step (c) is between about −12° C. and about −22° C.

26. The method of embodiment 25, wherein the holding temperature in the primary drying step (c) is between about −17° C. and about −19° C.

27. The method of embodiment 26, wherein the holding temperature in the primary drying step (c) is about −18° C.

28. The method of any preceding embodiment, wherein the primary drying step (c) comprises increasing the temperature to the holding temperature at a rate of about 1° C. per minute.

29. The method of any preceding embodiment, wherein the primary drying step (c) is for about 25 hours to about 35 hours.

30. The method of any preceding embodiment, wherein the end of the primary drying step (c) is about 12 to about 16 hours after the composition has reached holding temperature.

31. The method of any preceding embodiment, wherein the primary drying step (c) is at a vacuum pressure of about 0.09 mbar.

32. The method of any preceding embodiment, wherein the holding temperature in the secondary drying step (d) is between about −5° C. and about 20° C.

33. The method of embodiment 32, wherein the holding temperature in the secondary drying step (d) is between about −5° C. and about 5° C.

34. The method of embodiment 33, wherein the holding temperature in the secondary drying step (d) is about 0° C.

35. The method of any preceding embodiment, wherein the secondary drying step (d) comprises increasing the temperature to the holding temperature at a rate of about 0.2° C. per minute.

36. The method of any preceding embodiment, wherein the secondary drying step (d) is for about 1 hour to about 10 hours.

37. The method any preceding embodiment, wherein the secondary drying step (d) comprises holding the composition at the holding temperature for about 2 hours to about 6 hours.

38. The method any embodiment 37, wherein the secondary drying step (d) comprises holding the composition at the holding temperature for about 5 hours to about 6 hours.

39. The method of any preceding embodiment, wherein the secondary drying step (d) is at a vacuum pressure of about 0.09 mbar.

40. The method of any preceding embodiment, wherein the residual moisture in the lyophilized composition is between about 1% and about 5%.

41. The method of embodiment 40, wherein the residual moisture in the lyophilized composition is between about 2% and about 4%.

42. The method of any preceding embodiment, wherein the residual moisture in the lyophilized composition is at least about 2.5%.

43. The method of embodiment 42, wherein the residual moisture in the lyophilized composition is at least about 3%.

44. The method of any preceding embodiment, wherein the lyophilized composition shows at least about 60% viability after storage at between about −20° C. and about 4° C. for about 12 months.

45. The method of embodiment 44, wherein the lyophilized composition shows at least about 75% viability after storage at between about −20° C. and about 4° C. for about 12 months.

46. The method of embodiment 45, wherein the lyophilized composition shows at least about 80% viability after storage at between about −20° C. and about 4° C. for about 12 months.

47. The method of any preceding embodiment, wherein the *Listeria* strain is a recombinant *Listeria monocytogenes* strain.

48. The method of any preceding embodiment, wherein the *Listeria* strain is a recombinant *Listeria monocytogenes* strain, and wherein the buffer is a phosphate buffer, and wherein the formulation comprises about 2% to about 3% w/v sucrose, and wherein the formulation does not comprise trehalose, MSG, or rHSA, and wherein the formulation comprises about 1×10E9 to about 1×10E10 colony forming units (CFU) of *Listeria* per milliliter, and wherein the holding temperature in the freezing step (a) is between about −40° C. and about −50° C., and wherein the holding temperature in the primary drying step (c) is between −17° C. and −19° C., and wherein the holding temperature in the secondary drying step (d) is between −1° C. and 1° C., and wherein the residual moisture in the lyophilized composition is between about 2.5% and about 4%.

49. The method of 48, wherein the *Listeria* strain used in the composition in step (a) is a frozen *Listeria* strain that is thawed prior to step (a), and wherein the concentration of the frozen *Listeria* strain being thawed is between about 1×10E9 to about 1×10E10 colony forming units (CFU) per milliliter, and wherein the frozen *Listeria* strain is thawed at about 37° C., and wherein the frozen *Listeria* strain is thawed for no more than 8 hours, and wherein the frozen *Listeria* strain is held at about 2° C. to about 8° C. for no more than 24 hours after thawing.

50. The method of any preceding embodiment, wherein the *Listeria* strain is a recombinant *Listeria* strain comprising a nucleic acid comprising a first open reading frame encoding a fusion polypeptide, wherein the fusion polypeptide comprises a PEST-containing peptide fused to a disease-associated antigenic peptide.

51. The method of embodiment 50, wherein the recombinant *Listeria* strain is an attenuated *Listeria monocytogenes* strain comprising a deletion of or inactivating mutation in prfA, wherein the nucleic acid is in an episomal plasmid and comprises a second open reading frame encoding a D133V PrfA mutant protein.

52. The method of embodiment 50, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

53. A formulation for lyophilization of a *Listeria* strain, comprising: (1) the *Listeria* strain; (2) a phosphate buffer; and (3) sucrose.

54. The formulation of embodiment 53, wherein the *Listeria* strain is a strain in which a stress response has been induced by exposing the *Listeria* strain to a decreased temperature.

55. The formulation of embodiment 53 or 54, wherein the *Listeria* strain is from a frozen *Listeria* stock.

56. The formulation of embodiment 53 or 54, wherein the *Listeria* strain is from a freshly cultured *Listeria* stock.

57. The formulation of any one of embodiments 53-56, wherein the formulation comprises about 1% to about 5% w/v sucrose.

58. The formulation of embodiment 57, wherein the formulation comprises about 2% to about 3% w/v sucrose.

59. The formulation of embodiment 58, wherein the formulation comprises about 2.5% w/v sucrose.

60. The formulation of any one of embodiments 53-59, wherein the formulation does not comprise one or more of trehalose, monosodium glutamate (MSG), and recombinant human serum albumin (rHSA).

61. The formulation of embodiment 60, wherein the formulation does not comprise trehalose, MSG, or rHSA.

62. The formulation of any one of embodiments 53-61, wherein the *Listeria* strain is a recombinant *Listeria monocytogenes* strain.

63. The formulation of any one of embodiments 53-62, wherein the *Listeria* strain is a recombinant *Listeria monocytogenes* strain, and wherein the formulation comprises about 2% to about 3% w/v sucrose, and wherein the formulation does not comprise trehalose, MSG, or rHSA.

64. The formulation of any one of embodiments 53-63, wherein the *Listeria* strain is a recombinant *Listeria* strain comprising a nucleic acid comprising a first open reading frame encoding a fusion polypeptide, wherein the fusion polypeptide comprises a PEST-containing peptide fused to a disease-associated antigenic peptide.

65. The formulation of embodiment 64, wherein the recombinant *Listeria* strain is an attenuated *Listeria monocytogenes* strain comprising a deletion of or inactivating mutation in prfA, wherein the nucleic acid is in an episomal plasmid and comprises a second open reading frame encoding a D133V PrfA mutant protein.

66. The formulation of embodiment 64, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

67. A lyophilized composition produced by the method of any one of embodiments 1-52.

68. A lyophilized composition comprising a *Listeria* strain, a phosphate buffer, and sucrose.

69. The lyophilized composition of embodiment 68, wherein the lyophilized composition does not comprise one or more of trehalose, monosodium glutamate (MSG), and recombinant human serum albumin (rHSA).

70. The lyophilized composition of embodiment 69, wherein the lyophilized composition does not comprise trehalose, MSG, or rHSA.

71. The lyophilized composition of any one of embodiments 67-70, wherein the residual moisture in the lyophilized composition is between about 1% and about 5%.

72. The lyophilized composition of embodiment 71, wherein the residual moisture in the lyophilized composition is between about 2% and about 4%.

73. The lyophilized composition of any one of embodiments 67-72, wherein the residual moisture in the lyophilized composition is at least about 2.5%.

74. The lyophilized composition of embodiment 73, wherein the residual moisture in the lyophilized composition is at least about 3%.

75. A lyophilized composition comprising a *Listeria* strain, wherein the residual moisture in the lyophilized composition is at least about 2.5%.

76. The lyophilized composition of any one of embodiments 67-75, wherein the lyophilized composition shows at least about 60% viability after storage at between about −20° C. and about 4° C. for about 12 months.

77. The lyophilized composition of embodiment 76, wherein the lyophilized composition shows at least about 75% viability after storage at between about −20° C. and about 4° C. for about 12 months.

78. The lyophilized composition of embodiment 77, wherein the lyophilized composition shows at least about 80% viability after storage at between about −20° C. and about 4° C. for about 12 months.

79. The lyophilized composition of any one of embodiments 67-78, wherein the *Listeria* strain is a recombinant *Listeria monocytogenes* strain.

80. The lyophilized composition of any one of embodiments 67-79, wherein the *Listeria* strain is a recombinant *Listeria monocytogenes* strain, and wherein the lyophilized composition does not comprise trehalose, MSG, or rHSA, and wherein the residual moisture in the lyophilized composition is between 2.5% and 4%.

81. The lyophilized composition of any one of embodiments 67-80, wherein the *Listeria* strain is a recombinant *Listeria* strain comprising a nucleic acid comprising a first open reading frame encoding a fusion polypeptide, wherein the fusion polypeptide comprises a PEST-containing peptide fused to a disease-associated antigenic peptide.

82. The lyophilized composition of embodiment 81, wherein the recombinant *Listeria* strain is an attenuated *Listeria monocytogenes* strain comprising a deletion of or inactivating mutation in prfA, wherein the nucleic acid is in an episomal plasmid and comprises a second open reading frame encoding a D133V PrfA mutant protein.

83. The lyophilized composition of embodiment 81, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

84. A method of preparing a frozen *Listeria* strain for lyophilization, comprising thawing the frozen *Listeria* strain at a temperature between about 20° C. and about 37° C.

85. The method of embodiment 84, wherein the temperature is between about 32° C. and about 37° C.

86. The method of embodiment 85, wherein the temperature is about 37° C.

87. The method of any one of embodiments 84-86, wherein the frozen *Listeria* strain is thawed for no more than 8 hours.

88. The method of any one of embodiments 84-87, wherein the frozen *Listeria* strain is held at about 2° C. to about 8° C. for no more than 24 hours after thawing.

89. The method of any one of embodiments 84-88, wherein the frozen *Listeria* strain is thawed in a formulation comprising a buffer and sucrose.

90. The method of embodiment 89, wherein the formulation comprises about 1% to about 5% w/v sucrose.

91. The method of embodiment 90, wherein the formulation comprises about 2% to about 3% w/v sucrose.

92. The method of embodiment 91, wherein the formulation comprises about 2.5% w/v sucrose.

93. The method of any one of embodiments 89-92, wherein the formulation does not comprise one or more of trehalose, monosodium glutamate (MSG), and recombinant human serum albumin (rHSA).

94. The method of embodiment 93, wherein the formulation does not comprise trehalose, MSG, or rHSA.

95. The method of any one of embodiments 89-94, wherein the *Listeria* strain is a recombinant *Listeria monocytogenes* strain.

96. The method of any one of embodiments 89-95, wherein the *Listeria* strain is a recombinant *Listeria monocytogenes* strain, and wherein the formulation comprises about 2% to about 3% w/v sucrose, and wherein the formulation does not comprise trehalose, MSG, or rHSA.

The subject matter disclosed herein also includes, but is not limited to, the following embodiments.

1. A method for producing a lyophilized composition comprising a *Listeria* strain, comprising: (a) providing a composition comprising a *Listeria* strain in a formulation comprising a buffer and sucrose; (b) cooling the composition provided in step (a) in a freezing step, optionally wherein the temperature is between about −32° C. and −80° C.; (c) exposing the composition produced by step (b) to a vacuum in a primary drying step, optionally wherein the temperature is between about −10° C. and −30° C.; and (d) exposing the composition produced by step (c) to a vacuum in a secondary drying step, optionally wherein the temperature is between about 5° C. and 25° C., optionally wherein the temperature is between about 5° C. and 20° C., whereby the lyophilized composition is produced.

2. The method of embodiment 1, wherein prior to step (a), a stress response is induced in the *Listeria* strain by exposing the *Listeria* strain to a decreased temperature.

3. The method of embodiment 1, wherein prior to step (a), a stress response is not induced in the *Listeria* strain by exposing the *Listeria* strain to a decreased temperature.

4. The method of any preceding embodiment, wherein the *Listeria* strain used in the composition in step (a) is a frozen *Listeria* strain that was thawed prior to step (a).

5. The method of any one of embodiments 1-3, wherein the *Listeria* strain used in the composition in step (a) was freshly cultured prior to step (a).

6. The method of any preceding embodiment, wherein the buffer is a phosphate buffer.

7. The method of any preceding embodiment, wherein the formulation comprises 1% to 5% w/v sucrose.

8. The method of embodiment 7, wherein the formulation comprises 2% to 3% w/v sucrose.

9. The method of any preceding embodiment, wherein the formulation does not comprise one or more of trehalose, monosodium glutamate (MSG), and recombinant human serum albumin (rHSA).

10. The method of embodiment 9, wherein the formulation does not comprise trehalose, MSG, or rHSA.

11. The method of any preceding embodiment, wherein the temperature in the freezing step (b) is between −40° C. and −50° C.

12. The method of any preceding embodiment, wherein the cooling in the freezing step (b) is for 2-4 hours.

13. The method of any preceding embodiment, wherein the temperature in the primary drying step (c) is between −12° C. and −22° C.

14. The method of embodiment 13, wherein the temperature in the primary drying step (c) is between −17° C. and −19° C.

15. The method of any preceding embodiment, wherein the primary drying the primary drying step (c) is for 20-30 hours.

16. The method of any preceding embodiment, wherein the temperature in the secondary drying step (d) is between 10° C. and 20° C.

17. The method of any preceding embodiment, wherein the secondary drying step (d) is for 1-10 hours.

18. The method of embodiment 17, wherein the secondary drying step (d) is for 1-3 hours.

19. The method of any preceding embodiment, wherein the residual moisture in the lyophilized composition is between 1% and 5%.

20. The method of embodiment 19, wherein the residual moisture in the lyophilized composition is between 3% and 4%.

21. The method of any preceding embodiment, wherein the lyophilized composition shows at least 60% viability after storage at −20° C. or 4° C. for 6 months.

22. The method of embodiment 21, wherein the lyophilized composition shows at least 75% viability after storage at −20° C. or 4° C. for 6 months.

23. The method of embodiment 22, wherein the lyophilized composition shows at least 80% viability after storage at −20° C. or 4° C. for 6 months.

24. The method of any preceding embodiment, wherein the *Listeria* strain is a recombinant *Listeria monocytogenes* strain.

25. The method of any preceding embodiment, wherein the *Listeria* strain is a recombinant *Listeria monocytogenes* strain, and wherein the buffer is a phosphate buffer, and wherein the formulation comprises 2% to 3% w/v sucrose, and wherein the formulation does not comprise trehalose, MSG, or rHSA, and wherein the temperature in the primary drying step (c) is between −17° C. and −19° C., wherein the temperature in the secondary drying step (d) is between 10° C. and 20° C., and wherein the residual moisture in the lyophilized composition is between 3% and 4%.

26. The method of any preceding embodiment, wherein the *Listeria* strain is a recombinant *Listeria* strain comprising a nucleic acid comprising a first open reading frame encoding a fusion polypeptide, wherein the fusion polypeptide comprises a PEST-containing peptide fused to a disease-associated antigenic peptide.

27. The method of embodiment 26, wherein the recombinant *Listeria* strain is an attenuated *Listeria monocytogenes* strain comprising a deletion of or inactivating mutation in prfA, wherein the nucleic acid is in an episomal plasmid and comprises a second open reading frame encoding a D133V PrfA mutant protein.

28. The method of embodiment 26, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

29. A formulation for lyophilization of a *Listeria* strain, comprising: (1) the *Listeria* strain; (2) a phosphate buffer; and (3) sucrose.

30. The formulation of embodiment 29, wherein the *Listeria* strain is a strain in which a stress response has been induced by exposing the *Listeria* strain to a decreased temperature.

31. The formulation of embodiment 29 or 30, wherein the *Listeria* strain is from a frozen *Listeria* stock.

32. The formulation of embodiment 29 or 30, wherein the *Listeria* strain is a from a freshly cultured *Listeria* stock.

33. The formulation of any one of embodiments 29-32, wherein the formulation comprises 1% to 5% w/v sucrose.

34. The formulation of embodiment 33, wherein the formulation comprises 2% to 3% w/v sucrose.

35. The formulation of any one of embodiments 29-34, wherein the formulation does not comprise one or more of trehalose, monosodium glutamate (MSG), and recombinant human serum albumin (rHSA).

36. The formulation of embodiment 35, wherein the formulation does not comprise trehalose, MSG, or rHSA.

37. The formulation of any one of embodiments 29-36, wherein the *Listeria* strain is a recombinant *Listeria monocytogenes* strain.

38. The formulation of any one of embodiments 29-37, wherein the *Listeria* strain is a recombinant *Listeria monocytogenes* strain, and wherein the formulation comprises 2% to 3% w/v sucrose, and wherein the formulation does not comprise trehalose, MSG, or rHSA.

39. The formulation of any one of embodiments 29-38, wherein the *Listeria* strain is a recombinant *Listeria* strain comprising a nucleic acid comprising a first open reading frame encoding a fusion polypeptide, wherein the fusion polypeptide comprises a PEST-containing peptide fused to a disease-associated antigenic peptide.

40. The formulation of embodiment 39, wherein the recombinant *Listeria* strain is an attenuated *Listeria monocytogenes* strain comprising a deletion of or inactivating mutation in prfA, wherein the nucleic acid is in an episomal plasmid and comprises a second open reading frame encoding a D133V PrfA mutant protein.

41. The formulation of embodiment 39, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

42. A lyophilized composition produced by the method of any one of embodiments 1-28.

43. A lyophilized composition comprising a *Listeria* strain, a phosphate buffer, and sucrose.

44. The lyophilized composition of embodiment 43, wherein the lyophilized composition does not comprise one or more of trehalose, monosodium glutamate (MSG), and recombinant human serum albumin (rHSA).

45. The lyophilized composition of embodiment 44, wherein the lyophilized composition does not comprise trehalose, MSG, or rHSA.

46. The lyophilized composition of any one of embodiments 42-45, wherein the residual moisture in the lyophilized composition is between 1% and 5%.

47. The lyophilized composition of embodiment 46, wherein the residual moisture in the lyophilized composition is between 2% and 4%.

48. The lyophilized composition of embodiment 47, wherein the residual moisture in the lyophilized composition is between 3% and 4%.

49. The lyophilized composition of any one of embodiments 42-48, wherein the lyophilized composition shows at least 60% viability after storage at −20° C. or 4° C. for 6 months.

50. The lyophilized composition of embodiment 49, wherein the lyophilized composition shows at least 75% viability after storage at −20° C. or 4° C. for 6 months.

51. The lyophilized composition of embodiment 50, wherein the lyophilized composition shows at least 80% viability after storage at −20° C. or 4° C. for 6 months.

52. The lyophilized composition of any one of embodiments 42-51, wherein the *Listeria* strain is a recombinant *Listeria monocytogenes* strain.

53. The lyophilized composition of any one of embodiments 42-52, wherein the *Listeria* strain is a recombinant *Listeria monocytogenes* strain, and wherein the lyophilized composition does not comprise trehalose, MSG, or rHSA, and wherein the residual moisture in the lyophilized composition is between 3% and 4%.

54. The formulation of any one of embodiments 42-53, wherein the *Listeria* strain is a recombinant *Listeria* strain comprising a nucleic acid comprising a first open reading frame encoding a fusion polypeptide, wherein the fusion polypeptide comprises a PEST-containing peptide fused to a disease-associated antigenic peptide.

55. The formulation of embodiment 54, wherein the recombinant *Listeria* strain is an attenuated *Listeria monocytogenes* strain comprising a deletion of or inactivating mutation in prfA, wherein the nucleic acid is in an episomal plasmid and comprises a second open reading frame encoding a D133V PrfA mutant protein.

56. The formulation of embodiment 54, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

TABLE 3

Description of Sequences.

| SEQ ID NO | Type | Description |
|---|---|---|
| 1 | DNA | SIINFEKL Tag v1 |
| 2 | DNA | SIINFEKL Tag v2 |
| 3 | DNA | SIINFEKL Tag v3 |
| 4 | DNA | SIINFEKL Tag v4 |
| 5 | DNA | SIINFEKL Tag v5 |
| 6 | DNA | SIINFEKL Tag v6 |
| 7 | DNA | SIINFEKL Tag v7 |
| 8 | DNA | SIINFEKL Tag v8 |
| 9 | DNA | SIINFEKL Tag v9 |
| 10 | DNA | SIINFEKL Tag v10 |
| 11 | DNA | SIINFEKL Tag v11 |
| 12 | DNA | SIINFEKL Tag v12 |
| 13 | DNA | SIINFEKL Tag v13 |
| 14 | DNA | SIINFEKL Tag v14 |
| 15 | DNA | SIINFEKL Tag v15 |
| 16 | Protein | SIINFEKL Tag |
| 17 | DNA | 3xFLAG Tag v1 |
| 18 | DNA | 3xFLAG Tag v2 |
| 19 | DNA | 3xFLAG Tag v3 |
| 20 | DNA | 3xFLAG Tag v4 |
| 21 | DNA | 3xFLAG Tag v5 |
| 22 | DNA | 3xFLAG Tag v6 |
| 23 | DNA | 3xFLAG Tag v7 |
| 24 | DNA | 3xFLAG Tag v8 |
| 25 | DNA | 3xFLAG Tag v9 |
| 26 | DNA | 3xFLAG Tag v10 |
| 27 | DNA | 3xFLAG Tag v11 |
| 28 | DNA | 3xFLAG Tag v12 |
| 29 | DNA | 3xFLAG Tag v13 |
| 30 | DNA | 3xFLAG Tag v14 |
| 31 | DNA | 3xFLAG Tag v15 |
| 32 | Protein | 3xFLAG Tag |
| 33 | Protein | Peptide Linker v1 |
| 34 | Protein | Peptide Linker v2 |
| 35 | Protein | Peptide Linker v3 |
| 36 | Protein | Peptide Linker v4 |
| 37 | Protein | Peptide Linker v5 |
| 38 | Protein | Peptide Linker v6 |
| 39 | Protein | Peptide Linker v7 |
| 40 | Protein | Peptide Linker v8 |
| 41 | Protein | Peptide Linker v9 |
| 42 | Protein | Peptide Linker v10 |
| 43 | Protein | PEST-Like Sequence v1 |
| 44 | Protein | PEST-Like Sequence v2 |
| 45 | Protein | PEST-Like Sequence v3 |
| 46 | Protein | PEST-Like Sequence v4 |
| 47 | Protein | PEST-Like Sequence v5 |
| 48 | Protein | PEST-Like Sequence v6 |
| 49 | Protein | PEST-Like Sequence v7 |
| 50 | Protein | PEST-Like Sequence v8 |
| 51 | Protein | PEST-Like Sequence v9 |
| 52 | Protein | PEST-Like Sequence v10 |
| 53 | Protein | PEST-Like Sequence v11 |
| 54 | Protein | PEST-Like Sequence v12 |
| 55 | Protein | LLO Protein v1 |
| 56 | Protein | LLO Protein v2 |
| 57 | Protein | N-Terminal Truncated LLO v1 |
| 58 | Protein | N-Terminal Truncated LLO v2 |
| 59 | Protein | N-Terminal Truncated LLO v3 |
| 60 | DNA | Nucleic Acid Encoding N-Terminal Truncated LLO v3 |
| 61 | Protein | ActA Protein v1 |

TABLE 3-continued

Description of Sequences.

| SEQ ID NO | Type | Description |
|---|---|---|
| 62 | Protein | ActA Protein v2 |
| 63 | Protein | ActA Fragment v1 |
| 64 | Protein | ActA Fragment v2 |
| 65 | Protein | ActA Fragment v3 |
| 66 | Protein | ActA Fragment v4 |
| 67 | Protein | ActA Fragment v5 |
| 68 | DNA | Nucleic Acid Encoding ActA Fragment v5 |
| 69 | Protein | ActA Fragment v6 |
| 70 | Protein | ActA Fragment v7 |
| 71 | DNA | Nucleic Acid Encoding ActA Fragment v7 |
| 72 | Protein | ActA Fragment Fused to Hly Signal Peptide |
| 73 | Protein | ActA Substitution |
| 74 | Protein | Cholesterol-Binding Domain of LLO |
| 75 | Protein | HLA-A2 restricted Epitope from NY-ESO-1 |
| 76 | Protein | Lm Alanine Racemase |
| 77 | Protein | Lm D-Amino Acid Aminotransferase |
| 78 | DNA | Nucleic Acid Encoding Lm Alanine Racemase |
| 79 | DNA | Nucleic Acid Encoding Lm D-Amino Acid Aminotransferase |
| 80 | Protein | Wild Type PrfA |
| 81 | DNA | Nucleic Acid Encoding Wild Type PrfA |
| 82 | Protein | D133V PrfA |
| 83 | DNA | Nucleic Acid Encoding D133V PrfA |
| 84 | DNA | 4X Glycine Linker G1 |
| 85 | DNA | 4X Glycine Linker G2 |
| 86 | DNA | 4X Glycine Linker G3 |
| 87 | DNA | 4X Glycine Linker G4 |
| 88 | DNA | 4X Glycine Linker G5 |
| 89 | DNA | 4X Glycine Linker G6 |
| 90 | DNA | 4X Glycine Linker G7 |
| 91 | DNA | 4X Glycine Linker G8 |
| 92 | DNA | 4X Glycine Linker G9 |
| 93 | DNA | 4X Glycine Linker G10 |
| 94 | DNA | 4X Glycine Linker G11 |
| 95 | Protein | Detoxified Listeriolysin O (dtLLO) |
| 96 | Protein | Modified Cholesterol-Binding Domain of dtLLO |
| 97 | Protein | LLO Signal Sequence |
| 98 | Protein | ActA Signal Sequence |
| 99 | Protein | Variant FLAG Tag |
| 100 | Protein | 10-Mer Peptide |

EXAMPLES

Example 1. Representative Drug Substance Preparation and Lyophilization Cycle

The typical current storage temperature for the ADXS-HER2 and ADXS-HPV (final liquid drug products) is −80° C., which interferes with the cold chain maintenance and poses supply chain challenges. Storage of *Listeria monocytogenes* final drug product (liquid) in a frozen state is inconvenient as the cold-chain must be strictly kept at all times to assure drug product efficacy and to avoid potential patient risks. ADXS-HER2, which is an attenuated, recombinant *Listeria monocytogenes* (Lm) transformed with a HER2/Neu fusion protein, is an Lm Technology™ immunotherapy product candidate being developed to target HER2 expressing cancers. Axalimogene filolisbac (ADXS-HPV) is an Lm Technology™ immunotherapy candidate developed for the treatment of HPV-associated cancers. It is an immunotherapy based on live attenuated *Listeria monocytogenes* that secretes fusion protein Lm-LLO-E7 targeting HPV-associated tumors. The storage of the final drug products in a frozen liquid state is inconvenient, as the cold chain must be kept at all times to assure drug efficacy and to avoid potential patient risks. Development of a lyophilization (lyo) cycle which favors the long term storage of the drug products at −20° C. while maintaining the cold chain would be beneficial. Hence, a study was performed to develop a lyophilization cycle which favors the long term storage of the drug products.

Drug Substance Process Overview for ADXS-HPV Liquid Frozen Formulations

ADXS-HPV propagation was carried out entirely within a single use closed system provided by rocking wave motion bioreactor technology. The single-use closed system consists of a product 20 L culture bag for fermentation, a tangential flow filtration (TFF) for concentration and buffer exchange and a product manifold for DS container filling. Each of these components were sterilized by gamma irradiation. The drug substance manufacturing process flow diagram with in-process controls is shown in FIG. 20.

1 M sodium hydroxide (NaOH) for pH control was prepared and sterile-filtered using two 0.2 μm filters in series into a 1 L pH control bag. The sterilizing filters were removed by cutting through a heat-sealed section of tubing. Fermentation media and pH control solution were prepared per Table 4 and sterile-filtered through two 0.2 μm filters in series into a sterile 5 L media addition bag. The sterilizing filters were removed by cutting through a heat-sealed section of tubing.

TABLE 4

Fermentation Media Formulation.

| Formulation | Components | Component Weights |
|---|---|---|
| Chloramphenicol Stock Solution | Chloramphenicol | 0.68 g |
|  | Ethanol, anhydrous | 20 mL |
| Fermentation Media (5 L) | TSB | QS to 5 kg |
|  | D (+) Glucose | 32.54 g |
|  | Chloramphenicol Stock Solution | 5 mL |
| pH Control Solution | 1M NaOH | 1 L |
| Overnight Culture | TSB | 100 mL |
|  | Chloramphenicol Stock | 100 μL |
| Glucose Feed | D (+) Glucose | 45.04 g |
|  | WFI | 250 mL |

Diafiltration/wash buffer was prepared per Table 5 and sterile-filtered through two 0.2 μm filters in series into a sterile 2×10 L bag. The sterilizing filters were removed by cutting through a heat-sealed section of tubing.

TABLE 5

Diafiltration Wash Buffer Formulation.

| Formulation | Components | Component Weights |
|---|---|---|
| Formulation Buffer (20 L, 2 × 10 L) | Potassium dihydrogen phosphate ($KH_2PO_4$), | 4.0 g |
|  | Disodium hydrogen orthophosphate ($Na_2HPO_4$) | 22.8 g |
|  | Sodium chloride (NaCl) | 160 g |
|  | Potassium chloride (KCl) | 4.0 g |
|  | Sucrose | 400 g |
|  | Water for Injection (WFI) | QS to 20.00 kg |

A 20 L culture bag was pre-connected with probes for dissolved oxygen and pH monitoring. It was then aseptically filled with 5 L of growth medium. The media addition bag was then removed by cutting through a heat-sealed section of tubing.

The wave bag was inflated with sterile-filtered compressed $O_2$. Sterile-filtered compressed $O_2$ was continuously fed during propagation at a rate of 1 L/minute and removed through an outlet port. The rocking angle was set at 10° with a rocking rate of 18 per minute.

The pH control bag and the glucose feed bag were aseptically connected to the culture bag. During propagation, the process was automatically monitored and controlled for temperature, pH, and dissolved oxygen by an integrated controlling system.

An overnight culture was initiated from the WCB by pipetting 1 mL of WCB into 100 mL of TSB and grown for approximately 12-16 hours until an OD600 of approximately 4. Then, 100 mL of the overnight culture was used to inoculate the production culture by aseptically transferring to the WAVE bag.

At four hours after inoculation, 200 mL of glucose was added to the culture. Growth proceeded to an $OD_{600}$ between 7.5 and 8.5. This corresponds to approximately $1 \times 10^{10}$ CFU/mL.

When the $OD_{600}$ reached the target concentration, the culture bag was connected, using Readymates, to the sterile TFF manifold for concentration and diafiltration against the formulation buffer. The TFF module used a 0.2 μm pore size hollow fiber filter for low shear requirements of cell separation applications.

A peristaltic pump was used to feed the fermentation culture into the TFF system primed with formulation buffer. The bulk culture in the recirculation loop was set to a flow rate of 8 L/hr. The fermentation broth was concentrated 5-fold to a mass of approximately 1000 g.

The diafiltration/washing of the harvest concentrate was performed with ≥8 diavolumes (≥8 L). The harvest DS was sampled from the TFF assembly using a sampling manifold welded to the TFF. Each sample bag port was heat-sealed for removal.

The $OD_{600}$ of the sample was measured and used to calculate the amount of dilution volume needed to reach an $OD_{600}$ of 8.0±0.5. The required amount of formulation buffer was pumped into the retentate bag to dilute the harvest to the required concentration. All volume transfers were controlled by weight change in the respective bags. The harvest was sampled and measured to confirm the required product concentration of $1 \times 10^{10}$ CFU/mL was achieved. DS was sampled for QC analysis using the sampling manifold.

The DS was distributed into 1 L aliquots in four 1 L product bags with the fifth bag being filled with all the remaining DS. Each bag was heat-sealed for removal from the assembly. Each bag was individually labeled with the appropriate information and then stored at −80±10° C.

TABLE 6

Drug Substance Processing Parameters.

| Control Description | Operating Set-Point or Range |
| --- | --- |
| Fermentation Media pH | 6.6-7.4 |
| Rocking Rate | 18 Rocks/minute |
| Rocking Angle | 10° |
| Dissolved O$_2$ Set Point | 35% |

Drug Product Process Overview for ADXS-HPV Liquid Frozen Formulations

The manufacturing process of drug product (DP) involved dilution of the BDS to a final concentration of $1 \times 10^9$ CFU/mL and aseptic filling of the formulated axalimogene filolisbac into sterile 4 mL glass vials, stoppering with 13 mm chlorobutyl stoppers and over-sealing with aluminum flip-off seals with polypropylene discs. The process flow diagram is shown in FIG. 21.

Frozen drug substance (DS), in 1 L bags, containing up to 5 L in 1 L aliquots, was stored at −80±10° C. until manufacture of DP. DS was thawed at ambient temperature with a target of 3 hours to initiate manufacture of DP.

Under Grade A conditions, up to 5 L was aseptically transferred via a pump into a dedicated sterile glass carboy assembly. The pooled bulk material in the carboy was stirred from 80-300 rpm during the material transfer and was then connected to the sterile disposable filling module using a sterile tube welder. For the proposed commercial process a 1:10 dilution step was performed with final formulation buffer to a targeted CFU of $1 \times 10^9$ CFU/mL.

Depyrogenated 4 mL (DIN 2R Type I borosilicate) glass vials were semi-automatically filled by a peristaltic pump with 1.2 mL of DS using a sterile, single use filling line and filling needle. Filled vials were immediately stoppered with sterilized chlorobutyl stoppers. During filling, the fill volume was controlled by weight checks on 1 vial in every 300±50 filled vials.

The finished vials were over sealed with aluminum crimp flip-off seals with polypropylene discs. The vials were externally wiped with a 0.35% acetic acid solution and were transferred to a Grade D room for 100% visual inspection.

Vials were visually inspected for container-closure defects or atypical appearance of product. Bulk packaged vials were stored at −80±10° C. until shipping to the labeling and packaging site.

TABLE 7

Drug Product Process Parameters

| Process Stage | In-Process Control Description | Set Point or Operating Range |
| --- | --- | --- |
| Bulk mixing | Stirring speed sample bottle, >3 L volume | 190-300 rpm |
| Bulk mixing | Stirring speed sample bottle, 2-3 L volume | 140-240 rpm |
| Bulk mixing | Stirring speed sample bottle, 1-2 L volume | 100-160 rpm |
| Bulk mixing | Stirring speed sample bottle, 0-1 L volume | 80-120 rpm |
| Aseptic filling | Average line speed | 1300 ± 200 vials/hr |
| Aseptic filling | Adjustment filling volume | 1.2 mL |
| Aseptic filling | Filling weight max. | 1.279 g |
| Aseptic filling | Filling weight min. | 1.181 g |
| Aseptic filling | Reverse impulse setting (peristaltic dosing system) | 2-3 |
| Aseptic filling | Acceleration setting (peristaltic dosing system) | 200 |
| Aseptic filling | Timer delay setting (peristaltic dosing system) | 0.3 s |
| Over sealing | Average line speed | 300 ± 50 vials/hr |
| Over sealing | Stopper safety setting | 12.2 cm |
| Over sealing | Capping station vertical height | 9.6 cm |
| Over sealing | Capping station horizontal height | 3.2 cm |
| Over sealing | Closure station top dead center | 7.2 cm |
| Over sealing | Closure station bottom dead center | 4.2 cm |

TABLE 8A

Specifications for Axalimogene Filolisbac Drug Product.

| Test | Test Type | Acceptance Criteria |
|---|---|---|
| Identification | | |
| Western Blot for HPV16-E7 | In-house method | Principal bands conform to reference standard |
| Western Blot for tLLO | In-house method | Principal bands conform to reference standard |
| Purity | | |
| Microbiological Examination | In-house method based on Ph. Eur. 2.6.12, 2.6.13 | Single species |
| Potency | | |
| J774 Infectivity | In-house method (Cell based plate assay) | $\geq 1 \times 10^3$ CFU/mL |
| Content | | |
| Viable Cell Count | In-house method | $3 \times 10^8$ CFU/mL- $5 \times 10^{10}$ CFU/mL |
| General | | |
| Appearance | Based on USP <1> | Free-flowing cream-colored suspension |
| Osmolality | Ph. Eur. 2.2.35 | 280 to 420 mOsm/kg |
| pH | Ph. Eur. 2.2.3 | 6.0 to 7.9 |
| Safety | | |
| Endotoxin | Ph. Eur. 2.6.14 | $\leq 35$ EU/mL |

TABLE 8B

Specifications for Axalimogene Filolisbac Drug Substance.

| Test | Test Type | Acceptance Criteria |
|---|---|---|
| Identity | | |
| Western blot for HPV16-E7[1] | In-house method | Principal bands conform to reference standard |
| Western blot for tLLO[1] | In-house method | Principal bands conform to reference standard |
| prfA Deletion[1] | In-house method (PCR) | prfA gene is not present on the chromosome |
| prfA Mutation[1] | In-house method (PCR) | Point mutation in prfA gene is present on the plasmid |
| Purity | | |
| Microbiological Examination[2] | In-house method based on Ph. Eur. 2.6.12 and Ph. Eur. 2.6.13 | Single species (Negative for the presence of Bacterial and Fungal contamination) |
| Percentage of Viable cells | In-house method (Fluorometric plate assay) | $\geq 60\%$ Viable cells |
| Potency | | |
| J774 Infectivity | In-house method (cell-based plate assay) | $\geq 1 \times 10^3$ CFU/mL |
| Content | | |
| Extractable Volume[1] | Based on USP <1> | $\geq 1$ mL |
| Viable Cell Count | In-house method | $3 \times 10^8$ CFU/mL- $5 \times 10^{10}$ CFU/mL |
| Plasmid Copy Number[1] | In-house method | 5 to 100 copies |
| General | | |
| Appearance | Based on USP <1> | Free-flowing cream-colored suspension |
| Osmolality[1] | Ph. Eur. 2.2.35 | 280 to 420 mOsm/kg |
| pH | Ph. Eur. 2.2.3 | 6.0 to 7.9 |
| Safety | | |
| Antibiotic Sensitivity[1] | In-House method | Resistant to 50 µg/mL streptomycin Resistant to 34 µg/mL chloramphenicol Sensitive to 0.25 µg/mL ampicillin Sensitive to 1 µg/mL tetracycline Sensitive to 1.5 µg/mL ciprofloxacin |
| Reversion of prfA Mutation[1] | In-house method (PCR) | No detectable reversion of point mutation in prfA gene on the plasmid |
| Endotoxin[2] | Ph. Eur. 2.6.14 | $\leq 35$ EU/mL |
| Container Closure Integrity[3] | USP<1207> | No ingress of dye |

Notes
[1] Tested only at release
[2] Tested at release and at the end of shelf life
[3] Tested for stability only
PCR = polymerase chain reaction, Ph. Eur. = European Pharmacopoeia, USP = United States Pharmacopeia.

Lyophilization as an Alternative

Drug product can also be lyophilized for long-term storage. Vials with drug product were loaded onto lyophilizer shelves that have been chilled to a refrigerated temperature, in some embodiments, about 4° C. The chamber door was closed, and the vials were cooled to a temperature just above the freezing point of the formulation by reducing the shelf temperature to around −4° C. and holding it there for about 30 minutes. The formulation was then frozen by ramping the shelf temperature at a rate of approximately 0.5° C./min to a temperature between −40° C. and −50° C., or about −45° C., and maintaining that temperature for several hours until all vials were frozen and the product temperatures were close to the shelf temperature. To conduct primary drying, the chamber was evacuated, and the pressure was maintained at about 0.09 mbar with sterile nitrogen. The shelf temperature was raised at about 1° C./min to a temperature between −18° C. and −22° C., or about −18° C., and maintained at that value until all product temperatures exceeded the shelf temperature for a minimum of about 10 hours. To conduct secondary drying, the shelf temperature was raised at about 0.2° C./min to a final value of 20° C. and kept there for at least 2 hours, while the pressure was maintained at about 0.09 mbar. At the end of this secondary drying time, the shelf temperature was reduced to about 10° C., then the pressure was increased to about 500 mbar with nitrogen, and the vials were stoppered within the lyophilizer. A representative lyophilization cycle is shown in Table 9.

TABLE 9

Representative Lyophilization Cycle.

| Step | Duration [hh:mm] | Shelf Temp. [° C.] | Vacuum [mbar] |
|---|---|---|---|
| Loading | N/A | 4 | Off |
| Freezing | 00:20 | −4 | Off |
|  | 00:30 | −4 | Off |
|  | 01:30 | −45 | Off |
|  | 02:00 | −45 | Off |
| Primary drying | N/A | −45 | 0.090 |
|  | 00:30 | −45 | 0.090 |
|  | 00:18 | −18 | 0.090 |
|  | 26:00* | −18 | 0.090 |
| Secondary drying | 03:10 | 20 | 0.090 |
|  | 02:00 | 20 | 0.090 |
| End of cycle | 00:10 | 10 | 0.090 |
|  | N/A | 10 | 0.090 |
| Stoppering | N/A | 10 | 500 |

*Until all product temperature probes have been above shelf temperature for at least 10 h.

Example 2. Optimization of Lyophilization Parameters for *Listeria monocytogenes*

The ADXS *Listeria monocytogenes* (Lm) drug products are currently formulated in a phosphate buffered saline ($KH_2PO_4$, $Na_2HPO_4$, KCl, NaCl) containing 2.0% sucrose with recommended storage conditions of −80° C. The ultra-low storage temperature poses challenges for cold chain maintenance and supply chain. Hence, a development program was initiated for the development of a stable lyophilized drug product (DP). The goal of the program was to develop a lyophilization (Lyo) process which favored the long-term storage of the drug products at −20° C. or 2-8° C. A series of experiments were performed with different parameters to develop and optimize the formulation, the pre-conditioning of cells, storage/handling of the drug substance and the lyophilization cycle. Through optimization of various parameters, a stable lyophilized formulation was developed which has demonstrated long-term (18 months) stability at both 2-8° C. and −20° C.

Parameters tested in the experiments below include formulation parameters (buffer composition (the solution in which the cells are lyophilized in), excipient composition (the inactive substance used to aid in stability), and $OD_{600}$ at the time of lyophilization), A series of experiments were performed with different test parameters to develop and optimize the formulation, the pre-conditioning of cells, and the lyophilization cycle. Formulation parameters tested included buffer composition (the solution in which the cells are lyophilized in), excipient composition (the inactive substance used to aid in stability), and $OD_{600}$ at the time of lyophilization. Preconditioning of cell parameters tested included fresh/frozen (the storage condition of the drug substance before lyophilization), induction of stress response prior to lyophilization (shift in pH and/or temperature), and drug substance hold time/temperature (conditions at which drug substance is thawed and held prior to lyophilization). Lyophilization cycle parameters tested included primary drying shelf temperature (heat input for sublimation of the frozen water), secondary drying shelf temperature (heat input for desorption of moisture remaining after primary drying), and addition of an annealing step (heating the frozen formulation to a temperature below 0° C. to allow rearrangement of the ice pore structure and possibly improve primary drying). Outcomes measured to assess the success of a lyophilization run included viable cell count (VCC) over time and under different conditions (stability at −80° C., stability at 2-8° C., stability at −20° C., and accelerated stability at 30° C.), residual moisture, and reconstitution time.

The experiments described below identified several findings that appeared to enhance the stability of the lyophilized product: (1) higher residual moisture improved the stability of the lyophilized product (WP7-Lyo4); (2) a higher shelf temperature during primary drying improved the stability of the lyophilized product (WP7-Lyo9); (3) preconditioning of the cells prior to lyophilization through heat shock improved the stability of the lyophilized product (WP7-Lyo5); (4) higher VCC demonstrated slight improvement in stability of the lyophilized drug product relative to lower VCC (WP7, Cycle 3); and (5) the data demonstrate that the storage of the drug substance in a 1 L LDPE bag and thawing at 37° C. prior to lyophilization improved stability of the lyophilized drug product (WP7, Cycle 3). The data show that a lyophilized drug product that is stable at both −20° C. and 2-8° C. long term has been successfully developed. The resulting drug product demonstrated good stability at both accelerated and intended storage conditions and low loss in potency due to lyophilization.

To identify and characterize lead formulations, Lyo1 and Lyo2 experiments were performed, which led to the identification of two phosphate-based formulations with 5% sucrose and with 5% sucrose plus amino acid (AA) mix (final concentrations: 36 mM arginine, 57 mM glutamic acid, and 7 mM isoleucine). The characterization of these lead formulations showed their critical temperatures to be close together, allowing for the development of one cycle for both formulations. The residual moisture targeting and evaluation experiments, Lyo3 and Lyo4, showed the best results for higher moisture levels at a sucrose level of 2.5% and allowed for the optimization of the sucrose level at 2.5% for further cycle development.

The three main areas of evaluation for the lyophilization cycle development study included: (1) formulation development for the screening of buffer and excipient; (2) cell culture development for the pre-conditioning of the cells prior to lyophilization; and (3) optimization of the lyophilization cycle for targeted residual moisture (RM). The series of experiments performed in the lyophilization (lyo) cycle development with the different parameters tested are summarized in Table 10.

TABLE 10

Summary of Experiments Performed in Lyophilization (Lyo) Cycle Development

| Process Step | Expt. No. | Expt. Description | Construct | Buffer | Excipients | OD | Primary Drying Shelf Temp. (° C.) | Secondary Drying Shelf Temp. (° C.) |
|---|---|---|---|---|---|---|---|---|
| Formulation | Lyo1 | Buffer Screen | HER2 | Citrate Phosphate MOPS | Sucrose, Trehalose, MSG, rHSA | 10 | −12 | 20 |

TABLE 10-continued

Summary of Experiments Performed in Lyophilization (Lyo) Cycle Development

| | | | | | | | | |
|---|---|---|---|---|---|---|---|---|
| | Lyo2 | | | Phosphate | Sucrose, rHSA, AA mix (amino acid mix) | 10, 2 | −12 | 20 |
| | | Characterization of Tc, Tg, and Tg' | HER2 | Phosphate | 5% sucrose 5% sucrose + AA mix | 10 | −22 | 20 |
| Lyo cycle | Lyo3 | Residual moisture targeting | HER2 | Phosphate | 5% sucrose 2.5% sucrose | 10 | −22 | 20 |
| | Lyo4 | Evaluation of residual moisture on stability | HER2 | Phosphate | 5% sucrose 2.5% sucrose | 10 | −22 | 20 |
| Cell culture/ pre-conditioning of cells | Lyo5 | Evaluation of stress treatments pre-lyophilization on stability | HER2 | Phosphate | 2.5% sucrose | 10 | −22 | 20 |
| | Lyo6 | Evaluation of temp-shift pre-lyophilization on stability | HPV | Phosphate | 2.5% sucrose | 10 | −22 | 20 |
| Lyo cycle | Lyo7 | Evaluation of temp-shift pre-lyophilization on stability | HPV | Phosphate | 2.5% sucrose | 10 | −30 | 20 |
| Cell culture/ pre-conditioni | Lyo8 | Hold time study | HPV | Phosphate | 2.5% sucrose | 10 | −22 | |
| Lyo cycle | Lyo9 | Evaluation of increased primary drying shelf temperature | HPV | Phosphate | 2.5% sucrose | 10 | −18 | 20 |
| | Lyo10 | Comparison of plus/minus temperature shift | HPV | Phosphate | 2.5% sucrose | 10 | −18 | 20 |
| | Lyo11 | Stability study without temperature shift | HPV | Phosphate | 2.5% sucrose | 10 | −18 | 20 |
| Cell-culture/ pre-conditioning of cells | Lyo12 | Stability study of fresh vs. frozen material using different thawing | HPV | Phosphate | 2.5% sucrose | 10 | −18 | 20 |
| Cell-culture/ pre-conditioning of cells | Lyo13 | Stability study of Fresh vs Fresh/formulated material stored 3 days at 2-8° C. | HPV | Phosphate | 2.5% sucrose | 10 | −18 | 20 |
| Lyo Cycle | Lyo14 | Evaluation of commercial presentation in 2R vials | HPV | Phosphate | 2.5% sucrose | 1.5 | −18 | 20 |
| Cell-culture/ Pre-conditioning of cells | Lyo15 | Stability study of Fresh vs. Frozen pellet/reconstituted material in 2R vials | HPV | Phosphate | 2.5% sucrose | 1.8 | −18 | 20 |

| Process Step | Expt. No. | Temp/pH Shift | DS Hold | % RM | Conditions Evaluated | Results and Conclusions |
|---|---|---|---|---|---|---|
| Formulation | Lyo1 Lyo2 | | | | 2-8° C., accelerated stability conditions 25° C. for 3 days. | Two phosphate-based formulations with 5% sucrose and 5% sucrose + AA mix performed well. These 2 formulations were used for further cycle development. The critical |

TABLE 10-continued

Summary of Experiments Performed in Lyophilization (Lyo) Cycle Development

| | | | | | | |
|---|---|---|---|---|---|---|
| | | | | | | temperatures were close together. Development of one cycle for both formulations. |
| Lyo cycle | Lyo3 | | | | | |
| | Lyo4 | | | ~5%, ~3%, and 1% | 2-8° C., accelerated stability conditions for 1, 2, and 3 days at 30° C. | Best results were at higher moisture levels for the sucrose level of 2.5%. The sucrose level was fixed at 2.5% and the moisture level was fixed at 3.5%. |
| Cell culture/ pre-conditioning of cells | Lyo5 | Group 1: control; Group 2: temp-shift; Group 3: pH-shift; Group 4: pH- and temp-shift | | 3.5% | 2-8° C., accelerated stability conditions for 1, 2, and 3 days at 30° C. | |
| | Lyo6 | Only temp-shift, no control | | 3.5% | | |
| Lyo cycle | Lyo7 | Only temp-shift, no control | | 3.5% | 2-8° C., −20° C., and accelerated stability conditions for 1, 2, and 3 days at 30° C. | Significant losses on accelerated stability with the decreased shelf temperature. |
| Cell culture/ pre-conditioni | Lyo8 | | Part A: fresh Part B: frozen hold | | 2-8° C., −20° C., and accelerated stability conditions for 1, 2, and 3 days at 30° C. | Part A showed better stability profile under accelerated conditions than Part B. |
| Lyo cycle | Lyo9 | Only temp-shift, no control | | 3.5% | 2-8° C., −20° C., and accelerated stability conditions for 1, 2, and 3 days at 30° C. | Improvement in accelerated stability was observed with increased shelf temperature. |
| | Lyo10 | Part A: without temp-shift Part B: with temp-shift | | 3.0% | 2-8° C., −20° C., and accelerated stability conditions for 1, 2, and 3 days at 30° C. | The results were comparable for with and without the temperature shift. |
| | Lyo11 | Without temp-shift | | 2.5%-3.0% | 2-8° C., −20° C., and accelerated stability conditions for 1, 2, and 3 days at 30° C. | |
| Cell-culture/ pre-conditioning of cells | Lyo12 | Without temp-shift | Part A: fresh Part B: frozen, thawed at 2-8° C. Part C: frozen, thawed at 37° C. and incubated 4 h | 2.5%-3.0% | 2-8° C., −20° C., and accelerated stability conditions for 1, 2, and 3 days at 30° C. | |
| Cell-culture/ pre-conditioning of cells | Lyo13 | Without temp-shift | Part A: Fresh; Part B: Stored 3 days at 2-8° C. | 2.5-3.0% | 2-8° C., −20° C. and Accelerated conditions for 1, 2, and 3 days and 30° C. | |
| Lyo Cycle | Lyo14 | Without temp-shift | | 2.5-3.0% | 2-8° C., −20° C. and Accelerated conditions for 1, 2, and 3 days and 30° C. | |
| Cell-culture/ Pre-conditioning of cells | Lyo15 | | Suspension A: Fresh; Suspension B: Frozen, thawed at 37° C. and resuspended | 2.5-3.0% | 2-8° C., −20° C. and Accelerated conditions for 1, 2, and 3 days and 30° C. | |

Description of Experiments
2.1. Screening and Characterization of a Lyophilization Formulation.

For the identification, optimization and characterization of 2-3 lead formulations with good stability that could be continued with during further cycle development, two lyophilization experiments (Lyo1, Lyo2) were executed and 6-month stability data was generated. The lead formulations from this study were then characterized for their critical temperatures Tc (collapse temperature), Tg' (glass transition temperature of the frozen formulation), and Tg (glass transition temperature of the lyophilized product).

The formulations used in Lyo1 were citrate-, phosphate- and MOPS-based formulations. The formulations used in Lyo2 were only phosphate-based formulations because phosphate-based formulation had better performance compared to citrate- and MOPS-based buffers and required the smallest process change as they were closest to the current drug substance formulation.

2.1.1. WP5-Lyo1.

Materials and Methods.

The ADXS-HER2 drug product was used for this study. $OD_{600}=10$ was evaluated. The buffers and excipients used in the formulations were as follows: Three different buffers were used in the formulations: citrate; phosphate; and MOPS (3-(N-morpholino)propanesulfonic acid). The stabilizer mix components (excipients) used in the formulations included various combinations of sucrose, trehalose, monosodium glutamate (MSG), and recombinant human serum albumin (rHSA).

Study Design.

Three different pH buffers combined with 6 different excipient combinations resulted in 18 different formulations. For each formulation, 20×6R vials were filled with 2 mL, resulting in a cake height of ~6.54 mm. The 360 vials were randomly distributed on the 3 shelves of the lyophilization machine to average out edge effects. The lyophilization run was completed after ~44 h and 30 min. Vials were closed with 0.2 µm filtered air at 600 m bar. The vials were transferred to 2° C.-8° C. storage and crimped. Residual moisture was measured directly after lyophilization and after 6 months storage. Viable cell count (VCC) before and after lyophilization and the corresponding % survival data was analyzed. The spread plate method was used for determining the total viable cell count of microorganisms present per mL of cell culture. The medium used to perform viable cell count may vary and is determined by the growth requirements of the organism. *Listeria monocytogenes* samples were cultured in Trypticase Soy Agar (TSA).

Results.

Figure 1:
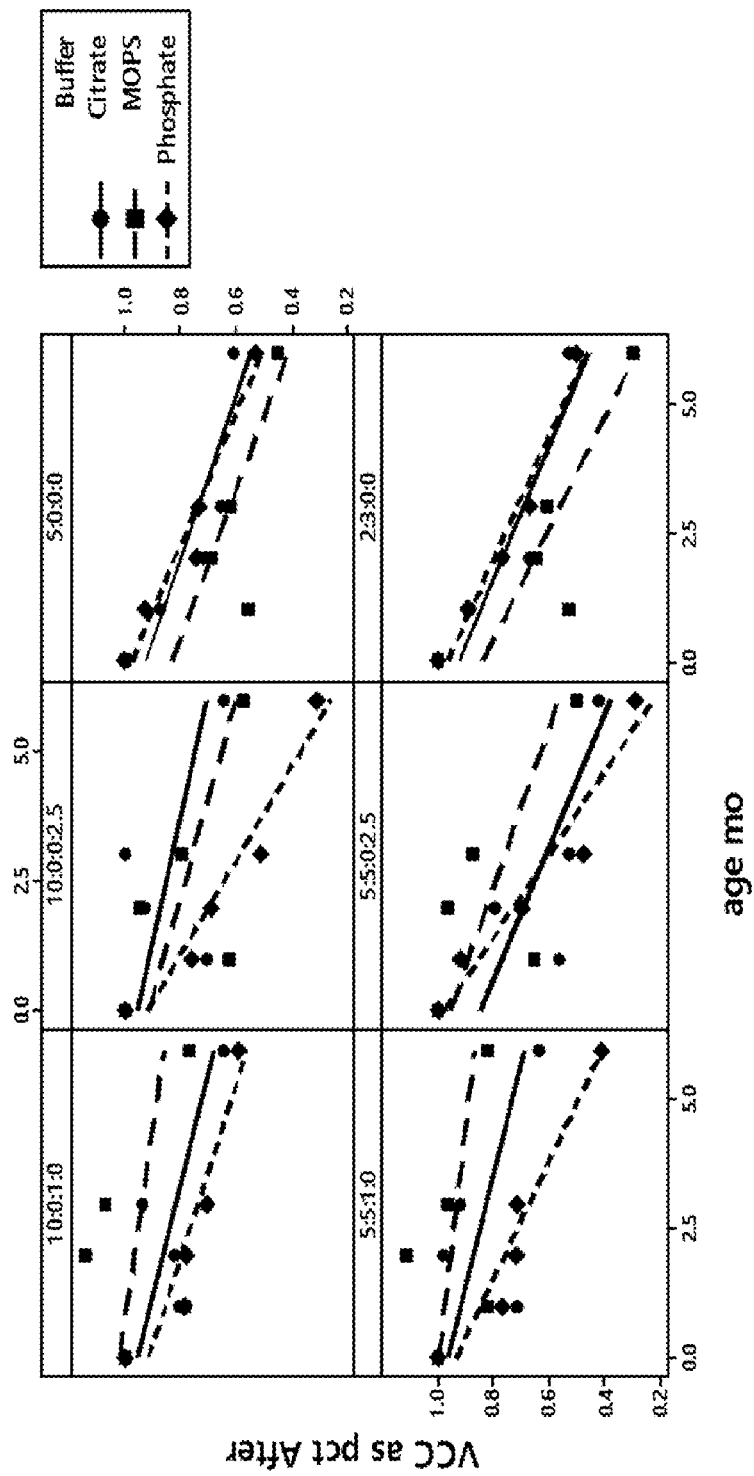
FIG. 1 shows viable cell count (VCC) data for different formulation buffers (citrate, phosphate, and MOPS (3-(N-morpholino)propanesulfonic acid)) and for different ratios of sucrose (Suc) to trehalose (Treh) to monosodium glutamate (MSG) to recombinant human serum albumin (rHSA) over time.

Phosphate- and citrate-based buffers yielded comparable recovery results. See FIG. 1. Residual moisture (RM) analysis revealed that the addition of MSG increased the RM in all buffer systems by ~1.0%-1.5%. Without MSG, the RM values ranged from ~1.8% to ~3.0%. There was no clear tendency for increase or decrease of % RM, indicating inter-assay variability Multivariate data analysis (MVDA) confirmed the decision to continue formulation development based on phosphate as there was no clear superiority of one buffer system, and phosphate requires only modest process change. See FIG. 1. The regression lines using stability at 4° C. showed the most consistency under the 5:0:0:0 stabilizer mix combination (sucrose:trehalose:MSG:rHSA). See FIG. 1.

Figure 2A:
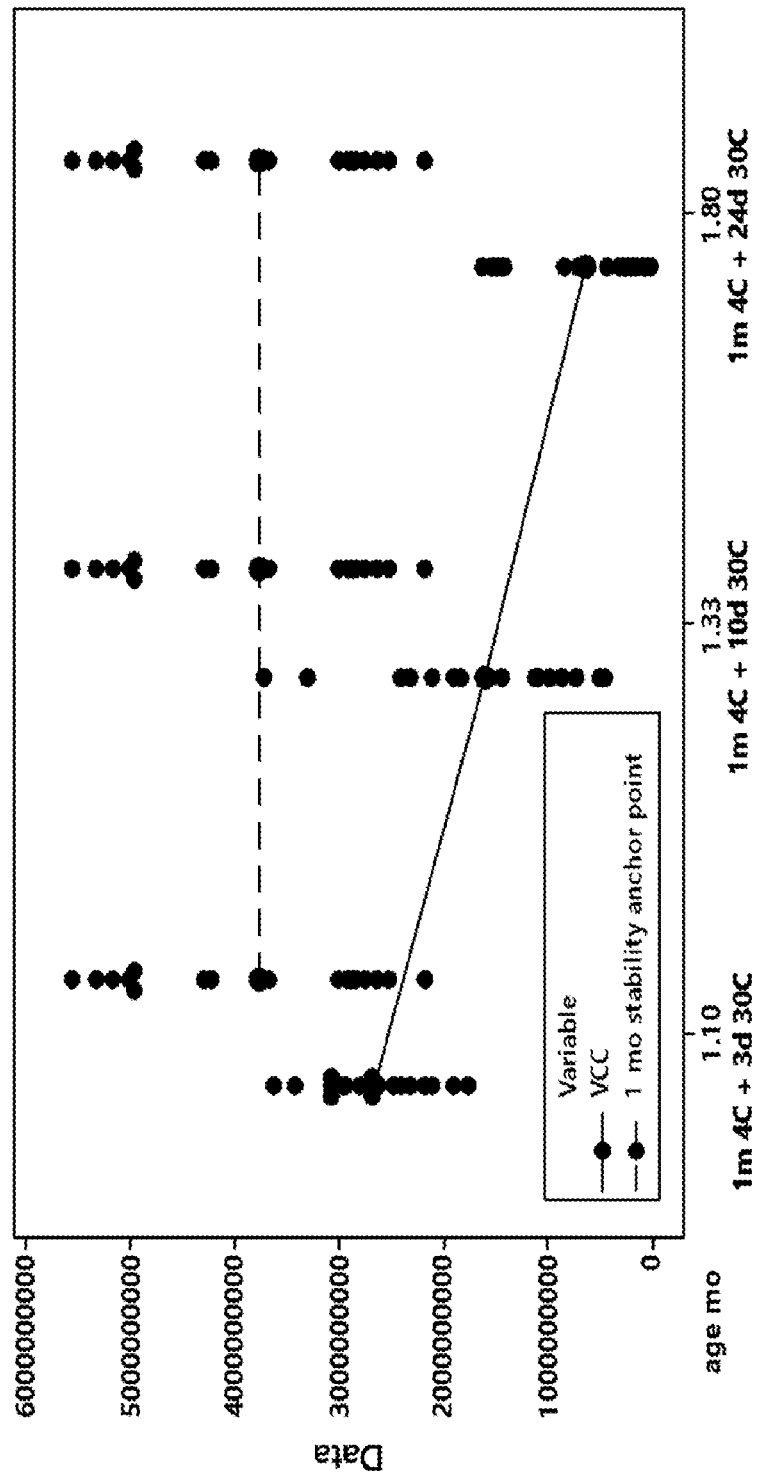
FIGS. 2A and 2B show VCC multivariate data analysis (MVDA) in an accelerated stability study at a 1 month stability anchor point (FIG. 2A) and at a 6 month stability anchor point (FIG. 2B).
Figure 2B:
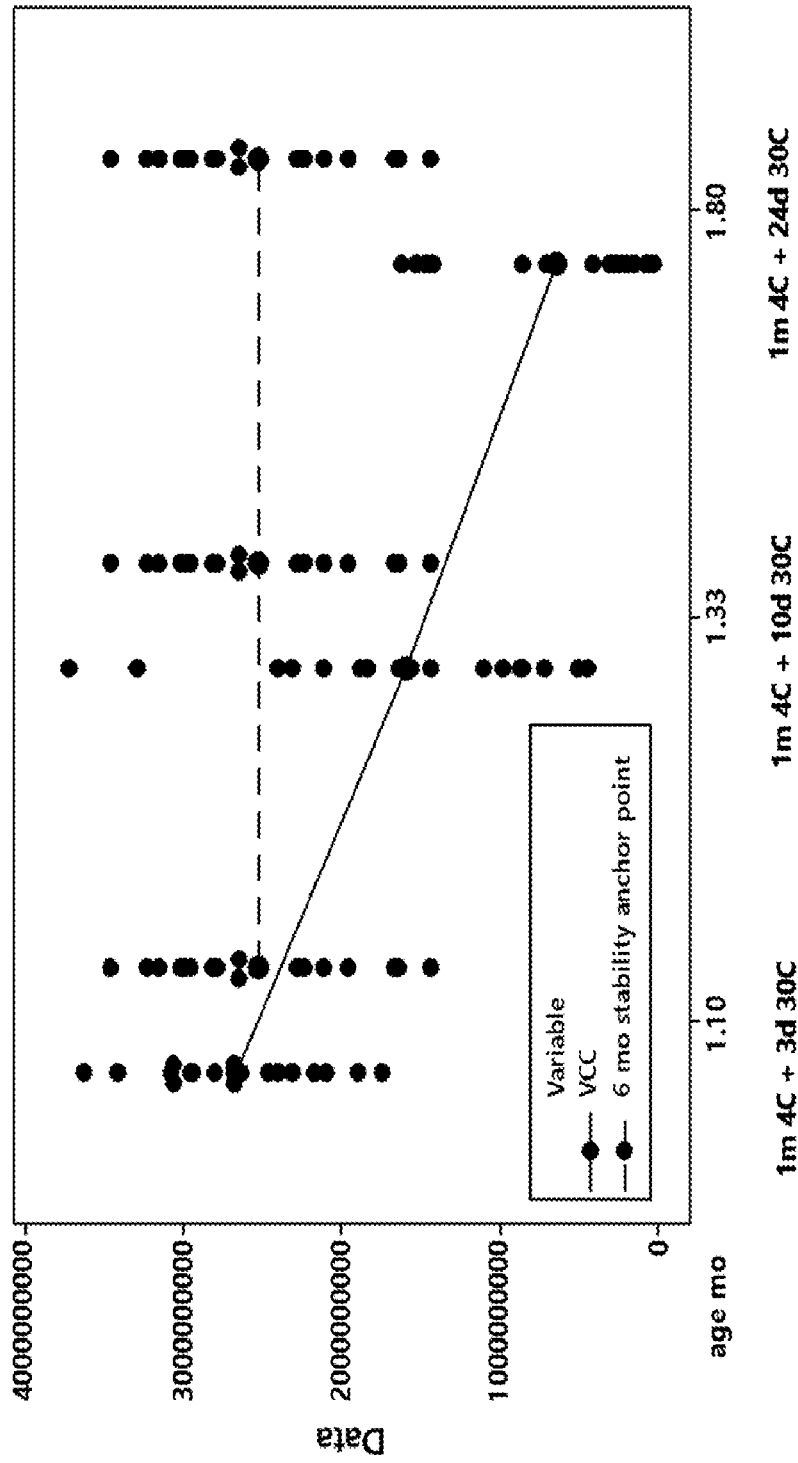

MVDA analysis also showed that in the accelerated stability study, the samples stored at 30° C. for 3 days showed a comparable recovery as the samples stored at 4° C. for 6 months. See FIGS. 2A and 2B. This indicated that higher storage temperature resulted in faster loss of viability and that accelerated conditions might be predictable data for long term storage at 2° C.-8° C. The lyo-cake appearance was good overall with no major defects or melt-backs. The sucrose based formulations showed slight cake shrinkages at the edges (top-crown and bottom of the vials). The change in VCC at 3 days at 30° C. was similar to that seen at 6 months at 4° C. FIG. 22A shows VCC data (percent of average pre-lyophilization VCC) before lyophilization and post-lyophilization after storage at different temperatures for different amounts of time in the Lyo1 experiment. Accelerated stability for 3 days at 30° C. was similar to 6 months stability at 4° C. FIG. 22B shows residual moisture immediately after lyophilization and after 6 months at 2-8° C. in the Lyo1 experiment.

2.1.2. WP7-Lyo2.

Materials and Methods.

The ADXS-HER2 drug product was used for this study. $OD_{600}$ values (OD in vial is representative of cell concentration) ranging from 2 to 20 were evaluated, and two different final $OD_{600}$ values were evaluated: $OD_{600}=10$ (same as Lyo1); and $OD_{600}=2.0$. The buffer used was phosphate-based buffer, and the stabilizer mix components (excipients) used included sucrose, amino acid (AA) mix, and rHSA.

Study Design.

One pH buffer, 9 different excipient combinations, and 2 bacterial concentrations resulted in 18 different formulations. The lyophilization run was performed similar to Lyo1. VCC was assessed on samples before lyophilization, on frozen samples (−80° C.) before lyophilization, on samples after lyophilization, and on samples after lyophilization and after storage for 1, 2, 3, 6, 9, 12, or 18 months at 2-8° C., −20° C., and −80° C.

Results.

Figure 3:
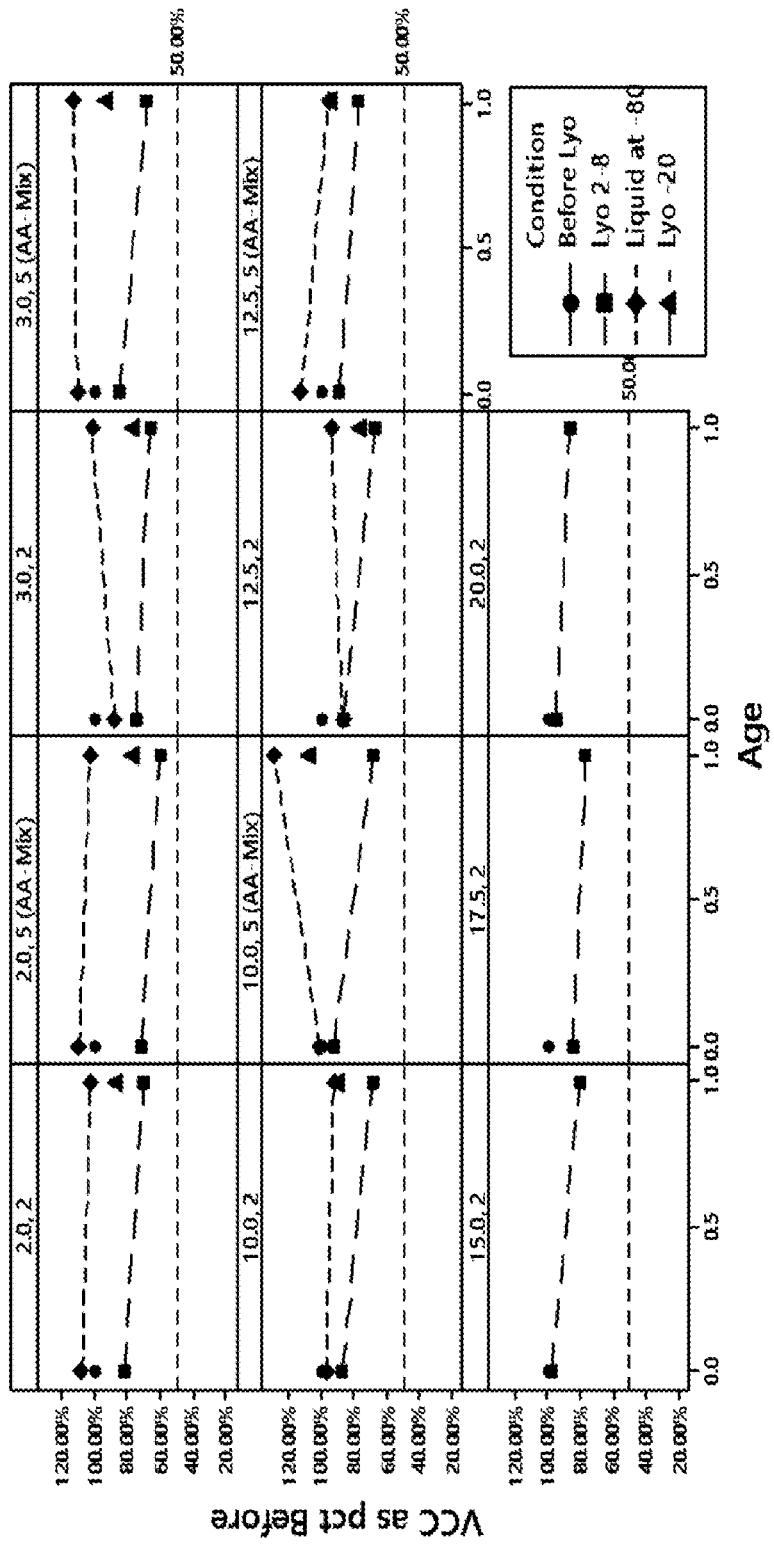
FIG. 3 shows VCC data for different OD levels and stabilizer combinations. Heading for each plot indicates OD in vial (2.0, 3.0, 10.0, 12.5, 15.0, 17.5, or 20.0), stabilizer (buffer 2 (2.5% sucrose) or buffer 5 (5% sucrose with amino acid mix).

In both the $OD_{600}=2$ and $OD_{600}=10$ groups, the highest recoveries were with sucrose-only formulations: 2.5% in $OD_{600}=10$; and 5% sucrose in $OD_{600}=2.0$. Parallel to Lyo1, there was a correlation between formulation and residual moisture. Formulations containing sucrose-only or a mixture of sucrose+AA had better residual moisture compared to rHSA formulations, which were drier. Percent RM at 6 months compared to after lyophilization was increased for all samples. MVDA analysis showed that rHSA had detrimental effects on stability. Highest recoveries (and lowest variability) were observed at lowest sucrose concentration (2.5%) and with higher $OD_{600}$ values (10 versus 2). The lyo-cake appearance was similar to Lyo1, and there was no significant difference between the two $OD_{600}$ vials. FIG. 3 shows VCC data for different OD levels and stabilizer combinations (OD, stabilizer). OD levels of 2.0, 3.0, 10.0, 12.5, 15.0, 17.5, and 20.0 were tested. Stabilizers including 2% and 5% sucrose were tested, optionally in combination with AA mix. VCC as a percentage of the count before lyophilization showed similar slopes at all OD levels and stabilizer combinations. Lyophilization samples stored at −20° C. for 1 month showed VCC results in between. FIG. 23A shows VCC data (percent of average pre-lyophilization VCC) before lyophilization and post-lyophilization after storage at different temperatures for different amounts of time (months) in the Lyo2 experiment. FIG. 23B shows residual moisture immediately after lyophilization and after 6 months at 2-8° C. in the Lyo2 experiment.

TABLE 11

Summary of Conditions in FIG. 23B.

| Target | Buffer # | $OD_{600}$ in Vial | $OD_{600}$ of 2-fold Stock | #6R Vials | Fill Volume (mL) | Formulations | X-fold increase in CFU/vial compared to WP5 |
|---|---|---|---|---|---|---|---|
| High $OD_{600}$ Formulation | 1 | 12.5 | 25 | 40 | 3 | Phosphate + 5% Sucrose | 1.88 (compared to $OD_{600}$ = 10) |
| | 2 | 12.5 | 25 | 40 | 3 | Phosphate + 5% Sucrose + Amino Acid | |
| | 3 | 10 | 20 | 40 | 3 | Phosphate + 5% Sucrose | 1.50 (compared to $OD_{600}$ = 10) |
| | 4 | 10 | 20 | 40 | 3 | Phosphate + 5% Sucrose + Amino Acid | |
| Low $OD_{600}$ Formulation | 5 | 3 | 6 | 40 | 3 | Phosphate + 5% Sucrose | 2.25 (compared to $OD_{600}$ = 2) |
| | 6 | 3 | 6 | 40 | 3 | Phosphate + 5% Sucrose + Amino Acid | |
| | 7 | 2 | 4 | 40 | 3 | Phosphate + 5% Sucrose | 2.25 (compared to $OD_{600}$ = 2) |
| | 8 | 3 | 4 | 40 | 3 | Phosphate + 5% Sucrose + Amino Acid | |
| $OD_{600}$ Maximum Evaluation | 9 | 20 | 40 | 12 | 3 | Phosphate + 5% Sucrose | 3.00 (compared to $OD_{600}$ = 10) |
| | 10 | 17.5 | 35 | 12 | 3 | Phosphate + 5% Sucrose | 3.63 (compared to $OD_{600}$ = 10) |
| | 11 | 15 | 30 | 12 | 3 | Phosphate + 5% Sucrose | 2.25 (compared to $OD_{600}$ = 10) |

Conclusions.

During this study, 18 different formulations in Lyo1 and 9 different formulations in Lyo2 were analyzed. Two formulations from Lyo1 and Lyo2 were identical, hence a total of 18+7=25 different formulations were analyzed (formulation-1 of Lyo1 is formulation-2 of Lyo2 and formulation-5 of Lyo1 is formulation-6 of Lyo2). Based on VCC results from Lyo1, optimization in Lyo2 was performed with phosphate-based formulations based on superior performance of phosphate and only modest change to current process. The lead formulation of Lyo1 was 5% sucrose, which performed better or equally well compared to the other buffers in Lyo2. In Lyo2, an amino acid mixture was expected to exhibit additional protective effects during long-term storage. Both the lead formulation of Lyo1 (5% sucrose) and the formulation with amino acids were then characterized for their critical temperatures (Tc, Tg, and Tg'), which were found to be close together, allowing for the development of one single cycle for both formulations.

2.2. Residual Moisture Targeting.

To obtain information about the process of drying samples during lyophilization cycle and establish correlation between secondary drying and residual moisture content, the Lyo3 experiment was performed. This enabled targeting for specific residual moisture contents in future lyophilization experiments.

2.2.1. WP5-Lyo3.

Materials and Methods.

The ADXS-HER2 drug product was used for this study. The formulations used were phosphate-based with 2.5% sucrose, 5% sucrose, and 10% sucrose. The stabilizer mix included different combinations of sucrose, AA mix, and rHSA. Two different $OD_{600}$ values were evaluated: $OD_{600}$=10 and $OD_{600}$=2.0.

Study Design.

Stability was tested at 4° C. for 13 days, 1 month, 3 months, and 6 months. Accelerated stability was tested using samples stored at 13 days at 4° C. before accelerating at 30° C. for 1 day, 2 days, or 3 days. VCC was measured before lyophilization, VCC and RM were measured after lyophilization and on stability, and RM was measured after lyophilization.

To obtain information about the process of drying, the cycle was aborted at different time points to take samples to analyze residual moisture (RM). The first samples were taken directly at the end of primary drying. A heating rate of 0.2° C./min was used in the ramp to secondary drying, and further samples were taken directly after the ramp to secondary drying. Secondary drying was performed at +20° C. for 8 h (3 h longer than in Lyo2). Samples were taken every 2 h and analyzed immediately. Based on the live RM data, secondary drying might be extended if the target of <1% is not reached.

Results/Conclusions.

Figure 4:
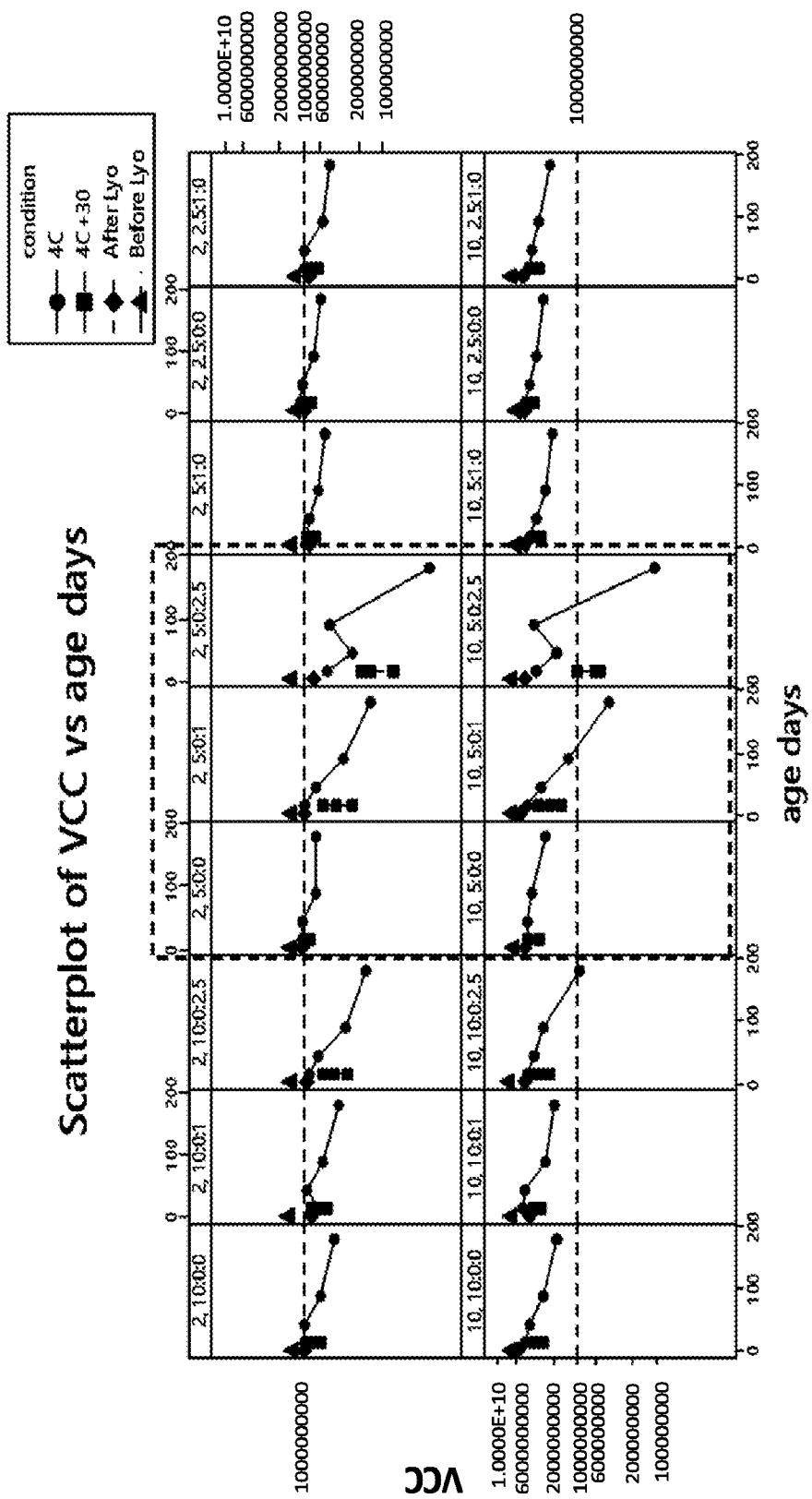
FIG. 4 shows VCC data for different OD levels and ratios of sucrose (Suc) to amino acid mix (AA Mix) to recombinant human serum albumin (rHSA). Heading for each plot indicates OD in vial (2 or 10), sucrose (10, 5, 2.5):amino acid mix (presence (1) or absence (0)):rHSA (0, 1, or 2.5).

As shown in FIG. 4, it is clear from the raw VCC levels that an increase in rHSA is associated with instability, counts are higher at $OD_{600}$=10, and the lowest variability of results is seen at the low level of sucrose (2.5%). This is reinforced by 6-month data.

Figure 5:
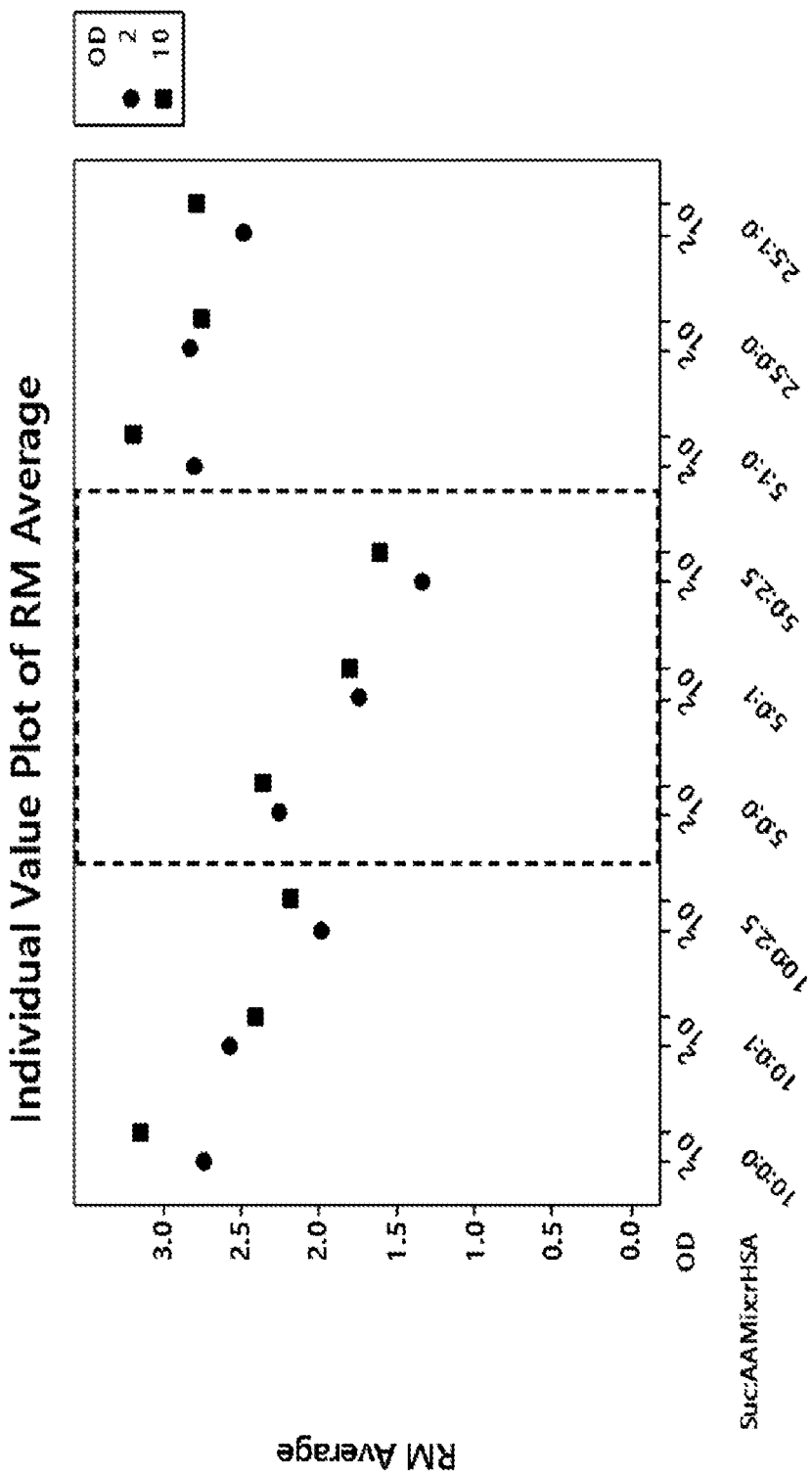
FIG. 5 shows residual moisture (RM) data for different OD levels and ratios of sucrose (Suc) to amino acid mix (AA Mix) to recombinant human serum albumin (rHSA).

As shown in FIG. 5, the moisture results show little distinction based on OD, lower RM with increased rHSA at sucrose levels of 10% and 5%, and lowest variability of results at the lowest level of sucrose (2.5%) and without rHSA.

These experiments also showed that material with RM within a desired range of ~5% to <1% can be generated by taking the product out of the freeze-dryer at distinct process steps, including the end of primary drying, the end of the ramp to secondary drying, and different time points during secondary drying.

2.3 Evaluation of Optimal Residual Moisture on Stability.

To optimize the target residual moisture and recovery after lyophilization, the Lyo4 stability study was performed.

2.3.1 WP7-Lyo4.

Data generated under WP7-Lyo3 demonstrated proof of principle that material with Residual Moisture within the targeted range of ~5% to <1% can be generated by removing samples from the freeze-dryer at distinct process steps: (1) end of primary drying; (2) end of ramp to secondary drying; and (3) at different time points during secondary drying. Based on the initial data material for long-term stability studies at 2-8° C. and at 30° C., 65% RH for short-term accelerated stress stability, was generated. The % residual moisture (RM) targets were ~5%, ~3% and about 1%. Based on all data available that was available at the time material was generated for two lead formulations: (1) phosphate buffer, pH 7.2, 5% sucrose; and (2) phosphate buffer, pH 7.2, 2.5% sucrose.

Materials and Methods.

The ADXS-HER2 drug product was used for this study. The formulations used were phosphate-based with 2.5% sucrose and 5% sucrose. $OD_{600}$ values were $OD_{600}$=20 ($2\times10^{10}$ CFU/mL). Moisture levels were controlled by removing the samples out of the freeze-dryer at distinct process steps: (1) end of primary drying (residual moisture target ~5%); (2) end of ramp to secondary drying (residual moisture target ~3%); and (3) end of secondary drying (residual moisture target ~1%).

Study Design.

The lyophilization run was performed similar to Lyo3 except initial OD value was 20. Bacteria were cultivated and concentrated by centrifugation as described in Lyo2 to an $OD_{600}$~20 (~$2\times10^{10}$ CFU/mL). Moisture levels were controlled by where the samples were taken in the lyophilization cycle: (1) high moisture; after primary drying; moistures ~5.4-5.8%; (2) mid moisture; after ramp (immediately after the ramp of the shelf temperature from the primary drying temperature to the secondary drying temperature); moistures ~3.7-4.5%; and (3) low moisture; after secondary drying; moistures ~1.1-1.3%. The first samples were taken directly at the end of primary drying (RM target is ~5%), and the second lot of samples were taken directly after the ramp to secondary drying (RM target is ~3%). Secondary drying was performed for 12 h, after which the third lot of samples were removed (RM target is ~1%). After removal, all vials were crimped and stored at 2-8° C. (including vials for later stress stability study). RM and VCC before lyophilization, after lyophilization, and at accelerated conditions for 1, 2 and 3 days (30° C.) were analyzed. VCC titer was measured, as both count and percent of count before lyophilization.

Results.

Figure 6:
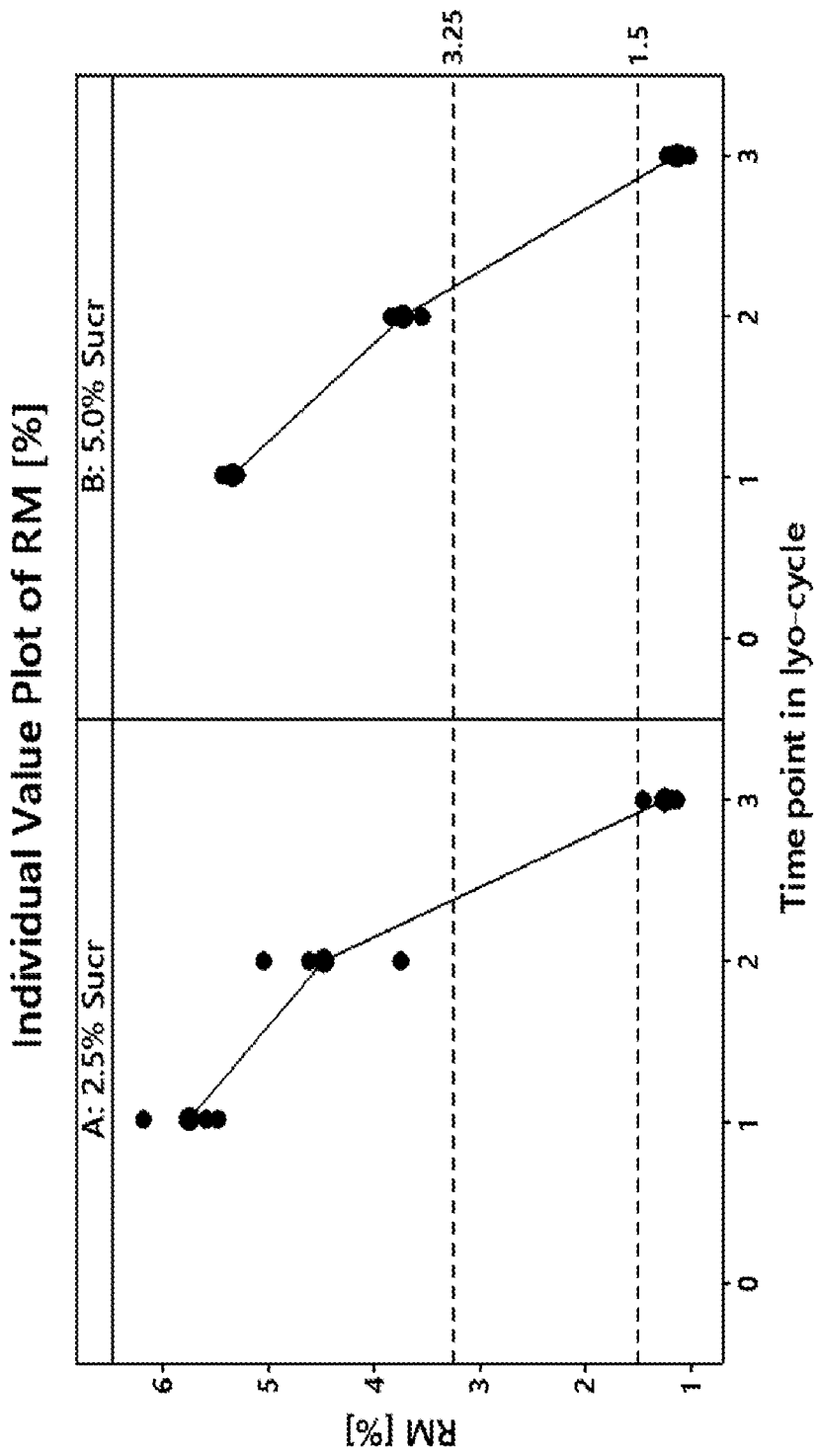
FIG. 6 shows residual moisture data for different percentages of sucrose (weight per volume) at different time points in the lyophilization cycle.
Figure 7A:
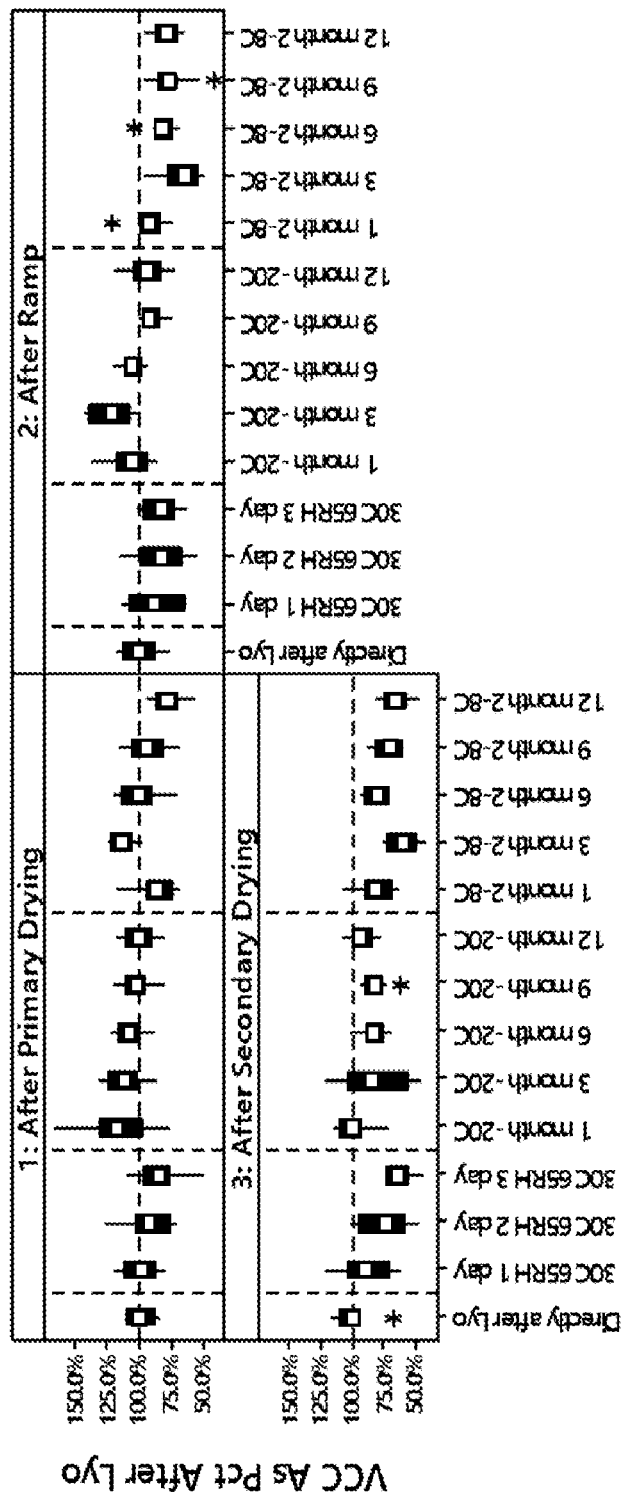
FIGS. 7A and 7B show VCC data post-lyophilization after storage at different temperatures for different amounts of time in Lm samples after the primary drying step, after the ramp, or after the secondary drying step in the Lyo4 experiment.
Figure 7B:
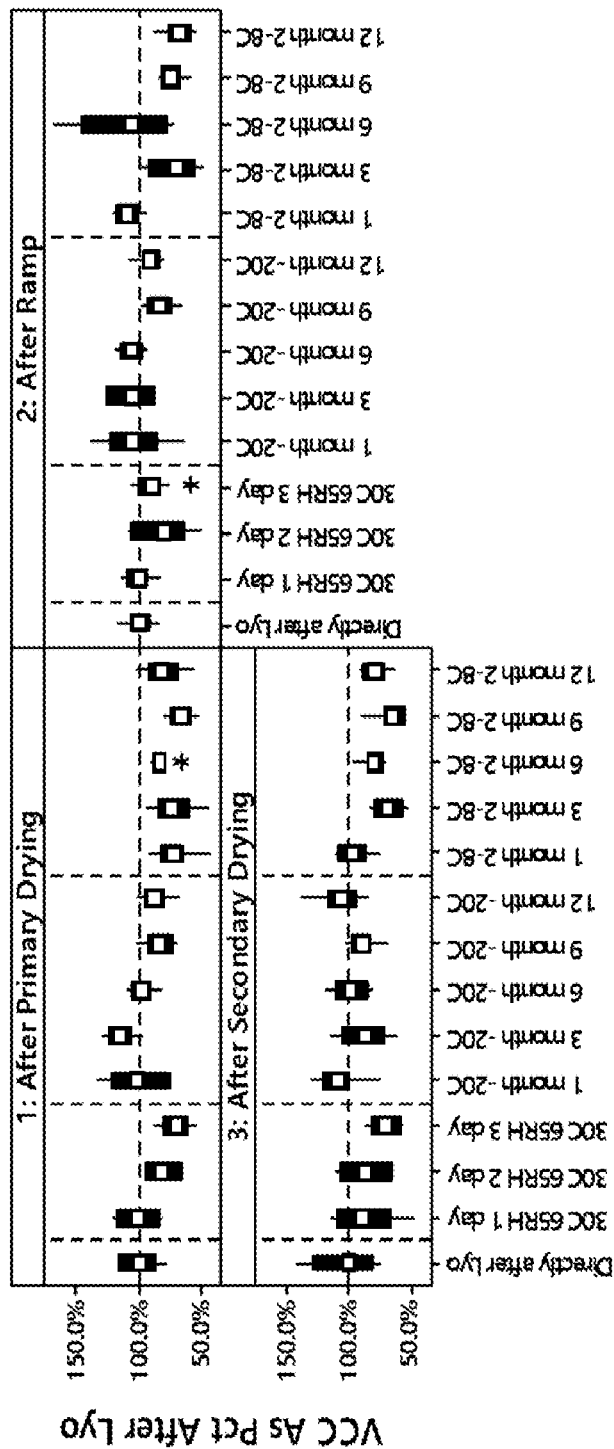

Moistures achieved in this study bracket moistures seen before. Combining Lyo4 and Lyo2 studies, focusing only on sucrose 2.5% and 5.0%, and removing all reference to studies with rHSA, comparability at accelerated conditions was seen. Best results were at higher moisture levels for the sucrose level of 2.5%. As shown in FIG. 6, RM achieved in this study "bracket" moistures previously seen. RM results are shown as both the individual values and the average. The dotted lines outline the range (high and low) of results that had been seen in the long-term study on Lyo2. The comparability at accelerated conditions is shown in FIGS. 7A, 7B, 24A, and 24B. As shown in FIGS. 7A and 7B, the best results are at higher moisture levels for sucrose levels of 2.5%. FIG. 24A shows residual moisture (RM) using 2.5% sucrose after primary drying, after ramp, and after secondary drying after storage at different temperatures for different amounts of time in the Lyo4 experiment. FIG. 24B shows residual moisture (RM) using 5.0% sucrose after primary drying, after ramp, and after secondary drying after storage at different temperatures for different amounts of time in the Lyo4 experiment.

Conclusions.

This study confirmed that higher residual moisture (RM) resulted in a better VCC profile under accelerated conditions at $OD_{600}$=20. The best VCC profiles obtained on accelerated stability were at higher moisture levels for the sucrose level of 2.5%. Hence, the sucrose level was fixed at 2.5% and the target residual moisture level for future development experiments was targeted at 2.5-3.5%.

2.4. Evaluation of Stress Treatments Pre-Lyophilization.

To evaluate stress treatments pre-lyophilization and its effects on stability of the lyophilized material, Lyo5 was performed. This study simulated stress conditions potentially experienced during the fermentation process.

Cold shock, heat shock, and osmotic shock to cells, may induce expression of genes involved in the general stress response. The genetic response to these shock conditions are necessary for defending the cell against stress damage and death. Thus, greater cell survival during lyophilization may be achieved by activating the stress response. To evaluate the induction of a stress response in the Lm prior to lyophilization and its effects on stability of the lyophilized material, WP7-Lyo5 was performed. This study induced a stress response either by a pH shift or cold shock prior to formulation and lyophilization.

2.4.1. WP7-Lyo5.

The study goal for WP7-Lyo5 was to evaluate if induction of a stress response (cold shock and pH shift) in the Lm could improve viability in the reconstituted drug product.

Materials and Methods.

The ADXS-HER2 drug product was used for this study. The experiment comprised of the following four arms: (1) Group-1: control culture; (2) Group-2: temperature-shift culture; (3) Group-3: pH-shift culture; and (4) Group-4: pH- and temperature-shift culture (pH-shift first followed by temperature-shift). To achieve the temperature-shift and pH-shift, immediately after harvesting the cells from the bioreactor, the cells were either placed in an ice bath or the pH was dropped by the addition of acid. This induces a stress response in the cells that activates a set of genes that seem to better prepare the cells for lyophilization. The formulation was phosphate-based with 2.5% sucrose, the residual moisture target was 3.5% and the $OD_{600}$=10 (~$1\times10^{10}$ CFU/mL). 6R vials were filled with approximately 2 mL of Drug Product. Accelerated stability was evaluated at 30° C. for 1, 2, and 3 days.

Study Design.

Once the material in the bioreactor reached the target $OD_{600}$, materials for group-1 (control) and group-2 (temperature-shift) were removed. Material for group-1 was processed further until formulated bulk (bulk drug substance) was obtained, which was then stored at 2-8° C. until vial filling. For group-2, the temperature-shift was performed in an ice/salt/water bath, after which the material was stored at 2-8° C. for 30 min. Then the material was processed further until formulated bulk was obtained, which was stored at 2-8° C. until vial filling. In the meantime, the pH-shift was performed in the bioreactor using 2M HCl to pH=5.25. Then the material for group-3 (pH-shift) and group-4 (pH-/temp-shift) was removed. Material from group-3 was processed further until formulated bulk was obtained and was stored at 2-8° C. until vial filling. For group-4, the temperature-shift was performed as described above and the material was stored at 2-8° C. for 30 min. Then the material was processed further until formulated bulk was obtained. Once formulated bulks for all groups were obtained, VCC was analyzed and lyophilization was initiated.

The lyophilization run was performed similar to Lyo4. For a target residual moisture of 3.5%, 2 h secondary drying time was used. VCC was analyzed before lyophilization, after lyophilization, and at accelerated conditions for 1, 2, and 3 days (30° C.). VCC titer was measured, expressed as both count and percent of count before lyophilization.

Results.

Figure 8:
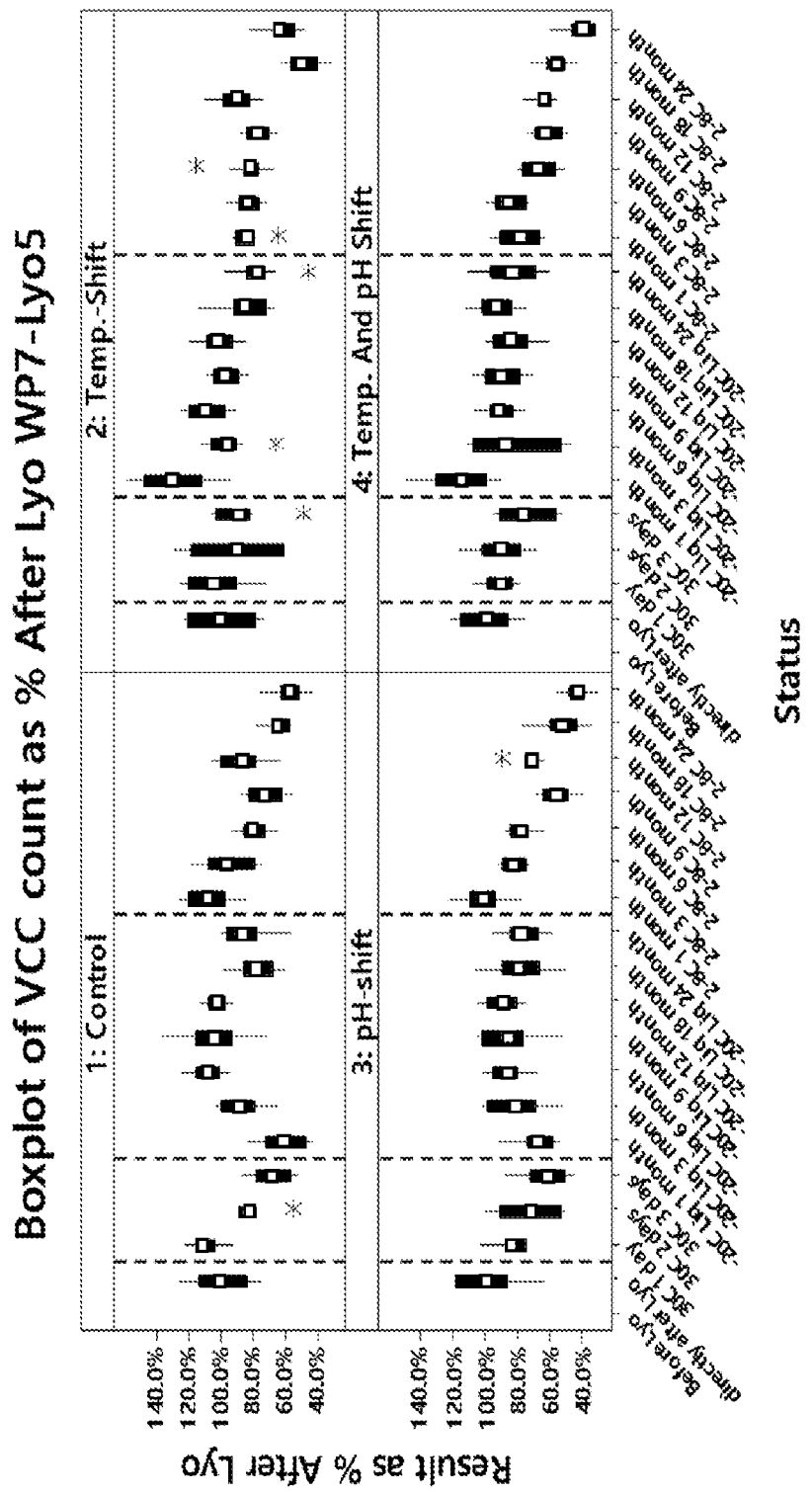

The data at 3 and 6 months (and 9, 12, and 18 months) at both −20° C. and 2-8° C. demonstrate good comparability across all four groups. See FIG. 8 (VCC) and FIG. 25 (RM). FIG. 8 shows the percentage of VCC after lyophilization for each experimental condition (pH shift, temperature shift, pH/temperature shift and control) evaluated on stability at −20° C., 2-8° C., and accelerated stability. FIG. 25 shows residual moisture levels at T=0 for each experimental condition (pH shift, temperature shift, pH/temperature shift, and control) evaluated on stability at 2-8° C. The temperature shift condition showed a more stable profile on long term stability compared to control or pH shift.

The data demonstrated a good stability profile both at −20° C. and 2-8° C. for the temperature shift sample relative to the other arms of the study. There does not appear to be a benefit to the pH shift or the pH+temperature shift pre-treatment. The data indicate that preconditioning the cells prior to lyophilization may increase the long-term stability of the product. The data do not show any clear trends in Residual Moisture across treatment arms or upon long-term storage.

Conclusion.

This study showed that a more stable profile on long term stability and accelerated stability conditions was obtained with the temperature shift condition compared to control or pH shift.

2.5. Evaluation of Temperature Shift Pre-Lyophilization

To evaluate temperature shift treatment pre-lyophilization and its effects on stability of the lyophilized material, Lyo6 was performed. This study simulated stress conditions potentially experienced during the fermentation process and was a measure to condition cells for the freezing process during lyophilization.

2.5.1. WP7-Lyo6.

Materials and Methods.

The ADXS-HPV drug product was used for this study. No control group was included. The formulation was phosphate-based with 2.5% sucrose, the residual moisture target was 3.5%, and the $OD_{600}$=10.

Study Design.

Once the material in the bioreactor reached the target $OD_{600}$, the required volume was harvested and the temperature shift was performed in an ice/salt/water bath, after which the material was stored at 2-8° C. for 30 min. Then the material was processed further until formulated bulk was obtained. VCC was analyzed before and after the lyophilization run, which was performed similar to Lyo5, and at accelerated conditions for 1, 2, and 3 days (30° C.). VCC titer was measured, expressed both as count and percent of count before lyophilization.

Results.

Figure 9:
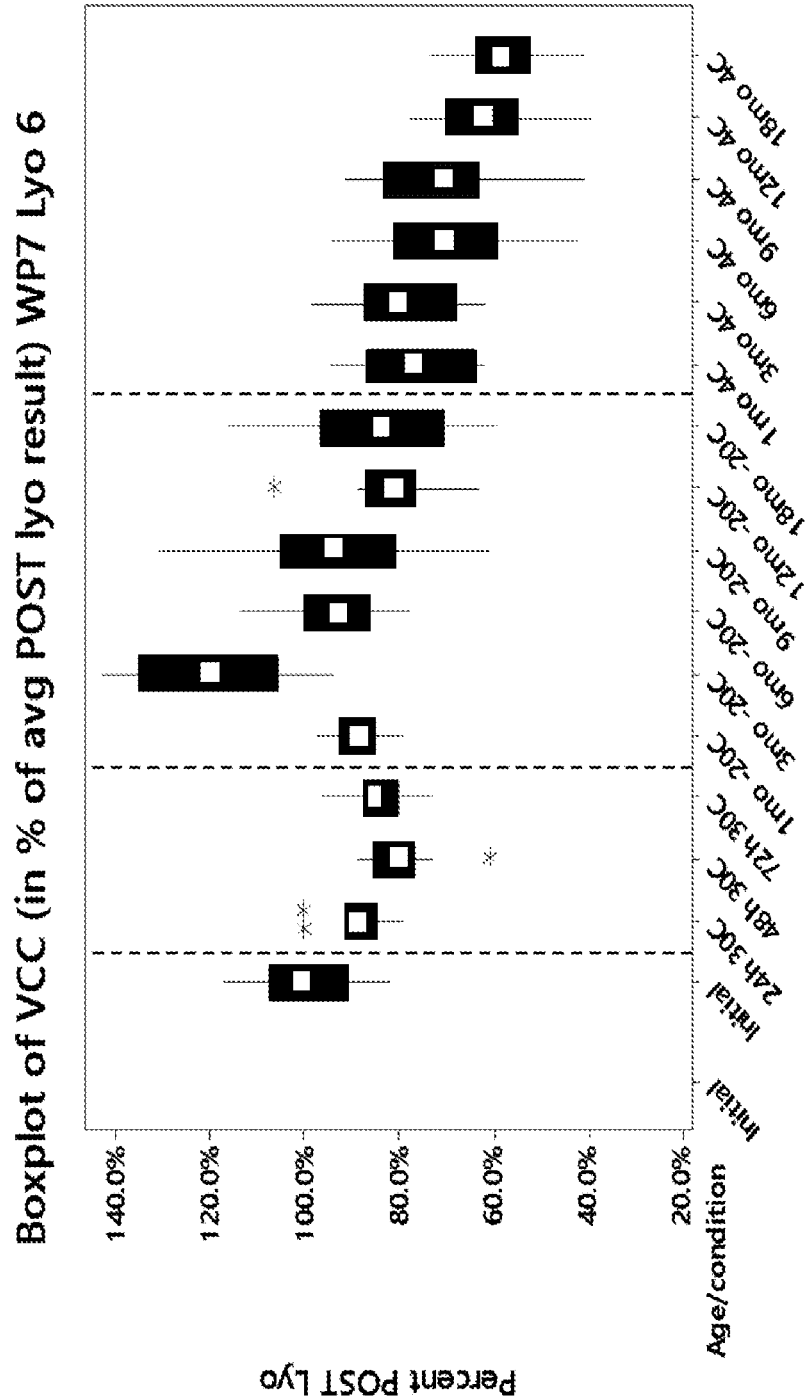

Accelerated results for ADXS-HPV were comparable to ADXS-HER2. One month stability was consistent with accelerated stability results. See FIG. 9 (VCC) and FIG. 26 (RM). The data demonstrate good stability under short-term accelerated conditions. The data at −20° C. shows good stability at 12 months while the 2-8° C. storage begins to show a loss in VCC after 12 months. The data show no clear trends in RM upon long-term storage at either −20° C. or 2-8° C.

Conclusion.

This study confirmed that the lyophilized ADXS-HPV construct produced results consistent with ADXS-HER2 and demonstrated the applicability of the lyophilization platform across constructs.

2.6. Evaluation of Reduced Primary Drying Shelf Temperature and Reduced Freezing Temperature.

To evaluate freezing temperature and primary drying shelf temperature and their effects on stability of the lyophilized material, Lyo7 was performed.

2.6.1. WP7-Lyo7.

Materials and Methods.

The ADXS-HPV drug product was used for this study. No control group was included. The formulation was phosphate-based with 2.5% sucrose, the residual moisture target was 3.5%, and the $OD_{600}$=10. The stability conditions used were 2-8° C., −20° C., and accelerated conditions for 1, 2, and 3 days at 30° C.

Study Design.

Once the material in the bioreactor reached the target $OD_{600}$, the required volume was harvested and the temperature-shift was performed in an ice/salt/water bath, after which the material was stored at 2-8° C. for 30 min. Then the material was processed further until formulated bulk was obtained. The lyophilization run was performed with freezing temperature decreased from −40° C. to −45° C., and primary drying shelf temperature was decreased from −22° C. to −30° C. VCC was analyzed before and after lyophilization and at accelerated conditions. VCC titer was measured, expressed both as count and percent of count before lyophilization.

Results.

Figure 10:
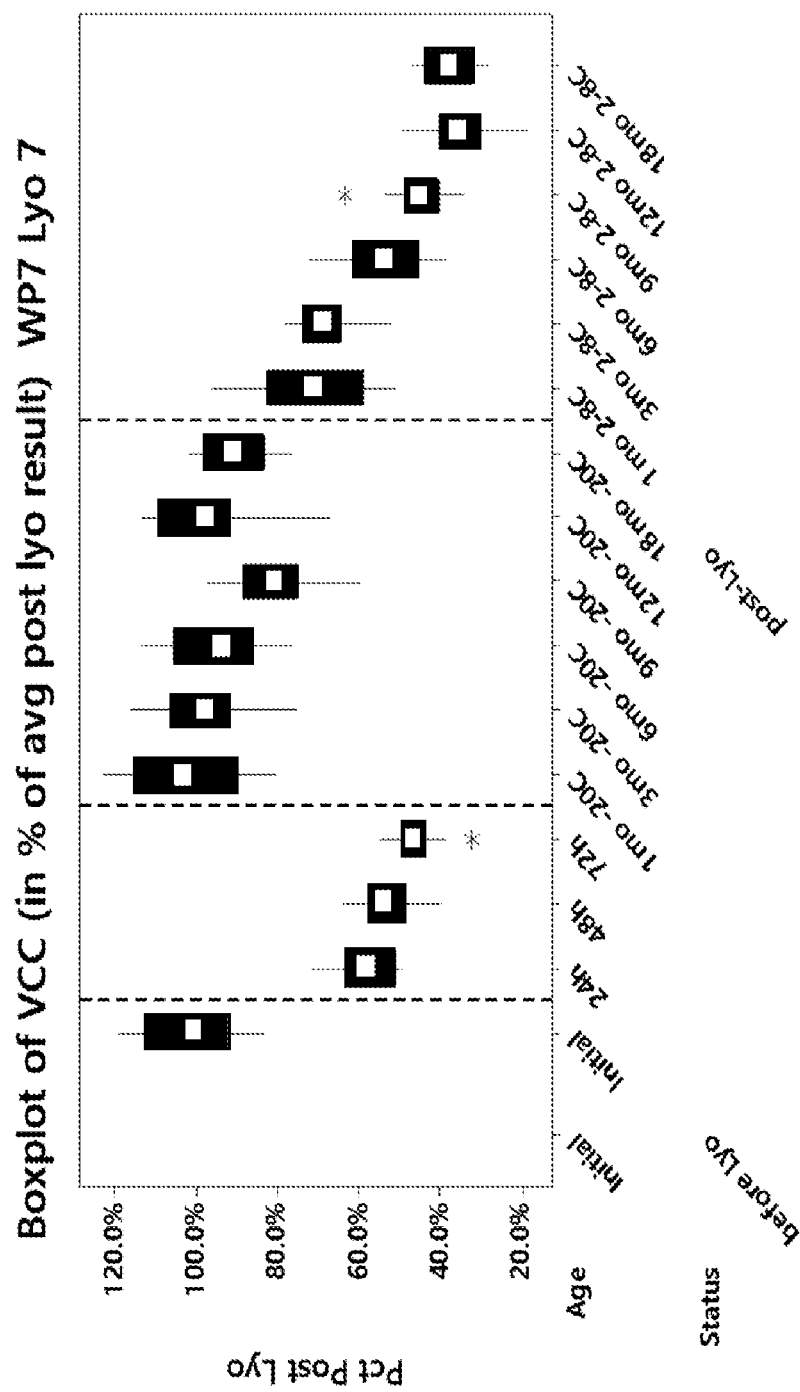

Significant losses were observed on accelerated stability with the decreased shelf temperature. See FIG. 10 (VCC) and FIG. 27 (RM). Decreasing shelf temperature during freezing did not improve stability of the lyophilized product.

2.7. Hold Time Study.

A hold time study was performed where the drug product (DP) was either lyophilized immediately after formulation or was frozen, thawed, and then lyophilized. 2.7.1. WP7-Lyo8.

Materials and Methods.

The ADXS-HPV drug product was used for this study. The formulation was phosphate-based with 2.5% sucrose, the residual moisture target was 3.5%, and the $OD_{600}$ of the final formulated material=10. The stability conditions used were 2-8° C., −20° C., and accelerated conditions for 1, 2, and 3 days at 30° C.

Study Design.

In some groups (Part A), samples were lyophilized immediately. In other groups (Part B), samples were frozen at −80° C., thawed at 2-8° C. overnight, and then lyophilized. VCC before lyo, after lyo, and at accelerated conditions for 1, 2 and 3 days (30° C.) was analyzed. VCC titer was measured, expressed both as count and percent of count before lyophilization.

Results.

Figure 11:
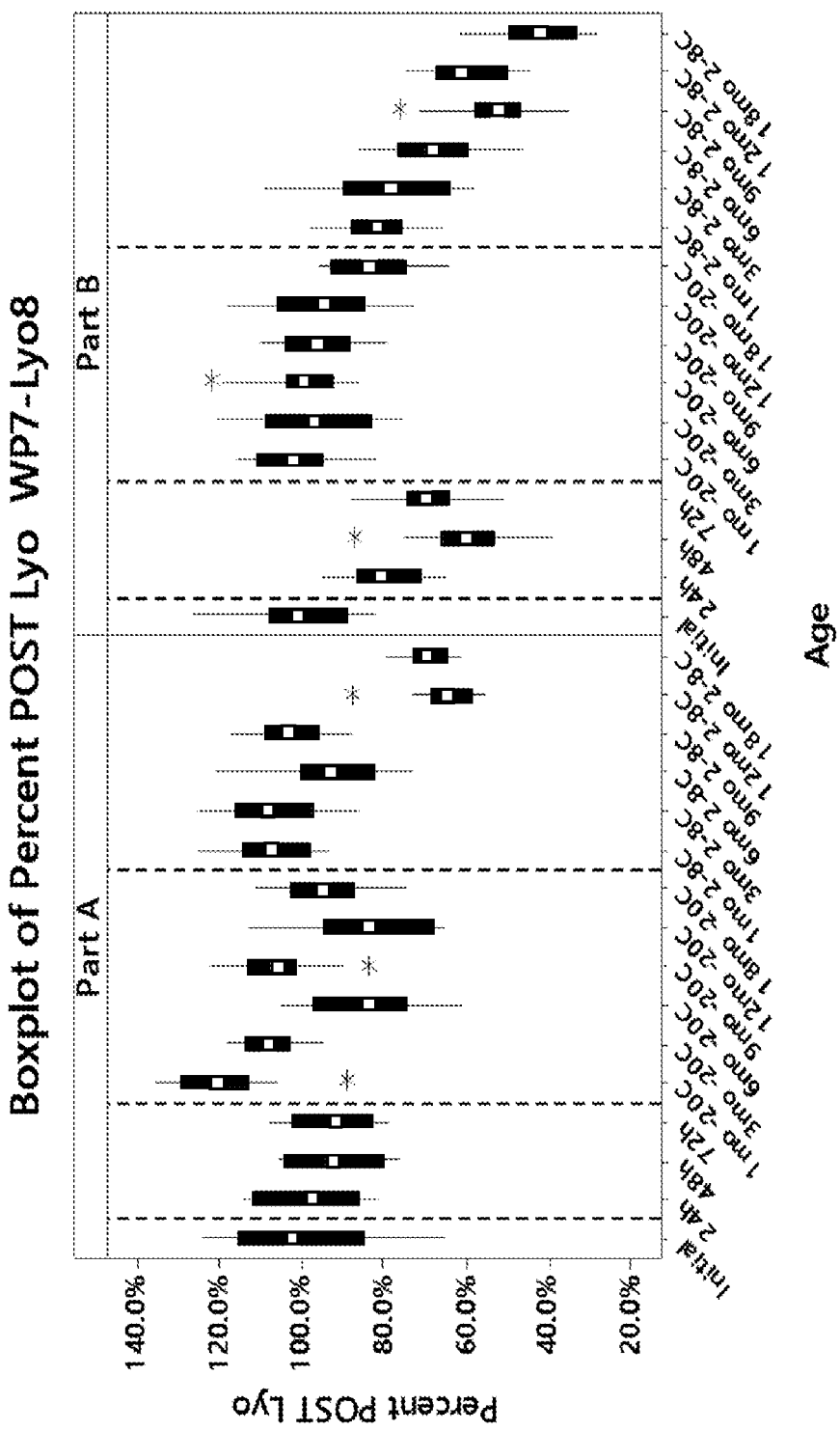

Part A (continuous processing) demonstrated a better stability profile under accelerated conditions compared to Part B (frozen hold). See FIG. 11 (VCC) and FIG. 28 (RM).

2.8. Evaluation of Increased Primary Drying Shelf Temperature.

To evaluate an increased shelf temperature during primary drying and its effect on stability of the lyophilized material, Lyo9 was performed.

2.8.1. WP7-Lyo9.

Based on previous observations that a lower primary drying shelf temperature reduced the stability of the resulting drug product, the goal of WP7-Lyo9 was to evaluate the effect of a higher shelf temperature during primary drying on the stability of freshly (continuously processed) lyophilized drug substance ADXS11-001 (HPV). A shelf-temperature of −18° C. during primary drying was evaluated. Lyophilized material was staged on stability at 2-8° C. and −20° C. Further accelerated stability for 1, 2, and 3 days at 30° C./65% RH.

Materials and Methods.

The ADXS-HPV drug product was used for this study. A shelf temperature of −18° C. was evaluated. The temperature shift was performed similar to prior experiments. The formulation was phosphate-based with 2.5% sucrose, the residual moisture target was 3.5%, and the $OD_{600}$=10. The stability conditions used were 2-8° C., −20° C., and accelerated conditions for 1, 2, and 3 days at 30° C.

Study Design.

Once the material in the bioreactor reached the target $OD_{600}$, the required volume was harvested and the temperature-shift was performed in an ice/salt/water bath, after which the material was stored at 2-8° C. for 30 min. Then the material was processed further until formulated bulk was obtained. The lyophilization run was performed with a primary drying shelf temperature of −18° C. VCC was analyzed before and after lyophilization and at accelerated conditions. VCC titer was measured, expressed both as count and percent of count before lyophilization.

Results.

Figure 12:
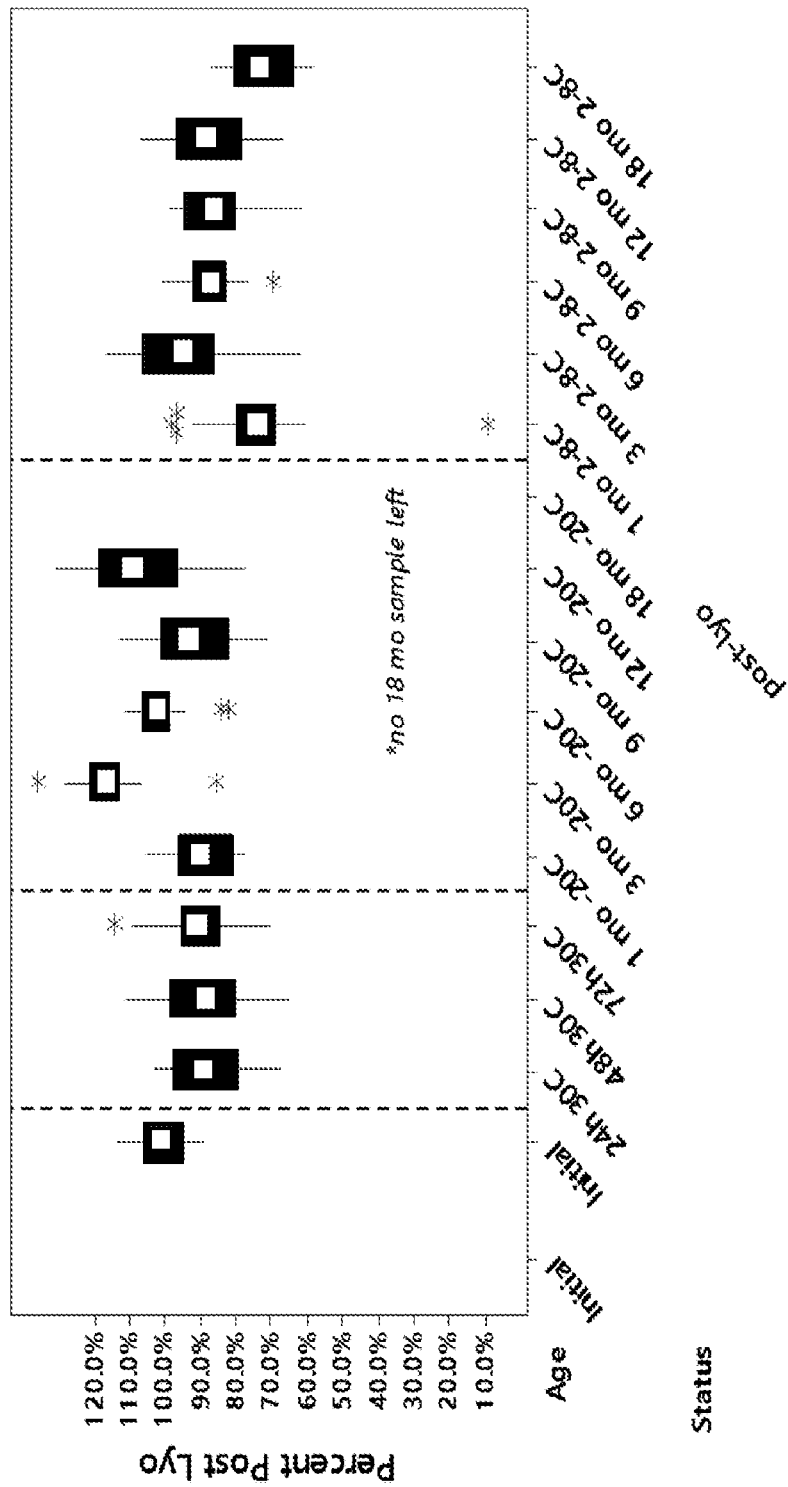

FIG. 12 shows % VCC after lyophilization evaluated on stability at 30° C., −20° C. and 2-8° C. FIG. 29 shows residual moisture levels evaluated on stability at 30° C., −20° C. and 2-8°. The data demonstrates that both −20° C. and 2-8° C. are stable up to 12 months. An improvement in accelerated stability was observed with increased shelf temperature. See FIG. 12 (VCC) and FIG. 29 (RM). In general, lyophilization of proteins at primary drying shelf temperatures high enough to cause the type of collapse seen in this study leads to reduced stability in the lyophilized cake. However, the trend for this whole bacteria formulation appears to be the opposite.

Conclusion.

This study showed that increased primary drying shelf temperature resulted in improvement in accelerated and long-term stability for the lyophilized product.

2.9 Comparison of Plus/Minus Temperature Shift at Increased Primary Drying Temperature (−18° C.).

To compare the minus [Part-A]/plus [Part-B] temperature shift at elevated primary drying temperature of Ts=−18° C., the Lyo10 stability study was performed.

2.9.1. WP7-Lyo10.

Materials and Methods.

The ADXS-HPV drug product was used for this study. A shelf temperature of −18° C. was evaluated for two groups of materials: (1) Part-A material—processed immediately after harvest (without temperature shift); and (2) Part-B material—temperature shift was performed.

The formulation was phosphate-based with 2.5% sucrose, the residual moisture target was 3.0%, and the $OD_{600}$=10. The stability conditions used were 2-8° C., −20° C. and accelerated conditions for 1, 2, and 3 days at 30° C.

Study Design.

Once the material in the bioreactor reached the target $OD_{600}$, the required volume for both Part-A and Part-B was harvested. Part-A was immediately processed until vial filling and for Part-B, temperature-shift was performed in an ice/salt/water bath, after which the material was stored at 2-8° C. for 30 min. Then the Part-A and Part-B materials were processed further until formulated bulk was obtained. The lyophilization run was performed with a primary drying shelf temperature of −18° C. and 2 h secondary drying time to target a residual moisture of 3.0%. VCC was analyzed before and after lyophilization and at accelerated conditions. VCC titer was measured, expressed both as count and percent of count before lyophilization.

Results.

Figure 13:
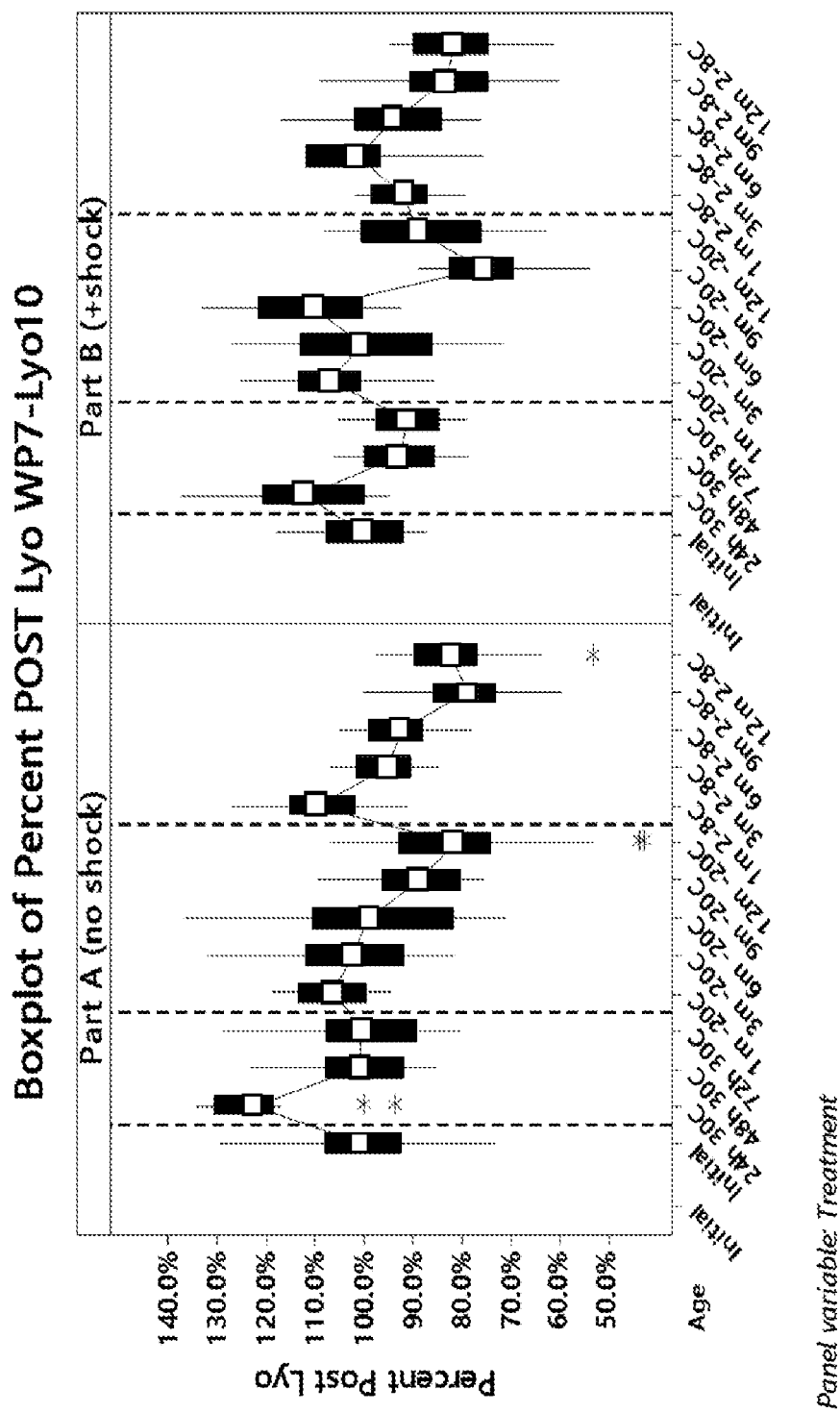

With the increased shelf temperature, the results were comparable with and without the temperature shift. See FIG. 13 (VCC) and FIG. 30 (RM). The results confirmed the good stability profile previously observed for the increased shelf temperature.

2.10. Stability Study without Temperature Shift at Primary Drying Temperature of −18° C. and Bioactivity Determination.

To confirm the results of Lyo10, a Lyo11 stability study was performed without temperature shift at elevated primary drying temperature of −18° C. Bioactivity of the lyophilized drug product was then compared to liquid frozen drug product.

2.10.1. WP7-Lyo11.

Materials and Methods.

The ADXS-HPV drug product was used for this study. A shelf temperature of −18° C. was evaluated without temperature shift. The formulation was phosphate-based with 2.5% sucrose, the residual moisture target was 2.5-3.0%, and the $OD_{600}$=10. The stability conditions used were 2-8° C., −20° C. and accelerated conditions for 1, 2, and 3 days at 30° C.

Study Design.

Once the material in the bioreactor reached the target $OD_{600}$, the required volume was harvested and immediately processed until formulated bulk was obtained. The lyophilization run was performed with a primary drying shelf temperature of −18° C., and a residual moisture of 2.5-3.0% was targeted. VCC was analyzed before and after lyophilization and at accelerated conditions. VCC titer was measured, expressed both as count and percent of count before lyophilization.

Results.

The data show that the temperature shift is not needed in order to achieve acceptable results when the shelf temperature is increased. See FIG. 14 (VCC) and FIG. 31 (RM). Lyophilized samples are stable out to 12 months for both 2-8° C. and −20° C. storage.

Advs11 frozen formulation (5271-15-01), lyo11 (5277 WP7 Lyo11) lyophilized formulation, and XFL7-tLLO-negative control strain were used to infect THP1 cells at MOI of 2 and 20. 10-mer peptide (YMLDLQPETT, SEQ ID NO: 100) was used as a positive control. Infected cells were then invocated for 20-24 hours, collected, and combined with T cells specific for the 10-mer peptide. After 18-24 hours, T cell IFNγ secretion was determined. A t low MOI, lyophilized formulation induced higher IFNγ production in the T cells. At higher MOI, lyophilized formulation showed similar induction of IFNγ production. The percent live for the lyophilized formulation was 95%. No loss in bioactivity was observed for the lyophilized product and for low MOI, bioactivity was increased. See FIG. 39.

2.11. Stability Study of Fresh Vs. Frozen Material with Different Thawing

To confirm the results obtained from Lyo8, Lyo10, and Lyo11, a stability study Lyo12 was performed where a comparison was made between fresh and frozen material with the frozen material being thawed in different ways.

2.11.1. WP7-Lyo12.

Materials and Methods.

The ADXS-HPV drug product was used for this study, and no temperature shift was performed. The formulation was phosphate-based with 2.5% sucrose, the residual moisture target was 2.5-3.0%, and the $OD_{600}$=10. The stability conditions used were 2-8° C., −20° C. and accelerated conditions for 1, 2, and 3 days at 30° C. The groups tested were: (1) Group A: control, lyophilized directly; (2) Group B: frozen at <−70° C., thawed at 2-8° C.; and (3) Group C: frozen at <−70° C., thawed at 37° C. in water bath, then incubated for 4 h at 37° C.

Study Design.

Once the material in the bioreactor reached the target $OD_{600}$, material was harvested and split into 3 aliquots for Parts A, B and C. Part A was immediately processed until formulated bulk was obtained and VCC analysis was performed before lyophilization. Part B and Part C materials were processed, aliquoted and frozen at <−70° C. Part B material was thawed at 2-8° C. overnight and Part C material was thawed completely in a water bath at 37° C. and was then incubated in the water bath at 37° C. for 4 h before lyophilization. Materials were then diluted to $OD_{600}$=10, and processed for lyophilization. The lyophilization run was performed for a target residual moisture of 2.5-3.0%. VCC was analyzed before and after lyophilization and at accelerated conditions. VCC titer was measured, expressed both as count and percent of count before lyophilization.

Results.

The data show that continually processed material has the better stability profile compare to frozen and thawed material. The data also demonstrate the drug substance may be stored prior to lyophilization. See FIG. 15 (VCC) and FIG. 32 (RM).

2.11.2. WP7-Lyo13.

Materials and Methods.

The ADXS-HPV drug product was used for this study. The formulation was phosphate-based with 2.5% sucrose, the residual moisture target was 2.5-3.0%, and the $OD_{600}$=10. The stability conditions used were 2-8° C., −20° C. and accelerated conditions for 1, 2, and 3 days at 30° C. The groups tested were: (1) Group A: fresh, lyophilized directly; (2) Group B: stored at 2-8° C. for 3 days.

Study Design.

Once the material in the bioreactor reached the target $OD_{600}$, material was harvested and split into 2 aliquots for Parts A and B. Part A was immediately processed until formulated bulk was obtained and VCC analysis was performed before lyophilization. Part B materials were processed, aliquoted and frozen at <−70° C. Part B material was stored at 2-8° C. for 3 days before lyophilization. Materials were then diluted to $OD_{600}$=10, and processed for lyophilization. The lyophilization run was performed for a target residual moisture of 2.5-3.0%. VCC was analyzed before and after lyophilization and at accelerated conditions. VCC titer was measured, expressed both as count and percent of count before lyophilization.

Results.

The data show good results for both continually processed material (straight through processing) and material stored at 2-8° C. for up to three days. See FIG. 16 (VCC) and FIG. 33 (RM). The data show that bulk drug substance (BDS) may be stored for three days at 2-8° C. before processing and still achieve acceptable results post-lyophilization.

Conclusion.

This study demonstrates that a 3 day hold of the drug substance at 2-8° C. can still result in acceptable long-term stability of the lyophilized drug product allowing for adding flexibility during routine manufacturing.

2.12. Presentation of Product.

2.12.1. WP7-Lyo14.

Materials and Methods.

The ADXS-HPV drug product was used for this study. The formulation was phosphate-based with 2.5% sucrose, the residual moisture target was 2.5-3.0%, and the $OD_{600}$=10. The stability conditions used were 2-8° C., −20° C. and accelerated conditions for 1, 2, and 3 days at 30° C. The factors tested were 2R vials, 1×10$^9$ VCC, and 1.2 mL fill.

Study Design.

Once the material in the bioreactor reached the target $OD_{600}$, material was harvested and processed for lyophilization. The lyophilization run was performed for a target residual moisture of 2.5-3.0%. VCC was analyzed before and after lyophilization and at accelerated conditions. VCC titer was measured, expressed both as count and percent of count before lyophilization.

Results.

The data show a decrease in viability under accelerated conditions but still within specifications. The data also indicate 2R vial presentation is suitable for use in lyophilization using the described compositions and methods. See FIG. 17 (VCC) and FIG. 34 (RM). The residual moisture was ~2% and below the target of 3-4%.

2.13 Batch Scale

Materials and Methods.

The ADXS-HPV drug product was used for this study. The formulation was phosphate-based with 2.5% sucrose, the residual moisture target was 2.5-3.0%, and the $OD_{600}$=10 with a target of 1×10$^{10}$ CFU/mL. 2 mL ADXS-HPV drug product were added to each of about 1500 R6 vials. The stability conditions used were 2-8° C., −20° C. and accelerated conditions for 1, 2, and 3 days at 30° C.

Study Design.

Once the material in the bioreactor reached the target $OD_{600}$, material was harvested and processed for lyophilization. The lyophilization run was performed for a target residual moisture of 2.5-3.0%. VCC was analyzed before and after lyophilization and at accelerated conditions. VCC titer was measured, expressed both as count and percent of count before lyophilization. Residual moisture (RM) was also determined.

Results.

The described compositions and methods are suitable for use with scale batch lyophilization. Accelerated stability is consistent with development of scale batches. Batch scale demonstrated suitability for clinical supply of drug substance in 6R vial presentation. See FIGS. 35-36 (VCC), FIGS. 37-38 (RM), and Table 12. "H" and "C" in FIG. 37 refer to hot and cold snots respectively within the lyophilizer.

TABLE 12

| Test | Test Method | Raw Data Reference | Result |
|---|---|---|---|
| Visual appearance | LAB-GEN-810 rev. 1.0 | LAB-GEN-810-TR01: T17L004 | 20 vials with white to off white cake 20 vials with white to off white solution |
| pH | LAB-GEN-840 rev. 1.0 | LAB-GEN-840-TR01: T17L007 | pH: 6.77 |
| Osmolality | LAB-GEN-800 rev. 1.0 | LAB-GEN-800-TR01: T17L008 | 372 mOsm/kg |
| Extractable volume | LAB-GEN-820 Rev. 1.0 | LAB-GEN-820-TR01: T17L005 | 1.92 mL per vial |
| CCIT | LAB-GEN-830 rev. 1.0 | LAB-GEN-830-TR01: T17L006 | No ingress of dye in 10 vials |
| Viable cell count | TM-SB-532 Rev. 2.0 | TM-SB-532-TR01: T17L017 | $6.4 \times 10^9$ CFU/mL |

2.14. Exemplary Materials and Methods.

pH-Buffer Stock Solutions.

pH-buffer solutions were prepared as 4-fold stock solutions.

Phosphate Buffer Stock Solution.

The phosphate buffer stock solution was prepared to resemble the current drug substance formulation as closely as possible, however without NaCl and KCl. It was prepared as a 4-fold stock: 0.8 g of $KH_2PO_4$ (anhydrous) and 4.6 g of $Na_2HPO_4$ (anhydrous) were dissolved in 800 mL of WFI. pH was adjusted to 7.2 with 10% HCl. Solution was filled up to 1000 mL of WFI and was filtered sterile with a 0.2 μm filter. The final formulated drug product would contain 0.2 g/L $KH_2PO_4$ (anhydrous) and 1.15 g/L of $Na_2HPO_4$ (anhydrous).

Citrate Buffer Stock Solution.

A 40 mM (=4-fold) stock solution of citric acid was prepared by dissolving 0.84 g of citric acid ad 100 mL WFI. A 40 mM (=4-fold) stock solution of Na-citrate was prepared by dissolving 2.94 g of Na-citrate ad 250 mL WFI. A 40 mM (=4-fold) stock solution of citrate buffer was prepared by adjusting the pH of the 40 mM Na-citrate solution to pH=7.2 using the 40 mM citric acid solution. Solution was filtered sterile with a 0.2 μm filter.

MOPS-Buffer Stock Solution.

A 40 mM (=4-fold) stock solution of MOPS was prepared by dissolving 2.3125 g MOPS in 200 mL of WFI. pH was adjusted to pH=7.2 with 10% HCl. Solution was filled up ad 250 mL WFI and was filtered sterile with a 0.2 μm filter.

40% w/v Sucrose Stock Solution.

200 g of sucrose were dissolved ad 500 mL WFI. Solution was filtered sterile with a 0.2 μm filter.

40% w/v Trehalose Stock Solution.

40 g of trehalose were dissolved ad 100 mL WFI. Solution was filtered sterile with a 0.2 μm filter.

20% w/v MSG Stock Solution.

8 g of L-Glutamic acid monosodium salt hydrate were dissolved ad 40 mL WFI. Solution was filtered sterile with a 0.2 μm filter.

20% w/v rHSA Stock Solution.

10 g of lyophilized rHSA (Kerry, rAlbumin EG) were dissolved ad 50 mL WFI. Solution was filtered sterile with a 0.2 μm filter.

Buffers for Resuspension of the Bacterial Pellet.

1-fold buffers for resuspension of the bacterial pellet were prepared by mixing 140 mL WFI, 10 mL of 40% sucrose and 50 mL of the respective 4-fold pH-buffer stock resulting in 1×pH buffer/2% sucrose.

AA-Mix Stock Solution.

200 mL of a 4-fold amino acid stock solution were prepared that contained 144 mM arginine, 228 mM glutamine and 28 mM isoleucine. See, e.g., Paik et. al. (Biotechnol Prog. 2012 November-December; 28(6), herein incorporated by reference in its entirety for all purposes). Final amino acid concentrations in formulated drug substance were 36 mM, 57 mM and 7 mM, respectively. It was prepared as follows: 5.17 g of arginine (Mw=174.2 g/mol) were weighed and dissolved ad 50 mL WFI. 48.52 mL (representing 5.017 g) of this solution were transferred into a 250 mL bottle. 0.8 g of isoleucine (Mw=131.17 g/mol) were weighed and dissolved ad 50 mL WFI. 45.91 mL of this solution (representing 0.735 g) were transferred into the same 250 mL bottle. 6.71 g of glutamine (Mw=147.13 g/mol) were weighed and transferred directly into the 250 mL bottle. Total volume was filled up to 160 mL WFI and the pH was carefully adjusted to pH=7.2 by adding 2N NaOH under constant stirring. When all glutamine was dissolved and the pH was stable, volume was filled up to 200 mL WFI. Solution was filtered sterile with a 0.2 μm filter.

Preparation of 2-Fold Excipient Stocks.

2-fold excipient stocks were used for mixing 1:1 with the bacterial stock solution to obtain the final formulations with an $OD_{600}$~10 or $OD_{600}$~2.0. They were prepared by mixing appropriate volumes of 4-fold pH-buffer stock solutions and excipient stock solutions to obtain the desired concentrations.

Cultivation of Lm.

100 mL of TSB (30 g TSB/1 kg WFI, 5 g yeast extract/1 kg WFI, additional 7.5 g glucose/1 kg WFI giving a final concentration of glucose of 10 g/1 kg WFI) were pre-warmed in a 500 mL baffled shake flask to 37° C. Medium was incubated overnight. On the next day, the medium was clear. One vial of the Lm RCB (5277-2015-01.01; VCC=$2.44 \times 10^9$ CFU/mL) was thawed at room temperature. Medium was inoculated with 900 μL of vial content. Lm were incubated at 37° C., 110 rpm for 5 h 15 minutes (P1). At this point the $OD_{600}$ was 3.59. For P2, 5×3 L Fernbach bottles containing 500 mL of TSB were inoculated with 2.5 mL of P1, respectively. The cultures were incubated at 37° C., 110 rpm for 14 h 50 min. Cultures were pooled and $OD_{600}$ was 5.96.

Alternatively, 50 mL of TSB were pre-warmed in a 250 mL baffled shake flask to 37° C. Medium was incubated overnight. On the next day, the medium was clear. One vial of the Lm RCB (5277-2015-01.01; VCC=$2.44 \times 10^9$ CFU/mL) was thawed at room temperature. Medium was inoculated with 600 μL of vial content. Lm were incubated at 37° C., 110 rpm for 7 h 55 min (P1). At this point the $OD_{600}$ was 4.78. For P2 3×3 L Fernbach bottles containing 500 mL of TSB were inoculated with 5.0 mL of P1, respectively. The cultures were incubated at 37° C., 110 rpm for 14 h 30 min. At this point the $OD_{600}$ was 5.96.

Concentration and Formulation of Lm.

For each pH-buffer (phosphate, citrate & MOPS) 520 mL of P2 were centrifuged at 2,000 g, 10 min, RT. Supernatant was discarded and the pellets were each resuspended in 155 mL of 1×pH-buffer 2% sucrose, respectively and the $OD_{600}$ values checked. Target $OD_{600}$ was 20 after concentration: $OD_{600}$ phosphate buffer=19.2. $OD_{600}$ citrate buffer=18.6. $OD_{600}$ MOPS buffer=18.8. Final formulations were obtained by mixing equal volumes of concentrated bacteria with 2×-concentrated excipient stocks resulting in a formulation with an $OD_{600}$~10. Excipient concentrations are described elsewhere herein. After formulation a sample was taken for VCC analysis (before Lyo).

Alternatively, 1,000 mL of P2 were centrifuged at 2,000 g, 10 min, RT. Supernatant was discarded and the pellets were each resuspended in 300 mL of 1× phosphate buffer 2% sucrose. $OD_{600}$ was 18.3 after resuspension. This stock was used for generation of the samples of $OD_{600}$~10. For generation of the samples of $OD_{600}$~2 this stock was diluted by a factor of 4.58 with 1× phosphate buffer 2% sucrose. $OD_{600}$ was 4.12 after dilution. Final formulations were obtained by mixing equal volumes of concentrated bacteria with 2× concentrated excipient stocks resulting in formulations with an $OD_{600}$~10 or $OD_{600}$~2.

2.15. Summary.

In summary, the data show that accelerated conditions appear to be a good predictor of long-term stability and that storage of lyophilized drug product at 2-8° C. and −20° C. is possible. The data for ADVX-HPV are comparable to the data for ADXS-HER2, indicating that the data is predicted to be consistent across different Lm drug products. The data also indicate that higher RM is more desirable. For example, moistures below about 1% may not provide a stable Lm product, but moistures as high as 6-7% appear to be as stable as moistures around 3-4%. The data also indicate that the temperature shift improves stability, and that higher shelf temperature (primary drying step) improves stability. 2R and 6R vial presentation is suitable for use in lyophilization using the described compositions and methods. Bioassay shows good activity of lyophilized material compared to frozen liquid formulation. Batch scale is suitable clinical supply in a 6R presentation. In some embodiments, the drug product is presented in 6R vials at $1\times10^{10}$ CFU/mL. In some embodiments, the drug product is presented in 2R vials at $1\times10^{9}$ CFU/mL.

Induction of a stress response through a temperature shift significantly improves the viability after lyophilization. In addition, despite phosphate buffers generally not being ideal buffers for lyophilization products, phosphate-based formulation had better performance compared to citrate- and MOPS-based buffers and required the smallest process change as they were closest to the current drug substance formulation. The best stability was seen in formulations including sucrose but no trehalose, MSG, or rHSA. Formulations containing sucrose-only or a mixture of sucrose+AA had better residual moisture compared to rHSA formulations, which were drier. Highest recoveries (and lowest variability) were observed at lowest sucrose concentration (about 2.5% w/v). Improvement in stability was observed with increased shelf temperature during the primary drying step (e.g., about 18° C.) and with increased residual moisture levels (e.g., about 3.5%). For increased residual moisture levels such as 3.5% (which are higher than typical residual moisture levels for lyophilized products), secondary drying temperatures as low as 5° C. may be feasible (e.g., between about 5° C. and about 20° C.).

Example 3. Reproduction and Further Optimization of Lyophilization Parameters for Listeria monocytogenes A series of experiments were performed with different test parameters to reproduce lyophilization cycles from Example 2 and to further optimize the formulation, the pre-conditioning of cells, and the lyophilization cycle.

3.1. Reproduce Previous Lyophilization Cycle as Basis of Comparison.

A series of experiments (WP2A) were performed with 6R vials and 2 mL fills using the same lyophilization cycle parameters as Lyo9 through Lyo13.

Study Design.

Once the material in the bioreactor reached the target $OD_{600}$, material was harvested and processed for lyophilization. The lyophilization run was performed for a target residual moisture of 2.5-3.0%. VCC was analyzed before and after lyophilization and at accelerated condition (1, 2, and 3 days at 30° C.). Residual moisture was also measured after lyophilization and at the 3 days accelerated condition. Micro-Flow Imaging (MFI) and Resonant Mass Measurement (RMM) were also performed before lyophilization, after lyophilization, and at accelerated conditions for 1, 2, and 3 days (30° C.). VCC titer was measured, expressed as both count and percent of count before lyophilization. Moisture and VCC data were compared to previous data from the same lyophilization cycle conditions.

Results.

A decrease of the VCC (CFU/mL) to 80% was observed after lyophilization. See FIG. 18. The VCC was constant throughout storage for up to 72 hours at 30° C. Initial residual moistures (direct sample injection) averaged 2.4%, and no increase was observed over 72 hours at 30° C. The number of subvisible particles of samples before and after lyophilization was comparable as measured by MFI and RMM. The particle size distribution remained constant. The previous lyophilization cycle was successfully reproduced.

3.2. Study Residual Moisture Content as Function of Secondary Drying Shelf Temperature.

A series of experiments (WP2B) were performed to study residual moisture (RM) content as a function of secondary drying shelf temperature to predict secondary drying shelf temperatures that would result in the target of 3.5% RM.

Study Design.

6R vials with 2 mL fills and the same freezing and primary drying as in the WP2A experiments. Secondary drying was conducted in stages: (1) end of primary drying, stopper shelf (for RM information only); (2) ramp to 0° C., hold for 6 hr, stopper shelf; (3) ramp to 5° C., hold for 6 hr, stopper shelf; (4) ramp to 15° C., hold for 6 hr, stopper shelf. VCC was analyzed before and after lyophilization and at accelerated condition (1, 2, and 3 days at 30° C.). Residual moisture was also measured after lyophilization and at the 3 days accelerated condition. MFI and RMM were also performed before lyophilization, after lyophilization, and at accelerated conditions for 1, 2, and 3 days (30° C.).

Results.

The target RM of 3.5% can be obtained by using a secondary drying temperature between 5° C. and 15° C. (e.g., 12° C.). See FIG. 19. The number of subvisible particles of samples at different sampling points was comparable as measured by MFI and RMM. Different SD temperatures had no influence on the subvisible particle level. Comparable particle levels were observed for WP2A samples. No significant change in VCC was observed from pre-lyophilization to post-lyophilization. A decrease of the VCC to 78%-85% of pre-lyophilization was observed after 72 hr at 30° C. There was no discernible trend of VCC with SD temperatures.

3.3. Evaluate Modified Freezing Steps.

A series of experiments (WP3) were performed to explore a modified freezing step with an extended hold time of vials at −4° C. to allow all vials to equilibrate just above freezing temperature.

Study Design.

6R vials with 2 mL fills and the cycle conditions from the WP2A experiments were used with the following changes: (1) extend hold at −4° C. from 30 min to approximately 1 hr 20 min; and (2) conduct secondary drying at 12° C. to target 3.5% RM. VCC was analyzed before and after lyophilization and at accelerated condition (1, 2, and 3 days at 30° C.). Residual moisture was also measured after lyophilization and at the 3 days accelerated condition. MFI and RMM were also performed before lyophilization, after lyophilization, and at accelerated conditions for 1, 2, and 3 days (30° C.).

Results.

Primary drying (PD) of samples was competed after about 23 hours process time. For front vials, PD was already finished after 18 hours. For back vials, PD was finished after 20 hours. After PD, the vials were equilibrated for 83 min at −4° C. After lyophilization, samples were analyzed immediately (Tlyo) or stored at 30° C. (Txxh). A decrease of the VCC to 80% was observed after lyophilization and to 70% after storage for up to 72 hr at 30° C. (T30 h). A RM of 2.3% was measured after lyophilization for the center vials instead of the expected 3.5%. The number of subvisible particles of the samples before and after lyophilization was comparable as measured by MFI. The particle size distribution remained constant. The enhanced freezing step may have changed the ice crystal formulation and thereby the drying behavior of the lyophilization cake, which may have influenced the cell viability and residual moisture. See FIGS. 40A-B.

3.4. Evaluate Modified Freezing Steps and Primary Drying Temperatures.

A two-factorial design study (WP4) is performed (freezing step and primary drying temperature).

Study Design.

Fast shelf cooling from 5° C. to −45° C. during the freezing step is tested. Adjusted primary drying conditions are tested to reduce cake shrinkage/collapse. VCC is analyzed before and after lyophilization and at accelerated condition (1, 2, and 3 days at 30° C.). Residual moisture is also measured after lyophilization and at the 3 days accelerated condition. MFI and RMM are also performed before lyophilization, after lyophilization, and at accelerated conditions for 1, 2, and 3 days (30° C.).

3.5. Evaluate Thawing Procedures (37° C. Thaw).

A series of experiments (WP6) were performed to evaluate a new thawing procedure for ADXS-HER2. The previous thawing procedure was to thaw formulated bulk material overnight at 2-8° C.

Study Design.

6R vials with 2 mL fills and the cycle conditions from the WP2B experiments were used. Formulated bulk material at an $OD_{600}$ of 10 was thawed at 37° C. The cell pellet was thawed at 37° C. and then diluted with formulation buffer to an $OD_{600}$ of 10. VCC was analyzed before and after lyophilization and at accelerated condition (1, 2, and 3 days at 30° C.). Residual moisture was also measured after lyophilization and at the 3 days accelerated condition. MFI and RMM were also performed before lyophilization, after lyophilization, and at accelerated conditions for 1, 2, and 3 days (30° C.). See FIGS. 41A-B.

Results.

The process of WP2B was reproduced until SD temperature of 5° C. Primary drying (PD) of samples completed after ~25 h process time. Lyo process was comparable to WP2B. After lyophilization, samples were immediately analyzed (Tlyo) or stored at 30° C. (Txxh). CFU/mL at Tliq were comparable between A (formulated bulk material (i.e., Drug Substance)) and B. (cell pellet (i.e., Drug Substance that has been highly concentrated to essentially remove all formulation buffer)). After lyophilization, a decrease to 70% and 80% VCC was observed. A further decrease to about 50% VCC was observed after storage for 24 hours at 30° C., which was unchanged after 72 Hr. at 30° C.

3.6. Evaluate Different Bacterial Target Concentrations (WP7).

Three different bacterial target concentrations were tested to determine the influence of the bacterial concentration on the cake appearance when the lyophilization cycle with an annealing step is used.

Study Design.

Three different formulations with different OD600 values were prepared:
(a) OD 10: F1000: use of delivered BDS as provided,
(b) OD 2: F0200: 31.37 ml BDS+118.63 ml formulation buffer, and
(c) OD 0.65: F0065: 10.20 ml BDS+139.80 ml formulation buffer.

HER2 material was provided using the ADXS platform manufacturing process (see Example 7).

| Parameter | Cell Pellet |
| --- | --- |
| Amount | 800 mL (by volume |
| OD600 (raw material) | 10.05 |
| Cells/mL | $1.69 \times 10^{10}$ |
| Viability | 98.45% |

VCC was analyzed before lyophilization, after lyophilization, and at accelerated conditions for 1, 2 and 3 days (30° C.). Residual moisture was analyzed after lyophilization and 3 days accelerated condition. MFI and RMM were analyzed before lyophilization, after lyophilization, and at accelerated conditions for 1, 2, and 3 days (30° C.).

Results:

Primary drying (PD) of samples was completed after ~40 h process time (indicated by both $Pt_{100}$ sensor and pressure sensor readout). The process was comparable to WP7 cycle 1; only the SD temperature was changed from 5° C. to 0° C. to target a residual moisture content of ca. 3.5%. After lyophilization, samples were immediately analyzed (Tlyo) or stored at 30° C. or 2-8° C., respectively. A correlation between bacterial concentration and optical appearance of the final product was observed. The lower the bacterial concentration, the more cake shrinkage was observed. Reconstitution of the lyophilized cake was faster for F0065 and F0200 (~20 s) than for F1000 (~100 s). See FIGS. 42A-B.

After lyophilization, a decrease in VCC to about 60% was observed, independent of the bacterial concentration. Also after lyophilization, no difference in VCC was observed for front and center vials. A slightly higher VCC was even detected for front vials. After 24 h at 30° C. a further 10% decrease in VCC was observed for the two lower bacterial concentrations. Results were unchanged after 72 h. at 30° C. After 7 days at 2-8° C., a decrease in VCC of about 20% was observed. See FIG. 43.

Viable cell count (VCC) and viability appeared stable under accelerated conditions. See FIGS. 44A-B.

3.7. Evaluate 2R Vial Presentation (WP8).

2R vial presentation at a target VCC of $1 \times 10^9$ wash was evaluated. In addition, stability of frozen and non-frozen BDS was compared.

Study Design.

Formulated bulk material at a target VCC of $1 \times 10^9$ and $1 \times 10^{10}$ plus about 30% to account for manufacturing losses was provided. VCC was analyzed before lyophilization, after lyophilization, and at accelerated conditions for 1, 2, and 3 days (30° C.). Residual moisture was analyzed after lyophilization and 3 days accelerated condition. MFI and RMM were analyzed before lyophilization, after lyophilization, and at accelerated conditions for 1, 2, and 3 days (30° C.).

Results.

Minimal losses due to lyophilization were observed. No significant changes observed in VCC or live/dead on accelerated stability were observed. % live at initial was higher relative to liquid-frozen formulation. See FIGS. 45A-B.

3.8 Large Scale Production (WP7).

In a large scale production the holding times of the BDS before starting a lyophilization run are longer compared to lyophilization runs during development in a pilot scale freeze dryer. The aim of this study is to evaluate whether this could have an influence on the product.

Study Design.

Non-frozen liquid bulk drug substance (BDS) was provided by APC one day prior to the start of the freeze drying cycle. The liquid BDS was diluted to an $OD_{600}$ value of 0.85 (target VCC of $1.3 \times 10^9$ CFU/ml) by using the delivered formulation buffer. The diluted material was stored at 2-8° C. during the conduct of the holding time study. The four shelves were filled with BDS and loaded into the freeze-dryer at four different time points: 20 h (H20 h), 8 h (H8 h), 5 h (H5 h), and 0 h (H0 h) before starting the freeze-drying process.

Results.

After lyophilization, a decrease in VCC was observed (relative to Tliq): 78% at H0 h, 74% at H5 h: 74%, 73% at H8 h, and 65% at H20 h. After storage for up to 72 h at 30° C. a further decrease of around 10% was observed for H20 h, H8 h, and H5 h. The VCC at T7 days after storage at 2-8° C. was comparable to the VCC after lyophilization. See FIGS. 46A, 46B, 47A, and 47B.

Example 4. Lyophilization of Drug Product and Long-Term Room Temperature Stability of the Lyophilized Drug Product 4.1 ADXS11-001 Pilot Batch 4.1.1 Materials and Methods Previous development experiments have all been performed using a small-scale development lyophilizer. Because scale up does not guarantee that the same dynamics of product temperature and ice content as those at the laboratory scale modifications to the lyophilization cycle may be needed for larger scale production. In order to evaluate potential scale up issues a pilot batch was manufactured for proof of concept and stability studies. The Drug Substance process is carried out within a single use closed system provided by rocking wave motion bioreactor technology. The Drug Substance manufacturing followed the ADXS platform manufacturing process. The platform consists of a single-use closed system of a product 20 L culture bag for fermentation, a tangential flow filtration (TFF) manifold for concentration and buffer exchange and a container manifold for DS filling. The Drug Substance was held overnight at 2-8° C., diluted to the target $OD_{600}$ with formulation buffer, filled into DIN 6R vials (2.0 mL) and lyophilized. The approximate batch size was 1500 vials.

TABLE 13

Primary Packaging Materials used for Pilot Batch.

| Primary Packing Material | Specifications | Supplier |
|---|---|---|
| 6R Glass vials | Rofa, 6R | HAL Allergy, MW005-002 |
| Lyo stoppers | West, 7000-5780 | Adelphi, FDW20RTS |
| Ready to sterilize (steam sterilization) | | |
| Crimp cap, flip-off seals | West, 5921-2032 | Adelphi, FOT20W |

The stoppers were delivered ready-to-process and were not dried before use.

4.1.2 Study Design

The lyophilization process was conducted in a Martin Christ Epsilon 2-12D pilot-scale lyophilizer. Because this lyophilizer uses a Pirani gauge as the controlling pressure sensor instead of an MKS sensor used in the laboratory-scale lyophilizer, a pressure set point for the Pirani gauge had to be selected. Based on a review of previous lyophilization cycles where the Pirani gauge pressure was measured (but not used for control), a Pirani pressure of 0.163 mbar was found to be equivalent to a MKS pressure of 0.090 mbar during the main portion of primary drying. Since Pirani gauge pressure is dependent upon the composition of the gas phase, as the partial pressure of water decreases towards the end of primary drying, the Pirani pressure readings approach the MKS pressure readings.

TABLE 14

Lyophilization Parameters for ADXS11-001 Pilot Batch

| Step | Phase | Item | Duration [hh:mm] | Temp, $T_s$ of Shelves [° C.] | Vacuum [mbar] |
|---|---|---|---|---|---|
| 1 | Preparation | Warm up of lyo, placement of temperature and Rx sensors | NA | 4 | off |
| 2 | Load | Loading of Shelves | NA | 4 | off |
| 3 | Ramp | Freezing | Ramp samples to −4° C. (0.4° C./min) | 00:20 | −4 | off |
| 4 | Hold | | Hold/anneal samples to −4° C. | 00:30 | −4 | off |
| 5 | Ramp | | Freeze ramp to −45° C. (0.45° C./min) | 01:30 | −45 | off |

TABLE 14-continued

Lyophilization Parameters for ADXS11-001 Pilot Batch

| Step | Phase | | Item | Duration [hh:mm] | Temp, $T_s$ of Shelves [° C.] | Vacuum [mbar] |
|---|---|---|---|---|---|---|
| 6 | Hold | | Hold at −45° C., temperature equilibration across load | 01:30 | −45 | off |
| 7 | Hold | | Hold and preparation of vacuum pump | 00:30 | — | — |
| 8 | Ramp | Primary | Vacuum[1] | 00:01 | −45 | 0.160*** |
| 9 | Hold | Drying | Vacuum[1] | 00:15 | −45 | 0.160 |
| 10 | Ramp | | Heating ramp (1.0° C./min) | 00:27 | −18 | 0.160 |
| 11 | Hold | | Stable shelf temp:primary drying | >tbc[2] | −18 | 0.160 |
| 12 | Ramp | Secondary Drying | Heating ramp (0.2° C./min) | 03:10 | 20 | 0.160 |
| 13 | Hold | | Stable shelf temp:secondary drying | 02:00 | 20 | 0.160 |
| 14 | Ramp- Hold | | Ramp to 10° C. | 00:10 | 10 | 0.160 |
| 15 | Hold | | Hold at 10° C. until unloading | NA | 10 | 1.0[3] |
| 15a | | | Ventilation and manual vial closure | NA | 10 | 500 mbar |

[1]Pirani vacuum sensor is process controlling (***0.163 was not programmable)
[2]End of primary drying is defined here 14 hours after $T_P$ P100 probe for the cold spot(s) have crossed the $T_s$ set point of −18° C.
[3]Only done to avoid vacuum pull after the cycle has finished during the night

4.1.3 Results and Discussion

TABLE 15

OD$_{600}$ and VCC for In-Process Samples

| Process Step | OD$_{600}$ | VCC |
|---|---|---|
| WAVE Harvest | 7.9 | $1.76 \times 10^{10}$ |
| Pre-Formulation | 17 | $3.09 \times 10^{10}$ |
| Final Bulk Formulation Post Hold/ Final Formulation | 10.2 | $1.27 \times 10^{10}$ |
| Final Formulated Bulk (before Lyo | 10.2 | $1.76 \times 10^{10}$ |

Preliminarily mapping of the lyophilizer was performed by determining the VCC (plate method) for hot (H) and cold (C) spots per shelf within the lyophilizer. The data are presented in FIG. 48 and Table 16.

TABLE 16

VCC and Residual Moisture Data from Hot and Cold Spots within the lyophilizer for the Pilot Batch

| Location | Sample | VCC (CFU/mL) | Residual Moisture |
|---|---|---|---|
| Hot | 1 | 7.00E+09 | 2.57 |
| | 2 | 7.60E+09 | 2.04 |
| | 3 | 6.58E+09 | 2.39 |
| | 4 | 6.94E+09 | 2.37 |
| | 5 | 7.28E+09 | 2.16 |
| Cold | 1 | 9.78E+09 | 2.45 |
| | 2 | 1.02E+10 | 2.53 |
| | 3 | 1.01E+10 | 2.81 |

TABLE 16-continued

VCC and Residual Moisture Data from Hot and Cold Spots within the lyophilizer for the Pilot Batch

| Location | Sample | VCC (CFU/mL) | Residual Moisture |
|---|---|---|---|
| | 4 | 1.03E+10 | 2.61 |
| | 5 | 1.12E+10 | 2.42 |

Summary statistics for the VCC data from the Hot and Cold spots within the lyophilizer demonstrate that the mean VCC for the Hot spots is 7.08E+09 CFU/mL and the mean for the Cold spots is 1.032E+10 CFU/mL. Hot spots and cold spots in the lyophilizer are determined based on temperatures from probes within the lyophilizer. Hot spots tend to be on the edges of the lyophilizer, and cold spots tend to be in the center of the lyophilizer. The sample numbers correspond to the shelf within the lyophilizer and show little variation with the H or C locations. Refer to the CV column in Table 17.

TABLE 17

Statistics Summary

| Variable | Location | N | Mean | StDev | Coef Var (CV) |
|---|---|---|---|---|---|
| VCC (CFU/mL) | Cold | 5 | 10316000000 | 531300292 | 5.15 |
| C | Hot | 5 | 7080000000 | 382883794 | 5.41 |

The data show a distinction in VCC and RM between the hot and cold Spots within the lyophilizer. It is not known if the difference in VCC is necessarily due to the difference in RM, or whether they are both functions of some other characteristic of the lyophilization cake.

Release and stability analysis was performed by Eurofins using validated methods. Vials are reconstituted with 2 mL or normal saline prior to analysis. The release and stability data are provided in Table 18.

TABLE 18

Release and Stability Testing for ADXS11-001 Pilot Batch (Lot# 5329PD-17-01)

| Test | Test method | | Specifications | Release testing | Accelerated stability Day 1 | Day 2 | Day 3 |
|---|---|---|---|---|---|---|---|
| Visual appearance | LAB-GEN-810 | Cake | White/off-white to slightly yellow powder | | | | |
| | | Color - Reconstituted Solution | White to off-white suspension | 20 vials with white to off white color | 12 vials with white to off white color | 12 vials with white to off white color | 12 vials with white to off white color |
| | | Particles- Reconstituted Solution | Essentially free of foreign particles | 20 vials with no particles present | 12 vials with no particles present | 12 vials with no particles present | 12 vials with no particles present |
| pH | LAB-GEN-840 | | 6.0-8.0 | 6.77 | 6.79 | 6.80 | 6.79 |
| Osmolality | LAB-GEN-800 | | 250-450 mOsm/kg | 372 | — | — | — |
| Extractable volume | LAB-GEN-820 | | >1 mL/vial | 1.92 mL | — | — | — |
| CCIT | LAB-GEN-830 | | No Dye Ingress | No ingress of dye in 10 vials | — | — | — |
| Reconstitution time | LAB-GEN-880 | | Report Result (seconds) | 56 | 24 | 28 | 27 |
| Viable cell count | TM-SG-110 | | $5 \times 10^9 - 5 \times 10^{10}$ CFU/mL | $1.12 \times 10^{10}$ | $1.16 \times 10^{10}$ | $1.09 \times 10^{10}$ | $1.10 \times 10^{10}$ |
| % of viable cells | TM-SG-110 | | >60% | 86% | 89% | 83% | 87% |
| Endotoxin | TM-SG-101 | | EU/mL | <10 EU/mL | — | — | — |
| Monosepsis | TM-SB-534 | TYMC < 10 CFU/mL | | <1 CFU/L | — | — | — |
| | | TYMC: Candida albicans | Absent in 1 mL | Absent in 1 mL | — | — | — |
| | | Absent in 1 mL Escherichia coli Bacillus subtilis Pseudomonas aeruginosa Staphylococcus aureus Clostridia sp. | Absent in 1 mL | Absent in 1 mL | — | — | — |
| | | Absent in 10 mL Salmonella sp. | Absent in 10 mL | Absent in 10 mL | — | — | — |
| | | Single Species (L. monocytogenes) | Pure culture | Pure culture | — | — | — |

| Test | Test method | | Results T1 5° C. | T1 −20° C. | T3 5° C. | T3 −20° C. | T6 5° C. | T6 −20° C. |
|---|---|---|---|---|---|---|---|---|
| Visual appearance | LAB-GEN-810 | Cake | | | | | Intact cake | Intact cake |
| | | Color - Reconstituted Solution | 12 vials with white to off white color | 12 vials with white to off white color | 12 vials with white to off white color | 12 vials with white to off white color | 12 vials with white to off white color | 12 vials with white to off white color |
| | | Particles- Reconstituted Solution | 12 vials with no particles present | 12 vials with no particles present | 12 vials with no particles present | 12 vials with no particles present | 12 vials with no particles present | 12 vials with no particles present |
| pH | LAB-GEN-840 | | 6.80 | 6.81 | 6.79 | 6.79 | 6.87 | 6.86 |
| Osmolality | LAB-GEN-800 | | — | — | — | — | — | — |
| Extractable volume | LAB-GEN-820 | | — | — | — | — | — | — |
| CCIT | LAB-GEN-830 | | — | — | — | — | — | — |
| Reconstitution time | LAB-GEN-880 | | 20 | 22 | 21 | 21 | 36 | 29 |
| Viable cell count | TM-SG-110 | | $1.24 \times 10^{10}$ | $1.22 \times 10^{10}$ | $1.15 \times 10^{10}$ | $1.11 \times 10^{10}$ | $1.15 \times 10^{10}$ | $1.21 \times 10^{10}$ |
| % of viable cells | TM-SG-110 | | 88% | 87% | 88% | 88% | 88% | 89% |
| Endotoxin | TM-SG-101 | | — | — | — | — | — | — |
| Monosepsis | TM-SB-534 | TYMC < 10 CFU/mL | — | — | — | — | — | — |
| | | TYMC: Candida albicans | — | — | — | — | — | — |

TABLE 18-continued

Release and Stability Testing for ADXS11-001 Pilot Batch (Lot# 5329PD-17-01)

| | | | | | | |
|---|---|---|---|---|---|---|
| Absent in 1 mL *Escherichia coli* *Bacillus subtilis* *Pseudomonas aeruginosa* *Staphylococcus aureus* *Clostridia* sp. | — | — | — | — | — | — |
| Absent in 10 mL *Salmonella* sp. | — | — | — | — | — | — |
| Single Species (*L. monocytogenes*) | — | — | — | — | — | — |

4.2.1 Accelerated Stability

Early development data demonstrated that accelerated stability at 30° C. may be predictive of long-term stability trends. The batch was stored at 30° C. and evaluated for up to 63 days to determine how long the product was stable for under accelerated conditions (FIGS. 49-53 and Table 19).

TABLE 19

VCC and % Live for ADXS11-001, Lot# 5329PD-17-01 Stored at 30° C.

| Day | Specification | % Live | VCC (cells/mL) |
|---|---|---|---|
| 0 | ≥60% | 86% | $1.12 \times 10^{10}$ |
| 1 | | 83% | $1.32 \times 10^{10}$ |
| 3 | | 86% | $1.35 \times 10^{10}$ |
| 7 | | 89% | $1.43 \times 10^{10}$ |
| 14 | | 91% | $1.09 \times 10^{10}$ |
| 21 | | 92% | $1.51 \times 10^{10}$ |
| 23 | | 88% | $1.46 \times 10^{10}$ |
| 28 | | 91% | $1.01 \times 10^{10}$ |
| 35 | | 90% | $1.11 \times 10^{10}$ |
| 42 | | 90% | $1.08 \times 10^{10}$ |

4.2.2 In Vivo Testing

ADXS11-001 (AXAL) is a live attenuated *Listeria monocytogenes*-listeriolysin O (Lm-LLO) immunotherapy that is under clinical development for the treatment of human papilloma virus (HPV)-associated cancers. ADXS11-001 is bioengineered to secrete an antigen-adjuvant fusion protein consisting of a truncated fragment of listeriolysin O (tLLO) fused to the full length E7 protein of HPV 16 (tLLO-E7). The proposed mechanism of action of the Lm-based immunotherapy is to stimulate both the innate and adaptive immune systems in order to initiate a coordinated anti-tumor response culminating in the de novo generation of tumor antigen-specific T cells that are capable of infiltrating and destroying the tumor. In order to confirm that the bioactivity of the product is not adversely impacted by lyophilization tumor-bearing mice immunized with ADXS11-001 generate CD4+ and CD8+ T cells specific to HPV16-E7 and HPV16-E6.

The abilities of lyophilized AXAL and clinical AXAL to control tumors and to prolong animal survival were evaluated and compared in TC-1 tumor-bearing mice. Adult female C57BL/6 mice were injected subcutaneously in the right flank with $1 \times 10^5$ TC-1 tumor cells and then immunized on Days 8, 15, and 22 after tumor implantation by IP injection with PBS or with various doses ($5 \times 10^7$ CFU, $1 \times 10^8$ CFU, $2 \times 10^8$ CFU) of lyophilized AXAL or clinical AXAL (see FIG. 54). Tumor growth and the general health of the mice were monitored for 62 days after tumor implantation. Mice were euthanized if tumor volume exceeded 2000 mm³.

In mice treated with PBS, tumor volume continued to increase, and no animals survived past Day 30 (FIGS. 55-56). In comparison, all doses of lyophilized AXAL and clinical AXAL significantly inhibited tumor growth and prolonged animal survival (FIGS. 55-56). Notably, for each dose, the tumor growth curves and survival curves for lyophilized AXAL and clinical AXAL were similar.

As shown in FIG. 55, tumor-bearing mice were treated on day 8 post-tumor implantation with PBS or with 3 different doses of lyophilized AXAL or clinical AXAL and at 7-day intervals thereafter for a total of 3 doses. Tumor volume was measured twice a week. Tumor growth curves for each dose group are shown. ****$P<0.0001$. NS, not significant.

As shown in FIG. 56, tumor-bearing mice were treated on day 8 post-tumor implantation with PBS or with 3 different doses of lyophilized AXAL or clinical AXAL and at 7-day intervals thereafter for a total of 3 doses. Tumor growth and the general health of the mice were monitored for 62 days after tumor implantation. Mice were euthanized if tumor volume exceeded 2000 mm³. Survival curves for each dose group are shown. **$P<0.01$. NS, not significant.

No significant differences were observed between lyophilized AXAL and clinical AXAL in their abilities to control tumor growth and to prolong animal survival in TC-1 tumor-bearing mice. These data indicate that the lyophilization process does not affect the antitumor activities of AXAL.

4.3 Conclusion

The pilot batch successfully demonstrated the application of the ADXS DS platform manufacturing process to support a lyophilized Drug Product. The % live and VCC on accelerated stability is consistent with previous development studies.

Example 5. Ability to Freeze/Thaw the Drug Substance and Obtain Comparable Results to Continuously Processed Material

5.1 WP7, Cycle 3

Different storage conditions of Drug Substance (frozen vs. non-frozen 2-8° C.) were evaluated to see if the improvements in the lyophilization cycle result in improved viability post lyophilization for DS that has been through a single freeze-thaw.

5.2 Materials and Methods

Frozen (A) and non-frozen liquid (B) BDS were provided by APC (Dublin, Ireland) one day prior to the freeze-drying cycle. Approximately 800 mL of both 2-8° C. and Frozen DS was formulated to an approximately $OD_{600}$ of 14 in 1 L LDPE bags. The frozen material was thawed in a water bath at 37° C. until the material contained no long contained ice crystals (thawing time: 2.5 h). The two Drug Substances (A and B) were diluted to two different $OD_{600}$ values by using the formulation buffer (prepared at Coriolis). Table 20 gives an overview of the prepared formulations and the target $OD_{600}$ values.

TABLE 20

Formulations and Target $OD_{600}$ values

| Formulation | BDS | $OD_{600}$ Value |
|---|---|---|
| A0085 | Frozen Drug Substance | 0.85 |
| A1300 | Frozen Drug Substance | 13 |
| B0085 | Non-Frozen Drug Substance | 0.85 |
| B1300 | Non-Frozen Drug Substance | 13 |

The measured $OD_{600}$ values of the Drug Substance as well as of the dilutions are shown in Table 21. The dilution scheme for the prepared formulation is given in Table 22.

TABLE 21

Measured $OD_{600}$ Values of the Delivered Material.

| | $OD_{600}$ values | |
|---|---|---|
| BDS (1000 mL, by volume) | A: frozen material | B: non-frozen material |
| According to shipping documents | 13.8 | 13.8 |
| Measured at Coriolis, n = 3 | 12.14 ± 0.12 | 11.33 ± 0.18 |

| Formulations | $OD_{600}$ Values |
|---|---|
| A0085 | 0.86 ± 0.00 |
| A1300 | 12.14 ± 0.12 |
| B0085 | 0.87 ± 0.00 |
| B1300 | 11.33 ± 0.18 |

TABLE 22

Dilution Scheme for the Three Formulations - F1000, F0200, and F0065.

| Formulation | DS | Formulation Buffer |
|---|---|---|
| A0085 | 14.00 mL | 186.00 mL |
| A1300 | 200.00 mL | — |
| B0085 | 15.01 mL | 184.99 mL |
| B1300 | 200.00 mL | — |

5.3 Study Design

Freezing during lyophilization was performed without an annealing step or hold at 4° C., since no positive effect on the cake appearance was observed with those steps in previous experiments. The vials were immediately frozen to −45° C. without a holding or annealing step. The secondary drying time was prolonged to 5 hours to obtain a more homogeneous batch and to reach the target residual moisture content (RM) of 3.5%. RM, VCC, MFI, RMM, reconstitution time, classification of the appearance of the lyophilized products, and determination of the water loss by weighing was performed after lyophilization. VCC, MFI, RMM were analyzed at 30° C. for 24 and 72 h. Additionally, VCC was analyzed for samples at 2-8° C. for 7 days.

TABLE 23

Lyophilization Cycle Parameters for WP7, Cycle3

| Step | Time | Temperature [° C.] | Pressure* [mbar] | Total Time [h] | Ramp [K/min] |
|---|---|---|---|---|---|
| loading | 00:00** | 4 | 1000 | 0.0 | |
| freezing | 00:49 | −45 | 1000 | 0.8 | 1.00 |
| freezing | 02:00 | −45 | 1000 | 2.8 | |
| Primary drying | 00:30 | −45 | 0.09 | 3.3 | |
| Primary drying | 00:15 | −45 | 0.09 | 3.6 | |
| Primary drying | 00:27 | −18 | 0.09 | 4.0 | 1.00 |
| Primary drying | 32:00:00 | −18 | 0.09 | 36.0 | |
| Secondary drying | 01:30 | 0 | 0.09 | 37.5 | 0.20 |
| Secondary drying hold | 05:00 | 0 | 0.09 | 42.5 | |
| aeration | 00:30 | 0 | 500 | 43.0 | |
| stoppering | 00:01** | 0 | 500 | 43.0 | |
| storage | 00:30** | 5 | 1000 | 43.1 | 0.50 |

*Pirani gauge controlling 5.4 Results and Discussion

Lyophilization was performed using an Epsilon 2-12D pilot scale freeze-dryer (Martin Christ, Osterode, Germany). During the freeze-drying process pressure (by Pirani and MKS), product temperature, shelf temperature, and ice condenser temperature were monitored. Center and front vials were monitored by $PT_{100}$ sensors.

No annealing step was included during freezing and the secondary drying step at 0° C. was set to 5 h. The primary drying of all samples was completed after about 34 h process time, as indicated by $PT_{100}$ sensors and pressure sensor readout. For front vials the primary drying was already finished after 18 h process time as indicated by $PT_{100}$ sensors. The drying of the samples was independent of the bacterial concentration.

For the freezing step, the samples were immediately frozen to −45° C. without a holding or annealing step. The front vials did not reach −45° C. before ramping to the PD temperature, according to the $PT_{100}$ sensors.

A video was recorded from the lyophilization process to determine when the shrinkage takes place. In the video, samples from all four formulations (A0085, A1300, B0085 and B1300) were visible and the shrinkage seems to occur during primary drying. The drying behavior of the center vials might be a slightly different as primary drying was finished earlier for front vials than for center vials.

5.5 Optical Evaluation of the Freeze-Dried Product

The optical appearance of the lyophilized cakes was documented for ten center vials of each formulation after lyophilization. The overall optical appearance of the lyophilization cakes of the four formulations was good. All cakes were compact and had no full contact to the glass vial. For the higher concentrated formulations (A1300 and B1300) the shrinkage in cake height and from the vial wall and bottom was comparable to that of samples of the previous cycle with similar $OD_{600}$ values (F1000). The same is true for the lower concentrated samples (A0085 and B0085). A similar lyophilization cake was observed as for the lower concentrated formulations of Cycle 2 (F0065). The lyophilization cake had a similar optical appearance as the lyophilized placebo. As with cycle 2, a correlation between bacterial concentration and optical appearance of the final product was observed.

5.6 Determination of the Cake Weight

The cake weight and the water loss were determined during cycle 3. The weight of five vials per formulation was gravimetrically determined. Based on the weight of the empty vial, the vial after filling and after lyophilization, the cake weight and the water loss were calculated (Table 24). The lyophilization cake of the lower concentrated formulations weighed 30 mg and that of the higher concentrated formulations 40 mg. After lyophilization, a water loss of 1.17-1.18 g was determined. Therefore, a reconstitution volume of 1.2 mL is suitable to obtain the same bacterial concentration as prior to lyophilization.

TABLE 24

Determination of the Cake Weight and the Water Loss.

| Sample | | Empty Vial (g) | Filled Vial (g) | Vial after Lyophilization (g) | Cake Weight (g) | Water Loss (g) | Water Loss (%) |
|---|---|---|---|---|---|---|---|
| A1300 | 1 | 5.20 | 6.41 | 5.24 | 0.04 | 1.17 | 82 |
|  | 2 | 5.27 | 6.48 | 5.30 | 0.04 | 1.18 | 82 |
|  | 3 | 5.23 | 6.44 | 5.27 | 0.04 | 1.18 | 82 |
|  | 4 | 5.16 | 6.37 | 5.20 | 0.04 | 1.17 | 82 |
|  | 5 | 5.17 | 6.38 | 5.21 | 0.04 | 1.17 | 82 |
| A0085 | 1 | 5.18 | 6.39 | 5.21 | 0.03 | 1.18 | 82 |
|  | 2 | 5.21 | 6.41 | 5.24 | 0.03 | 1.17 | 82 |
|  | 3 | 5.15 | 6.36 | 5.18 | 0.03 | 1.18 | 81 |
|  | 4 | 5.22 | 6.43 | 5.25 | 0.03 | 1.18 | 82 |
|  | 5 | 5.21 | 6.41 | 5.24 | 0.03 | 1.18 | 82 |
| B1300 | 1 | 5.28 | 6.49 | 5.31 | 0.04 | 1.17 | 82 |
|  | 2 | 5.27 | 6.48 | 5.31 | 0.04 | 1.17 | 82 |
|  | 3 | 5.21 | 6.42 | 5.25 | 0.04 | 1.17 | 82 |
|  | 4 | 5.18 | 6.38 | 5.21 | 0.04 | 1.17 | 82 |
|  | 5 | 5.21 | 6.42 | 5.24 | 0.04 | 1.17 | 82 |
| B0085 | 1 | 5.26 | 6.46 | 5.29 | 0.03 | 1.18 | 82 |
|  | 2 | 5.25 | 6.47 | 5.29 | 0.03 | 1.18 | 82 |
|  | 3 | 5.26 | 6.47 | 5.29 | 0.03 | 1.18 | 82 |
|  | 4 | 5.23 | 6.44 | 5.26 | 0.03 | 1.18 | 82 |
|  | 5 | 5.27 | 6.48 | 5.30 | 0.03 | 1.18 | 82 |

5.7 Reconstitution Time

The reconstitution time was measured for two samples per formulation and compared to the results of cycle 1 and cycle 2 (FIG. 57 and Table 25). The reconstitution time of the higher concentrated formulations (A1300 and B1300) was longer than for the lower concentrated formulations (A0085 and B0085). The reconstitution times were, in general, shorter than for the previous cycles of WP7. A direct freezing of the samples without including an annealing step seems to shorten the reconstitution times.

TABLE 25

Overview of the Measured Reconstitution Times of WP7 Cycle 1 to Cycle 3.
Reconstitution time

| Sample | Time (sec) Mean | SD | Foam | LP |
|---|---|---|---|---|
| Cycle 1_SD start_1 | 90 | 95 | 5 | — | yes |
| Cycle 1_SD start_2 | 100 |  |  | — | yes |
| Cycle 1_SD 2h_1 | 75 | 73 | 2 | — | yes |
| Cycle 1_SD 2h_2 | 71 |  |  | — | no |
| Cycle 1_SD end_1 | 77 | 69 | 8.5 | — | no |
| Cycle 1_SD end_2 | 60 |  |  | — | no |
| Cycle 2 F0065_2 | 24 | 22 | 2 | — | no |
| Cycle 2 F0065_3 | 20 |  |  | — | no |
| Cycle 2 F0200_1 | 21 | 21 | 0.5 | — | no |
| Cycle 2 F0200_2 | 20 |  |  | — | yes |
| Cycle 2 F1000_1 | 107 | 104 | 3.5 | — | no |
| Cycle 2 F1000_2 | 100 |  |  | — | yes |
| Cycle 3 A0085_1 | 13 | 12 | 1 | — | no |
| Cycle 3 A0085_2 | 11 |  |  | — | no |
| Cycle 3 A1300_1 | 47 | 53 | 6 | — | no |
| Cycle 3 A1300_2 | 59 |  |  | — | yes |
| Cycle 3 B0085_1 | 13 | 14 | 1 | — | no |
| Cycle 3 B0085_2 | 15 |  |  | — | no |
| Cycle 3 B1300_1 | 72 | 63 | 9.5 | — | no |
| Cycle 3 B1300_2 | 53 |  |  | — | no |

Score Foam: 0—no foam, 1 slight foam, 2—moderate foam, 3—strong foam, 4—strong and steady foam.
LP—low pressure.

5.8 Micro-Flow Imaging (MFI)

The number of subvisible particles was analyzed by MFI to determine whether the raw material (frozen or non-frozen) or the bacterial concentration has an influence on particle formation as well as on the size distribution of the particles. Subvisible particles are particulate matter that is not observable to the naked eye. Particulate matter in injections and parenteral infusions consists of mobile undissolved particles, other than gas bubbles, unintentionally present in the solutions. There are regulatory limits on the number of subvisible particles allowed in parenteral infusions. Samples were analyzed before lyophilization (Tliq), after lyophilization (Tlyo), and after storage for 24 hours and 72 hours at 30° C. (T24 h and T72 h). The results are shown in FIGS. 58A-D. The number of subvisible particles was unchanged for the frozen material (A0085 and A1300) before and after lyophilization as well as after storage at 30° C. for up to 72 h. For the non-frozen material, more particles were detected before lyophilization. Similar results were obtained in other experiments where non-frozen material was also used. The number of subvisible particles after lyophilization was comparable to the results of the frozen material.

5.9 Resonant Mass Measurement (Archimedes)

Results for RMM analysis of ADXS-HER2 samples regarding their content of negatively and positively buoyant particles are presented in FIGS. 59A-D.

The results for the frozen and the non-frozen material were similar Comparison of cumulative negatively buoyant particle counts for all time points and all storage conditions for bin size ≥0.3 μm. Note that particle counts below 300,000 particles per mL (LoQ), are given for information only (data not dilution-corrected, A0085 and B0085: 200-fold dilution, A1300 and B1300: 5,000-fold dilution).

After lyophilization a smaller second particle population appeared at around 300 nm. The particle distribution was comparable for all formulations throughout all analyzed time points. Comparison of the differential particle counts of negatively buoyant particles. Values below 0.3 μm size bins are given for information only (data not dilution-corrected, A0085 and B0085: 200-fold dilution, A1300 and B1300: 5,000-fold dilution).

Because of the different bacterial concentrations of the formulations, different dilutions had to be prepared. A0085 and B0085 were 200-fold diluted and A1300 and B1300 were diluted 5,000-fold. The cumulative counts are not corrected for the individual dilution, in order not to overestimate the multiplication error inherent to the measurement. Furthermore, since the Limit of Quantitation (LoQ) of the method is approximately 300,000 particles per mL, a dilution correction would elevate low particle counts for some measurements above the LoQ, which would otherwise not have been considered and might therefore not reflect the actual experimental conditions.

The number of submicron particles was unchanged for all four formulations before and after lyophilization (FIGS. 59A-D). The results for the frozen and the non-frozen material were similar Before lyophilization one main particle population was detected in the size range of 600-700 nm (FIGS. 60A-D). After lyophilization, a smaller second particle population appeared at around 300 nm. The particle distribution was comparable for all formulations throughout all analyzed time points.

5.10 Karl Fischer Titration

The RM at Tlyo was analyzed by direct injection (FIG. 61 and Table 26). A RM of about 3% was reached for the higher concentrated samples (A1300 and B1300) and a RM of about 3.5% for the lower concentrated samples (A0085 and B0085). The relative standard deviation of the five analyzed vials per formulation was lower than for cycle 2, which is most likely due to the extended SD time. The results of the frozen and non-frozen material were comparable.

TABLE 26

Overview of the KF Results Measured by Direct Injection for WP7 Cycle 3.

| Sample | RMC [%] | | | |
|---|---|---|---|---|
| | A0085 | A1300 | B0085 | B1300 |
| Vial 1 | 3.4 | 3.1 | 3.3 | 3.3 |
| Vial 2 | 3.1 | 3.0 | 3.5 | 3.4 |
| Vial 3 | 3.3 | 2.8 | 3.5 | 3.2 |
| Vial 4 | 3.7 | 3.2 | 4.1 | 2.7 |
| Vial 5 | 3.2 | 2.8 | 3.9 | 2.5 |
| Mean | 3.4 | 3.0 | 3.7 | 3.0 |
| SD | 0.2 | 0.2 | 0.3 | 0.3 |

5.11 VCC Assay

The concentration of viable bacteria (VCC, expressed as CFU/mL) was analyzed at Tliq, after lyophilization at Tlyo, after storage for 24 h and 72 h at 30° C. (T24 h and T72 h) and after storage for 7 days at 2-8° C. (T7 days) (FIG. 62 and Table 27). After lyophilization, a decrease in VCC to about 60% (relative to Tliq) for the lower bacterial concentration and to 70-78% for the higher bacterial concentration was observed. A further decrease of about 10% was observed for the lower bacterial concentration and of 20% for the higher bacterial concentration after an incubation time of 72 h at 30° C. The VCC results after storage for 7 days at 2-8° C. were comparable to the values after lyophilization. The results for the CFU/mL were, as in WP2, below the target values post-lyophilization:

A1300 (target $OD_{600}$ of 13): 1E+10 CFU/mL
A0085 (target $OD_{600}$ of 0.85): 1E+09 CFU/mL
B1300 (target $OD_{600}$ of 13): 1E+10 CFU/mL
B0085 (target $OD_{600}$ of 0.85): 1E+09 CFU/mL APC (Ireland, Dublin) performed flow cytometry again with samples of each formulation. The VCC and % live results are presented in FIG. 62 and Table 27.

TABLE 27

Overview of the CFU/mL and the Relative Viability.

| Sample | | CFU/mL | SD | % |
|---|---|---|---|---|
| A0085 | Tliq | 5.67E+08 | 1.21E+08 | 100 |
| | Tlyo | 3.17E+08 | 1.56E+07 | 56 |
| | T24h | 2.48E+08 | 2.00E+07 | 44 |
| | T72h | 2.43E+08 | 1.26E+07 | 43 |
| | T7days | 2.94E+08 | 2.06E+07 | 52 |
| A1300 | Tliq | 5.63E+09 | 1.43E+09 | 100 |
| | Tlyo | 4.40E+09 | 3.83E+08 | 78 |
| | T24h | 3.40E+09 | 2.08E+08 | 60 |
| | T72h | 3.39E+09 | 1.55E+08 | 60 |
| | T7days | 3.61E+09 | 2.56E+08 | 64 |
| B0085 | Tliq | 5.03E+08 | 8.06E+07 | 100 |
| | Tlyo | 3.41E+08 | 2.19E+07 | 68 |
| | T24h | 2.84E+08 | 1.89E+07 | 56 |
| | T72h | 2.69E+08 | 2.24E+07 | 54 |
| | T7days | 3.15E+08 | 1.45E+07 | 63 |
| B1300 | Tliq | 6.23E+09 | 6.94E+08 | 100 |
| | Tlyo | 4.37E+09 | 3.14E+08 | 70 |
| | T24h | 3.24E+09 | 2.76E+08 | 52 |
| | T72h | 3.20E+09 | 1.33E+08 | 51 |
| | T7days | 3.91E+09 | 1.72E+08 | 63 |

FIGS. 63A-B show the VCC and % live after Cycle 3 and on accelerated stability.

Minimal losses were observed due to lyophilization. No changes were observed in VCC or % live on accelerated stability. % live at initial is higher relative to the liquid-frozen formulation, which supports the further development of a lyophilized formulation. DS that had undergone a freeze/thaw demonstrated good accelerated stability with no decrease observed in either VCC or % live. There is a slight offset in % live observed between fresh and frozen material at the lower VCC levels which is consistent with prior observations that increased VCC is associated with better recoveries post-lyophilization.

TABLE 28

VCC and % Live for WP7, Cycle 4 Stored at 30° C.

| | Sample | | CFU/mL | % Live |
|---|---|---|---|---|
| 2-8° C. Stored DS | F1300 | PreLyo | 1.86E+10 | 96.6 |
| | | T = 0 h | 1.55E+10 | 94.7 |
| | | T = 24 h | 1.53E+10 | 94.7 |
| | | T = 48 h | 1.62E+10 | 94.5 |
| | | T = 72 h | 1.53E+10 | 94.3 |
| | F0085 | PreLyo | 1.38E+09 | 93.3 |
| | | T = 0 h | 1.40E+09 | 95.7 |
| | | T = 24 h | 1.32E+09 | 95.7 |
| | | T = 48 h | 1.37E+09 | 94.1 |
| | | T = 72 h | 1.33E+09 | 94.2 |
| Frozen DS | F1300 | PreLyo | 1.70E+10 | 96.1 |
| | | T = 0 h | 1.52E+10 | 93.4 |
| | | T = 24 h | 1.46E+10 | 93.9 |
| | | T = 48 h | 1.40E+10 | 93.7 |
| | | T = 72 h | 1.48E+10 | 93.4 |
| | F0085 | PreLyo | 1.28E+09 | 90.1 |
| | | T = 0 h | 1.24E+09 | 94.0 |
| | | T = 24 h | 1.19E+09 | 92.9 |
| | | T = 48 h | 1.19E+09 | 90.9 |
| | | T = 72 h | 1.18E+09 | 90.8 |

5.12 Conclusion

Lyophilization runs with non-frozen and frozen DS were performed. Two target bacterial concentrations were tested. No annealing step or hold was included during freezing, as there were no advantages during the previous cycles.

The optical appearance of the lyophilization cake of all formulations (two different bacterial concentrations, frozen and unfrozen raw material) was good. The shrinkage of the lyophilization cake appeared to be dependent on the bacterial concentration. Less shrinkage was observed for a higher bacterial concentration.

Reconstitution time was dependent on the bacterial concentration and on the freezing step. Longer reconstitution times were observed for a higher bacterial concentration. Shorter reconstitution times were observed in these experiments, which did not have an annealing step during freezing, compared to experiments having an annealing step during freezing (data not shown).

The number of subvisible and submicron particles was mainly unchanged after lyophilization and storage at 30° C. (analyzed by RMM and MFI). The number of particles of the non-frozen material was higher before lyophilization. After lyophilization, a small particle population with a size of about 300 nm was detected (analyzed by RMM).

A decrease of the plate based VCC to about 60-70% (relative to Tliq) was observed after lyophilization for the lowest bacterial concentration. A higher VCC (70-78% relative to Tliq) was observed for the two higher bacterial concentrations. A further decrease of 10-20% was observed after storage for up to 72 h at 30° C. Storage of the DS in a 1 L LDPE bag with thawing at 37° C. demonstrated comparable VCC and % live results on accelerated stability to the DS that was continuously processed.

Flow Cytometry Analysis for VCC and % live demonstrated good stability for both the frozen and fresh DS. There was a slight offset for the lower VCC level between the fresh and frozen DS.

A RM of about 3% (higher bacterial concentration) and 3.5% (lower bacterial concentration) was obtained after lyophilization (SD temperature of 0° C. for 6 h).

In general, no differences were observed between the frozen and the non-frozen material with the applied methods, indicating that long-term storage of the DS at −80° C. may be possible, thereby eliminating the need for continuous manufacturing.

Example 6. Effect of Temperature and Time in Thawing Frozen Drug Substance Prior to Lyophilization Temperature and the time for thawing can impact stability. Identifying appropriate conditions for thawing frozen drug substance allows freezing and holding of the drug substance prior to lyophilization. Ensuring high-quality healthy cells coming out of thaw ensures that the resulting lyophilized drug product is also of sufficient quality.

6.1 Freeze-Thawing (FT) of the Bulk Drug Substance

Throughout development, various studies evaluated the ability to store Drug Substance (DS) at −80° C., thaw and compound manufacture a Lyophilized Drug Product (DP) batch at a later date. This involves a freeze-thaw of the DS. A freeze/thaw cycle was defined as the complete thawing of the DS followed by storage at −80° C. for a minimum of 24 hours), until no ice crystals remain. The stress from the freeze-thaw could adversely impact the product quality (e.g. VCC, % live) of the lyophilized product. Hence, a series of experiments were performed to determine the optimal storage conditions and thawing procedure for the DS.

6.2 Evaluation of DS Container (Bag Vs. Bottle)

Early studies evaluated DS that was stored in bottles (Vibalogics Experiments Lyo8, Lyo12, and Lyo16, and Coriolis WP2A, WP2B, and WP3). Other studies thawed the DS at either 2-8° C. (Vibalogics Lyo8 and Lyo12 and Coriolis WP2B and WP3) overnight or 37° C. in a shorter span of time (Vibalogics Lyo16 and Coriolis WP2A, WP6, and WP7-Cycle 1). Later studies evaluated DS that was stored in a 1 L LDPE bag and thawed at 37° C. (WP7-Cycle 3).

6.3 Evaluation of DS Thaw Temperatures and DS Concentration

Since storage of the DS in LDPE bags is preferred over storage in bottles for GMP manufacturing, development efforts focused on conditions that resulted in higher VCC and % live profiles when stored in bags. A freeze/thaw cycle was defined as the complete thawing of the DS followed by storage at −80° C. for a minimum of 24 hours. Freeze-thaw studies were completed to evaluate the Drug Substance VCC and % live over three FT cycles for a range of DS VCC levels (concentration) and thawing temperatures.

The FT studies evaluated DS at $OD_{600}$ of 3.5 and 6.5. Approximately 1 L of DS was filled into 1 L LDPE bags and frozen at −80° C. and subjected to three FT cycles at either 2-8° C., Room Temperature (RT) or 37° C. DS bags, at an $OD_{600}$ of 6.5 or at an $OD_{600}$ 3.5, were thawed in a 4° C. refrigerator for 36 hours, at room temperature on a laboratory bench for approximately 12 hours or at 37° C. in an incubator for ≤8 hours. After thawing completely, a sample was taken for analysis and the bags were placed in −80° C. for a minimum of 24 hours prior to thawing at the respective conditions and re-freezing for the next cycle.

For the studied thawing conditions, VCC and viability values of BDS at an $OD_{600}$ of 6.5 demonstrated a higher VCC and viability over the three freeze-thaw cycles relative to the BDS at an OD600 of 3.5 as shown in FIG. 64 and FIG. 65.

The viability for the BDS at an $OD_{600}$ of 3.5 decreased with multiple freeze thaw cycles for all thaw temperatures except the 37° C. thaw. The 37° C. thaw demonstrated freeze-thaw stability for both $OD_{600}$ for 6.5 and 3.0.

The data demonstrate that thawing the DS at 37° C. results in improved product quality over the range of VCC values evaluated. The data are further supported by the Coriolis experiments which evaluated DS stored as a concentrated pellet, in a bottle and thawed at 2-8° C. which did not result in an acceptable accelerated stability profile. Based on the findings WP7 cycle 3 was performed to evaluate if the target storage and thaw conditions of the DS led to an improved in Lyo DP stability relative to DS that had not undergone a FT cycle. The results of WP7-cycle 3 which compared 2-8° C. and −80° C. stored DS with 1 L fill in a 1 L LDPE bag thawed at 37° C. demonstrated comparable results demonstrating that it is feasible to freeze and thaw DS prior to lyophilization.

Example 7. Exemplary Lyophilization Conditions

7.1 Formulation

TABLE 29

Exemplary Formulation. Target Buffer Composition for LYO Formulation

| Components | Component Weights (g/L) | Weight of component (g/mol) | Molarity (mol/L) | Molarity (millimol/L) |
|---|---|---|---|---|
| Potassium dihydrogen phosphate ($KH_2PO_4$) | 0.20 | 136.08 | 0.001470 | 1.5 |
| Disodium hydrogen phosphate ($Na_2HPO_4$) | 1.14-1.15 | 141.96 | 0.008030 | 8.0 |
| Sucrose | 25.00 | 342.30 | 0.073036 | 73.0 |
| Water for Injection (WFI) | Q.S to 1 L | | | |

The Drug Product is reconstituted with normal saline.

7.2 Drug Substance Manufacturing and Thawing

The DS manufacturing consists of a single-use closed system of a 20 L culture bag for fermentation, a tangential flow filtration (TFF) manifold for concentration and buffer exchange and a container manifold for DS filling. DS can either be held at 2-8° C. for up to three days or frozen at −80° C. prior to compounding, filling, and lyophilization. DS target concentration 3.5-6.5 $OD_{600}$. Thawing of the DS is performed at 37° C. in ≤8 hours.

7.3 Lyophilization Cycle

TABLE 30

Exemplary Lyophilization Cycle.

| Step | Phase | Item | Duration [hh:mm] | Temp, $T_s$ of Shelves [° C.] | Vacuum [mbar] |
|---|---|---|---|---|---|
| NA | Preparation | Warm up of Lyo, placement of temperature and Rx sensors | NA | 4 | Off |
| 1 | Load | Loading of Shelves | NA | 4 | Off |
| 2 | Ramp Freezing | Ramp samples to −4° C. (1.0° C./min) | 00:49 | −45 | Off |
| 3 | Hold | Hold at −45° C. | 02:00 | −45 | Off |
| 4 | Ramp Primary | Vacuum* | 00:01 | −45 | 0.09 |
| 5 | Hold Drying | Vacuum* | 00:15 | −45 | 0.09 |
| 6 | Ramp | Heating Ramp (1.0° C./min) | 00:27 | −18 | 0.09 |
| 7 | Hold | Stable Shelf Temp | >tbc** | −18 | 0.09 |
| 9 | Ramp Secondary | Heating Ramp (0.2° C./min) | 01:30 | 0 | 0.09 |
| 9 | Hold Drying | Stable Shelf Temp | 06:00 | 0 | 0.09 |
| 10 | Hold | Hold at 0° C. until unloading | NA | 0 | 1.0*** |
| 10a | | Ventilation and manual vial closure ($N_2$ sparging) | NA | 0 | 500 mbar |

*Pirani vacuum sensor is the process controlling probe

**End of primary drying is defined here as 14 hours after the $T_P$ P100 probe for the cold spots(s) has crossed the $T_s$ set-point of 18° C.

***Only done to avoid vacuum pull after the cycle is finished during the night

7.4 Residual Moisture Target

The residual moisture target is >3.0% at release.

7.4 ADXS DS Platform Process Description

Fermentation is carried out within a single-use closed system provided by rocking wave motion bioreactor technology. The single-use closed system consists of a product culture bag for fermentation, a tangential flow filtration (TFF) system for concentration and buffer exchange, and a product manifold for drug substance container filling. Each of these components are sterilized by gamma irradiation and received in accordance with site quality systems.

The platform uses the rocking wave motion technology for fermentation. This technology offers the ability to control the entire processing operation in a closed system. The bulk DS is harvested by TFF using a single-use hollow fiber module and single-use disposable filtration path.

The composition of the fermentation media and the pH control solution (1 M sodium hydroxide) are provided in Table 31. The media for the inoculum is sterile-filtered through two 0.2 µm filters in series into a sterile 1 L glass bottle. The fermentation media is sterile-filtered through two 0.2 µm filters in series into a sterile 10 L glass bottle.

TABLE 31

Fermentation Media Formulation Table.

| Formulation | Components | Component Weights |
| --- | --- | --- |
| Fermentation Media (1 kg) | Tryptic Soy Broth | 1 kg |
|  | D (+) Glucose (monohydrate) | 11.11 g |
| pH Control Solution (1M NaOH) | Sodium Hydroxide pellets | 40 g |
|  | WFI | 1000 g |

The culture bag is pre-connected with probes for dissolved oxygen (DO) and pH monitoring. It is then aseptically filled with 5 L of fermentation medium. The culture bag is inflated with 0.2 µm filtered compressed $O_2$ and air.

Filtered (0.2 µm) compressed air/$O_2$ is continuously fed during propagation at a rate of 1.0 L/minute, the $O_2$ flow set point is 50%, and is removed through a vent port. The rocking angle is set at 10°. The DO control is set to speed with a rocking rate between 18-36 rpm. The pH control bottle is aseptically connected to the culture bag. During propagation, the process is automatically monitored and controlled for temperature, pH and dissolved oxygen by an integrated controlling system.

A pre-culture is initiated from the working cell bank by pipetting 1 mL of the WCB into 170 mL of fermentation media and grown for approximately 10 hours until an $OD_{600}$ of ≥3.5 is reached. The pre-culture is used to inoculate the production culture by aseptically transferring it to the culture bag. Growth is proceeded to an $OD_{600}$≥7.5. When the $OD_{600}$ reaches the target value, the culture bag is connected, using Ready Mate connectors to the sterile TFF manifold for concentration and diafiltration against the formulation buffer. The TFF module uses a 0.2 µm pore size hollow fiber filter, meeting the low shear requirements of cell separation applications. A peristaltic pump is used to feed the fermentation culture into the TFF system. The bulk culture in the recirculation loop is initially set to a flow rate of approximately 75 rpm (approximately 4.5 L/min). The fermentation broth is concentrated 5-fold to a mass of approximately 1000 g. A permeate pump is used and set initially at 20% (approximately 275 mL/min).

The diafiltration/washing of the harvest concentrate is performed with ≥7 diavolumes. The retentate drug substance is sampled from the TFF assembly using an in-process sampling manifold. The $OD_{600}$ of the sample is measured and used to calculate the dilution volume needed to reach a target $OD_{600}$ of ≤6.5. The required amount of formulation buffer is pumped into the retentate bag to dilute the retentate to the required concentration. All volume transfers are controlled by weight change in the respective bags in addition to the complete TFF assembly to control volume transfers. The retentate is sampled and measured to confirm the $OD_{600}$ is ≤6.5. If the $OD_{600}$ has not been sufficiently diluted, it may be further diluted. The DS is then distributed into approximately 1 L aliquots into product bags.

Each bag is heat-sealed for removal from the assembly. Each bag is individually labeled with the appropriate information and then stored at −70±15° C.

7.6 Drug Substance Process Flow Diagram

See FIG. 20.

7.7 Drug Product Process Flow Diagram

See FIG. 21.

---

We claim:

1. A method for producing a lyophilized composition comprising a *Listeria* strain, comprising:
   (a) providing a composition comprising a *Listeria* strain in a formulation comprising a buffer and sucrose;
   (b) cooling the composition provided in step (a) at a holding temperature between about −32° C. and about −80° C. in a freezing step;
   (c) exposing the composition produced by step (b) to a vacuum at a holding temperature between about −10° C. and about −30° C. in a primary drying step; and
   (d) exposing the composition produced by step (c) to a vacuum at a holding temperature between about −5° C. and about 25° C. in a secondary drying step,
   whereby the lyophilized composition is produced.

2. The method of claim 1, wherein prior to step (a), a stress response is induced in the *Listeria* strain by exposing the *Listeria* strain to a decreased temperature.

3. The method of claim 1, wherein prior to step (a), a stress response is not induced in the *Listeria* strain by exposing the *Listeria* strain to a decreased temperature.

4. The method of claim 1, wherein the *Listeria* strain used in the composition in step (a) is a frozen *Listeria* strain that is thawed prior to step (a).

5. The method of claim 4, wherein the concentration of the frozen *Listeria* strain being thawed is between about 1x10E9 to about 1x10E10 colony forming units (CFU) per milliliter and/or wherein the formulation comprises about 1x10E9 to about 1x10E10 colony forming units (CFU) of *Listeria* per milliliter.

6. The method of claim 4, wherein the frozen *Listeria* strain is thawed at about 2° C. to about 37° C., about 20° C. to about 37° C., about 32° C. to about 37° C., or about 37° C.

7. The method of claim 4, wherein the frozen *Listeria* strain is thawed for no more than 8 hours and/or wherein the frozen *Listeria* strain is held at about 2° C. to about 8° C. for no more than 24 hours after thawing.

8. The method of claim 1, wherein the *Listeria* strain used in the composition in step (a) is freshly cultured prior to step (a).

9. The method of claim 1, wherein the buffer is a phosphate buffer.

10. The method of claim 1, wherein the formulation comprises about 1% to about 5% w/v sucrose, about 2% to about 3% w/v sucrose, or about 2.5% w/v sucrose.

11. The method of claim 1, wherein the formulation does not comprise one or more of trehalose, monosodium glutamate (MSG), and recombinant human serum albumin (rHSA).

12. The method of claim 1, wherein the holding temperature in the freezing step (b) is between about −40° C. and about −50° C. or is about −45° C.

13. The method of claim 1, wherein the freezing step (b) comprises decreasing the temperature to the holding temperature at a rate of about 1° C. per minute, and/or wherein the cooling in the freezing step (b) is for about 2 hours to about 4 hours, and/or wherein the cooling in the freezing step (b) comprises holding the composition at the holding temperature for about 2 hours.

14. The method of claim 1, wherein the holding temperature in the primary drying step (c) is between about −12° C. and about −22° C. is between about −17° C. and about −19° C., or is about −18° C.

15. The method of claim 1, wherein the primary drying step (c) comprises increasing the temperature to the holding temperature at a rate of about 1° C. per minute, and/or wherein the primary drying step (c) is for about 25 hours to about 35 hours, and/or wherein the end of the primary drying step (c) is about 12 to about 16 hours after the composition has reached holding temperature, and/or wherein the primary drying step (c) is at a vacuum pressure of about 0.09 mbar.

16. The method of claim 1, wherein the holding temperature in the secondary drying step (d) is between about −5° C. and about 20° C., is between about −5° C. and about 5° C., or is about 0° C.

17. The method of claim 1, wherein the secondary drying step (d) comprises increasing the temperature to the holding temperature at a rate of about 0.2° C. per minute and/or wherein the secondary drying step (d) is for about 1 hour to about 10 hours.

18. The method of claim 1, wherein the secondary drying step (d) comprises holding the composition at the holding temperature for about 2 hours to about 6 hours or about 5 hours to about 6 hours.

19. The method of claim 1, wherein the secondary drying step (d) is at a vacuum pressure of about 0.09 mbar.

20. The method of claim 1, wherein the residual moisture in the lyophilized composition is between about 1% and about 5% is between about 2% and about 4%, is at least about 2.5%, or is at least about 3%.

21. The method of claim 1, wherein the lyophilized composition shows at least about 60% viability after storage at between about −20° C. and about 4° C. for about 12 months, shows at least about 75% viability after storage at between about −20° C. and about 4° C. for about 12 months, or shows at least about 80% viability after storage at between about −20° C. and about 4° C. for about 12 months.

22. The method of claim 1, wherein the Listeria strain is a recombinant Listeria monocytogenes strain.

23. The method of claim 1, wherein the Listeria strain is a recombinant Listeria monocytogenes strain, and
wherein the buffer is a phosphate buffer, and
wherein the formulation comprises about 2% to about 3% w/v sucrose, and
wherein the formulation does not comprise trehalose, MSG, or rHSA, and
wherein the formulation comprises about 1×10E9 to about 1×10E10 colony forming units (CFU) of Listeria per milliliter, and
wherein the holding temperature in the freezing step (a) is between about −40° C. and about −50° C., and
wherein the holding temperature in the primary drying step (c) is between −17° C. and −19° C., and
wherein the holding temperature in the secondary drying step (d) is between −1° C. and 1° C., and
wherein the residual moisture in the lyophilized composition is between about 2.5% and about 4%.

24. The method of 23, wherein the Listeria strain used in the composition in step (a) is a frozen Listeria strain that is thawed prior to step (a), and
wherein the concentration of the frozen Listeria strain being thawed is between about 1×10E9 to about 1×10E10 colony forming units (CFU) per milliliter, and
wherein the frozen Listeria strain is thawed at about 37° C., and
wherein the frozen Listeria strain is thawed for no more than 8 hours, and
wherein the frozen Listeria strain is held at about 2° C. to about 8° C. for no more than 24 hours after thawing.

25. The method of claim 1, wherein the Listeria strain is a recombinant Listeria strain comprising a nucleic acid comprising a first open reading frame encoding a fusion polypeptide, wherein the fusion polypeptide comprises a PEST-containing peptide fused to a disease-associated antigenic peptide.

26. The method of claim 25, wherein the recombinant Listeria strain is an attenuated Listeria monocytogenes strain comprising a deletion of or inactivating mutation in prfA, wherein the nucleic acid is in an episomal plasmid and comprises a second open reading frame encoding a D133V PrfA mutant protein or wherein the recombinant Listeria strain is an attenuated Listeria monocytogenes strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

\* \* \* \* \*

SEQUENCE LISTING

<160> NUMBER OF SEQ ID NOS: 100

<210> SEQ ID NO 1
<211> LENGTH: 36
<212> TYPE: DNA
<213> ORGANISM: Artificial Sequence
<220> FEATURE:
<223> OTHER INFORMATION: Synthetic

<400> SEQUENCE: 1
gcacgtagta taatcaactt tgaaaaactg taataa      36

<210> SEQ ID NO 2
<211> LENGTH: 36
<212> TYPE: DNA
<213> ORGANISM: Artificial Sequence
<220> FEATURE:
<223> OTHER INFORMATION: Synthetic

<400> SEQUENCE: 2

```
gcacgttcta ttatcaactt cgaaaaacta taataa                                    36

<210> SEQ ID NO 3
<211> LENGTH: 36
<212> TYPE: DNA
<213> ORGANISM: Artificial Sequence
<220> FEATURE:
<223> OTHER INFORMATION: Synthetic

<400> SEQUENCE: 3
gcccgcagta ttatcaattt cgaaaaatta taataa                                    36

<210> SEQ ID NO 4
<211> LENGTH: 36
<212> TYPE: DNA
<213> ORGANISM: Artificial Sequence
<220> FEATURE:
<223> OTHER INFORMATION: Synthetic

<400> SEQUENCE: 4
gcgcgctcta taattaactt cgaaaaactt taataa                                    36

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
gcacgctcca ttattaactt tgaaaaactt taataa                                    36

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6
gctcgctcta tcatcaattt cgaaaaactt taataa                                    36

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
gcacgtagta ttattaactt cgaaaagtta taataa                                    36

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
gcacgttcca tcattaactt tgaaaaacta taataa                                    36

<210> SEQ ID NO 9
<211> LENGTH: 36
<212> TYPE: DNA
<213> ORGANISM: Artificial Sequence
```

```
<220> FEATURE:
<223> OTHER INFORMATION: Synthetic

<400> SEQUENCE: 9
gctcgctcaa tcatcaactt tgaaaagcta taataa                              36

<210> SEQ ID NO 10
<211> LENGTH: 36
<212> TYPE: DNA
<213> ORGANISM: Artificial Sequence
<220> FEATURE:
<223> OTHER INFORMATION: Synthetic

<400> SEQUENCE: 10
gctcgctcta tcatcaactt cgaaaaattg taataa                              36

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
gctcgctcta ttatcaattt tgaaaaatta taataa                              36

<210> SEQ ID NO 12
<211> LENGTH: 36
<212> TYPE: DNA
<213> ORGANISM: Artificial Sequence
<220> FEATURE:
<223> OTHER INFORMATION: Synthetic

<400> SEQUENCE: 12
gctcgtagta ttattaattt cgaaaaatta taataa                              36

<210> SEQ ID NO 13
<211> LENGTH: 36
<212> TYPE: DNA
<213> ORGANISM: Artificial Sequence
<220> FEATURE:
<223> OTHER INFORMATION: Synthetic

<400> SEQUENCE: 13
gctcgttcga ttatcaactt cgaaaaactg taataa                              36

<210> SEQ ID NO 14
<211> LENGTH: 36
<212> TYPE: DNA
<213> ORGANISM: Artificial Sequence
<220> FEATURE:
<223> OTHER INFORMATION: Synthetic

<400> SEQUENCE: 14
gcaagaagca tcatcaactt cgaaaaactg taataa                              36

<210> SEQ ID NO 15
<211> LENGTH: 36
<212> TYPE: DNA
<213> ORGANISM: Artificial Sequence
<220> FEATURE:
<223> OTHER INFORMATION: Synthetic

<400> SEQUENCE: 15
gcgcgttcta ttattaattt tgaaaaatta taataa                              36
```

```
<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Ala Arg Ser Ile Ile Asn Phe Glu Lys Leu
1               5                   10

<210> SEQ ID NO 17
<211> LENGTH: 66
<212> TYPE: DNA
<213> ORGANISM: Artificial Sequence
<220> FEATURE:
<223> OTHER INFORMATION: Synthetic

<400> SEQUENCE: 17
gattataaag atcatgacgg agactataaa gaccatgaca ttgattacaa agacgacgat      60
gacaaa                                                                66

<210> SEQ ID NO 18
<211> LENGTH: 66
<212> TYPE: DNA
<213> ORGANISM: Artificial Sequence
<220> FEATURE:
<223> OTHER INFORMATION: Synthetic

<400> SEQUENCE: 18
gactataaag accacgatgg cgattataaa gaccatgata ttgactacaa agatgatgat      60
gataag                                                                66

<210> SEQ ID NO 19
<211> LENGTH: 66
<212> TYPE: DNA
<213> ORGANISM: Artificial Sequence
<220> FEATURE:
<223> OTHER INFORMATION: Synthetic

<400> SEQUENCE: 19
gattataaag atcatgatgg cgactataaa gatcatgata tcgattacaa agatgacgat      60
gacaaa                                                                66

<210> SEQ ID NO 20
<211> LENGTH: 66
<212> TYPE: DNA
<213> ORGANISM: Artificial Sequence
<220> FEATURE:
<223> OTHER INFORMATION: Synthetic

<400> SEQUENCE: 20
gactacaaag atcacgatgg tgactacaaa gatcacgaca ttgattataa agacgatgat      60
gacaaa                                                                66

<210> SEQ ID NO 21
<211> LENGTH: 66
<212> TYPE: DNA
<213> ORGANISM: Artificial Sequence
<220> FEATURE:
<223> OTHER INFORMATION: Synthetic

<400> SEQUENCE: 21
```

```
gattacaaag atcacgatgg tgattataag gatcacgata ttgattacaa agacgacgac    60
gataaa                                                               66

<210> SEQ ID NO 22
<211> LENGTH: 66
<212> TYPE: DNA
<213> ORGANISM: Artificial Sequence
<220> FEATURE:
<223> OTHER INFORMATION: Synthetic

<400> SEQUENCE: 22
gattacaaag atcacgatgg cgattacaaa gatcatgaca ttgactacaa agacgatgat    60
gataaa                                                               66

<210> SEQ ID NO 23
<211> LENGTH: 66
<212> TYPE: DNA
<213> ORGANISM: Artificial Sequence
<220> FEATURE:
<223> OTHER INFORMATION: Synthetic

<400> SEQUENCE: 23
gattacaagg atcatgatgg tgattacaaa gatcacgata tcgactacaa agatgatgac    60
gataaa                                                               66

<210> SEQ ID NO 24
<211> LENGTH: 66
<212> TYPE: DNA
<213> ORGANISM: Artificial Sequence
<220> FEATURE:
<223> OTHER INFORMATION: Synthetic

<400> SEQUENCE: 24
gactacaaag atcatgatgg tgattacaaa gatcatgaca ttgattataa agatgatgat    60
gacaaa                                                               66

<210> SEQ ID NO 25
<211> LENGTH: 66
<212> TYPE: DNA
<213> ORGANISM: Artificial Sequence
<220> FEATURE:
<223> OTHER INFORMATION: Synthetic

<400> SEQUENCE: 25
gattataaag accatgatgg tgattataag gatcatgata tcgattataa ggatgacgac    60
gataaa                                                               66

<210> SEQ ID NO 26
<211> LENGTH: 66
<212> TYPE: DNA
<213> ORGANISM: Artificial Sequence
<220> FEATURE:
<223> OTHER INFORMATION: Synthetic

<400> SEQUENCE: 26
gattataaag atcacgatgg cgattataaa gaccacgata ttgattataa agacgacgat    60
gacaaa                                                               66

<210> SEQ ID NO 27
<211> LENGTH: 66
<212> TYPE: DNA
<213> ORGANISM: Artificial Sequence
```

```
<220> FEATURE:
<223> OTHER INFORMATION: Synthetic

<400> SEQUENCE: 27
gactataaag accacgatgg tgattataaa gatcacgaca tcgactacaa agacgatgat      60
gataaa                                                                66

<210> SEQ ID NO 28
<211> LENGTH: 66
<212> TYPE: DNA
<213> ORGANISM: Artificial Sequence
<220> FEATURE:
<223> OTHER INFORMATION: Synthetic

<400> SEQUENCE: 28
gactacaaag atcacgacgg cgattataaa gatcacgata ttgactataa agatgacgat      60
gataaa                                                                66

<210> SEQ ID NO 29
<211> LENGTH: 66
<212> TYPE: DNA
<213> ORGANISM: Artificial Sequence
<220> FEATURE:
<223> OTHER INFORMATION: Synthetic

<400> SEQUENCE: 29
gattataaag accatgatgg agattacaaa gatcatgata ttgactataa agacgacgac      60
gataaa                                                                66

<210> SEQ ID NO 30
<211> LENGTH: 66
<212> TYPE: DNA
<213> ORGANISM: Artificial Sequence
<220> FEATURE:
<223> OTHER INFORMATION: Synthetic

<400> SEQUENCE: 30
gattataaag atcacgatgg tgactacaaa gatcacgata tcgattataa agacgatgac      60
gataaa                                                                66

<210> SEQ ID NO 31
<211> LENGTH: 66
<212> TYPE: DNA
<213> ORGANISM: Artificial Sequence
<220> FEATURE:
<223> OTHER INFORMATION: Synthetic

<400> SEQUENCE: 31
gactacaaag atcacgatgg tgattataaa gaccatgata ttgattacaa agatgatgat      60
gacaaa                                                                66

<210> SEQ ID NO 32
<211> LENGTH: 22
<212> TYPE: PRT
<213> ORGANISM: Artificial Sequence
<220> FEATURE:
<223> OTHER INFORMATION: Synthetic

<400> SEQUENCE: 32

Asp Tyr Lys Asp His Asp Gly Asp Tyr Lys Asp His Asp Ile Asp Tyr
 1               5                  10                  15

Lys Asp Asp Asp Asp Lys
```

<210> SEQ ID NO 33
<211> LENGTH: 6
<212> TYPE: PRT
<213> ORGANISM: Artificial Sequence
<220> FEATURE:
<223> OTHER INFORMATION: Synthetic

<400> SEQUENCE: 33

Gly Ala Ser Gly Ala Ser
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Gly Ser Ala Gly Ser Ala
1               5

<210> SEQ ID NO 35
<211> LENGTH: 4
<212> TYPE: PRT
<213> ORGANISM: Artificial Sequence
<220> FEATURE:
<223> OTHER INFORMATION: Synthetic

<400> SEQUENCE: 35

Gly Gly Gly Gly
1

<210> SEQ ID NO 36
<211> LENGTH: 5
<212> TYPE: PRT
<213> ORGANISM: Artificial Sequence
<220> FEATURE:
<223> OTHER INFORMATION: Synthetic

<400> SEQUENCE: 36

Gly Gly Gly Gly Ser
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Val Gly Lys Gly Gly Ser Gly Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Pro Ala Pro Ala Pro
1               5

```
<210> SEQ ID NO 39
<211> LENGTH: 5
<212> TYPE: PRT
<213> ORGANISM: Artificial Sequence
<220> FEATURE:
<223> OTHER INFORMATION: Synthetic

<400> SEQUENCE: 39

Glu Ala Ala Ala Lys
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic

<400> SEQUENCE: 40

Ala Tyr Leu Ala Tyr Leu
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic

<400> SEQUENCE: 41

Leu Arg Ala Leu Arg Ala
1               5

<210> SEQ ID NO 42
<211> LENGTH: 4
<212> TYPE: PRT
<213> ORGANISM: Artificial Sequence
<220> FEATURE:
<223> OTHER INFORMATION: Synthetic

<400> SEQUENCE: 42

Arg Leu Arg Ala
1

<210> SEQ ID NO 43
<211> LENGTH: 32
<212> TYPE: PRT
<213> ORGANISM: Artificial Sequence
<220> FEATURE:
<223> OTHER INFORMATION: Synthetic

<400> SEQUENCE: 43

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 44
<211> LENGTH: 19
<212> TYPE: PRT
<213> ORGANISM: Artificial Sequence
<220> FEATURE:
<223> OTHER INFORMATION: Synthetic

<400> SEQUENCE: 44
```

```
Lys Glu Asn Ser Ile Ser Ser Met Ala Pro Pro Ala Ser Pro Pro Ala
1               5                   10                  15

Ser Pro Lys

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Lys Thr Glu Glu Gln Pro Ser Glu Val Asn Thr Gly Pro Arg
1               5                   10

<210> SEQ ID NO 46
<211> LENGTH: 28
<212> TYPE: PRT
<213> ORGANISM: Artificial Sequence
<220> FEATURE:
<223> OTHER INFORMATION: Synthetic

<400> SEQUENCE: 46

Lys Glu Ser Val Val Asp Ala Ser Glu Ser Asp Leu Asp Ser Ser Met
1               5                   10                  15

Gln Ser Ala Asp Glu Ser Thr Pro Gln Pro Leu Lys
            20                  25

<210> SEQ ID NO 47
<211> LENGTH: 20
<212> TYPE: PRT
<213> ORGANISM: Artificial Sequence
<220> FEATURE:
<223> OTHER INFORMATION: Synthetic

<400> SEQUENCE: 47

Lys Ser Glu Glu Val Asn Ala Ser Asp Phe Pro Pro Pro Pro Thr Asp
1               5                   10                  15

Glu Glu Leu Arg
            20

<210> SEQ ID NO 48
<211> LENGTH: 33
<212> TYPE: PRT
<213> ORGANISM: Artificial Sequence
<220> FEATURE:
<223> OTHER INFORMATION: Synthetic

<400> SEQUENCE: 48

Arg Gly Gly Arg Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Lys Gln Asn Thr Ala Ser Thr Glu Thr Thr Thr Thr Asn Glu Gln Pro
```

```
1               5                   10                  15

Lys

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Lys Gln Asn Thr Ala Asn Thr Glu Thr Thr Thr Thr Asn Glu Gln Pro
1               5                   10                  15

Lys

<210> SEQ ID NO 51
<211> LENGTH: 19
<212> TYPE: PRT
<213> ORGANISM: Artificial Sequence
<220> FEATURE:
<223> OTHER INFORMATION: Synthetic

<400> SEQUENCE: 51

Arg Ser Glu Val Thr Ile Ser Pro Ala Glu Thr Pro Glu Ser Pro Pro
1               5                   10                  15

Ala Thr Pro

<210> SEQ ID NO 52
<211> LENGTH: 28
<212> TYPE: PRT
<213> ORGANISM: Artificial Sequence
<220> FEATURE:
<223> OTHER INFORMATION: Synthetic

<400> SEQUENCE: 52

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
                20                  25

<210> SEQ ID NO 53
<211> LENGTH: 20
<212> TYPE: PRT
<213> ORGANISM: Artificial Sequence
<220> FEATURE:
<223> OTHER INFORMATION: Synthetic

<400> SEQUENCE: 53

Lys Asn Glu Glu Val Asn Ala Ser Asp Phe Pro Pro Pro Thr Asp
1               5                   10                  15

Glu Glu Leu Arg
                20

<210> SEQ ID NO 54
<211> LENGTH: 33
<212> TYPE: PRT
<213> ORGANISM: Artificial Sequence
<220> FEATURE:
<223> OTHER INFORMATION: Synthetic

<400> SEQUENCE: 54

Arg Gly Gly Ile Pro Thr Ser Glu Glu Phe Ser Ser Leu Asn Ser Gly
1               5                   10                  15
```

Asp Phe Thr Asp Asp Glu Asn Ser Glu Thr Thr Glu Glu Ile Asp
                20                  25                  30
Arg

<210> SEQ ID NO 55
<211> LENGTH: 529
<212> TYPE: PRT
<213> ORGANISM: Artificial Sequence
<220> FEATURE:
<223> OTHER INFORMATION: Synthetic

<400> SEQUENCE: 55

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Met Ala Pro Ala Ser Pro Pro Ala Ser
            35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
            130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala

```
                340                 345                 350
Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
            370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
                435                 440                 445

Gln His Lys Asn Trp Ser Glu Asn Asn Lys Ser Lys Leu Ala His Phe
            450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
                515                 520                 525

Glu

<210> SEQ ID NO 56
<211> LENGTH: 529
<212> TYPE: PRT
<213> ORGANISM: Artificial Sequence
<220> FEATURE:
<223> OTHER INFORMATION: Synthetic

<400> SEQUENCE: 56

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Val Ala Pro Pro Ala Ser Pro Pro Ala Ser
            35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175
```

```
Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu
```

<210> SEQ ID NO 57
<211> LENGTH: 441
<212> TYPE: PRT
<213> ORGANISM: Artificial Sequence
<220> FEATURE:
<223> OTHER INFORMATION: Synthetic

<400> SEQUENCE: 57

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Ala Ser
            35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
```

```
                420             425             430
Ile Ser Trp Asp Glu Val Asn Tyr Asp
            435             440

<210> SEQ ID NO 58
<211> LENGTH: 416
<212> TYPE: PRT
<213> ORGANISM: Artificial Sequence
<220> FEATURE:
<223> OTHER INFORMATION: Synthetic

<400> SEQUENCE: 58

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
```

```
                    340                 345                 350
Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
            370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 59
<211> LENGTH: 441
<212> TYPE: PRT
<213> ORGANISM: Artificial Sequence
<220> FEATURE:
<223> OTHER INFORMATION: Synthetic

<400> SEQUENCE: 59

Met Lys Lys Ile Met Leu Val Phe Ile Thr Leu Ile Leu Val Ser Leu
1               5                  10                  15

Pro Ile Ala Gln Gln Thr Glu Ala Lys Asp Ala Ser Ala Phe Asn Lys
                20                  25                  30

Glu Asn Ser Ile Ser Ser Met Ala Pro Pro Ala Ser Pro Ala Ser
            35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
```

```
            290                 295                 300
Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440

<210> SEQ ID NO 60
<211> LENGTH: 1323
<212> TYPE: DNA
<213> ORGANISM: Artificial Sequence
<220> FEATURE:
<223> OTHER INFORMATION: Synthetic

<400> SEQUENCE: 60
atgaaaaaaa taatgctagt ttttattaca cttatattag ttagtctacc aattgcgcaa      60
caaactgaag caaggatgc atctgcattc aataaagaaa attcaatttc atccatggca     120
ccaccagcat ctccgcctgc aagtcctaag acgccaatcg aaaagaaaca cgcggatgaa     180
atcgataagt atatacaagg attggattac aataaaaaca tgtattagt ataccacgga     240 gatgcagtga caaatgtgcc gccaagaaaa ggttacaaag atggaaatga atatattgtt     300
gtggagaaaa agaagaaatc catcaatcaa ataatgcag acattcaagt tgtgaatgca     360
atttcgagcc taacctatcc aggtgctctc gtaaaagcga attcggaatt agtagaaaat     420
caaccagatg ttctccctgt aaaacgtgat tcattaacac tcagcattga tttgccaggt     480
atgactaatc aagacaataa aatagttgta aaaaatgcca ctaaatcaaa cgttaacaac     540
gcagtaaata cattagtgga agatggaat gaaaaatatg ctcaagctta tccaaatgta     600
agtgcaaaaa ttgattatga tgacgaaatg gcttacagtg aatcacaatt aattgcgaaa     660
tttggtacag catttaaagc tgtaaataat agcttgaatg taaacttcgg cgcaatcagt     720
gaagggaaaa tgcaagaaga agtcattagt tttaaacaaa tttactataa cgtgaatgtt     780
aatgaaccta aagaccttc cagatttttc ggcaaagctg ttactaaaga gcagttgcaa     840
gcgcttggag tgaatgcaga aaatcctcct gcatatatct caagtgtggc gtatggccgt     900
caagtttatt tgaaattatc aactaattcc catagtacta agtaaaagc tgcttttgat     960 gctgccgtaa gcggaaaatc tgtctcaggt gatgtagaac taacaaatat catcaaaaat    1020
tcttccttca agccgtaat ttacggaggt tccgcaaaag atgaagttca aatcatcgac    1080 ggcaaccctcg agacttacg cgatattttg aaaaaggcg ctacttttaa tcgagaaaca    1140
ccaggagttc ccattgctta taacaaac ttcctaaaag acaatgaatt agctgttatt    1200
```

-continued

```
aaaaacaact cagaatatat tgaaacaact tcaaaagctt atacagatgg aaaaattaac    1260
atcgatcact ctggaggata cgttgctcaa ttcaacattt cttgggatga agtaaattat    1320
gat                                                                 1323
```

<210> SEQ ID NO 61
<211> LENGTH: 633
<212> TYPE: PRT
<213> ORGANISM: Artificial Sequence
<220> FEATURE:
<223> OTHER INFORMATION: Synthetic

<400> SEQUENCE: 61

```
Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Lys Thr Glu Gln Pro Ser Glu
        35                  40                  45

Val Asn Thr Gly Pro Arg Tyr Glu Thr Ala Arg Glu Val Ser Ser Arg
    50                  55                  60

Asp Ile Glu Glu Leu Glu Lys Ser Asn Lys Val Lys Asn Thr Asn Lys
65                  70                  75                  80

Ala Asp Leu Ile Ala Met Leu Lys Ala Lys Ala Glu Lys Gly Pro Asn
                85                  90                  95

Asn Asn Asn Asn Asn Gly Glu Gln Thr Gly Asn Val Ala Ile Asn Glu
            100                 105                 110

Glu Ala Ser Gly Val Asp Arg Pro Thr Leu Gln Val Glu Arg Arg His
        115                 120                 125

Pro Gly Leu Ser Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Ala Asn Lys Arg Lys Val Ala Lys Glu Ser Val Val
                165                 170                 175

Asp Ala Ser Glu Ser Asp Leu Asp Ser Ser Met Gln Ser Ala Asp Glu
            180                 185                 190

Ser Thr Pro Gln Pro Leu Lys Ala Asn Gln Lys Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Ser Glu Glu Val Asn Ala
                245                 250                 255

Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Thr Pro Ser Glu
        275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335
```

```
Glu Leu Glu Ile Met Arg Glu Thr Ala Pro Ser Leu Asp Ser Ser Phe
                340                 345                 350

Thr Ser Gly Asp Leu Ala Ser Leu Arg Ser Ala Ile Asn Arg His Ser
            355                 360                 365

Glu Asn Phe Ser Asp Phe Pro Leu Ile Pro Thr Glu Glu Leu Asn
370                 375                 380

Gly Arg Gly Arg Pro Thr Ser Glu Glu Phe Ser Ser Leu Asn Ser
385                 390                 395                 400

Gly Asp Phe Thr Asp Asp Glu Asn Ser Glu Thr Glu Glu Ile
                405                 410                 415

Asp Arg Leu Ala Asp Leu Arg Asp Arg Gly Thr Gly Lys His Ser Arg
                420                 425                 430

Asn Ala Gly Phe Leu Pro Leu Asn Pro Phe Ile Ser Ser Pro Val Pro
            435                 440                 445

Ser Leu Thr Pro Lys Val Pro Lys Ile Ser Ala Pro Ala Leu Ile Ser
            450                 455                 460

Asp Ile Thr Lys Lys Ala Pro Phe Lys Asn Pro Ser Gln Pro Leu Asn
465                 470                 475                 480

Val Phe Asn Lys Lys Thr Thr Thr Lys Thr Val Thr Lys Lys Pro Thr
                485                 490                 495

Pro Val Lys Thr Ala Pro Lys Leu Ala Glu Leu Pro Ala Thr Lys Pro
            500                 505                 510

Gln Glu Thr Val Leu Arg Glu Asn Lys Thr Pro Phe Ile Glu Lys Gln
            515                 520                 525

Ala Glu Thr Asn Lys Gln Ser Ile Asn Met Pro Ser Leu Pro Val Ile
530                 535                 540

Gln Lys Glu Ala Thr Glu Ser Asp Lys Glu Glu Met Lys Pro Gln Thr
545                 550                 555                 560

Glu Glu Lys Met Val Glu Glu Ser Glu Ser Ala Asn Ala Asn Gly
                565                 570                 575

Lys Asn Arg Ser Ala Gly Ile Glu Glu Gly Lys Leu Ile Ala Lys Ser
            580                 585                 590

Ala Glu Asp Glu Lys Ala Lys Glu Glu Pro Gly Asn His Thr Thr Leu
            595                 600                 605

Ile Leu Ala Met Leu Ala Ile Gly Val Phe Ser Leu Gly Ala Phe Ile
610                 615                 620

Lys Ile Ile Gln Leu Arg Lys Asn Asn
625                 630

<210> SEQ ID NO 62
<211> LENGTH: 639
<212> TYPE: PRT
<213> ORGANISM: Artificial Sequence
<220> FEATURE:
<223> OTHER INFORMATION: Synthetic

<400> SEQUENCE: 62

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Lys Thr
            35                  40                  45

Glu Glu Gln Pro Ser Glu Val Asn Thr Gly Pro Arg Tyr Glu Thr Ala
50                  55                  60
```

-continued

```
Arg Glu Val Ser Ser Arg Asp Ile Glu Glu Leu Glu Lys Ser Asn Lys
 65                  70                  75                  80

Val Lys Asn Thr Asn Lys Ala Asp Leu Ile Ala Met Leu Lys Ala Lys
                 85                  90                  95

Ala Glu Lys Gly Pro Asn Asn Asn Asn Asn Gly Glu Gln Thr Gly
            100                 105                 110

Asn Val Ala Ile Asn Glu Glu Ala Ser Gly Val Asp Arg Pro Thr Leu
            115                 120                 125

Gln Val Glu Arg Arg His Pro Gly Leu Ser Ser Asp Ser Ala Ala Glu
        130                 135                 140

Ile Lys Lys Arg Arg Lys Ala Ile Ala Ser Ser Asp Ser Glu Leu Glu
145                 150                 155                 160

Ser Leu Thr Tyr Pro Asp Lys Pro Thr Lys Ala Asn Lys Arg Lys Val
                165                 170                 175

Ala Lys Glu Ser Val Val Asp Ala Ser Glu Ser Asp Leu Asp Ser Ser
            180                 185                 190

Met Gln Ser Ala Asp Glu Ser Thr Pro Gln Pro Leu Lys Ala Asn Gln
        195                 200                 205

Lys Pro Phe Phe Pro Lys Val Phe Lys Lys Ile Lys Asp Ala Gly Lys
    210                 215                 220

Trp Val Arg Asp Lys Ile Asp Glu Asn Pro Glu Val Lys Lys Ala Ile
225                 230                 235                 240

Val Asp Lys Ser Ala Gly Leu Ile Asp Gln Leu Leu Thr Lys Lys Lys
                245                 250                 255

Ser Glu Glu Val Asn Ala Ser Asp Phe Pro Pro Pro Thr Asp Glu
            260                 265                 270

Glu Leu Arg Leu Ala Leu Pro Glu Thr Pro Met Leu Leu Gly Phe Asn
        275                 280                 285

Ala Pro Thr Pro Ser Glu Pro Ser Ser Phe Glu Phe Pro Pro Pro
    290                 295                 300

Thr Asp Glu Glu Leu Arg Leu Ala Leu Pro Glu Thr Pro Met Leu Leu
305                 310                 315                 320

Gly Phe Asn Ala Pro Ala Thr Ser Glu Pro Ser Ser Phe Glu Phe Pro
                325                 330                 335

Pro Pro Pro Thr Glu Asp Glu Leu Glu Ile Met Arg Glu Thr Ala Pro
            340                 345                 350

Ser Leu Asp Ser Ser Phe Thr Ser Gly Asp Leu Ala Ser Leu Arg Ser
        355                 360                 365

Ala Ile Asn Arg His Ser Glu Asn Phe Ser Asp Phe Pro Leu Ile Pro
    370                 375                 380

Thr Glu Glu Glu Leu Asn Gly Arg Gly Arg Pro Thr Ser Glu Glu
385                 390                 395                 400

Phe Ser Ser Leu Asn Ser Gly Asp Phe Thr Asp Glu Asn Ser Glu
                405                 410                 415

Thr Thr Glu Glu Glu Ile Asp Arg Leu Ala Asp Leu Arg Asp Arg Gly
            420                 425                 430

Thr Gly Lys His Ser Arg Asn Ala Gly Phe Leu Pro Leu Asn Pro Phe
        435                 440                 445

Ile Ser Ser Pro Val Pro Ser Leu Thr Pro Lys Val Pro Lys Ile Ser
    450                 455                 460

Ala Pro Ala Leu Ile Ser Asp Ile Thr Lys Lys Ala Pro Phe Lys Asn
465                 470                 475                 480

Pro Ser Gln Pro Leu Asn Val Phe Asn Lys Lys Thr Thr Thr Lys Thr
```

```
                    485                 490                 495
Val Thr Lys Lys Pro Thr Pro Val Lys Thr Ala Pro Lys Leu Ala Glu
                500                 505                 510

Leu Pro Ala Thr Lys Pro Gln Glu Thr Val Leu Arg Glu Asn Lys Thr
            515                 520                 525

Pro Phe Ile Glu Lys Gln Ala Glu Thr Asn Lys Gln Ser Ile Asn Met
        530                 535                 540

Pro Ser Leu Pro Val Ile Gln Lys Glu Ala Thr Glu Ser Asp Lys Glu
545                 550                 555                 560

Glu Met Lys Pro Gln Thr Glu Glu Lys Met Val Glu Glu Ser Glu Ser
                565                 570                 575

Ala Asn Asn Ala Asn Gly Lys Asn Arg Ser Ala Gly Ile Glu Glu Gly
            580                 585                 590

Lys Leu Ile Ala Lys Ser Ala Glu Asp Glu Lys Ala Lys Glu Glu Pro
        595                 600                 605

Gly Asn His Thr Thr Leu Ile Leu Ala Met Leu Ala Ile Gly Val Phe
    610                 615                 620

Ser Leu Gly Ala Phe Ile Lys Ile Ile Gln Leu Arg Lys Asn Asn
625                 630                 635

<210> SEQ ID NO 63
<211> LENGTH: 93
<212> TYPE: PRT
<213> ORGANISM: Artificial Sequence
<220> FEATURE:
<223> OTHER INFORMATION: Synthetic

<400> SEQUENCE: 63

Ala Thr Asp Ser Glu Asp Ser Ser Leu Asn Thr Asp Glu Trp Glu Glu
1               5                   10                  15

Glu Lys Thr Glu Glu Gln Pro Ser Glu Val Asn Thr Gly Pro Arg Tyr
            20                  25                  30

Glu Thr Ala Arg Glu Val Ser Ser Arg Asp Ile Glu Glu Leu Glu Lys
        35                  40                  45

Ser Asn Lys Val Lys Asn Thr Asn Lys Ala Asp Leu Ile Ala Met Leu
    50                  55                  60

Lys Ala Lys Ala Glu Lys Gly Pro Asn Asn Asn Asn Asn Asn Gly Glu
65                  70                  75                  80

Gln Thr Gly Asn Val Ala Ile Asn Glu Glu Ala Ser Gly
                85                  90

<210> SEQ ID NO 64
<211> LENGTH: 200
<212> TYPE: PRT
<213> ORGANISM: Artificial Sequence
<220> FEATURE:
<223> OTHER INFORMATION: Synthetic

<400> SEQUENCE: 64

Ala Thr Asp Ser Glu Asp Ser Ser Leu Asn Thr Asp Glu Trp Glu Glu
1               5                   10                  15

Glu Lys Thr Glu Glu Gln Pro Ser Glu Val Asn Thr Gly Pro Arg Tyr
            20                  25                  30

Glu Thr Ala Arg Glu Val Ser Ser Arg Asp Ile Glu Glu Leu Glu Lys
        35                  40                  45

Ser Asn Lys Val Lys Asn Thr Asn Lys Ala Asp Leu Ile Ala Met Leu
    50                  55                  60
```

```
Lys Ala Lys Ala Glu Lys Gly Pro Asn Asn Asn Asn Asn Gly Glu
 65                  70                  75                  80

Gln Thr Gly Asn Val Ala Ile Asn Glu Glu Ala Ser Gly Val Asp Arg
                 85                  90                  95

Pro Thr Leu Gln Val Glu Arg Arg His Pro Gly Leu Ser Ser Asp Ser
            100                 105                 110

Ala Ala Glu Ile Lys Lys Arg Lys Ala Ile Ala Ser Ser Asp Ser
            115                 120                 125

Glu Leu Glu Ser Leu Thr Tyr Pro Asp Lys Pro Thr Lys Ala Asn Lys
        130                 135                 140

Arg Lys Val Ala Lys Glu Ser Val Val Asp Ala Ser Glu Ser Asp Leu
145                 150                 155                 160

Asp Ser Ser Met Gln Ser Ala Asp Glu Ser Thr Pro Gln Pro Leu Lys
                165                 170                 175

Ala Asn Gln Lys Pro Phe Phe Pro Lys Val Phe Lys Lys Ile Lys Asp
            180                 185                 190

Ala Gly Lys Trp Val Arg Asp Lys
            195                 200
```

<210> SEQ ID NO 65
<211> LENGTH: 303
<212> TYPE: PRT
<213> ORGANISM: Artificial Sequence
<220> FEATURE:
<223> OTHER INFORMATION: Synthetic

<400> SEQUENCE: 65

```
Ala Thr Asp Ser Glu Asp Ser Ser Leu Asn Thr Asp Glu Trp Glu Glu
  1               5                  10                  15

Glu Lys Thr Glu Glu Gln Pro Ser Glu Val Asn Thr Gly Pro Arg Tyr
                 20                  25                  30

Glu Thr Ala Arg Glu Val Ser Ser Arg Asp Ile Glu Glu Leu Glu Lys
             35                  40                  45

Ser Asn Lys Val Lys Asn Thr Asn Lys Ala Asp Leu Ile Ala Met Leu
 50                  55                  60

Lys Ala Lys Ala Glu Lys Gly Pro Asn Asn Asn Asn Asn Gly Glu
 65                  70                  75                  80

Gln Thr Gly Asn Val Ala Ile Asn Glu Glu Ala Ser Gly Val Asp Arg
                 85                  90                  95

Pro Thr Leu Gln Val Glu Arg Arg His Pro Gly Leu Ser Ser Asp Ser
            100                 105                 110

Ala Ala Glu Ile Lys Lys Arg Lys Ala Ile Ala Ser Ser Asp Ser
            115                 120                 125

Glu Leu Glu Ser Leu Thr Tyr Pro Asp Lys Pro Thr Lys Ala Asn Lys
        130                 135                 140

Arg Lys Val Ala Lys Glu Ser Val Val Asp Ala Ser Glu Ser Asp Leu
145                 150                 155                 160

Asp Ser Ser Met Gln Ser Ala Asp Glu Ser Thr Pro Gln Pro Leu Lys
                165                 170                 175

Ala Asn Gln Lys Pro Phe Phe Pro Lys Val Phe Lys Lys Ile Lys Asp
            180                 185                 190

Ala Gly Lys Trp Val Arg Asp Lys Ile Asp Glu Asn Pro Glu Val Lys
            195                 200                 205

Lys Ala Ile Val Asp Lys Ser Ala Gly Leu Ile Asp Gln Leu Leu Thr
    210                 215                 220
```

```
Lys Lys Lys Ser Glu Glu Val Asn Ala Ser Asp Phe Pro Pro Pro
225                 230                 235                 240

Thr Asp Glu Glu Leu Arg Leu Ala Leu Pro Glu Thr Pro Met Leu Leu
            245                 250                 255

Gly Phe Asn Ala Pro Thr Pro Ser Glu Pro Ser Ser Phe Glu Phe Pro
            260                 265                 270

Pro Pro Pro Thr Asp Glu Glu Leu Arg Leu Ala Leu Pro Glu Thr Pro
            275                 280                 285

Met Leu Leu Gly Phe Asn Ala Pro Ala Thr Ser Glu Pro Ser Ser
            290                 295                 300

<210> SEQ ID NO 66
<211> LENGTH: 370
<212> TYPE: PRT
<213> ORGANISM: Artificial Sequence
<220> FEATURE:
<223> OTHER INFORMATION: Synthetic

<400> SEQUENCE: 66

Ala Thr Asp Ser Glu Asp Ser Ser Leu Asn Thr Asp Glu Trp Glu Glu
1               5                   10                  15

Glu Lys Thr Glu Glu Gln Pro Ser Glu Val Asn Thr Gly Pro Arg Tyr
            20                  25                  30

Glu Thr Ala Arg Glu Val Ser Ser Arg Asp Ile Glu Glu Leu Glu Lys
        35                  40                  45

Ser Asn Lys Val Lys Asn Thr Asn Lys Ala Asp Leu Ile Ala Met Leu
    50                  55                  60

Lys Ala Lys Ala Glu Lys Gly Pro Asn Asn Asn Asn Asn Gly Glu
65                  70                  75                  80

Gln Thr Gly Asn Val Ala Ile Asn Glu Glu Ala Ser Gly Val Asp Arg
                85                  90                  95

Pro Thr Leu Gln Val Glu Arg Arg His Pro Gly Leu Ser Ser Asp Ser
            100                 105                 110

Ala Ala Glu Ile Lys Lys Arg Lys Ala Ile Ala Ser Ser Asp Ser
            115                 120                 125

Glu Leu Glu Ser Leu Thr Tyr Pro Asp Lys Pro Thr Lys Ala Asn Lys
            130                 135                 140

Arg Lys Val Ala Lys Glu Ser Val Val Asp Ala Ser Glu Ser Asp Leu
145                 150                 155                 160

Asp Ser Ser Met Gln Ser Ala Asp Glu Ser Thr Pro Gln Pro Leu Lys
                165                 170                 175

Ala Asn Gln Lys Pro Phe Phe Pro Lys Val Phe Lys Lys Ile Lys Asp
            180                 185                 190

Ala Gly Lys Trp Val Arg Asp Lys Ile Asp Glu Asn Pro Glu Val Lys
            195                 200                 205

Lys Ala Ile Val Asp Lys Ser Ala Gly Leu Ile Asp Gln Leu Leu Thr
            210                 215                 220

Lys Lys Lys Ser Glu Glu Val Asn Ala Ser Asp Phe Pro Pro Pro
225                 230                 235                 240

Thr Asp Glu Glu Leu Arg Leu Ala Leu Pro Glu Thr Pro Met Leu Leu
            245                 250                 255

Gly Phe Asn Ala Pro Thr Pro Ser Glu Pro Ser Ser Phe Glu Phe Pro
            260                 265                 270

Pro Pro Pro Thr Asp Glu Glu Leu Arg Leu Ala Leu Pro Glu Thr Pro
            275                 280                 285
```

```
Met Leu Leu Gly Phe Asn Ala Pro Ala Thr Ser Glu Pro Ser Ser Phe
            290                 295                 300

Glu Phe Pro Pro Pro Thr Glu Asp Glu Leu Glu Ile Met Arg Glu
305                 310                 315                 320

Thr Ala Pro Ser Leu Asp Ser Ser Phe Thr Ser Gly Asp Leu Ala Ser
                325                 330                 335

Leu Arg Ser Ala Ile Asn Arg His Ser Glu Asn Phe Ser Asp Phe Pro
                340                 345                 350

Leu Ile Pro Thr Glu Glu Leu Asn Gly Arg Gly Arg Pro Thr
                355                 360                 365

Ser Glu
    370

<210> SEQ ID NO 67
<211> LENGTH: 390
<212> TYPE: PRT
<213> ORGANISM: Artificial Sequence
<220> FEATURE:
<223> OTHER INFORMATION: Synthetic

<400> SEQUENCE: 67

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
                20                  25                  30

Asn Thr Asp Glu Trp Glu Glu Lys Thr Glu Gln Pro Ser Glu
            35                  40                  45

Val Asn Thr Gly Pro Arg Tyr Glu Thr Ala Arg Glu Val Ser Ser Arg
50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
            115                 120                 125

Pro Gly Leu Pro Ser Asp Ser Ala Ala Glu Ile Lys Lys Arg Arg Lys
130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
            260                 265                 270
```

```
Pro Glu Thr Pro Met Leu Leu Gly Phe Asn Ala Pro Ala Thr Ser Glu
            275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
355                 360                 365

Gln Asn Phe Ser Asp Phe Pro Pro Ile Pro Thr Glu Glu Leu Asn
    370                 375                 380

Gly Arg Gly Gly Arg Pro
385                 390

<210> SEQ ID NO 68
<211> LENGTH: 1170
<212> TYPE: DNA
<213> ORGANISM: Artificial Sequence
<220> FEATURE:
<223> OTHER INFORMATION: Synthetic

<400> SEQUENCE: 68
atgcgtgcga tgatggtggt tttcattact gccaattgca ttacgattaa ccccgacata      60
atatttgcag cgacagatag cgaagattct agtctaaaca cagatgaatg ggaagaagaa     120
aaaacagaag agcaaccaag cgaggtaaat acgggaccaa gatacgaaac tgcacgtgaa     180
gtaagttcac gtgatattaa agaactagaa aaatcgaata aagtgagaaa tacgaacaaa     240
gcagacctaa tagcaatgtt gaaagaaaaa gcagaaaaag gtccaaatat caataataac     300
aacagtgaac aaactgagaa tgcggctata aatgagagg cttcaggagc cgaccgacca     360
gctatacaag tggagcgtcg tcatccagga ttgccatcgg atagcgcagc ggaaattaaa     420
aaaagaagga agccatagc atcatcggat agtgagcttg aaagccttac ttatccggat     480
aaaccaacaa aagtaaataa gaaaaaagtg gcgaaagagt cagttgcgga tgcttctgaa     540
agtgacttag attctagcat gcagtcagca gatgagtctt caccacaacc tttaaaagca     600
aaccaacaac cattttttccc taaagtattt aaaaaaataa aagatgcggg gaaatgggta     660
cgtgataaaa tcgacgaaaa tcctgaagta aagaaagcga ttgttgataa agtgcaggg     720 ttaattgacc aattattaac caaaagaaa agtgaagagg taaatgcttc ggacttcccg     780
ccaccaccta cggatgaaga gttaagactt gctttgccag agacaccaat gcttcttggt     840
tttaatgctc ctgctacatc agaaccgagc tcattcgaat tccaccacc acctacggat     900 gaagagttaa gacttgcttt gccagagacg ccaatgcttc ttggttttaa tgctcctgct     960
acatcggaac cgagctcgtt cgaatttcca ccgcctccaa cagaagatga actagaaatc    1020
atccgggaaa cagcatcctc gctagattct agttttacaa gagggatttt agctagtttg    1080
agaaatgcta ttaatcgcca tagtcaaaat ttctctgatt tcccaccaat cccaacagaa    1140
gaagagttga acgggagagg cggtagacca                                     1170

<210> SEQ ID NO 69
<211> LENGTH: 100
<212> TYPE: PRT
<213> ORGANISM: Artificial Sequence
```

<220> FEATURE:
<223> OTHER INFORMATION: Synthetic

<400> SEQUENCE: 69

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Lys Glu Leu Lys Ser Asn Lys
65                  70                  75                  80

Val Arg Asn Thr Asn Lys Ala Asp Leu Ile Ala Met Leu Lys Glu Lys
                85                  90                  95

Ala Glu Lys Gly
            100

<210> SEQ ID NO 70
<211> LENGTH: 390
<212> TYPE: PRT
<213> ORGANISM: Artificial Sequence
<220> FEATURE:
<223> OTHER INFORMATION: Synthetic

<400> SEQUENCE: 70

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Glu Glu Leu Glu Lys Ser Asn Lys Val Lys Asn Thr Asn Lys
65                  70                  75                  80

Ala Asp Leu Ile Ala Met Leu Lys Ala Lys Ala Glu Lys Gly Pro Asn
                85                  90                  95

Asn Asn Asn Asn Asn Gly Glu Gln Thr Gly Asn Val Ala Ile Asn Glu
            100                 105                 110

Glu Ala Ser Gly Val Asp Arg Pro Thr Leu Gln Val Glu Arg Arg His
        115                 120                 125

Pro Gly Leu Ser Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Ala Asn Lys Arg Lys Val Ala Lys Glu Ser Val Val
                165                 170                 175

Asp Ala Ser Glu Ser Asp Leu Asp Ser Ser Met Gln Ser Ala Asp Glu
            180                 185                 190

Ser Thr Pro Gln Pro Leu Lys Ala Asn Gln Lys Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly

```
                225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
                260                 265                 270

Pro Glu Thr Pro Met Leu Leu Gly Phe Asn Ala Pro Thr Pro Ser Glu
                275                 280                 285

Pro Ser Ser Phe Glu Phe Pro Pro Pro Thr Asp Glu Glu Leu Arg
                290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Met Arg Glu Thr Ala Pro Ser Leu Asp Ser Ser Phe
                340                 345                 350

Thr Ser Gly Asp Leu Ala Ser Leu Arg Ser Ala Ile Asn Arg His Ser
                355                 360                 365

Glu Asn Phe Ser Asp Phe Pro Leu Ile Pro Thr Glu Glu Leu Asn
                370                 375                 380

Gly Arg Gly Gly Arg Pro
385                 390

<210> SEQ ID NO 71
<211> LENGTH: 1170
<212> TYPE: DNA
<213> ORGANISM: Artificial Sequence
<220> FEATURE:
<223> OTHER INFORMATION: Synthetic

<400> SEQUENCE: 71
atgcgtgcga tgatggtagt tttcattact gccaactgca ttacgattaa ccccgacata      60
atatttgcag cgacagatag cgaagattcc agtctaaaca cagatgaatg ggaagaagaa     120
aaaacagaag agcagccaag cgaggtaaat acgggaccaa gatacgaaac tgcacgtgaa     180
gtaagttcac gtgatattga ggaactagaa aaatcgaata aagtgaaaaa tacgaacaaa     240
gcagacctaa tagcaatgtt gaaagcaaaa gcagagaaag gtccgaataa caataataac     300
aacggtgagc aaaacaggaa tgtggctata aatgaagagg cttcaggagt cgaccgacca     360
actctgcaag tggagcgtcg tcatccaggt ctgtcatcgg atagcgcagc ggaaattaaa     420
aaaagaagaa aagccatagc gtcgtcggat agtgagcttg aaagccttac ttatccagat     480
aaaccaacaa aagcaaataa gagaaaagtg gcgaaagagt cagttgtgga tgcttctgaa     540
agtgacttag attctagcat gcagtcagca gacgagtcta caccacaacc tttaaaagca     600
aatcaaaaac cattttttcc taaagtattt aaaaaaataa aagatgcggg gaaatgggta     660
cgtgataaaa tcgacgaaaa tcctgaagta agaaagcga ttgttgataa aagtgcaggg      720
ttaattgacc aattattaac caaaagaaa agtgaagagg taaatgcttc ggacttcccg      780
ccaccaccta cggatgaaga gttaagactt gctttgccag agacaccgat gcttctcggt      840
tttaatgctc ctactccatc ggaaccgagc tcattcgaat tccgccgcc acctacggat       900 gaagagttaa gacttgcttt gccagagacg ccaatgcttc ttggttttaa tgctcctgct     960
acatcggaac cgagctcatt cgaatttcca ccgcctccaa cagaagatga actagaaatt    1020
atgcgggaaa cagcaccttc gctagattct agttttacaa gcggggattt agctagtttg    1080
agaagtgcta ttaatcgcca tagcgaaaat ttctctgatt tcccactaat cccaacagaa    1140
```

```
gaagagttga acgggagagg cggtagacca                                    1170
```

<210> SEQ ID NO 72
<211> LENGTH: 226
<212> TYPE: PRT
<213> ORGANISM: Artificial Sequence
<220> FEATURE:
<223> OTHER INFORMATION: Synthetic

<400> SEQUENCE: 72

Met Lys Lys Ile Met Leu Val Phe Ile Thr Leu Ile Leu Val Ser Leu
1               5                   10                  15

Pro Ile Ala Gln Gln Thr Glu Ala Ser Arg Ala Thr Asp Ser Glu Asp
                20                  25                  30

Ser Ser Leu Asn Thr Asp Glu Trp Glu Glu Lys Thr Glu Glu Gln
        35                  40                  45

Pro Ser Glu Val Asn Thr Gly Pro Arg Tyr Glu Thr Ala Arg Glu Val
    50                  55                  60

Ser Arg Asp Ile Glu Glu Leu Glu Lys Ser Asn Lys Val Lys Asn
65                  70                  75                  80

Thr Asn Lys Ala Asp Leu Ile Ala Met Leu Lys Ala Lys Ala Glu Lys
                85                  90                  95

Gly Pro Asn Asn Asn Asn Asn Gly Glu Gln Thr Gly Asn Val Ala
            100                 105                 110

Ile Asn Glu Glu Ala Ser Gly Val Asp Arg Pro Thr Leu Gln Val Glu
        115                 120                 125

Arg Arg His Pro Gly Leu Ser Ser Asp Ser Ala Ala Glu Ile Lys Lys
    130                 135                 140

Arg Arg Lys Ala Ile Ala Ser Ser Asp Ser Glu Leu Glu Ser Leu Thr
145                 150                 155                 160

Tyr Pro Asp Lys Pro Thr Lys Ala Asn Lys Arg Lys Val Ala Lys Glu
                165                 170                 175

Ser Val Val Asp Ala Ser Glu Ser Asp Leu Asp Ser Ser Met Gln Ser
            180                 185                 190

Ala Asp Glu Ser Thr Pro Gln Pro Leu Lys Ala Asn Gln Lys Pro Phe
        195                 200                 205

Phe Pro Lys Val Phe Lys Lys Ile Lys Asp Ala Gly Lys Trp Val Arg
    210                 215                 220

Asp Lys
225

<210> SEQ ID NO 73
<211> LENGTH: 5
<212> TYPE: PRT
<213> ORGANISM: Artificial Sequence
<220> FEATURE:
<223> OTHER INFORMATION: Synthetic

<400> SEQUENCE: 73

Gln Asp Asn Lys Arg
1               5

<210> SEQ ID NO 74
<211> LENGTH: 11
<212> TYPE: PRT
<213> ORGANISM: Artificial Sequence
<220> FEATURE:
<223> OTHER INFORMATION: Synthetic

<400> SEQUENCE: 74

Glu Cys Thr Gly Leu Ala Trp Glu Trp Trp Arg
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic

<400> SEQUENCE: 75

Glu Ser Leu Leu Met Trp Ile Thr Gln Cys Arg
1               5                   10

<210> SEQ ID NO 76
<211> LENGTH: 368
<212> TYPE: PRT
<213> ORGANISM: Artificial Sequence
<220> FEATURE:
<223> OTHER INFORMATION: Synthetic

<400> SEQUENCE: 76

Met Val Thr Gly Trp His Arg Pro Thr Trp Ile Glu Ile Asp Arg Ala
1               5                   10                  15

Ala Ile Arg Glu Asn Ile Lys Asn Glu Gln Asn Lys Leu Pro Glu Ser
            20                  25                  30

Val Asp Leu Trp Ala Val Val Lys Ala Asn Ala Tyr Gly His Gly Ile
        35                  40                  45

Ile Glu Val Ala Arg Thr Ala Lys Glu Ala Gly Ala Lys Gly Phe Cys
    50                  55                  60

Val Ala Ile Leu Asp Glu Ala Leu Ala Leu Arg Glu Ala Gly Phe Gln
65                  70                  75                  80

Asp Asp Phe Ile Leu Val Leu Gly Ala Thr Arg Lys Glu Asp Ala Asn
                85                  90                  95

Leu Ala Ala Lys Asn His Ile Ser Leu Thr Val Phe Arg Glu Asp Trp
            100                 105                 110

Leu Glu Asn Leu Thr Leu Glu Ala Thr Leu Arg Ile His Leu Lys Val
        115                 120                 125

Asp Ser Gly Met Gly Arg Leu Gly Ile Arg Thr Thr Glu Glu Ala Arg
    130                 135                 140

Arg Ile Glu Ala Thr Ser Thr Asn Asp His Gln Leu Gln Leu Glu Gly
145                 150                 155                 160

Ile Tyr Thr His Phe Ala Thr Ala Asp Gln Leu Glu Thr Ser Tyr Phe
                165                 170                 175

Glu Gln Gln Leu Ala Lys Phe Gln Thr Ile Leu Thr Ser Leu Lys Lys
            180                 185                 190

Arg Pro Thr Tyr Val His Thr Ala Asn Ser Ala Ala Ser Leu Leu Gln
        195                 200                 205

Pro Gln Ile Gly Phe Asp Ala Ile Arg Phe Gly Ile Ser Met Tyr Gly
    210                 215                 220

Leu Thr Pro Ser Thr Glu Ile Lys Thr Ser Leu Pro Phe Glu Leu Lys
225                 230                 235                 240

Pro Ala Leu Ala Leu Tyr Thr Glu Met Val His Val Lys Glu Leu Ala
                245                 250                 255

Pro Gly Asp Ser Val Ser Tyr Gly Ala Thr Tyr Thr Ala Thr Glu Arg
            260                 265                 270

Glu Trp Val Ala Thr Leu Pro Ile Gly Tyr Ala Asp Gly Leu Ile Arg
            275                 280                 285

His Tyr Ser Gly Phe His Val Leu Val Asp Gly Glu Pro Ala Pro Ile
        290                 295                 300

Ile Gly Arg Val Cys Met Asp Gln Thr Ile Ile Lys Leu Pro Arg Glu
305                 310                 315                 320

Phe Gln Thr Gly Ser Lys Val Thr Ile Ile Gly Lys Asp His Gly Asn
            325                 330                 335

Thr Val Thr Ala Asp Asp Ala Ala Gln Tyr Leu Asp Thr Ile Asn Tyr
            340                 345                 350

Glu Val Thr Cys Leu Leu Asn Glu Arg Ile Pro Arg Lys Tyr Ile His
            355                 360                 365

<210> SEQ ID NO 77
<211> LENGTH: 289
<212> TYPE: PRT
<213> ORGANISM: Artificial Sequence
<220> FEATURE:
<223> OTHER INFORMATION: Synthetic

<400> SEQUENCE: 77

Met Lys Val Leu Val Asn Asn His Leu Val Glu Arg Glu Asp Ala Thr
1               5                   10                  15

Val Asp Ile Glu Asp Arg Gly Tyr Gln Phe Gly Asp Gly Val Tyr Glu
            20                  25                  30

Val Val Arg Leu Tyr Asn Gly Lys Phe Phe Thr Tyr Asn Glu His Ile
        35                  40                  45

Asp Arg Leu Tyr Ala Ser Ala Lys Ile Asp Leu Val Ile Pro Tyr
    50                  55                  60

Ser Lys Glu Glu Leu Arg Glu Leu Leu Glu Lys Leu Val Ala Glu Asn
65                  70                  75                  80

Asn Ile Asn Thr Gly Asn Val Tyr Leu Gln Val Thr Arg Gly Val Gln
                85                  90                  95

Asn Pro Arg Asn His Val Ile Pro Asp Asp Phe Pro Leu Glu Gly Val
            100                 105                 110

Leu Thr Ala Ala Ala Arg Glu Val Pro Arg Asn Glu Arg Gln Phe Val
        115                 120                 125

Glu Gly Gly Thr Ala Ile Thr Glu Glu Asp Val Arg Trp Leu Arg Cys
    130                 135                 140

Asp Ile Lys Ser Leu Asn Leu Leu Gly Asn Ile Leu Ala Lys Asn Lys
145                 150                 155                 160

Ala His Gln Gln Asn Ala Leu Glu Ala Ile Leu His Arg Gly Glu Gln
                165                 170                 175

Val Thr Glu Cys Ser Ala Ser Asn Val Ser Ile Ile Lys Asp Gly Val
            180                 185                 190

Leu Trp Thr His Ala Ala Asp Asn Leu Ile Leu Asn Gly Ile Thr Arg
        195                 200                 205

Gln Val Ile Ile Asp Val Ala Lys Lys Asn Gly Ile Pro Val Lys Glu
    210                 215                 220

Ala Asp Phe Thr Leu Thr Asp Leu Arg Glu Ala Asp Glu Val Phe Ile
225                 230                 235                 240

Ser Ser Thr Thr Ile Glu Ile Thr Pro Ile Thr His Ile Asp Gly Val
                245                 250                 255

Gln Val Ala Asp Gly Lys Arg Gly Pro Ile Thr Ala Gln Leu His Gln
            260                 265                 270

Tyr Phe Val Glu Glu Ile Thr Arg Ala Cys Gly Glu Leu Glu Phe Ala
    275                 280                 285

Lys

<210> SEQ ID NO 78
<211> LENGTH: 1107
<212> TYPE: DNA
<213> ORGANISM: Artificial Sequence
<220> FEATURE:
<223> OTHER INFORMATION: Synthetic

<400> SEQUENCE: 78

| | | | |
|---|---|---|---|
| atggtgacag gctggcatcg tccaacatgg attgaaatag accgcgcagc aattcgcgaa | 60 |
| aatataaaaa atgaacaaaa taaactcccg gaaagtgtcg acttatgggc agtagtcaaa | 120 |
| gctaatgcat atggtcacgg aattatcgaa gttgctagga cggcgaaaga agctggagca | 180 |
| aaaggtttct gcgtagccat tttagatgag gcactggctc ttagagaagc tggatttcaa | 240 |
| gatgacttta ttcttgtgct tggtgcaacc agaaaagaag atgctaatct ggcagccaaa | 300 |
| aaccacattt cacttactgt ttttagagaa gattggctag agaatctaac gctagaagca | 360 |
| acacttcgaa ttcatttaaa agtagatagc ggtatggggc gtctcggtat tcgtacgact | 420 |
| gaagaagcac ggcgaattga agcaaccagt actaatgatc accaattaca actggaaggt | 480 |
| atttacacgc attttgcaac agccgaccag ctagaaacta gttattttga caacaatta | 540 |
| gctaagttcc aaacgatttt aacgagttta aaaaaacgac caacttatgt tcatacagcc | 600 |
| aattcagctg cttcattgtt acagccacaa atcgggtttg atgcgattcg ctttggtatt | 660 |
| tcgatgtatg gattaactcc ctccacagaa atcaaaacta gcttgccgtt tgagcttaaa | 720 |
| cctgcacttg cactctatac cgagatggtt catgtgaaag aacttgcacc aggcgatagc | 780 |
| gttagctacg gagcaactta tacagcaaca gagcgagaat gggttgcgac attaccaatt | 840 |
| ggctatgcgg atggattgat tcgtcattac agtggtttcc atgttttagt agacggtgaa | 900 |
| ccagctccaa tcattggtcg agtttgtatg gatcaaacca tcataaaact accacgtgaa | 960 |
| tttcaaactg gttcaaaagt aacgataatt ggcaaagatc atggtaacac ggtaacagca | 1020 |
| gatgatgccg ctcaatattt agatacaatt aattatgagg taacttgttt gttaaatgag | 1080 |
| cgcataccta gaaaatacat ccattag | 1107 |

<210> SEQ ID NO 79
<211> LENGTH: 870
<212> TYPE: DNA
<213> ORGANISM: Artificial Sequence
<220> FEATURE:
<223> OTHER INFORMATION: Synthetic

<400> SEQUENCE: 79

| | | | |
|---|---|---|---|
| atgaaagtat tagtaaataa ccatttagtt gaaagagaag atgccacagt tgacattgaa | 60 |
| gaccgcggat atcagtttgg tgatggtgta tatgaagtag ttcgtctata taatggaaaa | 120 |
| ttctttactt ataatgaaca cattgatcgc ttatatgcta gtgcagcaaa aattgactta | 180 |
| gttattcctt attccaaaga agagctacgt gaattacttg aaaaattagt tgccgaaaat | 240 |
| aatatcaata cagggaatgt ctatttacaa gtgactcgtg tgttcaaaa cccacgtaat | 300 |
| catgtaatcc ctgatgattt ccctctagaa ggcgttttaa cagcagcagc tcgtgaagta | 360 |
| cctagaaacg agcgtcaatt cgttgaaggt ggaacggcga ttacagaaga agatgtgcgc | 420 |
| tggttacgct gtgatattaa gagcttaaac ctttaggaa atattctagc aaaaaataaa | 480 |

| | | | | |
|---|---|---|---|---|
| gcacatcaac | aaaatgcttt | ggaagctatt | ttacatcgcg | gggaacaagt aacagaatgt | 540 |
| tctgcttcaa | acgtttctat | tattaaagat | ggtgtattat | ggacgcatgc ggcagataac | 600 |
| ttaatcttaa | atggtatcac | tcgtcaagtt | atcattgatg | ttgcgaaaaa gaatggcatt | 660 |
| cctgttaaag | aagcggattt | cactttaaca | gaccttcgtg | aagcggatga agtgttcatt | 720 |
| tcaagtacaa | ctattgaaat | tacacctatt | acgcatattg | acggagttca agtagctgac | 780 |
| ggaaaacgtg | gaccaattac | agcgcaactt | catcaatatt | ttgtagaaga aatcactcgt | 840 |
| gcatgtggcg | aattagagtt | tgcaaaataa | | | 870 |

<210> SEQ ID NO 80
<211> LENGTH: 237
<212> TYPE: PRT
<213> ORGANISM: Artificial Sequence
<220> FEATURE:
<223> OTHER INFORMATION: Synthetic

<400> SEQUENCE: 80

Met Asn Ala Gln Ala Glu Glu Phe Lys Lys Tyr Leu Glu Thr Asn Gly
1               5                   10                  15

Ile Lys Pro Lys Gln Phe His Lys Lys Glu Leu Ile Phe Asn Gln Trp
            20                  25                  30

Asp Pro Gln Glu Tyr Cys Ile Phe Leu Tyr Asp Gly Ile Thr Lys Leu
        35                  40                  45

Thr Ser Ile Ser Glu Asn Gly Thr Ile Met Asn Leu Gln Tyr Tyr Lys
    50                  55                  60

Gly Ala Phe Val Ile Met Ser Gly Phe Ile Asp Thr Glu Thr Ser Val
65                  70                  75                  80

Gly Tyr Tyr Asn Leu Glu Val Ile Ser Glu Gln Ala Thr Ala Tyr Val
                85                  90                  95

Ile Lys Ile Asn Glu Leu Lys Glu Leu Leu Ser Lys Asn Leu Thr His
            100                 105                 110

Phe Phe Tyr Val Phe Gln Thr Leu Gln Lys Gln Val Ser Tyr Ser Leu
        115                 120                 125

Ala Lys Phe Asn Asp Phe Ser Ile Asn Gly Lys Leu Gly Ser Ile Cys
    130                 135                 140

Gly Gln Leu Leu Ile Leu Thr Tyr Val Tyr Gly Lys Glu Thr Pro Asp
145                 150                 155                 160

Gly Ile Lys Ile Thr Leu Asp Asn Leu Thr Met Gln Glu Leu Gly Tyr
                165                 170                 175

Ser Ser Gly Ile Ala His Ser Ser Ala Val Ser Arg Ile Ile Ser Lys
            180                 185                 190

Leu Lys Gln Glu Lys Val Ile Val Tyr Lys Asn Ser Cys Phe Tyr Val
        195                 200                 205

Gln Asn Leu Asp Tyr Leu Lys Arg Tyr Ala Pro Lys Leu Asp Glu Trp
    210                 215                 220

Phe Tyr Leu Ala Cys Pro Ala Thr Trp Gly Lys Leu Asn
225                 230                 235

<210> SEQ ID NO 81
<211> LENGTH: 714
<212> TYPE: DNA
<213> ORGANISM: Artificial Sequence
<220> FEATURE:
<223> OTHER INFORMATION: Synthetic

<400> SEQUENCE: 81

-continued

```
atgaacgctc aagcagaaga attcaaaaaa tatttagaaa ctaacgggat aaaaccaaaa    60
caatttcata aaaaagaact tatttttaac caatgggatc cacaagaata ttgtattttt   120
ctatatgatg gtatcacaaa gctcacgagt attagcgaga acgggaccat catgaattta   180
caatactcaa aagggctttt cgttataatg tctggcttta ttgatacaga aacatcggtt   240
ggctattata atttagaagt cattagcgag caggctaccg catacgttat caaaataaac   300
gaactaaaag aactactgag caaaaatctt acgcactttt tctatgtttt ccaaaccta    360 caaaaacaag tttcatacag cctagctaaa tttaatgatt tttcgattaa cgggaagctt   420
ggctctattt gcggtcaact tttaatcctg acctatgtgt atggtaaaga aactcctgat   480
ggcatcaaga ttacactgga taatttaaca atgcaggagt taggatattc aagtggcatc   540
gcacatagct cagctgttag cagaattatt tccaaattaa agcaagagaa agttatcgtg   600
tataaaaatt catgctttta tgtacaaaat cttgattatc tcaaaagata tgcccctaaa   660
ttagatgaat ggttttattt agcatgtcct gctacttggg gaaaattaaa ttaa         714
```

<210> SEQ ID NO 82
<211> LENGTH: 237
<212> TYPE: PRT
<213> ORGANISM: Artificial Sequence
<220> FEATURE:
<223> OTHER INFORMATION: Synthetic

<400> SEQUENCE: 82

```
Met Asn Ala Gln Ala Glu Glu Phe Lys Lys Tyr Leu Glu Thr Asn Gly
1               5                   10                  15

Ile Lys Pro Lys Gln Phe His Lys Lys Glu Leu Ile Phe Asn Gln Trp
            20                  25                  30

Asp Pro Gln Glu Tyr Cys Ile Phe Leu Tyr Asp Gly Ile Thr Lys Leu
        35                  40                  45

Thr Ser Ile Ser Glu Asn Gly Thr Ile Met Asn Leu Gln Tyr Tyr Lys
    50                  55                  60

Gly Ala Phe Val Ile Met Ser Gly Phe Ile Asp Thr Glu Thr Ser Val
65                  70                  75                  80

Gly Tyr Tyr Asn Leu Glu Val Ile Ser Glu Gln Ala Thr Ala Tyr Val
                85                  90                  95

Ile Lys Ile Asn Glu Leu Lys Glu Leu Leu Ser Lys Asn Leu Thr His
            100                 105                 110

Phe Phe Tyr Val Phe Gln Thr Leu Gln Lys Gln Val Ser Tyr Ser Leu
        115                 120                 125

Ala Lys Phe Asn Val Phe Ser Ile Asn Gly Lys Leu Gly Ser Ile Cys
    130                 135                 140

Gly Gln Leu Leu Ile Leu Thr Tyr Val Tyr Gly Lys Glu Thr Pro Asp
145                 150                 155                 160

Gly Ile Lys Ile Thr Leu Asp Asn Leu Thr Met Gln Glu Leu Gly Tyr
                165                 170                 175

Ser Ser Gly Ile Ala His Ser Ser Ala Val Ser Arg Ile Ile Ser Lys
            180                 185                 190

Leu Lys Gln Glu Lys Val Ile Val Tyr Lys Asn Ser Cys Phe Tyr Val
        195                 200                 205

Gln Asn Arg Asp Tyr Leu Lys Arg Tyr Ala Pro Lys Leu Asp Glu Trp
    210                 215                 220

Phe Tyr Leu Ala Cys Pro Ala Thr Trp Gly Lys Leu Asn
225                 230                 235
```

-continued

<210> SEQ ID NO 83
<211> LENGTH: 713
<212> TYPE: DNA
<213> ORGANISM: Artificial Sequence
<220> FEATURE:
<223> OTHER INFORMATION: Synthetic

<400> SEQUENCE: 83

```
atgaacgctc aagcagaaga attcaaaaaa tatttagaaa ctaacgggat aaaaccaaaa      60
caatttcata aaaaagaact tattttaac caatgggatc cacaagaata ttgtattttt     120
ctatatgatg gtatcacaaa gctcacgagt attagcgaga acgggaccat catgaattta     180
caatactaca aagggctttt cgttataatg tctggcttta ttgatacaga aacatcggtt     240
ggctattata atttagaagt cattagcgag caggctaccg catacgttat caaaataaac     300
gaactaaaag aactactgag caaaaatctt acgcactttt tctatgtttt ccaaacccta     360
caaaaacaag tttcatacag cctagctaaa tttaatgttt tttcgattaa cgggaagctt     420
ggctctattt gcggtcaact tttaatcctg acctatgtgt atggtaaaga aactcctgat     480
ggcatcaaga ttacactgga taatttaaca atgcaggagt taggatattc aagtggcatc     540
gcacatagct cagctgttag cagaattatt tccaaattaa agcaagagaa agttatcgtg     600
tataaaaatt catgctttta tgtacaaaat ctgattatct caaaagatat gcccctaaat     660
tagatgaatg gttttattta gcatgtcctg ctacttgggg aaaattaaat taa           713
```

<210> SEQ ID NO 84
<211> LENGTH: 12
<212> TYPE: DNA
<213> ORGANISM: Artificial Sequence
<220> FEATURE:
<223> OTHER INFORMATION: Synthetic

<400> SEQUENCE: 84
ggtggtggag ga                                                         12

<210> SEQ ID NO 85
<211> LENGTH: 12
<212> TYPE: DNA
<213> ORGANISM: Artificial Sequence
<220> FEATURE:
<223> OTHER INFORMATION: Synthetic

<400> SEQUENCE: 85
ggtggaggtg ga                                                         12

<210> SEQ ID NO 86
<211> LENGTH: 12
<212> TYPE: DNA
<213> ORGANISM: Artificial Sequence
<220> FEATURE:
<223> OTHER INFORMATION: Synthetic

<400> SEQUENCE: 86
ggtggaggag gt                                                         12

<210> SEQ ID NO 87
<211> LENGTH: 12
<212> TYPE: DNA
<213> ORGANISM: Artificial Sequence
<220> FEATURE:
<223> OTHER INFORMATION: Synthetic

<400> SEQUENCE: 87

```
ggaggtggtg ga                                              12

<210> SEQ ID NO 88
<211> LENGTH: 12
<212> TYPE: DNA
<213> ORGANISM: Artificial Sequence
<220> FEATURE:
<223> OTHER INFORMATION: Synthetic

<400> SEQUENCE: 88
ggaggaggtg gt                                              12

<210> SEQ ID NO 89
<211> LENGTH: 12
<212> TYPE: DNA
<213> ORGANISM: Artificial Sequence
<220> FEATURE:
<223> OTHER INFORMATION: Synthetic

<400> SEQUENCE: 89
ggaggtggag gt                                              12

<210> SEQ ID NO 90
<211> LENGTH: 12
<212> TYPE: DNA
<213> ORGANISM: Artificial Sequence
<220> FEATURE:
<223> OTHER INFORMATION: Synthetic

<400> SEQUENCE: 90
ggaggaggag gt                                              12

<210> SEQ ID NO 91
<211> LENGTH: 12
<212> TYPE: DNA
<213> ORGANISM: Artificial Sequence
<220> FEATURE:
<223> OTHER INFORMATION: Synthetic

<400> SEQUENCE: 91
ggaggaggtg ga                                              12

<210> SEQ ID NO 92
<211> LENGTH: 12
<212> TYPE: DNA
<213> ORGANISM: Artificial Sequence
<220> FEATURE:
<223> OTHER INFORMATION: Synthetic

<400> SEQUENCE: 92
ggaggtggag ga                                              12

<210> SEQ ID NO 93
<211> LENGTH: 12
<212> TYPE: DNA
<213> ORGANISM: Artificial Sequence
<220> FEATURE:
<223> OTHER INFORMATION: Synthetic

<400> SEQUENCE: 93
ggtggaggag ga                                              12

<210> SEQ ID NO 94
<211> LENGTH: 12
<212> TYPE: DNA
```

<210> SEQ ID NO 95
<211> LENGTH: 529
<212> TYPE: PRT
<213> ORGANISM: Artificial Sequence
<220> FEATURE:
<223> OTHER INFORMATION: Synthetic

<400> SEQUENCE: 95

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
```

```
                    325                 330                 335
Ile Ile Lys Asn Ser Ser Phe Lys Ala Val Ile Tyr Gly Gly Ser Ala
                340                 345                 350
Lys Asp Glu Val Gln Ile Ile Asp Gly Asn Leu Gly Asp Leu Arg Asp
                355                 360                 365
Ile Leu Lys Lys Gly Ala Thr Phe Asn Arg Glu Thr Pro Gly Val Pro
                370                 375                 380
Ile Ala Tyr Thr Thr Asn Phe Leu Lys Asp Asn Glu Leu Ala Val Ile
385                 390                 395                 400
Lys Asn Asn Ser Glu Tyr Ile Glu Thr Thr Ser Lys Ala Tyr Thr Asp
                405                 410                 415
Gly Lys Ile Asn Ile Asp His Ser Gly Gly Tyr Val Ala Gln Phe Asn
                420                 425                 430
Ile Ser Trp Asp Glu Val Asn Tyr Asp Pro Glu Gly Asn Glu Ile Val
                435                 440                 445
Gln His Lys Asn Trp Ser Glu Asn Asn Lys Ser Lys Leu Ala His Phe
                450                 455                 460
Thr Ser Ser Ile Tyr Leu Pro Gly Asn Ala Arg Asn Ile Asn Val Tyr
465                 470                 475                 480
Ala Lys Glu Ala Thr Gly Leu Ala Trp Glu Ala Arg Thr Val Ile
                485                 490                 495
Asp Asp Arg Asn Leu Pro Leu Val Lys Asn Arg Asn Ile Ser Ile Trp
                500                 505                 510
Gly Thr Thr Leu Tyr Pro Lys Tyr Ser Asn Lys Val Asp Asn Pro Ile
                515                 520                 525
Glu

<210> SEQ ID NO 96
<211> LENGTH: 11
<212> TYPE: PRT
<213> ORGANISM: Artificial Sequence
<220> FEATURE:
<223> OTHER INFORMATION: Synthetic

<400> SEQUENCE: 96

Glu Ala Thr Gly Leu Ala Trp Glu Ala Arg
1               5                   10

<210> SEQ ID NO 97
<211> LENGTH: 25
<212> TYPE: PRT
<213> ORGANISM: Artificial Sequence
<220> FEATURE:
<223> OTHER INFORMATION: Synthetic

<400> SEQUENCE: 97

Met Lys Lys Ile Met Leu Val Phe Ile Thr Leu Ile Leu Val Ser Leu
1               5                   10                  15

Pro Ile Ala Gln Gln Thr Glu Ala Lys
            20                  25

<210> SEQ ID NO 98
<211> LENGTH: 29
<212> TYPE: PRT
<213> ORGANISM: Artificial Sequence
<220> FEATURE:
<223> OTHER INFORMATION: Synthetic

<400> SEQUENCE: 98
```

```
Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala
            20                  25

<210> SEQ ID NO 99
<211> LENGTH: 21
<212> TYPE: PRT
<213> ORGANISM: Artificial Sequence
<220> FEATURE:
<223> OTHER INFORMATION: Synthetic

<400> SEQUENCE: 99

Asp Tyr Lys Asp His Asp Gly Asp Tyr Lys His Asp Ile Asp Tyr
1               5                   10                  15

Lys Asp Asp Asp Lys
            20

<210> SEQ ID NO 100
<211> LENGTH: 10
<212> TYPE: PRT
<213> ORGANISM: Artificial Sequence
<220> FEATURE:
<223> OTHER INFORMATION: Synthetic

<400> SEQUENCE: 100

Tyr Met Leu Asp Leu Gln Pro Glu Thr Thr
1               5                   10
```

UNITED STATES PATENT AND TRADEMARK OFFICE
CERTIFICATE OF CORRECTION

| | | |
|---|---|---|
| PATENT NO. | : 11,179,339 B2 | Page 1 of 1 |
| APPLICATION NO. | : 16/647977 | |
| DATED | : November 23, 2021 | |
| INVENTOR(S) | : David Fela et al. | |

It is certified that error appears in the above-identified patent and that said Letters Patent is hereby corrected as shown below:

In the Claims

In Claim 20, Column 203, Line 22, delete "5% is between" and insert --5%, is between--

In Claim 24, Column 204, Line 9, delete "method of 23" and insert --method of claim 23--

Signed and Sealed this
Twenty-fifth Day of April, 2023

Katherine Kelly Vidal
*Director of the United States Patent and Trademark Office*